US012773202B2

(12) United States Patent
Halabi et al.

(10) Patent No.: US 12,773,202 B2
(45) Date of Patent: Oct. 27, 2026

(54) TISSUE ANCHORS AND TECHNIQUES FOR USE THEREWITH

(71) Applicant: Edwards Lifesciences Innovation (Israel) Ltd., Caesarea (IL)

(72) Inventors: Ido Halabi, Givatayim (IL); Yuval Kasher, Kfar Shmuel (IL); Michael Lis, Rishon Letzion (IL); Sam Shafigh, Irvine, CA (US); Tomer Shoham, Kibbutz Einat (IL); Anna Khodos, Harish (IL); Or Cohen, Modi'in (IL); Rohan Yogee Katbamna, Irvine, CA (US); Eyal Shaolian, Newport Beach, CA (US); Ehud Aviv, Costa Mesa, CA (US); Ernest William Heflin, Pleasanton, CA (US); Philip Jiun-An Chen, Mission Viejo, CA (US)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 432 days.

(21) Appl. No.: 18/446,409

(22) Filed: Aug. 8, 2023

(65) Prior Publication Data

US 2024/0032908 A1 Feb. 1, 2024

Related U.S. Application Data

(63) Continuation of application No. PCT/IB2022/051099, filed on Feb. 8, 2022.

(Continued)

(51) Int. Cl.
*A61B 17/04* (2006.01)

(52) U.S. Cl.
CPC .. *A61B 17/0401* (2013.01); *A61B 2017/0409* (2013.01)

(58) Field of Classification Search
CPC ... A61B 17/0401; A61B 17/04; A61B 17/068; A61B 2017/0409; A61B 2017/0488;
(Continued)

(56) References Cited

U.S. PATENT DOCUMENTS 3,604,488 A 9/1971 Wishart et al.
3,656,185 A 4/1972 Carpentier et al.
(Continued)

FOREIGN PATENT DOCUMENTS

CN 113331995 A 9/2021
EP 1034753 B1 2/2005
(Continued)

OTHER PUBLICATIONS

Agarwal S., et al., "Interventional Cardiology Perspective Functional Tricuspid Regurgitation," Circulation: Cardiovascular Interventions, 2009, vol. 2, No. 2, pp. 565-573 (11 Pages).
(Continued)

*Primary Examiner* — Dianne Dornbusch
(74) *Attorney, Agent, or Firm* — Anya Adams

(57) ABSTRACT

A catheter device includes a tube that has a distal opening that is configured to be transluminally advanced into the subject; and an extracorporeal unit that is coupled to a proximal end of the tube. A series of cartridges is arranged along the extracorporeal unit, each of the cartridges having an initial position in which the cartridge holds a respective anchor. Each of the cartridges is, moveable from the initial position to a deployment position while remaining coupled to the extracorporeal unit. A driver is configured to, for each of the anchors, sequentially, while the respective cartridge is in the deployment position, move the anchor out of the respective cartridge and through the tube toward the distal opening. Other embodiments are also described.

20 Claims, 76 Drawing Sheets

Related U.S. Application Data

(60) Provisional application No. 63/162,443, filed on Mar. 17, 2021, provisional application No. 63/147,699, filed on Feb. 9, 2021.

(58) Field of Classification Search
CPC ........... A61B 2017/00407; A61B 2017/00725; A61B 2017/00243; A61B 2017/00269; A61B 2017/00818; A61B 2017/00823; A61B 2017/00827; A61B 2017/0414; A61B 2017/0416; A61B 2017/0441; A61B 2017/0464; A61B 2017/0496; A61B 2017/0649; A61B 90/08; A61B 2090/0807; A61F 2/2445; A61F 2/2442; A61F 2/2466; A61F 2/2427; A61F 2/2448; A61F 2/2451; A61F 2/2454; A61F 2/2457; A61F 2/246; A61F 2/2463; A61F 2/2433; A61F 2/2436; A61F 2/2439; A61F 2220/0016; A61F 5/0083; A61F 5/0086
See application file for complete search history.

(56) References Cited

U.S. PATENT DOCUMENTS

| | | | | |
|---|---|---|---|---|
| 3,840,018 | A | 10/1974 | Heifetz et al. | |
| 3,881,366 | A | 5/1975 | Bradley et al. | |
| 3,898,701 | A | 8/1975 | La Russa | |
| 4,042,979 | A | 8/1977 | Angell | |
| 4,118,805 | A | 10/1978 | Reimels | |
| 4,214,349 | A | 7/1980 | Munch | |
| 4,261,342 | A | 4/1981 | Aranguren Duo | |
| 4,290,151 | A | 9/1981 | Massana | |
| 4,434,828 | A | 3/1984 | Trincia | |
| 4,473,928 | A | 10/1984 | Johnson | |
| 4,518,384 | A * | 5/1985 | Tarello | F41A 9/84 604/61 |
| 4,602,911 | A | 7/1986 | Ahmadi et al. | |
| 4,625,727 | A | 12/1986 | Leiboff | |
| 4,712,549 | A | 12/1987 | Peters et al. | |
| 4,778,468 | A | 10/1988 | Hunt et al. | |
| 4,917,698 | A | 4/1990 | Carpentier et al. | |
| 4,935,027 | A | 6/1990 | Yoon | |
| 4,961,738 | A | 10/1990 | Mackin | |
| 5,042,707 | A | 8/1991 | Taheri | |
| 5,061,277 | A | 10/1991 | Carpentier et al. | |
| 5,064,431 | A | 11/1991 | Gilbertson et al. | |
| 5,104,407 | A | 4/1992 | Lam et al. | |
| 5,108,420 | A | 4/1992 | Marks | |
| 5,201,880 | A | 4/1993 | Wright et al. | |
| 5,258,008 | A | 11/1993 | Wilk | |
| 5,300,034 | A | 4/1994 | Behnke et al. | |
| 5,325,845 | A | 7/1994 | Adair | |
| 5,346,498 | A | 9/1994 | Greelis et al. | |
| 5,383,852 | A | 1/1995 | Stevens-Wright et al. | |
| 5,449,368 | A | 9/1995 | Kuzmak | |
| 5,450,860 | A | 9/1995 | O'Connor | |
| 5,464,404 | A | 11/1995 | Abela et al. | |
| 5,474,518 | A | 12/1995 | Farrer Velazquez | |
| 5,477,856 | A | 12/1995 | Lundquist | |
| 5,593,424 | A | 1/1997 | Northrup III | |
| 5,601,572 | A | 2/1997 | Middleman et al. | |
| 5,626,609 | A | 5/1997 | Zvenyatsky et al. | |
| 5,643,317 | A | 7/1997 | Pavcnik et al. | |
| 5,669,919 | A | 9/1997 | Sanders et al. | |
| 5,676,653 | A | 10/1997 | Taylor et al. | |
| 5,683,402 | A | 11/1997 | Cosgrove et al. | |
| 5,702,397 | A | 12/1997 | Goble et al. | |
| 5,702,398 | A | 12/1997 | Tarabishy | |
| 5,716,370 | A | 2/1998 | Williamson, IV et al. | |
| 5,716,397 | A | 2/1998 | Myers | |
| 5,728,116 | A | 3/1998 | Rosenman | |
| 5,730,150 | A | 3/1998 | Peppel et al. | |
| 5,749,371 | A | 5/1998 | Zadini et al. | |
| 5,752,963 | A | 5/1998 | Allard et al. | |
| 5,782,844 | A | 7/1998 | Yoon et al. | |
| 5,810,882 | A | 9/1998 | Bolduc et al. | |
| 5,824,066 | A | 10/1998 | Gross | |
| 5,830,221 | A | 11/1998 | Stein et al. | |
| 5,843,120 | A | 12/1998 | Israel et al. | |
| 5,855,614 | A | 1/1999 | Stevens et al. | |
| 5,876,373 | A | 3/1999 | Giba et al. | |
| 5,935,098 | A | 8/1999 | Blaisdell et al. | |
| 5,957,953 | A | 9/1999 | DiPoto et al. | |
| 5,961,440 | A | 10/1999 | Schweich, Jr. et al. | |
| 5,961,539 | A | 10/1999 | Northrup, III et al. | |
| 5,984,959 | A | 11/1999 | Robertson et al. | |
| 5,993,459 | A | 11/1999 | Larsen et al. | |
| 6,042,554 | A | 3/2000 | Rosenman et al. | |
| 6,045,497 | A | 4/2000 | Schweich, Jr. et al. | |
| 6,050,936 | A | 4/2000 | Schweich, Jr. et al. | |
| 6,059,715 | A | 5/2000 | Schweich, Jr. et al. | |
| 6,074,341 | A | 6/2000 | Anderson et al. | |
| 6,074,401 | A | 6/2000 | Gardiner et al. | |
| 6,074,417 | A | 6/2000 | Peredo | |
| 6,086,582 | A | 7/2000 | Altman et al. | |
| 6,102,945 | A | 8/2000 | Campbell | |
| 6,106,550 | A | 8/2000 | Magovern et al. | |
| 6,110,200 | A | 8/2000 | Hinnenkamp | |
| 6,132,390 | A | 10/2000 | Cookston et al. | |
| 6,143,024 | A | 11/2000 | Campbell et al. | |
| 6,159,240 | A | 12/2000 | Sparer et al. | |
| 6,165,119 | A | 12/2000 | Schweich, Jr. et al. | |
| 6,174,332 | B1 | 1/2001 | Loch et al. | |
| 6,183,411 | B1 | 2/2001 | Mortier et al. | |
| 6,187,040 | B1 | 2/2001 | Wright | |
| 6,210,347 | B1 | 4/2001 | Forsell | |
| 6,217,610 | B1 | 4/2001 | Carpentier et al. | |
| 6,228,032 | B1 | 5/2001 | Eaton et al. | |
| 6,231,602 | B1 | 5/2001 | Carpentier et al. | |
| 6,251,092 | B1 | 6/2001 | Qin et al. | |
| 6,296,656 | B1 | 10/2001 | Bolduc et al. | |
| 6,315,784 | B1 | 11/2001 | Djurovic | |
| 6,319,281 | B1 | 11/2001 | Patel | |
| 6,328,746 | B1 | 12/2001 | Gambale | |
| 6,332,893 | B1 | 12/2001 | Mortier et al. | |
| 6,355,030 | B1 | 3/2002 | Aldrich et al. | |
| 6,361,559 | B1 | 3/2002 | Houser et al. | |
| 6,368,348 | B1 | 4/2002 | Gabbay | |
| 6,402,780 | B2 | 6/2002 | Williamson, IV et al. | |
| 6,406,420 | B1 | 6/2002 | McCarthy et al. | |
| 6,406,493 | B1 | 6/2002 | Tu et al. | |
| 6,419,696 | B1 | 7/2002 | Ortiz et al. | |
| 6,451,054 | B1 | 9/2002 | Stevens | |
| 6,458,076 | B1 | 10/2002 | Pruitt | |
| 6,461,336 | B1 | 10/2002 | Larre | |
| 6,461,366 | B1 | 10/2002 | Seguin | |
| 6,470,892 | B1 | 10/2002 | Forsell | |
| 6,503,274 | B1 | 1/2003 | Howanec, Jr. et al. | |
| 6,524,338 | B1 | 2/2003 | Gundry | |
| 6,527,780 | B1 | 3/2003 | Wallace et al. | |
| 6,530,952 | B2 | 3/2003 | Vesely | |
| 6,533,772 | B1 | 3/2003 | Sherts et al. | |
| 6,537,314 | B2 | 3/2003 | Langberg et al. | |
| 6,547,801 | B1 | 4/2003 | Dargent et al. | |
| 6,554,845 | B1 | 4/2003 | Fleenor et al. | |
| 6,564,805 | B2 | 5/2003 | Garrison et al. | |
| 6,565,603 | B2 | 5/2003 | Cox | |
| 6,569,198 | B1 | 5/2003 | Wilson et al. | |
| 6,579,297 | B2 | 6/2003 | Bicek et al. | |
| 6,589,160 | B2 | 7/2003 | Schweich, Jr. et al. | |
| 6,592,593 | B1 | 7/2003 | Parodi et al. | |
| 6,602,288 | B1 | 8/2003 | Cosgrove et al. | |
| 6,602,289 | B1 | 8/2003 | Colvin et al. | |
| 6,613,078 | B1 | 9/2003 | Barone | |
| 6,613,079 | B1 | 9/2003 | Wolinsky et al. | |
| 6,619,291 | B2 | 9/2003 | Hlavka et al. | |
| 6,626,899 | B2 | 9/2003 | Houser et al. | |
| 6,626,917 | B1 | 9/2003 | Craig | |
| 6,626,930 | B1 | 9/2003 | Allen et al. | |
| 6,629,534 | B1 | 10/2003 | St. Goar et al. | |
| 6,651,671 | B1 | 11/2003 | Donlon et al. | |
| 6,652,556 | B1 | 11/2003 | VanTassel et al. | |

(56) References Cited

U.S. PATENT DOCUMENTS 6,682,558 B2 1/2004 Tu et al.
6,689,125 B1 2/2004 Keith et al.
6,689,164 B1 2/2004 Seguin
6,695,866 B1 2/2004 Kuehn et al.
6,702,826 B2 3/2004 Liddicoat et al.
6,702,846 B2 3/2004 Mikus et al.
6,709,385 B2 3/2004 Forsell
6,711,444 B2 3/2004 Koblish
6,719,786 B2 4/2004 Ryan et al.
6,723,038 B1 4/2004 Schroeder et al.
6,726,716 B2 4/2004 Marquez
6,726,717 B2 4/2004 Alfieri et al.
6,749,630 B2 6/2004 McCarthy et al.
6,752,813 B2 6/2004 Goldfarb et al.
6,764,310 B1 7/2004 Ichihashi et al.
6,764,510 B2 7/2004 Vidlund et al.
6,764,810 B2 7/2004 Ma et al.
6,786,924 B2 9/2004 Ryan et al.
6,786,925 B1 9/2004 Schoon et al.
6,790,231 B2 9/2004 Liddicoat et al.
6,797,001 B2 9/2004 Mathis et al.
6,797,002 B2 9/2004 Spence et al.
6,802,319 B2 10/2004 Stevens et al.
6,805,711 B2 10/2004 Quijano et al.
6,855,126 B2 2/2005 Flinchbaugh
6,858,039 B2 2/2005 McCarthy
6,884,250 B2 4/2005 Monassevitch et al.
6,893,459 B1 5/2005 Macoviak
6,908,478 B2 6/2005 Alferness et al.
6,908,482 B2 6/2005 McCarthy et al.
6,918,917 B1 7/2005 Nguyen et al.
6,926,730 B1 8/2005 Nguyen et al.
6,960,217 B2 11/2005 Bolduc
6,976,995 B2 12/2005 Mathis et al.
6,986,775 B2 1/2006 Morales et al.
6,989,028 B2 1/2006 Lashinski et al.
6,997,951 B2 2/2006 Solem et al.
7,004,176 B2 2/2006 Lau
7,007,798 B2 3/2006 Happonen et al.
7,011,669 B2 3/2006 Kimblad
7,018,406 B2 3/2006 Seguin et al.
7,037,334 B1 5/2006 Hlavka et al.
7,077,850 B2 7/2006 Kortenbach
7,077,862 B2 7/2006 Vidlund et al.
7,087,064 B1 8/2006 Hyde
7,101,396 B2 9/2006 Artof et al.
7,118,595 B2 10/2006 Ryan et al.
7,125,421 B2 10/2006 Tremulis et al.
7,150,737 B2 12/2006 Purdy et al.
7,159,593 B2 1/2007 McCarthy et al.
7,166,127 B2 1/2007 Spence et al.
7,169,187 B2 1/2007 Datta et al.
7,172,625 B2 2/2007 Shu et al.
7,186,262 B2 3/2007 Saadat
7,186,264 B2 3/2007 Liddicoat et al.
7,189,199 B2 3/2007 McCarthy et al.
7,192,443 B2 3/2007 Solem et al.
7,220,277 B2 5/2007 Arru et al.
7,226,467 B2 6/2007 Lucatero et al.
7,226,477 B2 6/2007 Cox
7,226,647 B2 6/2007 Kasperchik et al.
7,229,452 B2 6/2007 Kayan
7,238,191 B2 7/2007 Bachmann
7,294,148 B2 11/2007 McCarthy
7,311,728 B2 12/2007 Solem et al.
7,311,729 B2 12/2007 Mathis et al.
7,314,485 B2 1/2008 Mathis
7,316,710 B1 1/2008 Cheng et al.
7,329,279 B2 2/2008 Haug et al.
7,335,213 B1 2/2008 Hyde et al.
7,390,329 B2 6/2008 Westra et al.
7,404,824 B1 7/2008 Webler et al.
7,431,692 B2 10/2008 Zollinger et al.
7,442,207 B2 10/2008 Rafiee
7,452,376 B2 11/2008 Lim et al.
7,485,142 B2 2/2009 Milo
7,485,143 B2 2/2009 Webler et al.
7,500,989 B2 3/2009 Solem et al.
7,510,575 B2 3/2009 Spenser et al.
7,527,647 B2 5/2009 Spence
7,530,995 B2 5/2009 Quijano et al.
7,549,983 B2 6/2009 Roue et al.
7,559,936 B2 7/2009 Levine
7,562,660 B2 7/2009 Saadat
7,569,062 B1 8/2009 Kuehn et al.
7,585,321 B2 9/2009 Cribier
7,588,582 B2 9/2009 Starksen et al.
7,591,826 B2 9/2009 Alferness et al.
7,604,646 B2 10/2009 Goldfarb et al.
7,608,103 B2 10/2009 McCarthy
7,625,403 B2 12/2009 Krivoruchko
7,632,303 B1 12/2009 Stalker et al.
7,635,329 B2 12/2009 Goldfarb et al.
7,635,386 B1 12/2009 Gammie
7,686,822 B2 3/2010 Shayani
7,699,892 B2 4/2010 Rafiee et al.
7,704,277 B2 4/2010 Zakay et al.
7,722,666 B2 5/2010 Lafontaine
7,748,389 B2 7/2010 Salahieh et al.
7,753,924 B2 7/2010 Starksen et al.
7,758,632 B2 7/2010 Hojeibane et al.
7,780,726 B2 8/2010 Seguin
7,871,433 B2 1/2011 Lattouf
7,883,475 B2 2/2011 Dupont et al.
7,883,538 B2 2/2011 To et al.
7,892,281 B2 2/2011 Seguin et al.
7,927,370 B2 4/2011 Webler et al.
7,927,371 B2 4/2011 Navia et al.
7,942,927 B2 5/2011 Kaye et al.
7,947,056 B2 5/2011 Griego et al.
7,955,315 B2 6/2011 Feinberg et al.
7,955,377 B2 6/2011 Melsheimer
7,981,152 B1 7/2011 Webler et al.
7,992,567 B2 8/2011 Hirotsuka et al.
7,993,397 B2 8/2011 Lashinski et al.
8,034,103 B2 10/2011 Burriesci et al.
8,052,592 B2 11/2011 Goldfarb et al.
8,062,355 B2 11/2011 Figulla et al.
8,070,804 B2 12/2011 Hyde et al.
8,070,805 B2 12/2011 Vidlund et al.
8,075,616 B2 12/2011 Solem et al.
8,100,964 B2 1/2012 Spence
8,123,801 B2 2/2012 Milo
8,142,493 B2 3/2012 Spence et al.
8,142,495 B2 3/2012 Hasenkam et al.
8,142,496 B2 3/2012 Berreklouw
8,147,542 B2 4/2012 Maisano et al.
8,152,844 B2 4/2012 Rao et al.
8,163,013 B2 4/2012 Machold et al.
8,187,324 B2 5/2012 Webler et al.
8,202,315 B2 6/2012 Hlavka et al.
8,206,439 B2 6/2012 Gomez Duran
8,216,302 B2 7/2012 Wilson et al.
8,231,671 B2 7/2012 Kim
8,262,725 B2 9/2012 Subramanian
8,265,758 B2 9/2012 Policker et al.
8,277,502 B2 10/2012 Miller et al.
8,287,584 B2 10/2012 Salahieh et al.
8,287,591 B2 10/2012 Keidar et al.
8,292,884 B2 10/2012 Levine et al.
8,303,608 B2 11/2012 Goldfarb et al.
8,328,868 B2 12/2012 Paul et al.
8,343,213 B2 1/2013 Salahieh et al.
8,349,002 B2 1/2013 Milo
8,353,956 B2 1/2013 Miller et al.
8,357,195 B2 1/2013 Kuehn
8,382,829 B1 2/2013 Call et al.
8,388,680 B2 3/2013 Starksen et al.
8,393,517 B2 3/2013 Milo
8,419,825 B2 4/2013 Buergler et al.
8,430,926 B2 4/2013 Kirson
8,449,573 B2 5/2013 Chu
8,449,599 B2 5/2013 Chau et al.
8,454,686 B2 6/2013 Alkhatib

(56) References Cited

U.S. PATENT DOCUMENTS

| | | | |
|---|---|---|---|
| 8,460,371 | B2 | 6/2013 | Hlavka et al. |
| 8,475,491 | B2 | 7/2013 | Milo |
| 8,475,525 | B2 | 7/2013 | Maisano et al. |
| 8,518,107 | B2 | 8/2013 | Tsukashima et al. |
| 8,523,940 | B2 | 9/2013 | Richardson et al. |
| 8,551,161 | B2 | 10/2013 | Dolan |
| 8,608,797 | B2 | 12/2013 | Gross et al. |
| 8,628,569 | B2 | 1/2014 | Benichou et al. |
| 8,628,571 | B1 | 1/2014 | Hacohen et al. |
| 8,641,727 | B2 | 2/2014 | Starksen et al. |
| 8,652,202 | B2 | 2/2014 | Alon et al. |
| 8,652,203 | B2 | 2/2014 | Quadri et al. |
| 8,679,174 | B2 | 3/2014 | Ottma et al. |
| 8,685,086 | B2 | 4/2014 | Navia et al. |
| 8,728,097 | B1 | 5/2014 | Sugimoto et al. |
| 8,728,155 | B2 | 5/2014 | Montorfano et al. |
| 8,734,467 | B2 | 5/2014 | Miller et al. |
| 8,734,699 | B2 | 5/2014 | Heideman et al. |
| 8,747,463 | B2 | 6/2014 | Fogarty et al. |
| 8,778,021 | B2 | 7/2014 | Cartledge |
| 8,784,481 | B2 | 7/2014 | Alkhatib et al. |
| 8,790,394 | B2 | 7/2014 | Miller et al. |
| 8,795,355 | B2 | 8/2014 | Alkhatib |
| 8,795,356 | B2 | 8/2014 | Quadri et al. |
| 8,795,357 | B2 | 8/2014 | Yohanan et al. |
| 8,808,366 | B2 | 8/2014 | Braido et al. |
| 8,845,717 | B2 | 9/2014 | Khairkhahan et al. |
| 8,852,272 | B2 | 10/2014 | Gross et al. |
| 8,858,623 | B2 | 10/2014 | Miller et al. |
| 8,864,822 | B2 | 10/2014 | Spence et al. |
| 8,870,948 | B1 | 10/2014 | Erzberger et al. |
| 8,870,949 | B2 | 10/2014 | Rowe |
| 8,888,843 | B2 | 11/2014 | Khairkhahan et al. |
| 8,889,861 | B2 | 11/2014 | Skead et al. |
| 8,894,702 | B2 | 11/2014 | Quadri et al. |
| 8,911,461 | B2 | 12/2014 | Traynor et al. |
| 8,926,696 | B2 | 1/2015 | Cabiri et al. |
| 8,926,697 | B2 | 1/2015 | Gross et al. |
| 8,932,343 | B2 | 1/2015 | Alkhatib et al. |
| 8,932,348 | B2 | 1/2015 | Solem et al. |
| 8,940,044 | B2 | 1/2015 | Hammer et al. |
| 8,945,211 | B2 | 2/2015 | Sugimoto |
| 8,961,602 | B2 | 2/2015 | Kovach et al. |
| 8,979,922 | B2 | 3/2015 | Jayasinghe et al. |
| 8,992,604 | B2 | 3/2015 | Gross et al. |
| 9,005,273 | B2 | 4/2015 | Salahieh et al. |
| 9,011,520 | B2 | 4/2015 | Miller et al. |
| 9,011,530 | B2 | 4/2015 | Reich et al. |
| 9,072,603 | B2 | 7/2015 | Tuval et al. |
| 9,107,749 | B2 | 8/2015 | Bobo et al. |
| 9,119,719 | B2 | 9/2015 | Zipory et al. |
| 9,125,632 | B2 | 9/2015 | Loulmet et al. |
| 9,125,742 | B2 | 9/2015 | Yoganathan et al. |
| 9,138,316 | B2 | 9/2015 | Bielefeld |
| 9,173,646 | B2 | 11/2015 | Fabro |
| 9,180,005 | B1 | 11/2015 | Lashinski et al. |
| 9,180,007 | B2 | 11/2015 | Reich et al. |
| 9,198,756 | B2 | 12/2015 | Aklog et al. |
| 9,265,608 | B2 | 2/2016 | Miller et al. |
| 9,414,921 | B2 | 8/2016 | Miller et al. |
| 9,427,316 | B2 | 8/2016 | Schweich, Jr. et al. |
| 9,561,104 | B2 | 2/2017 | Miller et al. |
| 9,579,090 | B1 | 2/2017 | Simms et al. |
| 9,730,793 | B2 | 8/2017 | Reich et al. |
| 9,788,941 | B2 | 10/2017 | Hacohen |
| 9,801,720 | B2 | 10/2017 | Gilmore et al. |
| 9,907,547 | B2 | 3/2018 | Gilmore et al. |
| 10,368,852 | B2 | 8/2019 | Gerhardt et al. |
| 2001/0021874 | A1 | 9/2001 | Carpentier et al. |
| 2002/0022862 | A1 | 2/2002 | Grafton et al. |
| 2002/0082525 | A1 | 6/2002 | Oslund et al. |
| 2002/0087048 | A1 | 7/2002 | Brock et al. |
| 2002/0103532 | A1 | 8/2002 | Langberg et al. |
| 2002/0120292 | A1 | 8/2002 | Morgan |
| 2002/0151916 | A1 | 10/2002 | Muramatsu et al. |
| 2002/0151970 | A1 | 10/2002 | Garrison et al. |
| 2002/0177904 | A1 | 11/2002 | Huxel et al. |
| 2002/0188301 | A1 | 12/2002 | Dallara et al. |
| 2002/0188350 | A1 | 12/2002 | Arru et al. |
| 2002/0198586 | A1 | 12/2002 | Inoue |
| 2003/0050693 | A1 | 3/2003 | Quijano et al. |
| 2003/0078465 | A1 | 4/2003 | Pai et al. |
| 2003/0078653 | A1 | 4/2003 | Vesely et al. |
| 2003/0083538 | A1 | 5/2003 | Adams et al. |
| 2003/0093148 | A1 | 5/2003 | Bolling et al. |
| 2003/0105519 | A1 | 6/2003 | Fasol et al. |
| 2003/0114901 | A1 | 6/2003 | Loeb et al. |
| 2003/0120340 | A1 | 6/2003 | Liska et al. |
| 2003/0144657 | A1 | 7/2003 | Bowe et al. |
| 2003/0167062 | A1 | 9/2003 | Gambale et al. |
| 2003/0171760 | A1 | 9/2003 | Gambale |
| 2003/0199974 | A1 | 10/2003 | Lee et al. |
| 2003/0204193 | A1 | 10/2003 | Gabriel et al. |
| 2003/0204195 | A1 | 10/2003 | Keane et al. |
| 2003/0229350 | A1 | 12/2003 | Kay |
| 2004/0002735 | A1 | 1/2004 | Lizardi et al. |
| 2004/0010287 | A1 | 1/2004 | Bonutti |
| 2004/0019359 | A1 | 1/2004 | Worley et al. |
| 2004/0019377 | A1 | 1/2004 | Taylor et al. |
| 2004/0024451 | A1 | 2/2004 | Johnson et al. |
| 2004/0044350 | A1 | 3/2004 | Martin et al. |
| 2004/0049211 | A1 | 3/2004 | Tremulis et al. |
| 2004/0059413 | A1 | 3/2004 | Argento |
| 2004/0068273 | A1 | 4/2004 | Fariss et al. |
| 2004/0106950 | A1 | 6/2004 | Grafton et al. |
| 2004/0111095 | A1 | 6/2004 | Gordon et al. |
| 2004/0122514 | A1 | 6/2004 | Fogarty et al. |
| 2004/0127982 | A1 | 7/2004 | Machold et al. |
| 2004/0133274 | A1 | 7/2004 | Webler et al. |
| 2004/0133374 | A1 | 7/2004 | Kattan |
| 2004/0138744 | A1 | 7/2004 | Lashinski et al. |
| 2004/0138745 | A1 | 7/2004 | Macoviak et al. |
| 2004/0148019 | A1 | 7/2004 | Vidlund et al. |
| 2004/0148020 | A1 | 7/2004 | Vidlund et al. |
| 2004/0148021 | A1 | 7/2004 | Cartledge et al. |
| 2004/0176788 | A1 | 9/2004 | Opolski |
| 2004/0181287 | A1 | 9/2004 | Gellman |
| 2004/0186566 | A1 | 9/2004 | Hindrichs et al. |
| 2004/0193191 | A1 | 9/2004 | Starksen et al. |
| 2004/0243227 | A1 | 12/2004 | Starksen et al. |
| 2004/0260317 | A1 | 12/2004 | Bloom et al. |
| 2004/0260344 | A1 | 12/2004 | Lyons et al. |
| 2004/0260393 | A1 | 12/2004 | Rahdert et al. |
| 2004/0260394 | A1 | 12/2004 | Douk et al. |
| 2004/0267358 | A1 | 12/2004 | Reitan |
| 2005/0004668 | A1 | 1/2005 | Aklog et al. |
| 2005/0010287 | A1 | 1/2005 | Macoviak et al. |
| 2005/0010787 | A1 | 1/2005 | Tarbouriech |
| 2005/0016560 | A1 | 1/2005 | Voughlohn |
| 2005/0049692 | A1 | 3/2005 | Numamoto et al. |
| 2005/0055038 | A1 | 3/2005 | Kelleher et al. |
| 2005/0055087 | A1 | 3/2005 | Starksen |
| 2005/0060030 | A1 | 3/2005 | Lashinski et al. |
| 2005/0065601 | A1 | 3/2005 | Lee et al. |
| 2005/0070999 | A1 | 3/2005 | Spence |
| 2005/0075654 | A1 | 4/2005 | Kelleher |
| 2005/0075727 | A1 | 4/2005 | Wheatley |
| 2005/0090827 | A1 | 4/2005 | Gedebou |
| 2005/0090834 | A1 | 4/2005 | Chiang et al. |
| 2005/0096740 | A1 | 5/2005 | Langberg et al. |
| 2005/0107871 | A1 | 5/2005 | Realyvasquez et al. |
| 2005/0119734 | A1 | 6/2005 | Spence et al. |
| 2005/0125002 | A1 | 6/2005 | Baran et al. |
| 2005/0125011 | A1 | 6/2005 | Spence et al. |
| 2005/0131533 | A1 | 6/2005 | Alfieri et al. |
| 2005/0137686 | A1 | 6/2005 | Salahieh et al. |
| 2005/0137688 | A1 | 6/2005 | Salahieh et al. |
| 2005/0137695 | A1 | 6/2005 | Salahieh et al. |
| 2005/0159728 | A1 | 7/2005 | Armour et al. |
| 2005/0159810 | A1 | 7/2005 | Filsoufi |
| 2005/0177180 | A1 | 8/2005 | Kaganov et al. |
| 2005/0177228 | A1 | 8/2005 | Solem et al. |
| 2005/0187568 | A1 | 8/2005 | Klenk et al. |
| 2005/0192596 | A1 | 9/2005 | Jugenheimer et al. |

(56) References Cited

U.S. PATENT DOCUMENTS

| | | | |
|---|---|---|---|
| 2005/0203549 | A1 | 9/2005 | Realyvasquez |
| 2005/0203606 | A1 | 9/2005 | VanCamp |
| 2005/0216039 | A1 | 9/2005 | Lederman |
| 2005/0216079 | A1 | 9/2005 | MaCoviak |
| 2005/0222665 | A1 | 10/2005 | Aranyi |
| 2005/0234481 | A1 | 10/2005 | Waller |
| 2005/0240199 | A1 | 10/2005 | Martinek et al. |
| 2005/0251177 | A1* | 11/2005 | Saadat .................. A61F 5/0086 606/153 |
| 2005/0256532 | A1 | 11/2005 | Nayak et al. |
| 2005/0267478 | A1 | 12/2005 | Corradi et al. |
| 2005/0273138 | A1 | 12/2005 | To et al. |
| 2005/0288778 | A1 | 12/2005 | Shaoulian et al. |
| 2006/0004442 | A1 | 1/2006 | Spenser et al. |
| 2006/0004443 | A1 | 1/2006 | Liddicoat et al. |
| 2006/0020326 | A9 | 1/2006 | Bolduc et al. |
| 2006/0020327 | A1 | 1/2006 | Lashinski et al. |
| 2006/0020336 | A1 | 1/2006 | Liddicoat |
| 2006/0025858 | A1 | 2/2006 | Alameddine |
| 2006/0030885 | A1 | 2/2006 | Hyde |
| 2006/0041319 | A1 | 2/2006 | Taylor et al. |
| 2006/0069429 | A1 | 3/2006 | Spence et al. |
| 2006/0074486 | A1 | 4/2006 | Liddicoat et al. |
| 2006/0085012 | A1 | 4/2006 | Dolan |
| 2006/0095009 | A1 | 5/2006 | Lampropoulos et al. |
| 2006/0106423 | A1 | 5/2006 | Weisel et al. |
| 2006/0122633 | A1 | 6/2006 | To et al. |
| 2006/0129166 | A1 | 6/2006 | Lavelle |
| 2006/0142694 | A1 | 6/2006 | Bednarek et al. |
| 2006/0149280 | A1 | 7/2006 | Harvie et al. |
| 2006/0149368 | A1 | 7/2006 | Spence |
| 2006/0161265 | A1 | 7/2006 | Levine et al. |
| 2006/0173251 | A1 | 8/2006 | Govari et al. |
| 2006/0184240 | A1 | 8/2006 | Jimenez et al. |
| 2006/0184242 | A1 | 8/2006 | Lichtenstein |
| 2006/0195134 | A1 | 8/2006 | Crittenden |
| 2006/0206203 | A1 | 9/2006 | Yang et al. |
| 2006/0212048 | A1 | 9/2006 | Crainich |
| 2006/0241656 | A1 | 10/2006 | Starksen et al. |
| 2006/0241748 | A1 | 10/2006 | Lee et al. |
| 2006/0247763 | A1 | 11/2006 | Slater |
| 2006/0259135 | A1 | 11/2006 | Navia et al. |
| 2006/0271175 | A1 | 11/2006 | Woolfson et al. |
| 2006/0276871 | A1 | 12/2006 | Lamson et al. |
| 2006/0282161 | A1 | 12/2006 | Huynh et al. |
| 2006/0287716 | A1 | 12/2006 | Banbury et al. |
| 2007/0001627 | A1 | 1/2007 | Lin et al. |
| 2007/0010800 | A1 | 1/2007 | Weitzner et al. |
| 2007/0016287 | A1 | 1/2007 | Cartledge et al. |
| 2007/0016288 | A1 | 1/2007 | Gurskis et al. |
| 2007/0021781 | A1 | 1/2007 | Jervis et al. |
| 2007/0027533 | A1 | 2/2007 | Douk |
| 2007/0027536 | A1 | 2/2007 | Mihaljevic et al. |
| 2007/0032823 | A1 | 2/2007 | Tegg |
| 2007/0038221 | A1 | 2/2007 | Fine et al. |
| 2007/0038293 | A1 | 2/2007 | St.Goar et al. |
| 2007/0038296 | A1 | 2/2007 | Navia et al. |
| 2007/0039425 | A1 | 2/2007 | Wang |
| 2007/0049942 | A1 | 3/2007 | Hindrichs et al. |
| 2007/0049970 | A1 | 3/2007 | Belef et al. |
| 2007/0051377 | A1 | 3/2007 | Douk et al. |
| 2007/0055206 | A1 | 3/2007 | To et al. |
| 2007/0060922 | A1 | 3/2007 | Dreyfuss |
| 2007/0061010 | A1 | 3/2007 | Hauser et al. |
| 2007/0066863 | A1 | 3/2007 | Rafiee et al. |
| 2007/0078297 | A1 | 4/2007 | Rafiee et al. |
| 2007/0083168 | A1 | 4/2007 | Whiting et al. |
| 2007/0083235 | A1 | 4/2007 | Jervis et al. |
| 2007/0088390 | A1* | 4/2007 | Paz .................... A61B 17/0401 606/232 |
| 2007/0100427 | A1 | 5/2007 | Perouse |
| 2007/0106328 | A1 | 5/2007 | Wardle et al. |
| 2007/0112359 | A1 | 5/2007 | Kimura et al. |
| 2007/0112422 | A1 | 5/2007 | Dehdashtian |
| 2007/0112425 | A1 | 5/2007 | Schaller et al. |
| 2007/0118151 | A1 | 5/2007 | Davidson |
| 2007/0118154 | A1 | 5/2007 | Crabtree |
| 2007/0118213 | A1 | 5/2007 | Loulmet |
| 2007/0118215 | A1 | 5/2007 | Moaddeb |
| 2007/0142907 | A1 | 6/2007 | Moaddeb et al. |
| 2007/0162111 | A1 | 7/2007 | Fukamachi et al. |
| 2007/0198082 | A1 | 8/2007 | Kapadia et al. |
| 2007/0219558 | A1 | 9/2007 | Deutsch |
| 2007/0239208 | A1 | 10/2007 | Crawford |
| 2007/0244554 | A1 | 10/2007 | Rafiee et al. |
| 2007/0255397 | A1 | 11/2007 | Ryan et al. |
| 2007/0255400 | A1 | 11/2007 | Parravicini et al. |
| 2007/0270755 | A1 | 11/2007 | Von Oepen et al. |
| 2007/0276437 | A1 | 11/2007 | Call et al. |
| 2007/0282375 | A1 | 12/2007 | Hindrichs et al. |
| 2007/0282429 | A1 | 12/2007 | Hauser et al. |
| 2007/0295172 | A1 | 12/2007 | Swartz |
| 2007/0299424 | A1 | 12/2007 | Cumming et al. |
| 2008/0004697 | A1 | 1/2008 | Lichtenstein et al. |
| 2008/0027483 | A1 | 1/2008 | Cartledge et al. |
| 2008/0027555 | A1 | 1/2008 | Hawkins |
| 2008/0033460 | A1 | 2/2008 | Ziniti et al. |
| 2008/0035160 | A1 | 2/2008 | Woodson et al. |
| 2008/0039935 | A1 | 2/2008 | Buch et al. |
| 2008/0058595 | A1 | 3/2008 | Snoke et al. |
| 2008/0065011 | A1 | 3/2008 | Marchand et al. |
| 2008/0071366 | A1 | 3/2008 | Tuval et al. |
| 2008/0086138 | A1 | 4/2008 | Stone et al. |
| 2008/0086203 | A1 | 4/2008 | Roberts |
| 2008/0091169 | A1 | 4/2008 | Heideman et al. |
| 2008/0091257 | A1 | 4/2008 | Andreas et al. |
| 2008/0097483 | A1 | 4/2008 | Ortiz et al. |
| 2008/0097523 | A1 | 4/2008 | Bolduc et al. |
| 2008/0103572 | A1 | 5/2008 | Gerber |
| 2008/0140116 | A1 | 6/2008 | Bonutti |
| 2008/0167713 | A1 | 7/2008 | Bolling |
| 2008/0177380 | A1 | 7/2008 | Starksen et al. |
| 2008/0195126 | A1 | 8/2008 | Solem |
| 2008/0195200 | A1 | 8/2008 | Vidlund et al. |
| 2008/0208265 | A1 | 8/2008 | Frazier et al. |
| 2008/0221672 | A1 | 9/2008 | Lamphere et al. |
| 2008/0228030 | A1 | 9/2008 | Godin |
| 2008/0228223 | A1 | 9/2008 | Alkhatib |
| 2008/0234729 | A1 | 9/2008 | Page et al. |
| 2008/0262480 | A1 | 10/2008 | Stahler et al. |
| 2008/0262609 | A1 | 10/2008 | Gross et al. |
| 2008/0275300 | A1 | 11/2008 | Rothe et al. |
| 2008/0275469 | A1 | 11/2008 | Fanton et al. |
| 2008/0275551 | A1 | 11/2008 | Alfieri |
| 2008/0281353 | A1 | 11/2008 | Aranyi et al. |
| 2008/0281411 | A1 | 11/2008 | Berreklouw |
| 2008/0287862 | A1 | 11/2008 | Weitzner et al. |
| 2008/0288044 | A1 | 11/2008 | Osborne |
| 2008/0288062 | A1 | 11/2008 | Andrieu et al. |
| 2008/0294251 | A1 | 11/2008 | Annest et al. |
| 2008/0300537 | A1 | 12/2008 | Bowman |
| 2008/0300629 | A1 | 12/2008 | Surti |
| 2008/0312506 | A1 | 12/2008 | Spivey et al. |
| 2009/0024110 | A1 | 1/2009 | Heideman et al. |
| 2009/0028670 | A1 | 1/2009 | Garcia et al. |
| 2009/0043381 | A1 | 2/2009 | Macoviak et al. |
| 2009/0054723 | A1 | 2/2009 | Khairkhahan et al. |
| 2009/0054969 | A1 | 2/2009 | Salahieh et al. |
| 2009/0062866 | A1 | 3/2009 | Jackson |
| 2009/0076586 | A1 | 3/2009 | Hauser et al. |
| 2009/0076600 | A1 | 3/2009 | Quinn |
| 2009/0082797 | A1 | 3/2009 | Fung et al. |
| 2009/0088837 | A1 | 4/2009 | Gillinov et al. |
| 2009/0093877 | A1 | 4/2009 | Keidar et al. |
| 2009/0099650 | A1 | 4/2009 | Bolduc et al. |
| 2009/0105816 | A1 | 4/2009 | Olsen et al. |
| 2009/0166913 | A1 | 7/2009 | Guo et al. |
| 2009/0171439 | A1 | 7/2009 | Nissl |
| 2009/0177266 | A1 | 7/2009 | Powell et al. |
| 2009/0177274 | A1 | 7/2009 | Scorsin et al. |
| 2009/0248148 | A1 | 10/2009 | Shaolian et al. |
| 2009/0254103 | A1 | 10/2009 | Deutsch |
| 2009/0264994 | A1 | 10/2009 | Saadat |
| 2009/0287231 | A1 | 11/2009 | Brooks et al. |

(56) References Cited

U.S. PATENT DOCUMENTS

2009/0287304 A1 11/2009 Dahlgren et al.
2009/0299409 A1 12/2009 Coe et al.
2009/0326648 A1 12/2009 Machold et al.
2010/0001038 A1 1/2010 Levin et al.
2010/0010538 A1 1/2010 Juravic et al.
2010/0023022 A1* 1/2010 Zeiner ................ A61B 17/0401 606/139
2010/0023118 A1 1/2010 Medlock et al.
2010/0030014 A1 2/2010 Ferrazzi
2010/0030328 A1 2/2010 Seguin et al.
2010/0042147 A1 2/2010 Janovsky et al.
2010/0049213 A1 2/2010 Serina et al.
2010/0063542 A1 3/2010 Van Der Burg et al.
2010/0063550 A1 3/2010 Felix et al.
2010/0076499 A1 3/2010 Mcnamara et al.
2010/0094248 A1 4/2010 Nguyen et al.
2010/0094314 A1 4/2010 Hernlund et al.
2010/0106141 A1 4/2010 Osypka et al.
2010/0114180 A1 5/2010 Rock et al.
2010/0121349 A1 5/2010 Meier et al.
2010/0121435 A1 5/2010 Subramanian et al.
2010/0121437 A1 5/2010 Subramanian et al.
2010/0130989 A1 5/2010 Bourque et al.
2010/0130992 A1 5/2010 Machold et al.
2010/0152845 A1 6/2010 Bloom et al.
2010/0161043 A1 6/2010 Maisano et al.
2010/0168845 A1 7/2010 Wright
2010/0174358 A1 7/2010 Rabkin et al.
2010/0179574 A1 7/2010 Longoria et al.
2010/0217184 A1 8/2010 Koblish et al.
2010/0217382 A1 8/2010 Chau et al.
2010/0234935 A1 9/2010 Bashiri et al.
2010/0249497 A1 9/2010 Peine et al.
2010/0249908 A1 9/2010 Chau et al.
2010/0249915 A1 9/2010 Zhang
2010/0249920 A1 9/2010 Bolling et al.
2010/0262232 A1 10/2010 Annest
2010/0262233 A1 10/2010 He
2010/0286628 A1 11/2010 Gross
2010/0298929 A1 11/2010 Thornton et al.
2010/0305475 A1 12/2010 Hinchliffe et al.
2010/0324598 A1 12/2010 Anderson
2011/0004210 A1 1/2011 Johnson et al.
2011/0004298 A1 1/2011 Lee et al.
2011/0009956 A1 1/2011 Cartledge et al.
2011/0011917 A1 1/2011 Loulmet
2011/0026208 A1 2/2011 Utsuro et al.
2011/0029066 A1 2/2011 Gilad et al.
2011/0066231 A1 3/2011 Cartledge et al.
2011/0067770 A1 3/2011 Pederson et al.
2011/0071626 A1 3/2011 Wright et al.
2011/0082538 A1 4/2011 Dahlgren et al.
2011/0087146 A1 4/2011 Ryan et al.
2011/0093002 A1 4/2011 Rucker et al.
2011/0118832 A1 5/2011 Punjabi
2011/0137410 A1 6/2011 Hacohen
2011/0144576 A1 6/2011 Rothe et al.
2011/0144703 A1 6/2011 Krause et al.
2011/0202074 A1* 8/2011 Talmo ................ A61B 17/0401 606/228
2011/0202130 A1 8/2011 Cartledge et al.
2011/0208283 A1 8/2011 Rust
2011/0230941 A1 9/2011 Markus
2011/0230961 A1 9/2011 Langer et al.
2011/0257433 A1 10/2011 Walker
2011/0264208 A1 10/2011 Duffy et al.
2011/0276062 A1 11/2011 Bolduc
2011/0288435 A1 11/2011 Christy et al.
2011/0301498 A1 12/2011 Maenhout et al.
2012/0053628 A1 3/2012 Sojka et al.
2012/0053642 A1 3/2012 Lozier et al.
2012/0065464 A1 3/2012 Ellis et al.
2012/0078355 A1 3/2012 Zipory et al.
2012/0078359 A1 3/2012 Li et al.
2012/0089022 A1 4/2012 House et al.
2012/0089125 A1 4/2012 Scheibe et al.
2012/0095552 A1 4/2012 Spence et al.
2012/0109155 A1 5/2012 Robinson et al.
2012/0143226 A1 6/2012 Belson et al.
2012/0150290 A1 6/2012 Gabbay
2012/0158021 A1 6/2012 Morrill
2012/0158023 A1 6/2012 Mitelberg et al.
2012/0179086 A1 7/2012 Shank et al.
2012/0226349 A1 9/2012 Tuval et al.
2012/0239142 A1 9/2012 Liu et al.
2012/0245604 A1 9/2012 Tegzes
2012/0271198 A1 10/2012 Whittaker et al.
2012/0296349 A1 11/2012 Smith et al.
2012/0296417 A1 11/2012 Hill et al.
2012/0310330 A1 12/2012 Buchbinder et al.
2012/0323313 A1 12/2012 Seguin
2013/0030522 A1 1/2013 Rowe et al.
2013/0046373 A1 2/2013 Cartledge et al.
2013/0053884 A1 2/2013 Roorda
2013/0079873 A1 3/2013 Migliazza et al.
2013/0085529 A1 4/2013 Housman
2013/0090724 A1 4/2013 Subramanian et al.
2013/0096673 A1 4/2013 Hill et al.
2013/0116776 A1 5/2013 Gross et al.
2013/0123910 A1 5/2013 Cartledge et al.
2013/0131791 A1 5/2013 Hlavka et al.
2013/0166017 A1 6/2013 Cartledge et al.
2013/0190863 A1 7/2013 Call et al.
2013/0204361 A1 8/2013 Adams et al.
2013/0218206 A1 8/2013 Gadlage
2013/0226289 A1 8/2013 Shaolian et al.
2013/0226290 A1 8/2013 Yellin et al.
2013/0231701 A1 9/2013 Voss et al.
2013/0297013 A1 11/2013 Klima et al.
2013/0304093 A1 11/2013 Serina et al.
2013/0331930 A1 12/2013 Rowe et al.
2014/0067054 A1 3/2014 Chau et al.
2014/0081394 A1 3/2014 Keraenen et al.
2014/0088368 A1 3/2014 Park
2014/0088646 A1 3/2014 Wales et al.
2014/0094826 A1 4/2014 Sutherland et al.
2014/0094906 A1 4/2014 Spence et al.
2014/0114390 A1 4/2014 Tobis et al.
2014/0135799 A1 5/2014 Henderson
2014/0142619 A1 5/2014 Serina et al.
2014/0142695 A1 5/2014 Gross et al.
2014/0148849 A1 5/2014 Serina et al.
2014/0155783 A1 6/2014 Starksen et al.
2014/0163615 A1 6/2014 Gadlage et al.
2014/0163690 A1 6/2014 White
2014/0188108 A1 7/2014 Goodine et al.
2014/0188140 A1 7/2014 Meier et al.
2014/0188215 A1 7/2014 Hlavka et al.
2014/0194976 A1 7/2014 Starksen et al.
2014/0207231 A1 7/2014 Hacohen et al.
2014/0209660 A1* 7/2014 Rogers ................ A61B 17/068 227/176.1
2014/0243859 A1 8/2014 Robinson
2014/0243894 A1 8/2014 Groothuis et al.
2014/0243963 A1 8/2014 Sheps et al.
2014/0251042 A1 9/2014 Asselin et al.
2014/0275757 A1 9/2014 Goodwin et al.
2014/0276648 A1 9/2014 Hammer et al.
2014/0296962 A1 10/2014 Cartledge et al.
2014/0303720 A1 10/2014 Sugimoto et al.
2014/0309661 A1 10/2014 Sheps et al.
2014/0309730 A1 10/2014 Alon et al.
2014/0343668 A1 11/2014 Zipory et al.
2014/0350660 A1 11/2014 Cocks et al.
2014/0379006 A1 12/2014 Sutherland et al.
2015/0018940 A1 1/2015 Quill et al.
2015/0081014 A1 3/2015 Gross et al.
2015/0094800 A1 4/2015 Chawla
2015/0100116 A1 4/2015 Mohl et al.
2015/0112432 A1 4/2015 Reich et al.
2015/0127097 A1 5/2015 Neumann et al.
2015/0133997 A1 5/2015 Deitch et al.
2015/0182336 A1 7/2015 Zipory et al.
2015/0230919 A1 8/2015 Chau et al.

(56) References Cited

U.S. PATENT DOCUMENTS

| | | | |
|---|---|---|---|
| 2015/0272586 A1 | 10/2015 | Herman et al. | |
| 2015/0272734 A1 | 10/2015 | Sheps et al. | |
| 2015/0282931 A1 | 10/2015 | Brunnett et al. | |
| 2015/0351910 A1 | 12/2015 | Gilmore et al. | |
| 2016/0008132 A1 | 1/2016 | Cabiri et al. | |
| 2016/0029920 A1 | 2/2016 | Kronstrom et al. | |
| 2016/0030034 A1 | 2/2016 | Graul et al. | |
| 2016/0058557 A1 | 3/2016 | Reich et al. | |
| 2016/0113767 A1 | 4/2016 | Miller et al. | |
| 2016/0120642 A1 | 5/2016 | Shaolian et al. | |
| 2016/0120645 A1 | 5/2016 | Alon | |
| 2016/0158008 A1 | 6/2016 | Miller et al. | |
| 2016/0242762 A1 | 8/2016 | Gilmore et al. | |
| 2016/0256149 A1 | 9/2016 | Sampson et al. | |
| 2016/0256274 A1 | 9/2016 | Hayoz | |
| 2016/0262755 A1* | 9/2016 | Zipory | A61B 17/068 |
| 2016/0302917 A1 | 10/2016 | Schewel | |
| 2016/0317302 A1 | 11/2016 | Madjarov et al. | |
| 2016/0346084 A1 | 12/2016 | Taylor et al. | |
| 2016/0361058 A1 | 12/2016 | Bolduc et al. | |
| 2016/0361168 A1 | 12/2016 | Gross et al. | |
| 2016/0361169 A1 | 12/2016 | Gross et al. | |
| 2017/0042670 A1 | 2/2017 | Shaolian et al. | |
| 2017/0100119 A1 | 4/2017 | Baird et al. | |
| 2017/0224489 A1 | 8/2017 | Starksen et al. | |
| 2017/0245993 A1 | 8/2017 | Gross et al. | |
| 2018/0008409 A1 | 1/2018 | Kutzik et al. | |
| 2018/0049875 A1 | 2/2018 | Iflah et al. | |
| 2018/0140420 A1 | 5/2018 | Hayoz et al. | |
| 2018/0153543 A1 | 6/2018 | Schneider et al. | |
| 2018/0168803 A1 | 6/2018 | Pesce et al. | |
| 2018/0256334 A1 | 9/2018 | Sheps et al. | |
| 2018/0280019 A1 | 10/2018 | Azar et al. | |
| 2018/0289480 A1 | 10/2018 | D'Ambra et al. | |
| 2018/0318083 A1 | 11/2018 | Bolling et al. | |
| 2019/0029498 A1 | 1/2019 | Mankowski et al. | |
| 2019/0091445 A1 | 3/2019 | House | |
| 2019/0111239 A1 | 4/2019 | Bolduc et al. | |
| 2019/0117400 A1 | 4/2019 | Medema et al. | |
| 2019/0125325 A1 | 5/2019 | Sheps et al. | |
| 2019/0151093 A1 | 5/2019 | Keidar et al. | |
| 2019/0175344 A1 | 6/2019 | Khairkhahan | |
| 2019/0175345 A1 | 6/2019 | Schaffner et al. | |
| 2019/0175346 A1 | 6/2019 | Schaffner et al. | |
| 2019/0183648 A1 | 6/2019 | Trapp et al. | |
| 2019/0240023 A1 | 8/2019 | Spence et al. | |
| 2019/0290260 A1 | 9/2019 | Caffes et al. | |
| 2019/0290431 A1 | 9/2019 | Genovese et al. | |
| 2019/0343633 A1 | 11/2019 | Garvin et al. | |
| 2020/0015810 A1 | 1/2020 | Piccirillo | |
| 2020/0015971 A1 | 1/2020 | Brauon et al. | |
| 2020/0178956 A1 | 6/2020 | Mitelberg et al. | |
| 2020/0390551 A1 | 12/2020 | McCarthy | |
| 2021/0015475 A1 | 1/2021 | Lau | |
| 2021/0052387 A1 | 2/2021 | Greenan et al. | |
| 2021/0059820 A1 | 3/2021 | Clark et al. | |
| 2021/0085461 A1 | 3/2021 | Neumark et al. | |
| 2021/0145584 A1 | 5/2021 | Kasher et al. | |
| 2022/0096232 A1 | 3/2022 | Skaro et al. | |
| 2022/0110656 A1 | 4/2022 | Azar et al. | |
| 2022/0233316 A1 | 7/2022 | Sheps et al. | |
| 2022/0313438 A1 | 10/2022 | Chappel-Ram | |
| 2022/0323221 A1 | 10/2022 | Sharon et al. | |
| 2023/0016867 A1 | 1/2023 | Tennenbaum | |
| 2023/0218291 A1 | 7/2023 | Zarbatany et al. | |
| 2023/0320856 A1 | 10/2023 | Zarbatany et al. | |
| 2024/0008985 A1 | 1/2024 | Yuan et al. | |
| 2024/0099736 A1 | 3/2024 | Elsheikh et al. | |

FOREIGN PATENT DOCUMENTS

| | | | |
|---|---|---|---|
| EP | 3531975 | B1 | 5/2020 |
| WO | WO-1992005093 | A1 | 4/1992 |
| WO | WO-1998046149 | A1 | 10/1998 |
| WO | WO-2002085250 | A2 | 10/2002 |
| WO | WO-2003047467 | A1 | 6/2003 |
| WO | WO-2007098512 | A1 | 9/2007 |
| WO | WO-2010000454 | A1 | 1/2010 |
| WO | WO-2012176195 | A2 | 12/2012 |
| WO | WO-2014064964 | A1 | 5/2014 |
| WO | WO-2015059699 | A2 | 4/2015 |
| WO | WO-2019145941 | A1 | 8/2019 |
| WO | WO-2019145947 | A1 | 8/2019 |
| WO | WO-2019182645 | A1 | 9/2019 |
| WO | WO-2019224814 | A1 | 11/2019 |
| WO | WO-2020240282 | A2 | 12/2020 |
| WO | WO-2021014440 | A2 | 1/2021 |
| WO | WO-2021038559 | A1 | 3/2021 |
| WO | WO-2021038560 | A1 | 3/2021 |
| WO | WO-2022064401 | A2 | 3/2022 |
| WO | WO-2022090907 | A1 | 5/2022 |
| WO | WO-2022101817 | A2 | 5/2022 |
| WO | WO-2022153131 | A1 | 7/2022 |
| WO | WO-2022157592 | A1 | 7/2022 |
| WO | WO-2022172108 | A1 | 8/2022 |
| WO | WO-2022172149 | A1 | 8/2022 |
| WO | WO-2022200972 | A1 | 9/2022 |
| WO | WO-2022224071 | A1 | 10/2022 |
| WO | WO-2022229815 | A1 | 11/2022 |
| WO | WO-2022250983 | A1 | 12/2022 |

OTHER PUBLICATIONS

Ahmadi A., et al., "Hemodynamic Changes Following Experimental Production and Correction of Acute Mitral Regurgitation With an Adjustable Ring Prosthesis," The Thoracic and Cardiovascular Surgeon, 1988, vol. 36, No. 6, pp. 313-319.

Ahmadi A., et al., "Percutaneously Adjustable Pulmonary Artery Band," The Annals of Thoracic Surgery, 1995, vol. 60, pp. S520-S522.

Alfieri O., et al., "An Effective Technique to Correct Anterior Mitral Leaflet Prolapse," Journal of Cardiac Surgery, 1999, vol. 14, No. 6, pp. 468-470.

Alfieri O., et al., "Novel Suture Device for Beating-Heart Mitral Leaflet Approximation," The Annals of Thoracic Surgery, 2002, vol. 74, pp. 1488-1493.

Alfieri O., et al., "The Double Orifice Technique in Mitral Valve Repair: A Simple Solution for Complex Problems," The Journal of Thoracic and Cardiovascular Surgery, Oct. 2001, vol. 122, No. 4, pp. 674-681 (10 Pages).

Alfieri O., "The Edge-to-Edge Repair of the Mitral Valve," [Abstracts] 6th Annual NewEra Cardiac Care: Innovation & Technology, Heart Surgery Forum, 2000, pp. 103 (102-123), (22 Pages).

Amplatzer: "AGA: Amplatzer Cardiac Plug Brochure, Instructions to Use," AGA Medical Corporation, 5050 Nathan Lane North, Plymouth, MN 55442 USA, Copyright 2008-2010, 16 Pages, [Retrieved on Jan. 11, 2011].

AMPLATZER: "Septal Occluder and Delivery System," A Patient Guide to the Non-surgical Closuer of the Atrial Septal Defect Using the AMPLATZER Septal Occluder System, AGA Med Ca Corporation, Apr. 2008, 17 Pages.

Amplatzer: "Multifenestracted Septal Occlunder—Cribriform," Cribriform Occluder, A patient, guide to Percutaneous, Transcatheter, Atrial Septal Defect Closuer, AGA Medical Corporation, Apr. 2008, 10 Pages.

Assad R.S., "Adjustable Pulmonary Artery Banding," InTech, 2014, pp. 149-179 (32 Pages).

Brennan J., "510(k) Summary of Safety and Effectiveness," Department of Health & Human Services, May 14, 2009, 6 Pages, (Jan. 19, 2008).

Dabritz S., et al., "Experience with an Adjustable Pulmonary Artery Banding Device in Two Cases: Initial Success—Midterm Failure," The Thoracic and Cardiovascular Surgeon, 1999, vol. 47, pp. 51-52.

Dang N.C., et al., "Simplified Placement of Multiple Artificial Mitral Valve Chords," The Heart Surgery Forum #2005-1005, 2005, vol. 8, No. 3, pp. E129-E131.

Dictionary: Definition of "Lock," Dictionary.com, Jul. 29, 2013, 10 Pages.

(56) References Cited

OTHER PUBLICATIONS

Dieter R.S., "Percutaneous Valve Repair: Update on Mitral Regurgitation and Endovascular Approaches to the Mitral Valve," Applications in Imaging, Cardiac Interventions, Supported by an Educational Grant From Amersham Health, 2003, pp. 11-14.

Elliott D.S., et al., "An Implantable Mechanical Urinary Sphincter: A New Nonhydraulic Design Concept," Urology, 1998, vol. 52, No. 6, pp. 1151-1154.

Langer F., et al., "Ring Plus String: Papillary Muscle Repositioning as an Adjunctive Repair Technique for Ischemic Mitral Regurgitation," The Journal of Thoracic Cardiovascular Surgery, Jan. 2007, vol. 133, No. 1, pp. 247-249.

Langer F., "Ring+String, Successful Repair Technique for Ischemic Intral Regurgitation with Severe Leaflet Tethering," The Department of Thoracic Cardiovascular surgery, Hamburg, Germany, Sep. 15, 2009, pp. S85-S91 (10 Pages), Nov. 8-12, 2008.

Maisano F., et al., "The Double-orifice Technique as a Standardized Approach to Treat Mitral Regurgitation Due to Severe Myxomatous Disease: Surgical Technique," European Journal of Cardiothoracic Surgery, 2000, vol. 17, pp. 201-205 (7 Pages).

Odell J.A., et al., "Early Results of a Simplified Method of Mitral Valve Annuloplasty," Circulation, 1995, vol. 92, pp. 150-154, 13 Pages.

O'Reilly S et al., "Heart Valve Surgery Pushes the Envelope," Medtech Insight, Mar. 2006, vol. 8, No. 3, p. 99 (73-108).

Park S.C., et al., "A Percutaneously Adjustable Device for Banding of the Pulmonary Trunk." International Journal of Cardiology, 1985, vol. 9, No. 4, pp. 477-484.

Swain C.P., et al., "An Endoscopically Deliverable Tissue-transfixing Device for Securing Biosensors in the Gastrointestinal Tract," Gastrointestinal Endoscopy, 1994, vol. 40, No. 6, pp. 730-734.

Swenson O., "An Experimental Implantable Urinary Sphincter," Journal—Invest Urol, Sep. 1976, vol. 14, No. 2, pp. 100-103.

Swenson O., et al., "An Improved Mechanical Device for Control of Urinary Incontinence," Investigative Urology, Mar. 1978, vol. 15, No. 5, pp. 389-391.

Swenson O., "Internal Device for Control of Urinary Incontinence," Journal of Pediatric Surgery, Oct.-Nov. 1972, vol. 7, No. 5, pp. 542-545.

Tajik A.J., et al., "Two-Dimensional Real-time Ultrasonic Imaging of the Heart and Great Vessels," Mayo Clinic Proceedings, May 1978, vol. 53, pp. 271-303, (05 pages).

* cited by examiner

FIG. 9A
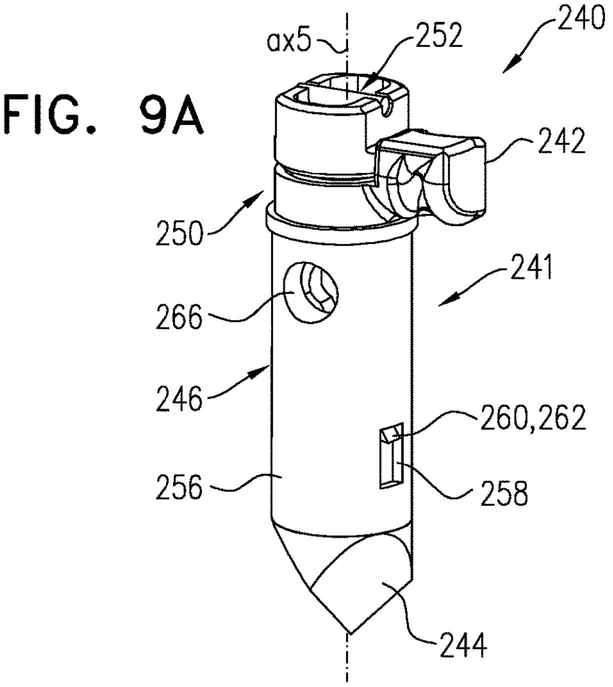
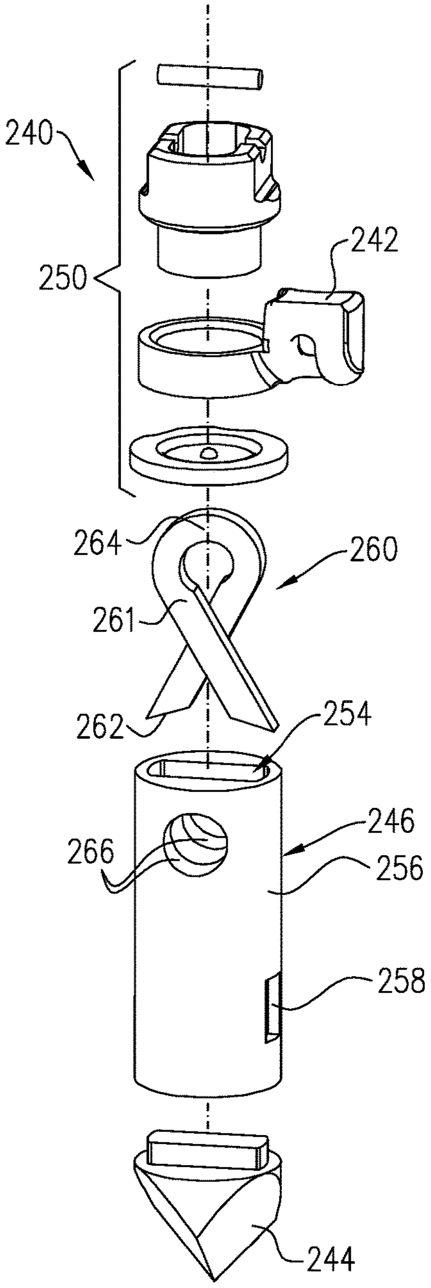
FIG. 9B
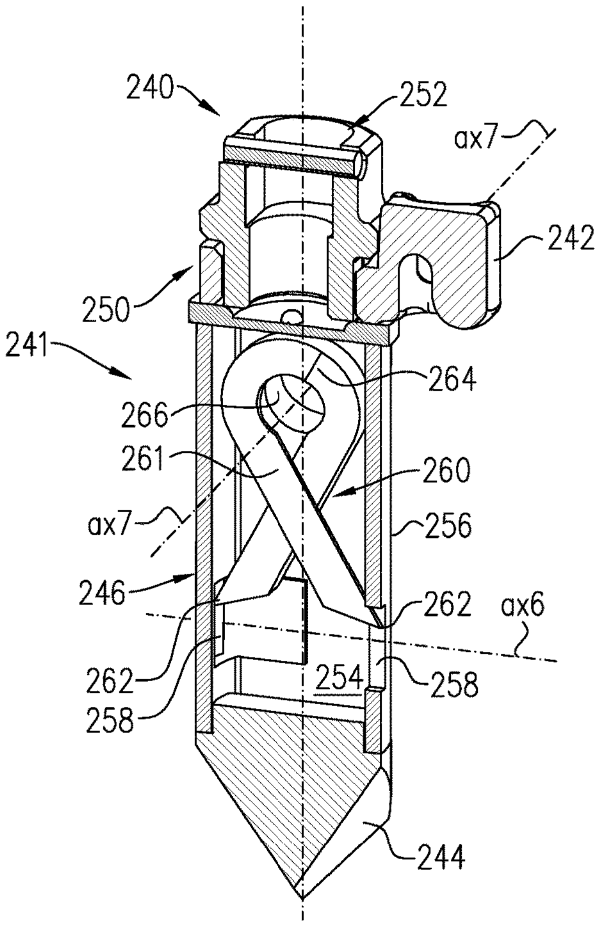
FIG. 9C

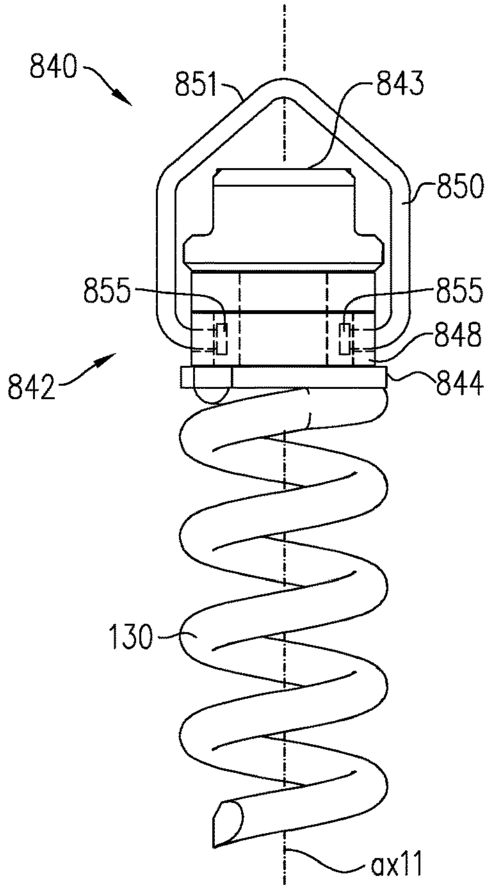
FIG. 39A
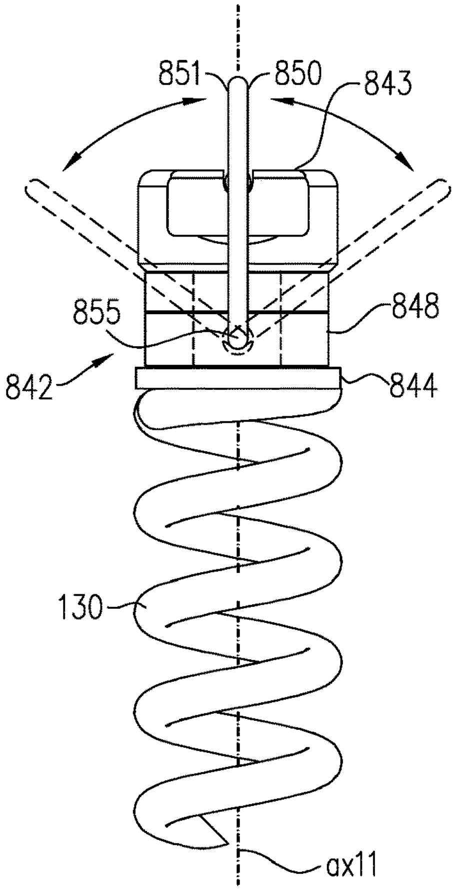
FIG. 39B
FIG. 39C
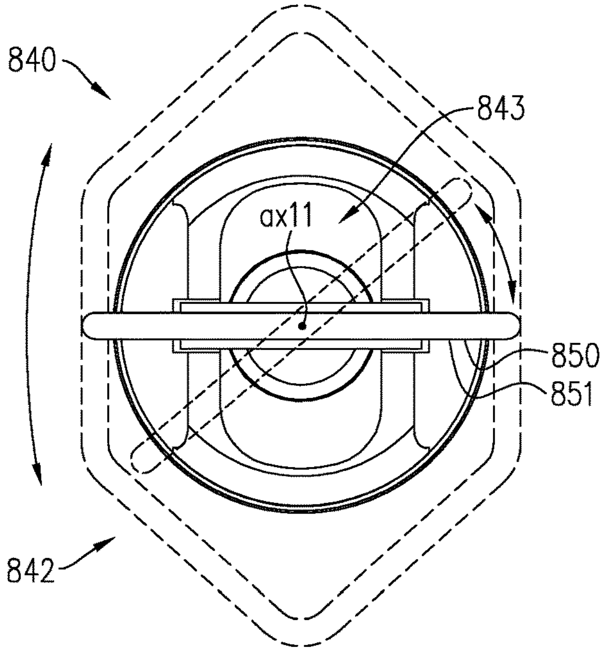

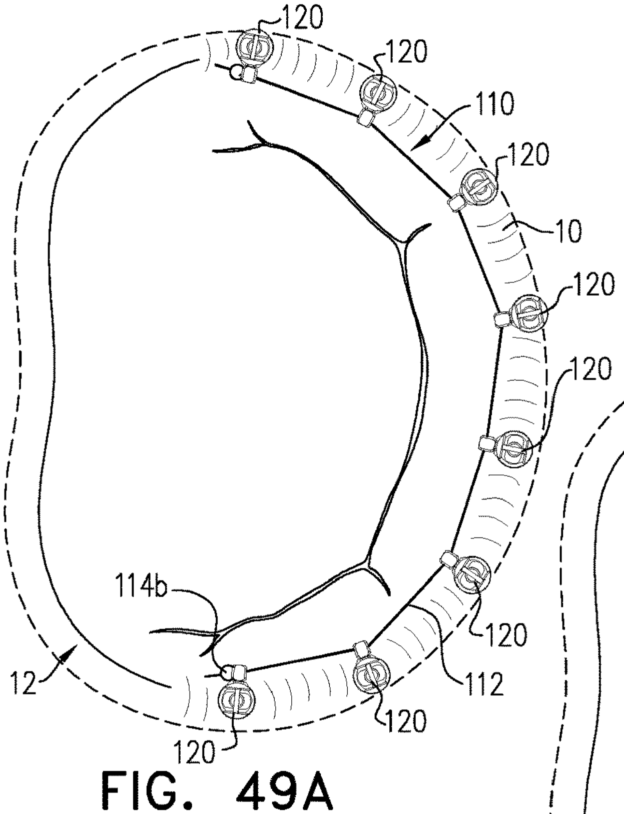
FIG. 49A
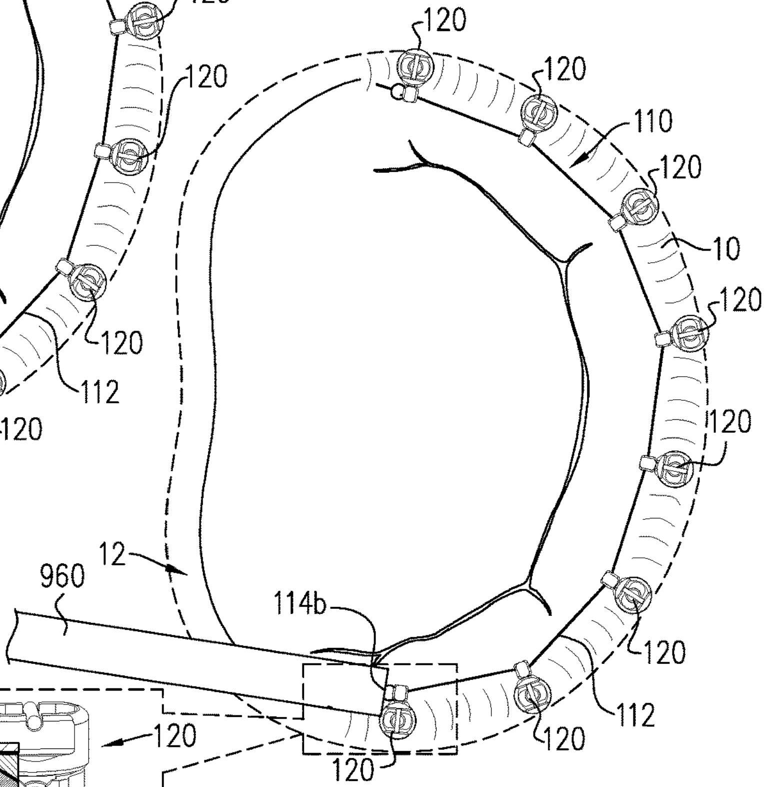
FIG. 49B
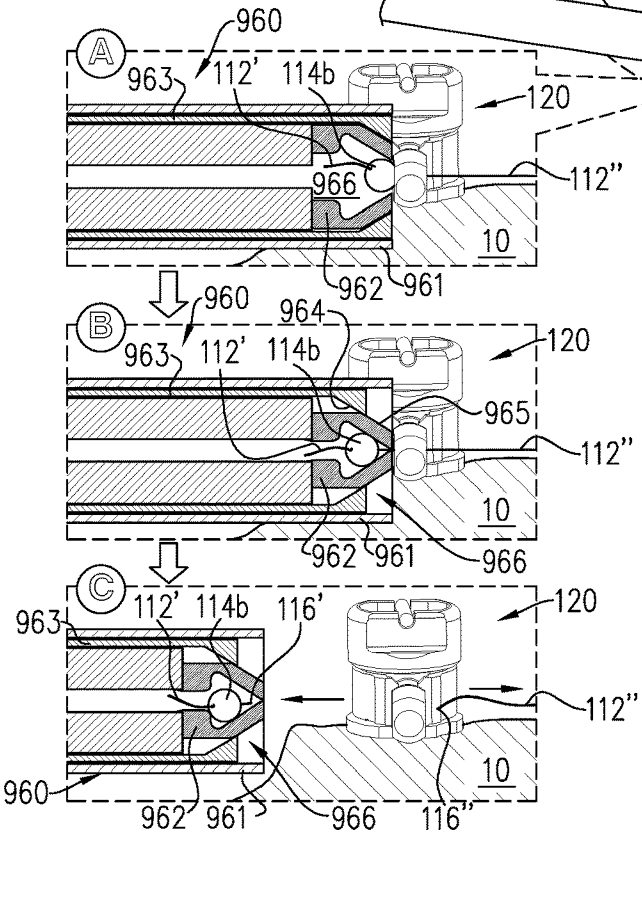

TISSUE ANCHORS AND TECHNIQUES FOR USE THEREWITH

CROSS-REFERENCES TO RELATED APPLICATIONS

The present application is a Continuation of International Patent Application PCT/IB2022/051099 to Shafigh et al., filed Feb. 8, 2022, and titled "Tissue anchors and techniques for use therewith;" which claims priority to:

U.S. Provisional Patent Application 63/147,699 to Shafigh et al., filed Feb. 9, 2021, and titled "Tissue anchors and techniques for use therewith;" and U.S. Provisional Patent Application 63/162,443 to Shafigh et al., filed Mar. 17, 2021, and titled "Tissue anchors and techniques for use therewith."

Each of the above applications is incorporated herein by reference.

BACKGROUND

Annuloplasty involves remodeling tissue of an annulus. This can be done by pulling tissue about the annulus to a new shape. Tissue anchors can be used to facilitate medical procedures including annuloplasty, other remodeling of tissues, and securing implants. In some instances, tissue anchors can be used as an alternative to sutures. For example, a tissue anchor may be used for a procedure in which there is no line-of-sight to the target.

SUMMARY

This summary is meant to provide some examples and is not intended to be limiting of the scope in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure can be included in the examples summarized here.

Some of the systems, apparatuses, and techniques described herein, and applications thereof, include or are configured to be used with an implant that includes multiple tissue anchors slidably coupled to a tether or contraction member or the like. The implant can be a tissue-adjustment implant that contracts tissue upon tensioning of the tether or the like. The implant can be for use at a heart of a subject. For example, the implant can be an annuloplasty implant.

Some applications relate to tissue anchors that are configured (e.g., shaped) to be slidable along a tether (e.g., a line, wire, ribbon, rope, braid, contraction member, suture, etc.) both (i) while aligned (i.e., parallel or coaxial) with the tether, and (ii) while oriented orthogonal to the tether. This is believed to facilitate, inter alia, (i) advancement of the anchor along the tether while aligned with the tether during transcatheter delivery, and (ii) subsequent sliding of the tether with respect to the anchor after implantation, e.g., while the tether is orthogonal to the anchor.

The tissue anchor can include (i) a tissue-engaging element, (ii) and a head at a proximal end of the tissue-engaging element. The head can define an eyelet or other connector that defines an aperture therethrough.

A variety of different tissue-engagement element configurations are possible for any of the various anchors described in this disclosure. In some applications, the tissue-engaging element can be shaped as a helix having an axis, define a central lumen along the axis, and be configured to be screwed into tissue along the axis. In some applications, the tissue-engaging element can be pushed axially into tissue, and in some circumstances, can include barbs or barbed portions to hold the tissue-engaging element in tissue. In some applications, the tissue-engaging element can comprise a hook or multiple hooks. In some applications, the tissue-engaging element can comprise one or more of a clamp, clip, pinching device, dart, staple, tines, etc. Other tissue-engaging elements or portions of anchors are also possible.

The eyelet can be disposed laterally from the axis of the tissue anchor. In some applications, the eyelet is rotatable in a manner that facilitates smooth sliding along the tether both (i) when the anchor is parallel with the tether and (ii) when the anchor is in an orthogonal orientation with respect to the tether. Rotation of the eyelet allows the eyelet to, in each of these orientations of the anchor with respect to the tether define a respective clear, straight pathway through the aperture of the eyelet for the tether to pass through.

In some applications, one or more spacers or dividers (e.g., tubes, solid-wall tubes, laser-cut tubes, rods coils, springs, etc.) are threaded on the tether between anchors. For some such applications, the eyelets define flat faces against which the spacers or dividers can abut in order to provide secure and stable spacing of the anchors and/or force distribution between the anchors.

In some applications, the tissue anchor includes a tissue-engaging element and a head. An anchor driver can engage the anchor at the head (e.g., reversibly attaching to the head), and drives the tissue-engaging element into the tissue. The tissue-engaging element can be the same as or similar to other tissue-engaging elements described herein.

In some applications, a catheter device is provided for advancement and anchoring of the anchors (e.g., an implant that includes the anchors threaded on the tether). The catheter device can include a tube and an extracorporeal unit, and a series of cartridges mounted on the extracorporeal unit can hold the anchors in order to facilitate bringing each of the anchors, in sequence, to a proximal opening of the tube for advancement, by a driver, through the tube. The extracorporeal unit can include a barrier that, along with the cartridges, facilitates verification of engagement between the driver and the anchor, and can obstruct advancement of the anchor in the absence of such verification.

In some applications, the anchor includes a case that has a tissue-facing opening, and the tissue-engaging element is helical, and is stored within the case such that rotation of the tissue-engaging element with respect to the case, while the tissue-facing opening faces tissue, causes the tissue-engaging element to helically exit the case via the tissue-facing opening, and screw into the tissue. For some such applications, the tissue-engaging element is axially compressed within the case, and axially expands as it exits the tissue-facing opening.

In some applications, the tissue anchor includes a sharpened distal tip, a hollow body proximal from the tip, and a spring constrained in the hollow body. The tissue anchor is configured to be driven into tissue tip-first such that the hollow body becomes disposed in the tissue, and the spring is then released such that it pushes sharpened ends laterally out of lateral ports in the hollow body, further securing anchoring of the anchor.

In some applications, the tissue anchor is delivered using a tool that includes a tube and a driver. The tool drives a distal opening of the tube into the tissue, and while the opening remains submerged in the tissue, the driver drives the tissue-engaging element of the anchor out of the opening and into the tissue.

In some applications, the tissue anchor has a head, and multiple tissue-engaging elements that are configured to be driven linearly into tissue where they move toward each other, pressing a tissue-facing side of the head against the tissue. The head can define grips, such that the movement of the tissue-engaging elements toward each other presses the grips against the tissue. For some such applications, each tissue-engaging element defines a lateral barb, and the barb may become exposed upon movement of the tissue-engaging elements toward each other.

In some applications, a tether-handling device is used to lock tension in a tether, e.g., before excess tether is cut and removed. For example, the tether-handling device can include a clamp that clamps onto the tether. The tether-handling device can also be configured to manage (e.g., move, confine, cover, and/or obscure) a vestigial piece of the tether left behind after the cutting, e.g., to reduce a likelihood of the cut end injuring adjacent tissue.

In some applications, the tether-handling device is used as a stopper (or fastener), configured to be locked to a tether of a tissue-adjustment implant that includes multiple anchors, in a vicinity of a final tissue anchor of the implant. When locked to the tether, the tether-handling device is configured to restrict movement of the tether with respect to the final tissue anchor. Therefore, if the tether-handling device is locked to the tether after tension is applied to the tether, the tether-handling device locks the tension in the tether.

Some applications relate to tensioners that include a spring and a restraint. The restraint restrains the spring in an elastically-deformed (i.e., strained) state, but is bioresorbable at a given rate. Therefore, after the restraint disintegrates within the body of the subject (e.g., after a predetermined duration after implantation), it ceases to restrain the spring, and the spring moves away from its elastically-deformed state, e.g., toward its resting state. The spring is coupled to at least one tether between two anchors, such that this movement of the spring pulls on (e.g., applies tension to) the tether, drawing the anchors toward each other. This delayed application of tension to the tether is hypothesized to allow physiological processes such as tissue recovery and growth to enhance anchoring of the anchors while the tether is under a lesser amount of tension, before increasing the tension to a degree that achieves the desired tissue adjustment.

Some applications relate to anchor-handling assemblies that can be used to transluminally de-anchor a tissue anchor from tissue of a subject, and to remove the anchor from the subject. Each of these anchor-handling assemblies can include a sleeve and a tool. A distal end of the sleeve can be advanced over the head of the anchor, and jaws of the tool can then be advanced within the sleeve and engaged with an anchor head of the anchor. An inner dimension of the distal portion of the sleeve can be such that it retains the jaws in a closed state, and the tool can be configured such that the jaws can be locked to an interface of the anchor head while in the closed state, e.g., a snap fit. The tool can then de-anchor the anchor, which is then removed from the subject using the anchor-handling assembly.

Some applications relate to anchor drivers that have a driver head that is locked to the driver interface of an anchor by moving a part of the driver head laterally and, for example, into a recess defined by the driver interface. For example, fins can be pushed laterally by a rod that is extended distally between the fins. Optionally, a cam of the driver head can be coupled to a distal part of a rod that extends through a shaft of the driver and that is eccentric with respect to the shaft, such that rotation of the shaft causes the cam to rotate and protrude laterally from the shaft.

In some applications, systems, apparatuses, and techniques are described for use with an implant that includes multiple anchors threaded on a tether, whereby after anchoring the anchors to tissue, an anchor is added to the tether between other anchors and is anchored, or is de-anchored and removed from the tether from between other anchors. In some applications, a magnet is disposed in the head of each anchor to facilitate navigation to the anchor. In some applications, the anchor head includes a shackle that facilitates this, by allowing the tether to be moved laterally through an opening of the shackle, rather than requiring axial threading of the tether that would be required had the anchor head instead included a regular eyelet.

There is provided, in accordance with some applications, a system for use with a subject, including a catheter device, including a tube and an extracorporeal unit. The tube can have a distal opening that is configured to be transluminally advanced into the subject, and a proximal end that defines a proximal opening. The extracorporeal unit can be coupled to the proximal end of the tube, and/or can define a deployment position. The extracorporeal unit can include a track that leads to the deployment position, and/or a barrier that is movable between (i) a closed state in which the barrier obstructs the proximal opening, and (ii) an open state. In some applications, a track is not used and the cartridge can be moved into position by other means, e.g., attached by hand, rotated into position, etc.

The system can further include a series of anchors.

In some applications, the system includes a series of cartridges, each of the cartridges holding a respective anchor of the series of anchors and being coupled to the extracorporeal unit at a respective initial position of a series of initial positions. Each of the cartridges can be configured to be, while remaining coupled to the extracorporeal unit, moveable along the track from the respective initial position to the deployment position (or otherwise moveable into the deployment position, e.g., if no track is included) such that (i) in the deployment position, the cartridge holds the respective anchor opposite the proximal opening, and (ii) the barrier is in its closed state.

The system can further include an anchor driver that, for each of the anchors, is configured to, while the anchor is held opposite the proximal opening by the respective cartridge in the deployment position, (i) engage the anchor, and (ii) while engaged with the anchor, apply a force to the anchor that transitions the barrier into its open state. For each of the anchors, the anchor driver can be configured to, while the barrier remains in its open state, advance the anchor distally out of the respective cartridge, through the proximal opening, and through the tube toward the distal opening.

In some applications, the force is an engagement-verification force that challenges the engagement of the anchor by the anchor driver.

In some applications, the barrier is configured to move from its closed state to its open state by pivoting.

In some applications, the force is a proximal pulling force, and the anchor driver, for each of the anchors, is configured to, while engaged with the anchor, apply the proximal pulling force to the anchor.

In some applications, the system is configured to define a threshold magnitude of the force, the barrier transitioning into the open state responsively to the force only upon the force exceeding the threshold magnitude.

In some applications, for each of the cartridges, the cartridge is configured to undergo conformational change in response to the force, and the anchor driver is configured to transition the barrier into its open state by inducing the conformational change by applying the force to the respective anchor.

In some applications, the barrier is biased toward being in its open state.

In some applications, the extracorporeal unit includes a spring-loaded displacement mechanism configured to transition the barrier into its open state responsively to the force applied to the anchor by the anchor driver.

In some applications, each of the cartridges is configured to lock to the extracorporeal unit upon arriving at the deployment position.

In some applications, each of the cartridges is shaped to be grasped by hand by a human operator and is configured to be moved along the track by hand by the operator.

In some applications, the catheter device further includes a port at the proximal opening of the tube. In some applications, the system further includes a flushing adapter that includes a fluid fitting, a nozzle, and a channel therebetween. In some applications, the flushing adapter is reversibly lockable to the extracorporeal unit in a flushing position in which (i) the fluid fitting is accessible from outside of the catheter device, and (ii) the nozzle in fluid communication with the port such that fluid driven into the flushing adapter via the fluid fitting is directed distally through the tube.

In some applications, in the flushing position, the barrier is in its open state, and the channel extends distally past the barrier.

In some applications, the flushing position is substantially coincident with the deployment position.

In some applications, the fluid fitting is a Luer fitting.

In some applications, the port includes a sealing membrane, the anchor driver configured, for each of the anchors, to advance the anchor distally through the membrane and into the tube.

In some applications, in the flushing position, the nozzle seals with the port proximally from the membrane.

In some applications, the port has a tapered inner wall that defines a lumen proximal from the membrane, the lumen of the port tapering distally toward the membrane.

In some applications, the nozzle is dimensioned such that, when the flushing adapter is locked to the extracorporeal unit in the flushing position, the nozzle seals against the tapered inner wall proximally from the membrane.

In some applications, the membrane is shaped to define a first aperture through the membrane, a second aperture through the membrane, and a closed slit connecting the first aperture with the second aperture.

In some applications, the first aperture is wider in diameter than the second aperture.

In some applications, the first aperture is 3-10 times larger than the second aperture.

In some applications, each of the anchors includes a tissue-engaging element. In some applications, each of the anchors includes a head that includes an eyelet. In some applications, the port is arranged such that, for each of the cartridges, while the cartridge is in the deployment position and holds the respective anchor opposite the proximal opening: (i) the tissue-engaging element of the respective tissue anchor is aligned with the first aperture, thereby defining an anchor-advancement axis from the respective tissue anchor, through the first aperture, and through the tube, and (ii) the eyelet of the respective tissue anchor is aligned with the second aperture. The tissue-engaging element can be the same as or similar to other tissue-engaging elements described herein.

In some applications, the system further includes a platform, and the proximal end of the tube defines a longitudinal axis. In some applications, the extracorporeal unit is configured to be mounted on the platform in a manner that facilitates rotation of the extracorporeal unit around the longitudinal axis. In some applications, the extracorporeal unit is rotationally fixed to the tube, such that rotation of the extracorporeal unit around the longitudinal axis rotates the tube.

In some applications, the system defines an array of discrete rotational orientations of the extracorporeal unit around the longitudinal axis, and the extracorporeal unit is configured to be mounted on the platform in a manner that facilitates orienting the extracorporeal unit in each of the discrete rotational orientations.

In some applications, the system further includes at least one detent, configured to secure the extracorporeal unit in each of the discrete rotational orientations.

In some applications, the at least one detent is configured to secure the extracorporeal unit in each of the discrete rotational orientations by providing a snap-fit of the extracorporeal unit in each of the discrete rotational orientations.

In some applications, the extracorporeal unit defines an array of recesses corresponding to the array of discrete rotational orientations. In some applications, the at least one detent is configured to secure the extracorporeal unit in each of the discrete rotational orientations by, for each of the discrete rotational orientations, protruding into the corresponding recess.

In some applications, the system further includes a bracket, the extracorporeal unit being configured to be mounted on the platform via coupling between the bracket and the platform. In some applications, the extracorporeal unit is rotatably coupled to the bracket in a manner that facilitates rotation of the extracorporeal unit around the longitudinal axis. In some applications, the at least one detent is configured to secure the extracorporeal unit in each of the discrete rotational orientations by, while the extracorporeal unit is disposed in any of the discrete rotational orientations, inhibiting rotation of the extracorporeal unit with respect to the bracket.

In some applications, the at least one detent is spring-loaded.

In some applications, for each of the cartridges, the barrier is configured to transition into its closed state responsively to movement of the cartridge toward the deployment position.

In some applications, for each of the cartridges, the barrier is configured to transition into its closed state responsively to arrival of the cartridge at the deployment position.

In some applications, for each of the cartridges, the cartridge is configured to push the barrier toward its closed state upon arrival of the cartridge at the deployment position.

In some applications, for each of the cartridges, the cartridge includes a first piece and a second piece that (i) holds the respective anchor, (ii) defines a face that, upon arrival of the cartridge at the deployment position, pushes the barrier toward the closed state, and (iii) is configured such that, while the cartridge remains in the deployment position with the barrier in the closed state, application of the force to the respective anchor displaces the face such that the barrier responsively transitions into its open state.

In some applications, the cartridge is configured such that, while the cartridge remains in the deployment position with the barrier in the closed state, application of the force to the respective anchor moves the face proximally. In some applications, the barrier is configured to transition into the open state responsively to the movement of the face proximally.

In some applications, the face is defined by the second piece, and the cartridge is configured such that, while the cartridge remains in the deployment position with the barrier in the closed state, application of the force to the respective anchor displaces the face by sliding the second piece with respect to the first piece.

In some applications, for each of the cartridges, the cartridge is coupled to the extracorporeal unit via coupling between the first piece and the extracorporeal unit.

In some applications, the second piece is mounted inside the first piece.

In some applications, the first piece is shaped to be grasped by hand by a human operator.

In some applications, from the deployment position, each of the cartridges is removable such that the deployment position becomes vacant for a successive cartridge of the series.

In some applications, from the deployment position, each of the cartridges is removable by being removed from the extracorporeal unit.

In some applications, the anchor driver is configured to, for each of the anchors, advance the anchor distally out of the respective cartridge, through the proximal opening, and through the tube toward the distal opening while the respective cartridge remains in the deployment position.

In some applications, for each of the cartridges, the cartridge is configured such that, while (i) the cartridge remains at the deployment position, and (ii) the anchor driver is extended distally beyond the cartridge and through the tube toward the distal opening, the anchor driver inhibits removal of the cartridge from the deployment position.

In some applications, each of the anchors includes a tissue-engaging element, and a head that includes an eyelet. In some applications, the system further includes a tether (e.g., a line, wire, ribbon, rope, braid, contraction member, suture, etc.) threaded through the eyelet of each of the anchors, having a proximal portion that includes a proximal end of the tether, and having a distal portion that includes a distal end of the tether. In some applications, the distal end of the tether is advanceable distally through the tube into the subject while the proximal end of the tether remains outside of the subject. The tissue-engaging element can be the same as or similar to other tissue-engaging elements described herein.

In some applications, the tube defines a lateral slit extending proximally from the distal end of the tube, and the lateral slit is dimensioned to allow the tether, but not the anchors, to exit the tube laterally, proximally from the distal end of the tube.

In some applications, the tube is shaped to define a narrowed inlet into the lateral slit, configured to inhibit but not preclude the tether from distally exiting the lateral slit via the narrowed inlet.

In some applications, the tube includes a tip frame that maintain the lateral slit and the narrowed inlet.

In some applications, the tip frame is resilient.

In some applications, for each of the anchors: (i) the tissue-engaging element defines a central longitudinal axis of the anchor, has a sharpened distal tip, and is configured to be driven into tissue of a subject, (ii) the head is coupled to a proximal end of the tissue-engaging element, and further includes an interface, configured to be reversibly engaged by the anchor driver, and (iii) the eyelet is mounted so as to be revolvable about the central longitudinal axis of the anchor.

In some applications, for each of the anchors, the eyelet: (i) defines an aperture and a slide axis through the aperture, (ii) is disposed laterally from the central longitudinal axis of the anchor thereby defining an eyelet axis that is orthogonal to the central longitudinal axis, and (iii) is mounted so as to be rotatable about the eyelet axis in a manner that constrains the slide axis to be orthogonal to the eyelet axis.

In some applications, for each of the anchors, the eyelet: (i) defines an aperture and a slide axis through the aperture, (ii) is disposed laterally from the central longitudinal axis of the anchor, and (iii) is mounted so as to be revolvable about the central longitudinal axis while the slide axis remains constrained to be orthogonal to the eyelet axis.

In some applications, the interface is disposed on the central longitudinal axis of the anchor.

In some applications, the tissue-engaging element is helical, defines the central longitudinal axis by extending in a helix around and along the central longitudinal axis, and is configured to be screwed into the tissue of the subject.

In some applications, the head includes a collar that circumscribes the central longitudinal axis and is rotatably coupled to the tissue-engaging element, and the eyelet is mounted on the collar, and is revolvable around the central longitudinal axis by rotation of the collar about the central longitudinal axis.

In some applications, the system further includes a series of tubular spacers, threaded on the tether alternatingly with the anchors.

In some applications, each of the spacers is elastically flexible in deflection.

In some applications, each of the spacers includes, at each end of the tubular spacer, a rigid ring.

In some applications, each of the spacers resists axial compression.

In some applications, each of the spacers is defined by a helical wire shaped as a coil.

In some applications, the anchor driver, for each of the anchors, is configured to advance the anchor distally out of the respective cartridge, through the proximal opening, and through the tube toward the distal opening, while the eyelet of the anchor remains threaded on the tether.

In some applications, the catheter device further includes a port at the proximal opening of the tube, the port including a membrane. In some applications, the membrane is shaped to define a first aperture through the membrane, a second aperture through the membrane, and a closed slit connecting the first aperture with the second aperture. In some applications, the port is arranged such that, for each of the anchors, the anchor driver is configured to advance the anchor distally out of the respective cartridge and through the membrane with the tissue-engaging element passing through the first aperture and the tether extending through the second aperture.

In some applications, the catheter device further includes a tensioner that includes a spring-loaded winch, coupled to the proximal portion of the tether, and configured to maintain tension on the tether.

There is provided, in accordance with some applications, a method for use with a catheter device, the method including (i) transluminally advancing a distal portion of a tube of the catheter device to a heart of a subject, the catheter device including an extracorporeal unit coupled to a proximal end of the tube, a cartridge coupled to the extracorporeal unit at an initial position and holding an anchor; and (ii) sliding the cartridge, from the initial position, along a track to a deployment position in which the cartridge holds the anchor opposite a proximal opening of the catheter, the extracorporeal unit including a barrier that obstructs the proximal opening. In some applications, a track is not used and the cartridge can be moved into position by other means, e.g., attached by hand, rotated into position, etc.

The method can further include subsequently, using an anchor driver engaged with the anchor, opening the barrier by applying a force to the anchor.

The method can further include, subsequently to opening the barrier, using the anchor driver, advancing the anchor distally out of the cartridge, through the proximal opening, and through the tube toward the distal portion of the tube.

There is provided, in accordance with some applications, a system for use with a subject, including a catheter device, that includes a tube and an extracorporeal unit. The tube can have a proximal opening, and a distal opening that is configured to be transluminally advanced into the subject. The extracorporeal unit can include a track that leads to a deployment position, and/or a barrier, movable between (i) a closed state in which the barrier obstructs the proximal opening, and (ii) an open state.

The system can further include a first cartridge holding a first anchor and being coupled to the extracorporeal unit and, while remaining coupled to the extracorporeal unit, being moveable along the track from a first initial position to the deployment position such that: (i) the first cartridge holds the first anchor opposite the proximal opening, and (ii) the barrier is in its closed state.

The system can further include a second cartridge holding a second anchor and being coupled to the extracorporeal unit and, while remaining coupled to the extracorporeal unit, being moveable along the track from a second initial position to the deployment position such that (i) the second cartridge holds the second anchor opposite the proximal opening, and (ii) the barrier is in its closed state.

The system can further include an anchor driver that is (i) couplable to the first anchor while the first anchor is held by the first cartridge opposite the proximal opening, and/or (ii) configured to, while the barrier is in its open state, advance the first anchor distally out of the first cartridge through the proximal opening and through the tube. The anchor driver can be subsequently couplable to the second anchor while the second anchor is held by the second cartridge opposite the proximal opening, and/or configured to, while the barrier is in its open state, advance the second anchor distally out of the second cartridge through the proximal opening and through the tube toward the first anchor.

In some applications, the driver is configured to advance the first anchor distally out of the first cartridge through the proximal opening and through the tube while: (i) the first cartridge is in the deployment position, (ii) the barrier is in its open state, and (iii) the second cartridge remains in the second initial position.

In some applications, each of the first cartridge and the second cartridge is configured to lock to the extracorporeal unit upon arriving at the deployment position.

In some applications, each of the first cartridge and the second cartridge is shaped to be grasped by hand by a human operator and is configured to be moved along the track by hand by the human operator.

In some applications, a track is not used and the cartridge can be moved into position by other means, e.g., attached by hand, rotated into position, etc.

In some applications, each of the first cartridge and the second cartridge is removable from the deployment position by being removed from the extracorporeal unit.

In some applications, the system further includes a third cartridge holding a third anchor and being coupled to the extracorporeal unit and, while remaining coupled to the extracorporeal unit, being moveable along the track from a third initial position to the deployment position such that the third cartridge holds the third anchor opposite the proximal opening.

In some applications, the first anchor includes a first tissue-engaging element and a first head including a first eyelet, and the second anchor includes a second tissue-engaging element and a second head including a second eyelet. The first tissue-engaging element and the second tissue-engaging element can be the same as or similar to other tissue-engaging elements described herein.

In some applications, the system further includes a tether (e.g., a line, wire, ribbon, rope, braid, contraction member, suture, etc.) threaded through the first eyelet and the second eyelet, the tether having a proximal portion that includes a proximal end of the tether and having a distal portion that includes a distal end of the tether, the distal end of the tether being advanceable distally through the tube into the subject while the proximal end of the tether remains outside of the subject.

In some applications, the anchor driver is configured to advance the first anchor distally out of the first cartridge, through the proximal opening, and through the tube, while the first eyelet of the first anchor remains threaded on the tether, and the anchor driver is configured to advance the second anchor distally out of the second cartridge, through the proximal opening, and through the tube, while the second eyelet of the second anchor remains threaded on the tether.

In some applications, the catheter device further includes a tensioning device configured to maintain tension on the tether during advancement of the first anchor and advancement of the second anchor.

In some applications, the tensioning device includes a spring and a spool, the spool coupled to the spring such that rotation of the spool in a first direction applies stress to the spring, and the proximal portion of the tether is wound around the spool such that advancing of the distal portion of the tether distally through the tube rotates the spool in the first direction.

There is provided, in accordance with some applications, a system, for use with a subject, the system including a catheter device that includes a tube and an extracorporeal unit. The tube can have a distal opening that is configured to be transluminally advanced to a tissue of the subject, and/or a proximal portion that defines a longitudinal tube-axis. The extracorporeal unit can be coupled to the proximal portion of the tube.

The system can further include a series of anchors, each of the anchors including (i) a tissue-engaging element, and/or a head, coupled to a proximal end of the tissue-engaging element, and including an interface and an eyelet. The tissue-engaging element can be the same as or similar to other tissue-engaging elements described herein.

The system can further include a tether (e.g., a line, wire, ribbon, rope, braid, contraction member, suture, etc.), threaded through the eyelet of each of the anchors.

The system can further include an anchor driver that, for each of the anchors, is configured to (i) engage the interface of the anchor, and/or (ii) while engaged with the anchor, advance the anchor distally through the tube toward the distal opening, and drive the tissue-engaging element into the tissue.

The system can further include a platform. The system can define an array of discrete rotational orientations of the extracorporeal unit around the longitudinal tube-axis. The extracorporeal unit can be configured to be mounted on the platform in a manner that facilitates rotation of the extracorporeal unit around the longitudinal tube-axis so as to become oriented in any of the discrete rotational orientations. The extracorporeal unit can be rotationally fixed to the tube, such that rotation of the extracorporeal unit around the longitudinal tube-axis rotates the tube.

In some applications, the tether has a proximal end, and a distal end that is advanceable distally through the tube into the subject while the proximal end of the tether remains outside of the subject.

In some applications, the tube defines a lateral slit extending proximally from the distal end of the tube. In some applications, the lateral slit is dimensioned to allow the tether, but not the anchors, to exit the tube laterally, proximally from the distal end of the tube.

In some applications, the tube is shaped to define a narrowed inlet into the lateral slit, configured to inhibit but not preclude the tether from distally exiting the lateral slit via the narrowed inlet.

In some applications, the tube includes a tip frame that maintain the narrowed slit and the narrowed inlet.

In some applications, the tip frame is resilient.

In some applications, the system further includes at least one detent, configured to secure the extracorporeal unit in each of the discrete rotational orientations.

In some applications, the at least one detent is spring-loaded.

In some applications, the at least one detent is configured to secure the extracorporeal unit in each of the discrete rotational orientations by providing a snap-fit of the extracorporeal unit in each of the discrete rotational orientations.

In some applications, the extracorporeal unit defines an array of recesses corresponding to the array of discrete rotational orientations. In some applications, the at least one detent is configured to secure the extracorporeal unit in each of the discrete rotational orientations by, for each of the discrete rotational orientations, protruding into the corresponding recess.

In some applications, the system further includes a bracket, the extracorporeal unit being configured to be mounted on the platform via coupling between the bracket and the platform. In some applications, the extracorporeal unit is rotatably coupled to the bracket in a manner that facilitates rotation of the extracorporeal unit around the longitudinal tube-axis. In some applications, the at least one detent is configured to secure the extracorporeal unit in each of the discrete rotational orientations by, while the extracorporeal unit is disposed in any of the discrete rotational orientations, inhibiting rotation of the extracorporeal unit with respect to the bracket.

In some applications, the system further includes a series of tubular spacers, threaded on the tether alternately with the anchors.

In some applications, each of the spacers is elastically flexible in deflection.

In some applications, each of the spacers includes, at each end of the tubular spacer, a rigid ring.

In some applications, each of the spacers resists axial compression.

In some applications, each of the spacers is defined by a helical wire shaped as a coil.

In some applications, for each of the anchors: (i) the tissue-engaging element defines a central longitudinal anchor-axis of the anchor, and (ii) the eyelet is mounted so as to be revolvable about the central longitudinal anchor axis.

In some applications, for each of the anchors, the eyelet: (i) defines an aperture and a slide axis through the aperture, (ii) is disposed laterally from the central longitudinal anchor-axis thereby defining an eyelet axis that is orthogonal to the central longitudinal anchor-axis, and (iii) is mounted so as to be rotatable about the eyelet axis in a manner that constrains the slide axis to be orthogonal to the eyelet axis.

In some applications, for each of the anchors, the eyelet: (i) defines an aperture and a slide axis through the aperture, (ii) is disposed laterally from the central longitudinal anchor-axis, and (iii) is mounted so as to be revolvable about the central longitudinal anchor-axis while the slide axis remains constrained to be orthogonal to the eyelet axis.

In some applications, the interface is disposed on the central longitudinal axis of the anchor.

In some applications, the tissue-engaging element is helical, defines the central longitudinal anchor-axis by extending in a helix around and along the central longitudinal anchor-axis, and is configured to be screwed into the tissue of the subject.

There is provided, in accordance with some applications, a system, for use with a subject, the system including a catheter device that includes a tube and an extracorporeal unit, coupled to a proximal portion of the tube. The tube can have a distal opening that is configured to be transluminally advanced to a tissue of the subject. The proximal portion of the tube can define a longitudinal tube-axis.

The system can define an array of discrete rotational orientations of the extracorporeal unit around the longitudinal tube-axis.

The system can include a platform on which the extracorporeal unit is configured to be mounted in a manner that facilitates rotation of the extracorporeal unit around the longitudinal tube-axis so as to become oriented in any of the discrete rotational orientations.

The extracorporeal unit can be rotationally fixed to the tube, such that rotation of the extracorporeal unit around the longitudinal tube-axis rotates the tube.

In some applications, the system further includes a series of anchors, each of the anchors being advanceable through the tube, and including a tissue-engaging element and a head, coupled to a proximal end of the tissue-engaging element. The tissue-engaging element can be the same as or similar to other tissue-engaging elements described herein.

In some applications, the head of each of the anchors and includes an interface and an eyelet, and the system further includes a tether (e.g., a line, wire, ribbon, rope, braid, contraction member, suture, etc.), threaded through the eyelet of each of the anchors.

In some applications, the system further includes an anchor driver that, for each of the anchors, is configured to engage the interface of the anchor, and while engaged with the anchor, advance the anchor distally through the tube toward the distal opening, and drive the tissue-engaging element into the tissue.

There is provided, in accordance with some applications, a method for use with a heart of a subject, the method including transluminally advancing, to the heart, a distal portion of a tube of a catheter device of a system. The catheter device including an extracorporeal unit that is coupled to the proximal portion of the tube, the proximal portion of the tube defining a longitudinal tube-axis. In some applications, the system further includes a series of anchors, a tether (e.g., a line, wire, ribbon, rope, braid, contraction member, suture, etc.) threaded through an eyelet of each of the anchors, an anchor driver, and a platform.

In some applications, the extracorporeal unit mounted on the platform in a manner that defines an array of discrete rotational orientations of the extracorporeal unit around the longitudinal tube-axis.

In some applications, the method includes, while the extracorporeal unit is in a first of the discrete rotational orientations and using an anchor driver, advancing a first anchor of the series distally through the tube toward the distal opening, and anchoring the first anchor to a first site of tissue of the heart In some applications, the method includes, subsequently, rotating the tube by a predetermined angle of rotation by rotating the extracorporeal unit into a second of the discrete rotational orientations.

In some applications, the method includes, subsequently, while the extracorporeal unit remains in the second of the discrete rotational orientations, and using the anchor driver, advancing a second anchor of the series distally through the tube and over and along the tether toward the distal opening, and anchoring the second anchor to a second site of tissue of the heart.

In some applications, the method further includes, subsequently drawing the first anchor and the second anchor toward each other by applying tension to the tether.

There is provided, in accordance with some applications, a system, for use with a subject, the system including a catheter device that includes a tube and an extracorporeal unit. The tube can have (i) a proximal portion including a proximal end, (ii) a distal portion that is configured to be transluminally advanced to a tissue of the subject, and (iii) an intermediate portion extending between the proximal portion and the distal portion. The extracorporeal unit can be coupled to the proximal portion of the tube. The distal portion of the tube can define a lumen, a distal opening, and a lateral slit extending proximally from the distal opening. The distal portion of the tube can be rotatably coupled to the intermediate portion such that the lateral slit is revolvable about the lumen.

The system can further include a series of anchors, each of the anchors including (i) a tissue-engaging element, and (ii) a head, coupled to a proximal end of the tissue-engaging element, and including an interface and an eyelet.

The system can further include a tether (e.g., a line, wire, ribbon, rope, braid, contraction member, suture, etc.), threaded through the eyelet of each of the anchors.

The system can further include an anchor driver that, for each of the anchors, is configured to (i) engage the interface of the anchor, and/or while engaged with the anchor, advance the anchor distally through the tube toward the distal portion, and drive the tissue-engaging element into the tissue.

Each of the anchors can be dimensioned to be advanced by the anchor driver distally out of the lumen via the distal opening. The lateral slit can be dimensioned to allow the tether, but not the anchor, to exit the lumen laterally through the slit.

In some applications, the distal portion is shaped to define a narrowed inlet into the lateral slit, configured to inhibit but not preclude the tether from distally exiting the lateral slit via the narrowed inlet.

In some applications, the tether has a proximal end, and a distal end that is advanceable distally through the tube into the subject while the proximal end of the tether remains outside of the subject.

In some applications, the system further includes a series of tubular spacers, threaded on the tether alternately with the anchors.

In some applications, each of the spacers is elastically flexible in deflection.

In some applications, each of the spacers includes, at each end of the tubular spacer, a rigid ring.

In some applications, each of the spacers resists axial compression.

In some applications, each of the spacers is defined by a helical wire shaped as a coil.

In some applications, for each of the anchors: (i) the tissue-engaging element defines a central longitudinal anchor-axis of the anchor, and (ii) the eyelet is mounted so as to be revolvable about the central longitudinal anchor axis.

In some applications, for each of the anchors, the eyelet: (i) defines an aperture and a slide axis through the aperture, (ii) is disposed laterally from the central longitudinal anchor-axis thereby defining an eyelet axis that is orthogonal to the central longitudinal anchor-axis, and (iii) is mounted so as to be rotatable about the eyelet axis in a manner that constrains the slide axis to be orthogonal to the eyelet axis.

In some applications, for each of the anchors, the eyelet: (i) defines an aperture and a slide axis through the aperture, (ii) is disposed laterally from the central longitudinal anchor-axis, and (iii) is mounted so as to be revolvable about the central longitudinal anchor-axis while the slide axis remains constrained to be orthogonal to the eyelet axis.

In some applications, the interface is disposed on the central longitudinal axis of the anchor.

In some applications, the tissue-engaging element is helical, defines the central longitudinal anchor-axis by extending in a helix around and along the central longitudinal anchor-axis, and is configured to be screwed into the tissue of the subject.

There is provided, in accordance with some applications, a system and/or an apparatus including a tissue anchor, the tissue anchor including a helical tissue-engaging element and a head. The tissue-engaging element can have a proximal turn, and a distal turn that defines a sharpened distal tip. The tissue-engaging element can extend helically around a central anchor-axis of the tissue anchor. The head can include a core, a flange, and/or a cap. The core can be disposed on the central longitudinal axis. The flange can be fixed to the core and can have a proximal-facing surface. The proximal turn of the tissue-engaging element can lie on the proximal-facing surface of the flange. The cap can be fixed to the core in a manner that secures the tissue-engaging element to the head by sandwiching the proximal turn against the proximal-facing surface of the flange.

In some applications, the cap is fixed to the core via complimentary screw threads defined by the cap and the core.

In some applications, the flange is a first flange, the cap is shaped to define a second flange, and the cap is fixed to the core in a manner that secures the tissue-engaging element to the head by sandwiching the proximal turn between the second flange and the proximal-facing surface of the first flange.

In some applications, the flange is shaped such that the proximal-facing surface is inclined with respect to the central anchor-axis.

In some applications, the flange is shaped such that the proximal-facing surface defines a partial helix.

In some applications, the tissue-engaging element has a second turn immediately distally from the proximal turn, and the flange is disposed between the proximal turn and the second turn.

In some applications, the flange protrudes laterally beyond the core.

In some applications, the flange protrudes radially beyond the core.

In some applications, the apparatus further includes a washer, and the cap is fixed to the core in a manner that secures the tissue-engaging element to the head by sandwiching the proximal turn between the washer and the proximal-facing surface of the flange.

In some applications, the proximal turn has a notch therein, the washer is shaped to define a spur, and the cap is fixed to the core in a manner that secures the tissue-engaging element to the head by sandwiching the proximal turn between the washer and the proximal-facing surface of the flange, with the spur disposed in the notch.

In some applications, the core is shaped as a post, and the cap is shaped to define a cavity in which the post is disposed.

In some applications, the head further includes: (i) a collar, disposed axially between the flange and the cap, circumscribing the post and rotatable about the post, and (ii) an eyelet, mounted on the collar, and revolvable around the central anchor-axis by rotation of the collar about the post.

In some applications, the cap defines a tubular wall that defines the cavity and that is disposed coaxially between the post and the collar.

In some applications, the cap is fixed to the core in a manner that secures the tissue-engaging element to the head by sandwiching the proximal turn between a distal end of the tubular wall and the proximal-facing surface of the flange.

There is provided, in accordance with some applications, a method for manufacturing a tissue anchor, the anchor including a head and helical tissue-engaging element, the method including placing a proximal turn of the helical tissue-engaging element on a proximal-facing surface of a flange of the head. In some applications, the head includes a core disposed on a central anchor-axis of the tissue anchor, and the tissue-engaging element extends helically around the central anchor-axis and has a distal turn that defines a sharpened distal tip. In some applications, the method includes sandwiching the proximal turn against the proximal-facing surface of the flange by fixing a cap to the core.

In some applications, fixing the cap to the core includes screwing the cap onto the core.

In some applications, the flange is a first flange, the cap is shaped to define a second flange, and sandwiching the proximal turn against the proximal-facing surface of the flange includes sandwiching the proximal turn between the second flange and the proximal-facing surface of the first flange.

In some applications, sandwiching the proximal turn against the proximal-facing surface of the flange includes sandwiching the proximal turn between a washer and the proximal-facing surface of the flange by fixing the cap to the core.

In some applications, the proximal turn has a notch therein, the washer is shaped to define a spur, and sandwiching the proximal turn between the washer and the proximal-facing surface of the flange includes sandwiching the proximal turn between the washer and the proximal-facing surface of the flange by fixing the cap to the core such that the spur is disposed in the notch.

In some applications, the core is shaped as a post, the cap is shaped to define a cavity, and fixing the cap to the core includes positioning the post in the cavity.

In some applications, the method further includes placing a collar axially between the flange and the cap such that the collar circumscribes the post and is rotatable about the post, the collar having an eyelet mounted thereon such that the eyelet is revolvable around the central anchor-axis by rotation of the collar about the post.

In some applications, the cap defines a tubular wall that defines the cavity, and fixing the cap to the core includes positioning the tubular wall coaxially between the post and the collar.

In some applications, sandwiching the proximal turn against the proximal-facing surface of the flange by fixing a cap to the core includes sandwiching the proximal turn between a distal end of the tubular wall and the proximal-facing surface of the flange by fixing a cap to the core.

There is provided, in accordance with some applications, a system, for use with a subject, the system including a catheter device that includes a tube and an extracorporeal unit. The tube can have (i) a proximal portion including a proximal end, and (ii) a distal portion that is configured to be transluminally advanced to a tissue of the subject. The extracorporeal unit can be coupled to the proximal portion of the tube.

The system can further include a fluoroscopic guide that includes a flap that has a tip, a root, and an intermediate portion extending between the tip and the root.

At the root, the flap can be pivotably coupled to the distal portion of the tube in a manner in which the flap is deflectable with respect to the tube between (i) a retracted state in which the flap is substantially parallel with the tube, and (ii) an extended state in which the flap extends laterally from the tube.

The intermediate portion can be radiopaque, and flexible such that pressing on the intermediate portion changes a curvature of the intermediate portion.

The fluoroscopic guide can further include a control rod, extending from the distal portion of the tube to the tip of the flap such that (i) advancement of the control rod deflects the flap toward the extended state by pushing the tip of flap, and/or (ii) retraction of the control rod deflects the flap toward the retracted state by pulling the tip of the flap.

In some applications, the fluoroscopic guide is configured such that advancement of the control rod deflects the flap toward the extended state by pushing the tip of flap distally.

In some applications, the fluoroscopic guide is configured such that retraction of the control rod deflects the flap toward the extended state by pulling the tip of flap proximally.

In some applications, the system further includes an anchor, and an anchor driver configured to advance the anchor distally through the tube toward the distal portion and drive the anchor into the tissue.

In some applications, the control rod extends from the extracorporeal unit, along the tube, to an exit point at which the control rod extends from the tube to the tip of the flap.

In some applications, in the retracted state, the tip of the flap is disposed against the distal portion of the tube.

In some applications, in the retracted state, the tip of the flap is disposed proximally from the root of the flap.

In some applications, in the extended state, the flap extends distolaterally from the tube.

In some applications, the distal portion of the tube includes a distal end of the tube, and the root of the flap is pivotably coupled to the distal portion of the tube at the distal end of the tube.

In some applications, the control rod is flexible such that the advancement of the control rod that deflects the flap toward the extended state causes the control rod to flex laterally away from the distal portion of the tube.

In some applications, the flap is pivotably coupled to the distal portion of the tube such that an angular range of the flap between the retracted state and the extended state is 80-160 degrees.

In some applications, the flap is pivotably coupled to the distal portion of the tube such that the angular range of the flap between the retracted state and the extended state is 90-140 degrees.

In some applications, the flap is pivotably coupled to the distal portion of the tube such that the angular range of the flap between the retracted state and the extended state is 100-130 degrees.

In some applications, in the extended state, the flap is disposed at 80-160 degrees with respect to the tube.

In some applications, in the extended state, the flap is disposed at 90-140 degrees with respect to the tube.

In some applications, in the extended state, the flap is disposed at 100-130 degrees with respect to the tube.

There is provided, in accordance with some applications, a method, including transluminally advancing, to a heart of a subject, a distal portion of a tube of a catheter device, the catheter device including a fluoroscopic guide. In some applications, the fluoroscopic guide includes a flap, having: (i) a tip, (ii) a root at which the flap is pivotably coupled to the distal portion of the tube, and (iii) a flexible intermediate portion extending between the tip and the root. In some applications, the fluoroscopic guide also includes a control rod, extending from the distal portion of the tube to the tip of the flap.

In some applications, the method further includes placing a distal end of the tube against a tissue site of the heart proximate to a valve of the heart. In some applications, the method includes, within the heart, deflecting the flap toward an extended state thereof by advancing the control rod such that the control rod pushes the tip of the flap away from the tube.

In some applications, the method includes, while the distal end of the tube remains against the tissue site and the flap remains in its extended state, fluoroscopically observing a curvature of the intermediate portion.

In some applications, the method includes, responsively to the observing, determining whether to drive an anchor into the tissue site.

In some applications, the method includes, responsively to the determining, driving the anchor into the tissue site.

In some applications, deflecting the flap toward the extended state includes deflecting the flap toward the extended state by advancing the control rod such that the control rod pushes the tip of the flap distally.

In some applications, fluoroscopically observing the curvature includes fluoroscopically observing oscillation of the curvature.

In some applications, the catheter device includes an extracorporeal unit that is coupled to a proximal portion of the tube, and the control rod extends from the extracorporeal unit, along the tube, to an exit point at which the control rod extends from the tube to the tip of the flap. In some applications, the method includes deflecting the flap toward the extended state by advancing the control rod includes deflecting the flap toward an extended state thereof by pushing the control rod from the extracorporeal unit.

In some applications, transluminally advancing the distal portion of the tube includes transluminally advancing the distal portion of the tube while the flap is in a retracted state in which the tip of the flap is disposed against the distal portion of the tube.

In some applications, transluminally advancing the distal portion of the tube includes transluminally advancing the distal portion of the tube while the flap is in a retracted state in which the tip of the flap is disposed proximally from the root of the flap.

In some applications, in the extended state, the flap extends distolaterally from the tube, and deflecting the flap toward the extended state includes deflecting the flap toward the extended state in which the flap extends distolaterally from the tube.

In some applications, the distal portion of the tube includes a distal end of the tube, the root of the flap is pivotably coupled to the distal portion of the tube at a pivot point that is at the distal end of the tube, and deflecting the flap toward the extended state includes deflecting the flap about the pivot point that is at the distal portion of the tube.

In some applications, the control rod is flexible, and advancing the control rod includes advancing the control rod such that the control rod flexes laterally away from the distal portion of the tube and pushes the tip of the flap away from the distal portion of the tube.

In some applications, the method further includes, subsequently to the observing, deflecting the flap toward a retracted state thereof by retracting the control rod such that the control rod pulls the tip of the flap toward the tube.

In some applications, deflecting the flap toward the retracted state includes deflecting the flap toward the retracted state by retracting the control rod such that the control rod pulls the tip of the flap proximally.

In some applications, the tissue site is a site on an annulus of the valve, and placing the distal end of the tube against the tissue site includes placing the distal end of the tube against the site on the annulus of the valve.

In some applications, deflecting the flap toward the extended state includes deflecting the flap toward the extended state such that the intermediate portion of the flap becomes pressed against a hinge of the valve at which a leaflet of the valve connects to the annulus.

In some applications, the method further includes pressing the intermediate portion of the flap against a hinge of the valve at which a leaflet of the valve connects to the annulus.

In some applications, deflecting the flap toward the extended state includes deflecting the flap by 80-160 degrees.

In some applications, deflecting the flap toward the extended state includes deflecting the flap by 90-140 degrees.

In some applications, deflecting the flap toward the extended state includes deflecting the flap by 100-130 degrees.

In some applications, in the extended state, the flap is disposed at 80-160 degrees with respect to the tube, and deflecting the flap toward the extended state includes deflecting the flap such that the flap becomes disposed at 80-160 degrees with respect to the tube.

In some applications, in the extended state, the flap is disposed at 90-140 degrees with respect to the tube, and deflecting the flap toward the extended state includes deflecting the flap such that the flap becomes disposed at 90-140 degrees with respect to the tube.

In some applications, in the extended state, the flap is disposed at 100-130 degrees with respect to the tube, and deflecting the flap toward the extended state includes deflecting the flap such that the flap becomes disposed at 100-130 degrees with respect to the tube.

There is provided, in accordance with some applications, a system and/or apparatus, including an anchor for use with tissue of a subject, the anchor including: a case, having a tissue-facing side that defines a tissue-facing opening from inside the case to outside the case; and a tissue-engaging element that is shaped to define a helix that has multiple turns around an axis, and that has distal tip. Tissue-engaging element can be disposed (and can be axially compressed) within the case and positioned such that rotation of the tissue-engaging element about the axis feeds the helix distally out of the tissue-facing opening. The tissue-engaging element can be configured to be screwed into the tissue, and to anchor the case to the tissue, the tissue-facing side serving as a head of the anchor.

In some applications, the distal tip is sharpened.

In some applications, the anchor is configured such that screwing of the tissue-engaging element into the tissue presses the tissue-facing side against the tissue.

In some applications, the case side defines grips on the tissue-facing side, such that the screwing of the tissue-engaging element into the tissue presses the grips against the tissue.

In some applications, the anchor is configured such that screwing of the tissue-engaging element into the tissue moves a proximal part of the tissue-engaging element toward the tissue-facing side.

In some applications, the case further has a driver side opposite the tissue-facing side and defines a driver opening that provides access to the interface from outside the case, and the anchor is configured such that screwing of the tissue-engaging element into the tissue moves the proximal part of the tissue-engaging element away from the driver side.

In some applications, the case further has a driver side opposite the tissue-facing side and defines a driver opening that provides access to the interface from outside the case, and the case is configured to automatically contract as the helix is fed distally out of the tissue-facing opening, such that the driver side follows the proximal part of the tissue-engaging element toward the tissue-facing side.

In some applications, the anchor is configured such that screwing of the tissue-engaging element into the tissue sandwiches the tissue-facing side between the tissue and the proximal part of the tissue-engaging element.

In some applications, the tissue-engaging element is configured such that, as the helix is fed out of the tissue-facing opening, progressively proximal portions of the helix axially expand as they become disposed outside of the case.

In some applications, while the helix is entirely disposed within the case, the helix has a compressed pitch, and portions of the helix disposed outside of the case have an expanded pitch that is at least twice as great as the compressed pitch.

In some applications, the anchor includes an interface at a proximal part of the tissue-engaging element, and the case further has a driver side that defines a driver opening from inside the case to outside the case, the driver opening providing access to the interface.

In some applications, the anchor is configured such that screwing of the tissue-engaging element into the tissue moves the interface away from the driver side and toward the tissue-facing side.

In some applications, the anchor is configured such that screwing of the tissue-engaging element into the tissue sandwiches the tissue-facing side between the tissue and the interface.

In some applications, the interface is rotationally locked with the helix of the tissue-engaging element.

In some applications, the driver opening is disposed in front of the interface.

In some applications, the interface is visible via the driver opening.

In some applications, the interface includes a bar that is transverse to the axis and parallel to the driver opening.

In some applications, the driver side is opposite the tissue-facing side.

In some applications, the system and/or apparatus further includes a driver having a driver head at a distal portion of the driver, the driver head being dimensioned to access the interface from outside the case via the driver opening and being configured to engage the interface, and to rotate the tissue-engaging element by applying torque to the interface.

In some applications, the driver head has an introduction state and a locking state; the anchor head is shaped to define a proximal opening via which the interface is accessible by the driver head while the driver head is in the introduction state, and the anchor driver is configured to lock the driver head to the interface by transitioning the driver head into the locking state by moving a part of the driver head laterally.

In some applications, the anchor driver includes a flexible shaft, and a rod extending through the shaft, the anchor head is disposed at a distal end of the shaft, and the rod is configured to transition the driver head into the locking state by applying a force to the driver head.

In some applications, the driver head includes fins, and the rod is configured to transition the driver head into the locking state by being advanced distally between the fins such that the rod pushes the fins radially outward such that the fins lock to the interface.

In some applications, the fins are configured to, when pushed radially outward by the rod, lock to the interface via a friction fit.

In some applications, the driver head includes a cam, the rod being coupled to the cam, and configured to transition the driver head into the locking state by rotating the cam such that at least part of the cam protrudes laterally.

In some applications, the rod is eccentric with respect to the shaft.

In some applications, the rod is eccentric with respect to the cam.

In some applications, in the introduction state the cam is flush with the shaft.

In some applications, the anchor driver has a longitudinal axis defined by the shaft, and the shaft and the cam are circular in transverse cross-section.

In some applications, the interface is shaped to define multiple recesses, each dimensioned to receive the cam as it protrudes laterally.

There is provided, in accordance with some applications, a system and/or apparatus including a tissue anchor for use with an anchor driver, the tissue anchor including: a tissue-engaging element defining a central longitudinal axis of the anchor, having a sharpened distal tip, and configured to be driven into tissue of a subject; and an anchor head, coupled to a proximal end of the tissue-engaging element. The anchor head can include an interface, configured to be reversibly engaged by the anchor driver, and an eyelet. The eyelet defines an aperture and a slide axis through the aperture and can be disposed laterally from the central longitudinal axis thereby defining an eyelet axis that is orthogonal to the central longitudinal axis. The eyelet can be mounted such that the eyelet is rotatable about the eyelet axis in a manner that constrains the slide axis to be orthogonal to the eyelet axis.

In some applications, the interface is disposed on the central longitudinal axis of the anchor.

In some applications, the tissue-engaging element is helical, defines the central longitudinal axis by extending in a helix around and along the central longitudinal axis, and is configured to be screwed into the tissue of the subject.

In some applications, the eyelet is mounted such that the eyelet is revolvable around the central longitudinal axis while the slide axis remains constrained to be orthogonal to the eyelet axis.

In some applications, the anchor head includes a collar that circumscribes the central longitudinal axis and is rotatably coupled to the tissue-engaging element, and the eyelet is mounted on the collar, and is revolvable around the central longitudinal axis by rotation of the collar about the central longitudinal axis.

In some applications, the eyelet defines a flange disposed medially to the collar, and a stem that extends laterally past the collar, and couples the flange to the aperture.

In some applications, the collar is a closed collar that defines a recess that supports the stem.

In some applications, the collar is an open collar that has free ends that together support the stem.

In some applications, the eyelet is shaped to define a first flat face and a second flat face, the aperture extending through the eyelet from the first flat face to the second flat face, and the second flat face being opposite the first flat face.

In some applications, the system and/or apparatus includes an implant that includes the anchor, and a tether (e.g., a line, wire, ribbon, rope, braid, contraction member, suture, etc.) threaded through the aperture.

In some applications, the first flat face is parallel with the eyelet axis.

In some applications, the first flat face is orthogonal to the slide axis.

In some applications, the first flat face is parallel with the second flat face.

In some applications, the eyelet has an inner surface that defines the aperture between the first flat face and the second flat face, such that a narrowest part of the aperture is midway between the first flat face and the second flat face.

In some applications, the eyelet defines the inner surface of the eyelet as a hyperboloid.

In some applications, the eyelet defines the inner surface of the eyelet as a catenoid.

In some applications, the system and/or apparatus includes an implant that includes the anchor, and a tether (e.g., a line, wire, ribbon, rope, braid, contraction member, suture, etc.) threaded through the aperture.

In some applications, the anchor is a first anchor of the implant, the implant can further include a second anchor and a spacer or divider (e.g., rod, tube, solid-wall tube, laser-cut tube, coil, spring, etc.) that is tubular, having two spacer-ends and a lumen therebetween, and the spacer is threaded on the tether between the first anchor and the second anchor, with the tether passing through the spacer-lumen.

In some applications, the spacer is elastically flexible in deflection.

In some applications, the spacer is generally not compressible axially.

In some applications, the spacer is defined by a helical wire shaped as a coil that defines the spacer-lumen.

In some applications, the spacer is configured to limit a proximity between the first anchor and the second anchor.

In some applications, for each of the anchors, the eyelet is shaped to define two flat faces, the aperture extending through the eyelet between the flat faces, and the spacer is threaded on the tether between the first anchor and the second anchor such that one of the spacer-ends faces one of the flat faces of the eyelet of the first anchor, and the other of the spacer-ends faces one of the flat faces of the eyelet of the second anchor, and each of the spacer ends is dimensioned to abut, flush against, the flat face that it faces.

In some applications, the system and/or apparatus further includes the anchor driver.

In some applications, the anchor driver has a driver head that has an introduction state and a locking state, the anchor head is shaped to define a proximal opening via which the interface is accessible by the driver head while the driver head is in the introduction state, and the anchor driver is configured to lock the driver head to the interface by transitioning the driver head into the locking state by moving a part of the driver head laterally.

In some applications, the anchor driver includes a flexible shaft, and a rod extending through the shaft, the anchor head is disposed at a distal end of the shaft, and the rod is configured to transition the driver head into the locking state by applying a force to the driver head.

In some applications, the driver head includes fins, and the rod is configured to transition the driver head into the locking state by being advanced distally between the fins such that the rod pushes the fins radially outward such that the fins lock to the interface.

In some applications, the fins are configured to, when pushed radially outward by the rod, lock to the interface via a friction fit.

In some applications, the driver head includes a cam, the rod being coupled to the cam, and configured to transition the driver head into the locking state by rotating the cam such that at least part of the cam protrudes laterally.

In some applications, the rod is eccentric with respect to the shaft.

In some applications, the rod is eccentric with respect to the cam.

In some applications, in the introduction state the cam is flush with the shaft.

In some applications, the anchor driver has a longitudinal axis defined by the shaft, and the shaft and the cam are circular in transverse cross-section.

In some applications, the interface is shaped to define multiple recesses, each dimensioned to receive the cam as it protrudes laterally.

In some applications, the system and/or apparatus includes a delivery tool that includes the anchor driver and a percutaneously-advanceable tube and, while the anchor driver is engaged with the anchor, the anchor driver and the anchor are slidable through the tube.

In some applications, the tube defines an internal channel that has a keyhole-shaped orthogonal cross-section that defines a major channel region and a minor channel region, the major channel-region has a larger cross-sectional area than does the minor channel region, and the anchor is slidable through the channel with the tissue-engaging element sliding snugly through the major channel region, and the eyelet sliding snugly through the minor channel region.

In some applications, the system and/or apparatus includes an implant that includes a tether and the tissue anchor, and the eyelet is shaped to facilitate smooth sliding of the eyelet simultaneously (i) snugly though the minor channel region, and (ii) over the tether, while the tether is disposed within the minor channel region and is parallel with the central longitudinal axis.

In some applications, the anchor is advanceable out of a distal end of the tube, the tube defines a lateral slit extending proximally from the distal end of the tube, the slit is adjacent to the minor channel region, and the slit allows the tether, but not the anchor, to exit the tube laterally, proximally from the distal end of the tube.

In some applications, the system and/or apparatus includes an implant including a tether (e.g., a line, wire, ribbon, rope, braid, contraction member, suture, etc.) and the tissue anchor, and the eyelet is shaped to facilitate smooth sliding of the tether through the aperture both (i) while the tether is parallel with the central longitudinal axis, and (ii) while the tether is oriented orthogonal to the central longitudinal axis.

In some applications, the tether has a thickness, and a narrowest part of the aperture is no more than twice as wide as the thickness of the tether.

In some applications, the narrowest part of the aperture is no more than 50 percent wider than the thickness of the tether.

In some applications, the narrowest part of the aperture is no more than 20 percent wider than the thickness of the tether.

There is provided, in accordance with some applications, a system and/or apparatus including an implant for use in a heart of a subject, the implant including a first anchor, a second anchor, at least one tether (e.g., a line, wire, ribbon, rope, braid, contraction member, suture, etc.) coupling the first anchor to the second anchor, and a tensioner, coupled to the at least one tether between the first anchor and the second anchor.

In some applications, the tensioner includes a spring; and a restraint, restraining the spring in an elastically-deformed shape of the spring.

In some applications, the restraint is bioresorbable, such that after implantation of the implant within the heart, disintegration of the restraint releases the spring from the restraint, and the spring is configured to, upon release from the restraint, automatically move away from the elastically-deformed state toward a second shape.

In some applications, the coupling of the spring to the at least one tether is such that the movement of the spring away from the elastically-deformed state toward the second shape pulls, via the at least one tether, the first anchor and the second anchor toward each other.

In some applications, the restraint includes a suture. In some applications, the restraint includes a band.

In some applications, the restraint includes a spacer or divider.

In some applications, the restraint restrains the spring by holding portions of the spring together.

In some applications, the restraint restrains the spring by holding portions of the spring apart from each other.

In some applications, the first anchor is a tissue-piercing anchor. In some applications, the first anchor is a clip.

In some applications, the spring is a tension spring. In some applications, the spring has a coiled structure.

In some applications, the spring defines a cell, and the movement of the spring away from the elastically-deformed state toward the second shape includes the cell becoming smaller in a first dimension and larger in a second direction.

In some applications, the spring is a foreshortening spring, and the movement of the spring away from the elastically-deformed state toward the second shape includes foreshortening of the spring.

In some applications, the at least one tether (e.g., a line, wire, ribbon, rope, braid, contraction member, suture, etc.) defines a path from the first anchor via the spring to the second anchor, and the coupling of the spring to the at least one tether is such that the movement of the spring away from the elastically-deformed state toward the second shape pulls the first anchor and the second anchor toward each other by introducing tortuosity to the path of the at least one tether.

In some applications, the restraint is a first restraint, the tensioner further includes a second restraint, and the second restraint is configured to limit the movement of the spring away from the elastically-deformed state upon release of the spring from the first restraint, thereby applying a limit to the pulling of the first anchor and the second anchor toward each other.

In some applications, the second restraint is bioresorbable, such that disintegration of the second restraint releases the spring from the second restraint, thereby allowing the spring to further pull, beyond the limit, the first anchor and the second anchor toward each other.

In some applications, the first restraint is bioresorbable at a first rate, such that release of the spring from the first restraint occurs after a first duration after implantation of the implant within the heart, and the second restraint is bioresorbable at a second rate, such that release of the spring from the second restraint occurs after a second duration after implantation of the implant within the heart, the second duration being longer than the first duration.

In some applications, the first rate is such that the first duration is between 1 and 3 months.

In some applications, the second rate is such that the second duration is between 3 months and 1 year.

In some applications, the implant is an annuloplasty structure, the first anchor and the second anchor are configured to be driven into tissue of an annulus of a valve of the heart, and the implant is configured to reshape the annulus by the pulling of the first anchor and the second anchor toward each other.

In some applications, the at least one tether is a first at least one tether, the tensioner is a first tensioner, and the implant further includes: a third anchor, a second at least one tether coupled to the third anchor, and a second tensioner, coupled to the second at least one tether.

In some applications, the second at least one tether couples the third anchor to the second anchor, and the second tensioner is coupled to the second at least one tether between the third anchor and the second anchor.

In some applications, the at least one tether includes: a first tether that tethers the first anchor to a first part of the spring; and a second tether that is distinct from the first tether, and that tethers the second anchor to a second part of the spring, the first and second tethers thereby coupling the first anchor to the second anchor via the spring.

In some applications, an inter-part distance between the first part and the second part is smaller in the second state than in the elastically-deformed state.

There is provided, in accordance with some applications, a system and/or apparatus, including an anchor for use with tissue of a subject, the anchor including: a sharpened distal tip; a hollow body proximal from the distal tip; and a spring. The hollow body can be shaped to define a chamber, a lateral wall around the chamber, and one or more (e.g., two) ports in the lateral wall. An anchor axis of the anchor can pass through the chamber and the tip. The spring can include an elongate element that has one or more (e.g., two) ends and that can define a loop therebetween. Often, at least the loop is disposed within the chamber. In some applications, the anchor has a first state in which the spring is constrained by the lateral wall, and the anchor is transitionable from the first state into a second state in which, relative to the first state, the spring (e.g., the elongate element thereof) is under less strain, and each of the ends protrudes laterally from the hollow body via a respective one of the ports. In the second state, the ends can be disposed further apart from each other compared to in the first state.

In some applications, the ends are sharpened.

In some applications, in the first state, the ends do not protrude laterally from the hollow body.

In some applications, the anchor is configured such that, when the anchor transitions from the first state to the second state, the loop becomes smaller.

In some applications, the anchor is configured such that, when the anchor transitions from the first state to the second state, the loop moves axially within the chamber.

In some applications, the anchor further includes a head that defines an interface, configured to be reversibly engaged by an anchor driver.

In some applications, the system and/or apparatus further includes a tether (e.g., a line, wire, ribbon, rope, braid, contraction member, suture, etc.), and the head defines an eyelet that is threaded onto the tether.

In some applications, in the first state, the ends are disposed distally from the loop.

In some applications, in the second state, the ends are disposed distally from the loop.

In some applications, in the second state, the ends are disposed proximally from the loop.

In some applications, the system and/or apparatus further includes a retainer, and the hollow body is shaped to define at least one window in the lateral wall, and the retainer is configured to retain the anchor in the first state by extending through the window and into the loop.

In some applications, in the first state, each of the ends is disposed at the respective port, the anchor is configured such that, when the anchor transitions from the first state to the second state, the loop moves axially within the chamber, and the retainer is configured to retain the anchor in the first state by inhibiting the loop from moving axially within the chamber.

In some applications, the hollow body is shaped to define two windows in the lateral wall, the two windows being opposite each other and rotationally offset from the two ports.

In some applications, the retainer extends through one of the windows, through the loop, and out of the other of the windows.

In some applications, a port axis passes through the two ports and the anchor axis, and a window axis passes through the two windows and the anchor axis and is orthogonal to the port axis.

In some applications, the windows are axially offset from the ports.

There is provided, in accordance with some applications, a system and/or apparatus for use with tissue of a heart of a subject, the system and/or apparatus including a tool, and an anchor. The tool can be transluminally advanceable to the heart, and can include a tube, having a distal end that defines an opening; and a driver, extending through at least part of the tube. The anchor can be disposed at least partly within the tube, and includes a tissue-engaging element, the anchor being configured to be anchored to the tissue by the tissue-engaging element being driven into the tissue. The driver can extend through at least part of the tube, with a distal end of the driver reversibly engaged with the anchor within the tube. The tool can be configured to, while the anchor remains disposed at least partly within the tube, penetrate the distal end of the tube into the tissue such that the opening becomes submerged within the tissue. The driver can be configured to drive the tissue-engaging element out of the opening and into the tissue while the opening is disposed within the tissue. The tissue-engaging element can be the same as or similar to other tissue-engaging elements described herein.

In some applications, the distal end is tapered.

In some applications, the distal end is sharpened.

In some applications, the anchor is disposed entirely within the tube.

In some applications, the anchor further includes a head, the driver being reversibly engaged with the anchor by being reversibly engaged with the head.

In some applications, the system and/or apparatus further includes a tether (e.g., a line, wire, ribbon, rope, braid, contraction member, suture, etc.), and the anchor further includes a head that defines an eyelet through which the tether is threaded.

In some applications, at least a part of the tissue-engaging element is constrained by the tube and is configured to automatically change shape within the tissue upon exiting the opening.

In some applications, the part of the tissue-engaging element is a tine.

In some applications, the part of the tissue-engaging element is a flange.

In some applications, the flange includes a polymer.

In some applications, the flange includes a sheet and a self-expanding frame supporting the sheet.

In some applications, a distal tip of the tissue-engaging element is disposed outside of the opening, and the tool is configured to, while the distal tip is disposed outside of the opening, penetrate the distal end of the tube into the tissue such that the opening becomes submerged within the tissue.

In some applications, the tissue-engaging element is shaped to fit snugly within the opening such that, while the tool penetrates the distal end of the tube into the tissue, the tissue-engaging element blocks the opening.

In some applications, the distal tip is sharpened, and the distal tip of the tissue-engaging element and the distal end of the tube together define a tapered point, the distal tip being a distal portion of the tapered point and the distal end of the tube being a proximal portion of the tapered point.

In some applications, the tube defines a channel that has a central channel region and lateral channel regions, and the anchor includes a head and tines, the head disposed in the central channel region and each of the tines disposed in a respective lateral channel region, such that, within the channel, the anchor is slidable axially but is inhibited from rotating.

In some applications, the channel is wider at the central channel region than at the lateral channel region.

In some applications, the opening is defined by the channel reaching the distal end of the tube, and the shape of the opening shapes the distal end of the tube to resemble a beak.

There is provided, in accordance with some applications, a system and/or apparatus for use with tissue of a heart of a subject, the system and/or apparatus including a tissue anchor that includes a head and multiple tissue-engaging elements. The head can have a tissue-facing side, shaped to define a plurality of grips, and can also have an opposing side that defines an eyelet. The tissue-engaging elements can be disposed laterally from the grips. Each of the tissue-engaging elements often has a sharpened tip, a delivery state in which the tissue-engaging element is configured to be driven linearly into the tissue until the grips contact the tissue, and a gripping state. The tissue-engaging elements can be collectively configured such that, while the multiple tissue-engaging elements are disposed within the tissue with the grips contacting the tissue, transitioning of the tissue-engaging elements toward the gripping state brings the tips toward each other and presses the grips against the tissue. The tissue-engaging elements can be the same as or similar to other tissue-engaging elements described herein.

In some applications, the multiple tissue-engaging elements are collectively configured such that, while the multiple tissue-engaging elements are disposed within the tissue with the grips contacting the tissue, transitioning of the tissue-engaging elements toward the gripping state squeezes the tissue between the multiple tissue-engaging elements.

In some applications, each of the tissue-engaging elements has a deflecting portion, and a static portion that connects the deflecting portion to the head, both the deflecting portion and the static portion being configured to be driven linearly into the tissue while the tissue-engaging element is in the delivery state, and the tissue-engaging element is configured such that, when the tissue-engaging element transitions toward the gripping state (i) the static portion remains static with respect to the head, and (ii) the deflecting portion deflects with respect to the static portion and with respect to the head.

In some applications, the system and/or apparatus includes an implant that includes: the tissue anchor, and a tether (e.g., a line, wire, ribbon, rope, braid, contraction member, suture, etc.) threaded through the eyelet.

In some applications, in the delivery state, each of the tissue-engaging elements has a medial side and a lateral side, the medial side being closer than the lateral side to the other tissue-engaging elements, and each of the tissue-engaging elements is shaped to define a barb on the lateral side.

In some applications, each of the tissue-engaging elements is configured such that, in the delivery state the barb is obscured, and in the gripping state the barb is exposed.

In some applications, each of the tissue-engaging elements has a deflecting portion, and a static portion that connects the deflecting portion to the head, both the deflecting portion and the static portion being configured to be driven linearly into the tissue while the tissue-engaging element is in the delivery state, and the tissue-engaging element is configured such that, when the tissue-engaging element transitions toward the gripping state (i) the static portion remains static with respect to the head, and (ii) the deflecting portion deflects with respect to the static portion and with respect to the head.

In some applications, for each of the tissue-engaging elements, the barb is defined by the static portion.

In some applications, for each of the tissue-engaging elements, the barb is defined by the deflecting portion.

There is provided, in accordance with some applications, a system and/or apparatus for use with tissue of a heart of a subject, the system and/or apparatus including: an anchor; a tether (e.g., a line, wire, ribbon, rope, braid, contraction member, suture, etc.), coupled to the anchor; a tether-handling device; and a tool. The anchor is configured to be anchored to the tissue with the tether extending proximally from the anchor.

In some applications, the tether-handling device can include a housing that can be shaped to define a passage therethrough, the tether extending through the passage in a manner that facilitates transluminal sliding of the housing distally over and along the tether to the anchor. The tether-handling device can also include a clamp, coupled to the housing, and biased to clamp onto the tether within the passage in a manner that inhibits sliding of the housing with respect to the tether.

In some applications, the tether-handling device can also include an arm that can extend proximally from the housing, and that can include: a conduit, shaped to receive a portion of the tether proximally from the housing, and a lever, coupling the conduit to the housing.

In some applications, the lever can be being biased to place the conduit in an offset position with respect to the passage. The tool can include a tube.

In some applications, the system and/or apparatus can have a delivery state in which the tool is coupled to the tether-handling device, with the tube disposed within the passage in a manner that inhibits the clamp from clamping, and within the conduit in a manner that constrains the conduit in an in-line position with respect to the passage. In some applications, in the delivery state, the tool is configured to transluminally advance the tether-handling device distally over and along the tether toward the anchor.

In some applications, the conduit has an open lateral side.

In some applications, the tether extends out of a proximal side of the housing, and the lever is biased to place the conduit against the proximal side of the housing.

In some applications, the bias of the clamp is such that, absent the tube being disposed in the passage, the clamp automatically clamps onto the tether within the passage in the manner that inhibits sliding of the housing with respect to the tether.

In some applications, in the delivery state, the tube is disposed within the passage and within the conduit by extending distally through the conduit and into the passage.

In some applications, the system and/or apparatus is transitionable from the delivery state into an intermediate state by proximally retracting the tube out of the passage but not out of the conduit.

In some applications, in the intermediate state a distal part of the tube remains disposed in the housing.

In some applications, the tether has sufficient tensile strength relative to the bias of the lever that, absent the tube being disposed in the conduit, the lever is inhibitable from moving the conduit into the offset position by tensioning the tether proximally from the clamp.

In some applications, the system and/or apparatus further includes a cutter, advanceable over and along the tether, axially moveable with respect to the tube, and configured to cut the tether proximally from the conduit.

In some applications, while the tether is tensioned proximally from the clamp, cutting of the tether proximally from the conduit triggers the lever to move the conduit into the offset position.

In some applications, the cutter is configured to cut the tether proximally from the conduit in a manner that leaves a vestigial piece of the tether protruding proximally from the conduit, and the arm is configured such that the lever moving the conduit into the offset position draws the vestigial piece of the tether into the conduit.

In some applications, the tube is slidable within the cutter.

There is provided, in accordance with some applications, a system and/or apparatus for use with a tether, the system and/or apparatus including a clamp that can include a chuck and a spring. The chuck can include a sleeve and a collet. The chuck can have a longitudinal axis, the sleeve circumscribing the longitudinal axis. The sleeve can have a tapered inner surface. In some applications, the collet is disposed within the sleeve and is dimensioned to receive the tether therethrough. In some applications, the spring can axially push the collet against the tapered inner surface such that the collet is squeezed medially by the sleeve.

In some applications, the sleeve and the collet are concentric with the longitudinal axis.

In some applications, the spring is concentric with the longitudinal axis.

In some applications, the spring is a compression spring.

In some applications, the spring is helical.

In some applications, the spring circumscribes the longitudinal axis, the clamp configured to be threaded onto the tether such that the sleeve, the collet, and the spring circumscribe the tether.

In some applications, the sleeve has an opposing surface, and the spring is maintained under compression between the opposing surface and the collet.

In some applications, the system and/or apparatus further includes the tether, and the clamp is configured to receive the tether through the collet and the sleeve, and the spring axially pushes the collet against the tapered inner surface by pushing the collet in a first axial direction with respect to the sleeve, such that the collet clamps the tether thereby inhibiting sliding of the tether through the collet in at least the first axial direction.

In some applications, the clamp is configured to facilitate sliding of the tether through the collet in a second axial direction that is opposite to the first axial direction, by movement of the tether through the sleeve in the second axial direction axially pushing the collet away from the tapered inner surface, thereby reducing clamping of the tether by the collet.

In some applications, the sleeve has an opposing surface against which the spring applies an opposing force while axially pushing the collet.

In some applications, the system and/or apparatus further includes the tether, and the clamp has a proximal end and a distal end, the tapered inner surface tapering toward the distal end, the chuck facilitates sliding of the clamp along the tether in a distal direction in which the distal end leads the proximal end, and the chuck inhibits sliding of the clamp along the tether in a proximal direction in which the proximal end leads the distal end.

In some applications, the system and/or apparatus further includes a sheath that extends proximally from the sleeve, and that is elastically coupled to the sleeve in a manner in which: the sheath is retractable distally over the sleeve by application of a distally-directed force to the sheath and, in response to removal of the distally-directed force, the sheath automatically re-extends proximally.

In some applications, the sheath is rigid.

In some applications, the system and/or apparatus further includes a tool that includes a cutter, the tool being configured to: retract the sheath distally over the sleeve by applying the distally-directed force to the sheath. In some applications, the tool is configured, while maintaining the distally-directed force on the sheath, to tension the tether by applying a proximally-directed force to the tether, such that the tether slides proximally through the collet. In some applications, the tool is configured, subsequently, to cut the tether proximally from the sleeve in a manner that leaves a vestigial piece of the tether protruding proximally from the sleeve and remove the distally-directed force such that the sheath automatically re-extends proximally and ensheathes the vestigial piece of the tether.

In some applications, the tool is configured to cut the tether proximally from the sleeve in a manner that leaves a vestigial piece of the tether protruding proximally from the chuck.

In some applications, the spring is a first spring, and the clamp further includes a second spring, disposed laterally from the sleeve, and providing the elastic coupling of the sheath to the sleeve.

In some applications, the sleeve defines a flange extending laterally from the sleeve, the second spring is a compression spring, disposed laterally from the sleeve such that application of the distally-directed force to the sheath compresses the spring against the flange.

In some applications, the second spring is a helical spring.

In some applications, the second spring circumscribes the sleeve.

There is provided, in accordance with some applications, a system and/or apparatus including an implant configured to be implanted in a heart of a subject, the implant including a tether (e.g., a line, wire, ribbon, rope, braid, contraction member, suture, etc.); anchors slidably coupled to the tether, and configured to anchor the tether to tissue of the heart; a spring; and a restraint. The spring has a resting state and can be coupled to the tether in a manner in which movement of the spring toward the resting state applies tension to the tether. In some applications, the restraint can be coupled to the spring in a manner that inhibits the spring from moving toward the resting state. The restraint can include a material that is configured to disintegrate within the heart (e.g., a bioresorbable material) and can be configured such that disintegration of the material reduces the inhibition of the spring by the restraint.

In some applications, the spring is a helical coil spring.

In some applications, the restraint is configured such that, after a threshold amount of disintegration of the restraint, the restraint no longer inhibits the spring, and the material is configured such that the threshold amount of disintegration is reached between 1 day and 2 years after implantation of the implant in the heart.

In some applications, the material is configured such that the threshold amount of disintegration is reached between 15 days and 2 years after implantation of the implant in the heart.

In some applications, the material is configured such that the threshold amount of disintegration is reached between 15 days and 1 year after implantation of the implant in the heart.

In some applications, the material is configured such that the threshold amount of disintegration is reached between 15 days and 6 s after implantation of the implant in the heart.

In some applications, the material is configured such that the threshold amount of disintegration is reached between 1 and 3 months after implantation of the implant in the heart.

In some applications, the material is configured such that the threshold amount of disintegration is reached between 1 and 2 months after implantation of the implant in the heart.

In some applications, the restraint is a first restraint, and is configured to have a first lifespan after implantation of the implant such that, upon expiry of the first lifespan, the first restraint no longer inhibits the spring, and the implant further includes a second restraint, configured to have a second lifespan after implantation of the implant, the second lifespan being greater than the first lifespan.

In some applications, the second restraint is coupled to the spring in a manner that inhibits the spring from moving toward the resting state, thereby configuring the system and/or apparatus such that, after implantation of the implant: (i) upon expiry of the first lifespan, the spring moves partway toward the resting state but remains inhibited by the second restraint; and (ii) upon expiry of the second lifespan, the second restraint no longer inhibits the spring, and the spring moves further toward the resting state.

In some applications, the spring is a first spring, and the implant further includes a second spring, having a resting state, and coupled to the tether in a manner in which movement of the second spring toward the resting state applies tension to the tether.

In some applications, the second restraint is coupled to the second spring in a manner that inhibits the second spring from moving toward the resting state of the second spring, and is configured such that upon expiry of the second lifespan, the second restraint no longer inhibits the second spring.

In some applications, the first restraint and the second restraint are configured such that second lifespan is at least twice as great as the first lifespan.

In some applications, the first restraint and the second restraint are configured such that second lifespan is at least three times as great as the first lifespan.

In some applications, the first restraint and the second restraint are configured such that the first lifespan is between 1 and 3 months, and the second lifespan is between 3 months and 1 year.

In some applications, the first restraint and the second restraint are configured such that the first lifespan is between 1 and 3 months, and the second lifespan is between 3 and 6 months.

In some applications, the first restraint and the second restraint are configured such that the first lifespan is between 1 and 2 months, and the second lifespan is between 3 months and 1 year.

In some applications, the first restraint and the second restraint are configured such that the first lifespan is between 1 and 2 months, and the second lifespan is between 3 and 6 months.

In some applications, the restraint is extension-resistant, and is coupled to the spring in a manner that inhibits the spring from moving toward the resting state by the restraint resisting extension.

In some applications, the restraint is a tether that tethers one part of the spring to another part of the spring, thereby inhibiting the one part of the spring from moving away from the other part of the spring.

In some applications, the restraint is a tube in which the spring is disposed.

In some applications, the restraint is compression-resistant, and is coupled to the spring in a manner that inhibits the spring from moving toward the resting state by the restraint resisting compression.

In some applications, the restraint is an obstruction disposed between one part of the spring and another part of the spring, thereby inhibiting the one part of the spring from moving toward from the other part of the spring.

In some applications, the spring is shaped to define a cell that has a first dimension and a second dimension and is configured to move toward the resting state by contracting in the first dimension and expanding in the second dimension.

In some applications, while inhibited by the restraint, the spring is longer in the first dimension than in the second dimension.

In some applications, the cell is a first cell, and the spring is shaped to further define a second cell.

There is provided, in accordance with some applications, a system and/or apparatus, for use with tissue of a heart of a subject, the system and/or apparatus including: an anchor and an anchor-handling assembly. The anchor generally includes a tissue-engaging element that can have a sharpened distal tip, and that can be configured to anchor the anchor to the tissue by being driven into the tissue. The anchor head is coupled to a proximal end of the tissue-engaging element and includes an interface. The anchor-handling assembly can include a sleeve and a tool. The sleeve has a distal portion that includes a distal end of the sleeve, the distal portion being transluminally advanceable to the anchor anchored to the tissue. The distal end can be dimensioned to snugly fit over the anchor head. The tissue-engaging element can be the same as or similar to other tissue-engaging elements described herein.

In some applications, the tool includes a flexible shaft, and a tool head that is coupled to a distal end of the flexible shaft. The tool head can include jaws that are biased to assume an open state, and that are reversibly squeezable into a closed state. The tool head can be dimensioned, relative to an inner dimension of the distal portion of the sleeve, such that disposition of the tool head in the distal portion of the sleeve squeezes the jaws into the closed state.

In some applications, the tool can be configured to: advance the tool head distally through the sleeve to the distal portion, while the jaws remain in the closed state, lock the jaws to the interface, and while the jaws remain locked to the interface, apply a de-anchoring force to the anchor head.

In some applications, while the tool head is locked to the interface and the distal end of the sleeve is disposed snugly over the anchor head, the jaws are unlockable from the interface by retracting the sleeve proximally with respect to the anchor head and the tool head, such that the distal portion of the sleeve ceases to squeeze the jaws into the closed state, and the jaws automatically move apart.

In some applications, the tool is configured to lock the jaws to the interface while the jaws remain in the closed state by pushing the driver head against the anchor head.

In some applications, in the closed state, the jaws define a gap therebetween, and while remaining in the closed state, the jaws are configured: (i) to become locked to the interface by receiving the interface into the gap in response to the jaws being pushed onto the interface with a distally-directed force having a magnitude, by the interface deflecting the jaws apart, and (ii) to resist becoming unlocked from the interface by the interface leaving the gap and pulling of the jaws with a proximally-directed force having the magnitude is insufficient to pull the jaws off of the interface.

In some applications, the sleeve has an intermediate portion that is proximal from the distal portion, and that is internally dimensioned such that disposition of the tool head in the intermediate portion of the sleeve does not squeeze the jaws into the closed state.

In some applications, the jaws and the interface are configured to define a snap-fitting, and the tool is configured to lock the jaws to the interface while the jaws remain in the closed state by snap-fitting the jaws to the interface.

In some applications, the de-anchoring force is a de-anchoring torque, and the tool is configured to apply the de-anchoring torque to the anchor head while the jaws remain locked to the interface.

There is provided, in accordance with some applications, a system and/or apparatus for use with a tether secured along tissue of a heart of a subject, the system and/or apparatus including an anchor and an anchor-handling assembly. The anchor includes a tissue-engaging element and a head that is coupled to a proximal part of the tissue-engaging element. The head can include a shackle that has a reversibly openable opening. The anchor-handling assembly is transluminally advanceable to the heart and includes a driver and a link tool. The driver is configured to anchor the tissue-engaging element to the tissue. The link tool can be configured to, within the heart, temporarily open the opening and pass the tether laterally through the opening.

In some applications, the link tool is configured to, within the heart, slidably couple the anchor to the tether by temporarily opening the opening and passing the tether laterally through the opening and into the shackle.

In some applications, the driver is configured to drive the tissue-engaging element into the tissue by screwing the tissue-engaging element into the tissue.

In some applications, at the opening, the shackle includes a spring-loaded gate.

In some applications, the spring-loaded gate is a single gate.

In some applications, the spring-loaded gate is a double gate.

In some applications, the spring-loaded gate is configured to open inwardly but not outwardly.

In some applications, the link tool is configured to, within the heart, decouple the anchor from the tether by temporarily opening the opening and passing the tether laterally through the opening and out of the shackle.

In some applications, the head further includes a magnet, and the tool is configured to be magnetically-attracted to the magnet.

There is provided, in accordance with some applications, a method for use with tissue of a heart of a subject, the method including transluminally securing a tether (e.g., a line, wire, ribbon, rope, braid, contraction member, suture, etc.) along the tissue by anchoring a plurality of anchors to respective sites of the tissue such that the tether extends between the anchors of the plurality and along the tissue, each anchor of the plurality having a respective eyelet through which the tether passes.

In some applications, the method includes, while the plurality of anchors remains anchored to the tissue, transluminally: (i) slidably coupling an additional anchor to the tether between two of the anchors of the plurality, and (ii) anchoring the additional anchor to the tissue.

In some applications, anchoring the additional anchor to the tissue includes anchoring the additional anchor to the tissue subsequently to slidably coupling the additional anchor to the tether.

In some applications, anchoring the additional anchor to the tissue includes anchoring the additional anchor to the tissue prior to slidably coupling the additional anchor to the tether.

In some applications, for each anchor of the plurality, anchoring the anchor to the respective site of the tissue includes driving a tissue-engaging element of the anchor into the respective site of the tissue.

In some applications, for each anchor of the plurality, driving the tissue-engaging element of the anchor into the respective site of the tissue includes screwing the tissue-engaging element of the anchor into the respective site of the tissue.

In some applications, the method further includes contracting the tissue by tensioning the tether.

In some applications, tensioning the tether includes tensioning the tether subsequently to anchoring the additional anchor to the tissue.

In some applications, tensioning the tether includes tensioning the tether prior to slidably coupling the additional anchor to the tether.

In some applications, the method further includes relaxing the tether subsequently to tensioning the tether and prior to slidably coupling the additional anchor to the tether.

In some applications, the method further includes re-tensioning the tether subsequently to anchoring the additional anchor to the tissue.

In some applications, slidably coupling the additional anchor to the tether includes clipping the additional anchor to the tether.

In some applications, the additional anchor includes a head that includes a shackle, and clipping the additional anchor to the tether includes, subsequently to anchoring the additional anchor to the tissue, transluminally grasping the tether and pressing the tether laterally into the shackle such that the shackle becomes slidably coupled to the tether.

In some applications, the shackle is a snap shackle, and pressing the tether laterally into the shackle includes pressing the tether laterally into the snap shackle such that the tether snaps into the snap shackle.

The above method(s) and steps can be performed on a living animal or on a simulation, such as on a cadaver, cadaver heart, simulator (e.g., with the body parts, heart, tissue, etc. being simulated), etc.

There is provided, in accordance with some applications, a method for use with tissue of a heart of a subject, the method including: transluminally securing a tether (e.g., a line, wire, ribbon, rope, braid, contraction member, suture, etc.) along the tissue by anchoring a plurality of anchors to respective sites of the tissue such that the tether extends between the anchors of the plurality and along the tissue, each anchor of the plurality having a respective eyelet through which the tether passes; and transluminally decoupling from the tether one anchor of the plurality from between two other anchors of the plurality.

In some applications, the one anchor includes a tissue-engaging element having a sharpened distal tip, and a head coupled to a proximal part of the tissue-engaging element, the head including a magnetic element, and the method further includes transluminally advancing a tool to the one anchor, facilitated by magnetic attraction between the tool and the magnetic element, and decoupling the one anchor from the tether includes decoupling the one anchor from the tether using the tool. The tissue-engaging element can be the same as or similar to other tissue-engaging elements described herein.

In some applications, the method further includes, while the two other anchors of the plurality remain anchored to the tissue, de-anchoring the one anchor from the tissue.

In some applications, de-anchoring the one anchor from the tissue includes de-anchoring the one anchor from the tissue prior to decoupling the one anchor from the tether.

In some applications, de-anchoring the one anchor from the tissue includes de-anchoring the one anchor from the tissue subsequently to decoupling the one anchor from the tether.

In some applications, for each anchor of the plurality, anchoring the anchor to the respective site of the tissue includes driving a tissue-engaging element of the anchor into the respective site of the tissue.

In some applications, for each anchor of the plurality, driving the tissue-engaging element of the anchor into the respective site of the tissue includes screwing the tissue-engaging element of the anchor into the respective site of the tissue.

In some applications, the method further includes contracting the tissue by tensioning the tether.

In some applications, tensioning the tether includes tensioning the tether subsequently to decoupling the one anchor from the tether.

In some applications, tensioning the tether includes tensioning the tether prior to decoupling the one anchor from the tether.

In some applications, the method further includes relaxing the tether subsequently to tensioning the tether and prior to decoupling the one anchor from the tether.

In some applications, the method further includes re-tensioning the tether subsequently to decoupling the one anchor from the tether.

In some applications, decoupling the one anchor from the tether includes unclipping the additional anchor from the tether.

In some applications, the one anchor includes a head that includes a shackle, and unclipping the one anchor from the tether includes transluminally opening the shackle.

The above method(s) and steps can be performed on a living animal or on a simulation, such as on a cadaver, cadaver heart, simulator (e.g., with the body parts, heart, tissue, etc. being simulated), etc.

There is provided, in accordance with some applications, a system and/or an apparatus including a tissue anchor. The anchor can include a tissue-engaging element defining a central longitudinal axis of the anchor, having a sharpened distal tip, and configured to be driven into tissue of a subject. The anchor can further include an anchor head, coupled to a proximal end of the tissue-engaging element. The anchor head can include a stock, a ball joint, and an eyelet, coupled to the stock via the ball joint. The tissue-engaging element can be the same as or similar to other tissue-engaging elements described herein.

In some applications, the ball joint is disposed on the central longitudinal axis.

In some applications, the anchor head defines an eyelet axis through the ball joint and the eyelet, and the ball joint allows the eyelet to be moved into a position in which the eyelet axis is orthogonal to the central longitudinal axis.

In some applications, the stock is fixedly coupled to the tissue-engaging element.

In some applications, the tissue-engaging element is helical, defines the central longitudinal axis by extending in a helix around and along the central longitudinal axis, and is configured to be screwed into the tissue of the subject.

In some applications, the eyelet is disposed laterally from the central longitudinal axis.

In some applications, the ball joint is disposed laterally from the central longitudinal axis.

In some applications, the anchor head includes a collar that circumscribes and is rotatably coupled to the stock, and the ball joint is mounted on the collar such that the ball joint is revolvable around the central longitudinal axis by rotation of the collar about the stock.

In some applications, the stock is disposed on the central longitudinal axis.

In some applications, the ball joint includes a socket, and a bearing stud; the bearing stud defines a ball at a first end of the stud, the ball disposed within the socket; and a second end of the stud defines the eyelet.

The ball joint can define (i) a spherical-sector of deflection within which the ball joint allows deflection of the bearing stud into any angular disposition with respect to the socket, and (ii) a deflection plane on which the ball joint allows deflection of the bearing stud beyond the spherical-sector of deflection, outside of the deflection plane the ball joint inhibiting deflection of the bearing stud beyond spherical-sector of deflection.

In some applications, the spherical-sector of deflection has a midpoint, and the ball joint is positioned such that the midpoint lies on the central longitudinal axis.

In some applications, the ball joint is disposed on the central longitudinal axis.

In some applications, the ball joint defines the spherical-sector of deflection to have a solid angle of at least one steradian.

In some applications, the ball joint defines the solid angle to be least two steradians.

In some applications, the ball joint defines the solid angle to be 2-5 steradians.

In some applications, the ball joint defines the solid angle to be 3-5 steradians.

In some applications, the ball joint defines, on the deflection plane, a planar angular arc of deflection of at least 110 degrees; and on the deflection plane, the ball joint allows deflection of the bearing stud beyond the boundary only within the planar angular arc of deflection.

In some applications, the ball joint defines the planar angular arc of deflection to be at least 120 degrees.

In some applications, the ball joint defines the planar angular arc of deflection to be at least 140 degrees.

In some applications, the ball joint defines the planar angular arc of deflection to be at least 160 degrees.

In some applications, the ball joint defines the planar angular arc of deflection to be at least 180 degrees.

In some applications, the ball joint defines the planar angular arc of deflection to be at least 200 degrees.

In some applications, the ball joint defines the planar angular arc of deflection to be no greater than 180 degrees.

In some applications, the ball joint defines the planar angular arc of deflection to be no greater than 160 degrees.

In some applications, the ball joint defines the planar angular arc of deflection to be no greater than 140 degrees.

In some applications, the eyelet is shaped to define a first face, and a second face opposite the first face; and the eyelet has an aperture defined by an inner surface of the eyelet, the aperture extending between the first face and the second face, and a narrowest part of the aperture being midway between the first face and the second face.

In some applications, the inner surface of the eyelet is a hyperboloid.

In some applications, the inner surface of the eyelet is a catenoid.

In some applications, the system/apparatus includes an implant that includes a tether (e.g., a line, wire, ribbon, rope, braid, contraction member, suture, etc.) and the anchor, the eyelet being threaded onto the tether.

In some applications, the anchor is a first anchor of the implant; and the implant further includes a second anchor, an eyelet of the second anchor being threaded onto the tether.

In some applications, the implant further includes a spacer or divider that is tubular, having two spacer-ends and a lumen therebetween; and the spacer is threaded on the tether between the first anchor and the second anchor, with the tether passing through the spacer-lumen.

In some applications, the spacer is elastically flexible in deflection.

In some applications, the spacer resists axial compression.

In some applications, the spacer is defined by a helical wire shaped as a coil that defines the spacer-lumen.

In some applications, the eyelet defines an aperture therethrough, the eyelet being threaded onto the tether by the tether being threaded through the aperture, and the anchor head being configured to facilitate smooth sliding of the tether through the aperture both (i) while the tether is parallel with the central longitudinal axis, and (ii) while the tether is oriented orthogonal to the central longitudinal axis.

In some applications, the tether has a thickness, and a narrowest part of the aperture is no more than twice as wide as the thickness of the tether.

In some applications, the narrowest part of the aperture is no more than 50 percent wider than the thickness of the tether.

In some applications, the narrowest part of the aperture is no more than 20 percent wider than the thickness of the tether.

In some applications, the anchor head further includes a driver interface, and the system/apparatus further includes an anchor driver, configured to reversibly engage the driver interface, and configured to, while engaged with the driver interface, (i) transluminally advance the anchor to the tissue, and (ii) drive the tissue-engaging element into the tissue.

In some applications, the interface is disposed on the central longitudinal axis of the anchor.

In some applications, the system/apparatus includes a delivery tool that includes a percutaneously-advanceable tube and the anchor driver; and the anchor driver is, while engaged with the driver interface, configured to transluminally advance the anchor to the tissue by sliding the anchor through the tube.

In some applications, the tube defines an internal channel that has a cross-section that defines a major channel region and a minor channel region; the major channel-region has a larger cross-sectional area than does the minor channel region; and the anchor is slidable through the channel with the tissue-engaging element sliding through the major channel region, and the eyelet sliding through the minor channel region.

There is provided, in accordance with some applications, a system and/or an apparatus including a tissue anchor, the anchor including a tissue-engaging element defining a central longitudinal axis of the anchor, having a sharpened distal tip, and configured to be driven into tissue of a subject; and an anchor head. The anchor head can include a stock, coupled to a proximal end of the tissue-engaging element; a driver interface coupled to the stock; and an eyelet, hingedly coupled to the stock such that the eyelet is pivotable over the driver interface. The tissue-engaging element can be the same as or similar to other tissue-engaging elements described herein.

In some applications, the stock is fixedly coupled to the proximal end of the tissue-engaging element.

In some applications, the driver interface is fixedly coupled to the stock.

In some applications, the stock is coupled to the proximal end of the tissue-engaging element and to the driver interface in a manner that transfers torque from the driver interface to the tissue-engaging element.

In some applications, the eyelet is positionable on the central longitudinal axis.

In some applications, the hinged coupling of the eyelet to the stock is such that the eyelet is positionable on a first side of the driver interface, and is pivotable over the driver interface to a second side of the driver interface, the second side being opposite the first side.

In some applications, the hinged coupling of the eyelet to the stock is such that the eyelet is pivotable over the driver interface in an arc that is greater than 180 degrees.

In some applications, the tissue-engaging element is helical, defines the central longitudinal axis by extending in a helix around and along the central longitudinal axis, and is configured to be screwed into the tissue of the subject.

In some applications, the anchor head includes an arch that defines at least part of the eyelet, the arch having two base termini, each of the base termini being hingedly coupled to the stock at respective hinge points opposite each other.

In some applications, the anchor head includes a collar that circumscribes and is rotatably coupled to the stock; and the eyelet is hingedly coupled to the stock by each of the base termini being hingedly coupled to the collar at a respective one of the hinge points.

In some applications, at each of the hinge points, the collar defines a respective recess, and the respective base terminus is hingedly coupled to the collar by protruding into the recess.

In some applications, the eyelet is disposed centrally on the arch.

In some applications, the eyelet is disposed eccentrically on the arch.

In some applications, the system/apparatus includes an implant that includes a tether (e.g., a line, wire, ribbon, rope, braid, contraction member, suture, etc.) and the anchor, the eyelet being threaded onto the tether.

In some applications, the anchor is a first anchor of the implant; and the implant further includes a second anchor, an eyelet of the second anchor being threaded onto the tether.

In some applications, the implant further includes a spacer or divider that is tubular, having two spacer-ends and a lumen therebetween; and the spacer is threaded on the tether between the first anchor and the second anchor, with the tether passing through the spacer-lumen.

In some applications, the spacer is elastically flexible in deflection.

In some applications, the spacer resists axial compression.

In some applications, the spacer is defined by a helical wire shaped as a coil that defines the spacer-lumen.

In some applications, the eyelet defines an aperture therethrough, the eyelet being threaded onto the tether by the tether being threaded through the aperture, and the anchor head being configured to facilitate smooth sliding of the tether through the aperture both (i) while the tether is parallel with the central longitudinal axis, and (ii) while the tether is oriented orthogonal to the central longitudinal axis.

In some applications, the system/apparatus further includes an anchor driver, configured to reversibly engage the driver interface, and configured to, while engaged with the driver interface, (i) transluminally advance the anchor to the tissue, and (ii) drive the tissue-engaging element into the tissue.

In some applications, the interface is disposed on the central longitudinal axis of the anchor.

In some applications, the system/apparatus includes a delivery tool that includes a percutaneously-advanceable tube and the anchor driver; and the anchor driver is, while engaged with the driver interface, configured to transluminally advance the anchor to the tissue by sliding the anchor through the tube.

There is provided, in accordance with some applications, a method, including, to an implant that is coupled to a heart of a subject, transluminally advancing an elongate tool that includes a holder and a cutter. The implant can include a tether (e.g., a line, wire, ribbon, rope, braid, contraction member, suture, etc.) under tension, and a stopper locking the tension in the tether by being locked to a first portion of the tether. The method can further include securing the stopper to the holder; and while the stopper remains secured to the holder and locked to the first portion of the tether: (i) relieving the tension on the tether by cutting the tether with the cutter, and (ii) withdrawing the tool, the stopper, and the first portion of the tether from the subject while leaving a second portion of the tether coupled to the heart.

In some applications, the implant includes an anchor coupled to the tether and anchored to the heart, and withdrawing the tool, the stopper, and the first portion of the tether includes withdrawing the tool, the stopper, and the first portion of the tether from the subject while leaving the anchor anchored to the heart.

In some applications, the holder includes a chamber and an opening into the chamber, the cutter is disposed at the opening, and securing the stopper includes advancing the stopper past the cutter and the opening and into the chamber.

In some applications, securing the stopper includes using the cutter to inhibit the stopper from exiting the chamber via the opening.

In some applications, using the cutter to inhibit the stopper from exiting the chamber via the opening includes actuating the cutter to obstruct the opening.

In some applications, actuating the cutter to obstruct the opening includes moving a blade of the cutter to obstruct the opening, and cutting the tether includes cutting the tether with the blade by moving further the blade of the cutter.

In some applications, the implant is disposed inside the heart, and transluminally advancing the elongate tool to the implant includes transluminally advancing the elongate tool to the implant that is disposed inside the heart.

In some applications, the implant is an annuloplasty implant, coupled to an annulus of a valve of the heart, and transluminally advancing the elongate tool to the implant includes transluminally advancing the elongate tool to the annuloplasty implant that is coupled to the annulus.

In some applications, the method further includes, subsequently to relieving the tension on the tether, deploying a prosthetic valve within the annulus of the valve of the heart.

In some applications, the annuloplasty implant extends in a path at least partway around the annulus and is coupled to the annulus at multiple sites along the path, and transluminally advancing the elongate tool to the implant includes transluminally advancing the elongate tool to the annuloplasty implant that extends in the path at least partway around the annulus and is coupled to the annulus at the multiple sites along the path.

In some applications, the implant includes an anchor slidably coupled to the tether and anchored to the heart, the stopper locking the tension in the tether by inhibiting the first portion of the tether from sliding with respect to the anchor, and transluminally advancing the elongate tool to the implant includes transluminally advancing the elongate tool to the implant that includes the anchor slidably coupled to the tether and anchored to the heart, the stopper locking the tension in the tether by inhibiting the first portion of the tether from sliding with respect to the anchor.

In some applications, the stopper inhibits the first portion of the tether from sliding with respect to the anchor by the stopper abutting the anchor, and transluminally advancing the elongate tool to the implant includes transluminally advancing the elongate tool to the implant in which the stopper inhibits the first portion of the tether from sliding with respect to the anchor by the stopper abutting the anchor.

In some applications, cutting the tether includes cutting the tether between the stopper and the anchor.

In some applications, relieving the tension on the tether by cutting the tether includes cutting the tether such that the cutting forms first and second cut ends of the tether, and the second portion of the tether pulls the second cut end away from the cutter and past the anchor. Withdrawing the first portion of the tether can include withdrawing the first portion of the tether along with the first cut end. Leaving the second portion of the tether can include leaving the second portion of the tether along with the second cut end.

In some applications, the anchor is a first anchor; the implant includes a second anchor, slidably coupled to the tether and anchored to the heart; and cutting the tether includes cutting the tether such that the second portion of the tether pulls the second cut end away from the cutter, past the first anchor, but not past the second anchor.

In some applications, cutting the tether such that the second portion of the tether pulls the second cut end away from the cutter and past the anchor, includes cutting the tether such that the second portion of the tether decouples the anchor from the tether by pulling the second cut end away from the cutter and past the anchor.

In some applications the anchor is slidably coupled to the tether by an eyelet of the anchor being threaded onto the tether; and cutting the tether such that the second portion of the tether decouples the anchor from the tether includes cutting the tether such that the second portion of the tether unthreads the anchor from the tether by pulling the second cut end away from the cutter and through the eyelet.

The above method(s) and steps can be performed on a living animal or on a simulation, such as on a cadaver, cadaver heart, simulator (e.g., with the body parts, heart, tissue, etc. being simulated), etc.

There is provided, in accordance with some applications, a method, including transluminally advancing an elongate tool to a tether (e.g., a line, wire, ribbon, rope, braid, contraction member, suture, etc.) that is under tension and disposed within a heart of a subject. The elongate tool can include a holder and a cutter. The method can further include securing a first portion of the tether to the holder; and while the first portion of the tether remains secured to the holder, (i) relieving the tension on the tether by cutting the tether with the cutter, thereby separating the first portion of the tether from a second portion of the tether, and (ii) withdrawing the tool and the first portion of the tether from the subject while leaving the second portion of the tether coupled to the heart.

In some applications, the first portion of the tether includes a knot that locks the tension in the tether, and withdrawing the first portion of the tether includes withdrawing the knot from the subject.

In some applications, the first portion of the tether has a stopper locked thereto, the stopper locking the tension in the tether, and withdrawing the first portion of the tether includes withdrawing the stopper from the subject.

In some applications, the tether is coupled to an anchor that is anchored to the heart, and withdrawing the tool and the first portion of the tether includes withdrawing the tool and the first portion of the tether from the subject while leaving the anchor anchored to the heart.

The above method(s) and steps can be performed on a living animal or on a simulation, such as on a cadaver, cadaver heart, simulator (e.g., with the body parts, heart, tissue, etc. being simulated), etc.

There is provided, in accordance with some applications, a system and/or an apparatus, including a tissue anchor, the anchor including a revolute joint, defining a hinge axis; a first arm, and a second arm. The first arm can define a first coupling, and a first hook that curves about and away from the hinge axis, terminating in a first tip, the curving of the first hook being in a first direction about the hinge axis. The second arm can be hingedly coupled to the first arm via the revolute joint, and can define a second coupling, and a second hook that curves about and away from the hinge axis, terminating in a second tip, the curving of the second hook being in a second direction about the hinge axis, the second direction being opposite to the first direction.

The hinged coupling of the second arm to the first arm can be such that the anchor is transitionable between (i) an open state in which the first arm is in a first rotational position about the hinge axis; the first hook and the second hook define a space therebetween, the first tip and the second tip define therebetween a gap into the space, and the first coupling and the second coupling are disengaged from each other, and (ii) a closed state in which the first arm is in a second rotational position about the hinge axis; the gap is smaller than in the open state; and the first coupling and the second coupling are engaged with each other, the engagement between the first coupling and the second coupling inhibiting the anchor from transitioning out of the closed state.

In some applications, for each of the first hook and the second hook, a radius of curvature of the hook increases with distance from the revolute joint.

In some applications, in the closed state, the first tip and the second tip face away from each other.

In some applications, the anchor further includes a spring, configured to bias the first arm toward a given rotational position about the hinge axis.

In some applications, the spring is configured to bias the lock toward the closed state.

In some applications, the spring is a torsion spring.

In some applications, the revolute joint includes a pin that extends through the first arm and the second arm, and the torsion spring is mounted on the pin.

In some applications, the first arm defines a first beam; the second arm defines a second beam; and the revolute joint is disposed between the first beam and the first hook, and between the second beam and the second hook, such that the first arm is a class I lever whose fulcrum is the revolute joint.

In some applications, the anchor is a class I double-lever whose fulcrum is the revolute joint.

In some applications, the anchor is transitionable from the open state toward the closed state by driving the first beam about the hinge axis.

In some applications, the anchor is transitionable from the open state toward the closed state by increasing an alignment between the first beam and the second beam.

In some applications, the first coupling is disposed on the first beam; the second coupling is disposed on the second beam; and the hinged coupling of the second arm to the first arm is such that the anchor is transitionable into the closed state by bringing the first beam into alignment with the second beam such that the first coupling and the second coupling responsively engage each other.

In some applications, the first coupling includes a protrusion, and the second coupling includes a recess.

There is provided, in accordance with some applications, a system and/or an apparatus for use with tissue of a heart, the system/apparatus including a tether (e.g., a line, wire, ribbon, rope, braid, contraction member, suture, etc.) and a tissue anchor. The tissue anchor can include a stem, an arm, a hinge, and a head. The arm can be coupled to a distal end of the stem via the hinge. The head can be coupled to a proximal part of the stem. The tether can be slidably coupled to the head. The stem can have an intermediate part between the distal end and the proximal part.

The anchor can be anchorable into the tissue by advancing into the tissue, in succession, a first side of the arm, the hinge, and the intermediate part of the stem, such that stem extends, from the distal end and the hinge within the tissue, to the proximal part above the tissue. The arm can be pivotable about the hinge within the tissue such that the anchor is transitionable, within the tissue, toward a restraining state in which the arm extends transversally across the distal end of the stem. The head can be configured to sandwich the tissue between the arm and the head by being moved distally along the stem toward the hinge.

In some applications, the system/apparatus further includes a hollow needle, that has a sharpened tip, and is configured to be penetrated into the tissue. The arm can be configured to be delivered, within the needle, into the tissue. The stem can be biased to automatically curve, upon deployment from the needle within the tissue. The needle can be configured to inhibit the curving of the stem while the stem is disposed within the needle.

In some applications, the arm has a second side, the hinge coupled to the arm between the first side and the second side, such that transitioning of the anchor toward the restraining state pivots, within the tissue, the arm with respect to the stem such that the first side of the arm moves proximally with respect to the stem, and the second side of the arm moves distally with respect to the stem.

In some applications, the anchor is configured to, while the arm is disposed within the tissue, automatically transition toward the restraining state upon application of a proximal pulling force to the stem.

In some applications, the second side, measured between a tip of the second side and the hinge, is longer than the first side, measured between a tip of the first side and the hinge.

In some applications, the second side has an eccentric tip.

In some applications, the eccentric tip is sharpened.

In some applications, the first side has a centralized tip.

In some applications, the centralized tip is sharpened.

In some applications, the system/apparatus further includes a retrieval line, coupled to the second side in a manner in which proximal pulling of the retrieval line transitions the anchor away from the restraining state by pivoting, within the tissue, the arm with respect to the stem such that the first side of the arm moves distally with respect to the stem, and the second side of the arm moves proximally with respect to the stem.

In some applications, the system/apparatus further includes a tube, advanceable distally over and along the retrieval line and the stem, and the anchor is configured to be de-anchored from the tissue by pulling of the retrieval line, the stem, and the second side of the arm, into the tube.

In some applications, the retrieval line is intracorporeally decouplable from the anchor.

There is provided, in accordance with some applications, a method for implanting an implant into tissue of a heart of a subject, the method including, into the subject, introducing a tissue anchor including a stem, a head coupled to a proximal part of the stem, an arm, and a hinge via which the arm is coupled to the stem, the stem having an intermediate part between the distal end and the proximal part.

The method can further include, toward the heart, transluminally advancing the anchor along a tether (e.g., a line, wire, ribbon, rope, braid, contraction member, suture, etc.) with the head sliding over the tether; and advancing into the tissue, in succession, a first side of the arm, the hinge, and the intermediate part of the stem, such that a proximal part of the stem extends above the tissue.

The method can further include, within the tissue, transitioning the anchor toward a restraining state thereof by pivoting the arm about the hinge such that the arm extends transversally across the distal end of the stem; and subsequently, sandwiching the tissue between the arm and the head by moving the head distally along the stem toward the hinge.

In some applications, the method further includes advancing into the tissue a needle that has a sharpened tip, and advancing into the tissue the first end of the arm, the hinge, and the intermediate part of the stem includes advancing out of the needle and into the tissue, in succession, the first end of the arm, the hinge, and the intermediate part of the stem.

In some applications, advancing the first side of the arm into the tissue includes advancing the first side of the arm into an annulus of an atrioventricular valve of the heart while the arm is generally orthogonal to a coronary artery disposed alongside the annulus.

In some applications, pivoting the arm about the hinge includes pivoting the arm about the hinge such that the arm becomes generally parallel with the coronary artery.

In some applications, the arm has a second side, the hinge coupled to the arm between the first side and the second side, and transitioning the anchor toward the retaining state includes, within the tissue, pivoting the arm with respect to the stem such that the first side of the arm moves proximally with respect to the stem, and the second side of the arm moves distally with respect to the stem.

In some applications, pivoting the arm about the hinge includes pivoting the arm about the hinge while a retrieval line is coupled to the second side, and the method further includes subsequently intracorporeally decoupling the retrieval line from the anchor.

In some applications, pivoting the arm with respect to the stem includes applying a proximal pulling force to the stem such that the anchor automatically transitions to ward the restraining state.

In some applications, the second side, measured between a tip of the second side and the hinge, is longer than the first side, measured between a tip of the first side and the hinge, and pivoting the arm with respect to the stem includes applying a proximal pulling force to the stem such that interaction between the tissue and the longer second side pivots the arm with respect to the stem.

In some applications, the second side has an eccentric tip, and pivoting the arm with respect to the stem includes applying a proximal pulling force to the stem such that interaction between the tissue and the eccentric tip side pivots the arm with respect to the stem.

In some applications, the first side of the arm has a centralized tip, and advancing the first side of the arm into the tissue includes penetrating the tissue with the centralized tip.

In some applications, the method further includes de-anchoring the anchor from the tissue by (i) pivoting the arm with respect to the stem by proximally pulling on a retrieval line that is coupled to the second side such that, within the tissue, the first side of the arm moves distally with respect to the stem and the second side of the arm moves proximally with respect to the stem; and (ii) subsequently, pulling the arm, second-side first, out of the tissue.

In some applications, the method further includes advancing a tube over and along the retrieval line and the stem, and pulling the arm out of the tissue includes pulling the arm, second-side first, into the tube and out of the tissue.

The above method(s) and steps can be performed on a living animal or on a simulation, such as on a cadaver, cadaver heart, simulator (e.g., with the body parts, heart, tissue, etc. being simulated), etc.

There is provided, in accordance with some applications, a system and/or an apparatus for use with tissue of a heart of a subject, the system/apparatus including an implant that includes a tether (e.g., a line, wire, ribbon, rope, braid, contraction member, suture, etc.), a first anchor, and a second anchor. Each of the first and second anchors can include a head, slidably coupled to the tether; and a tissue-engaging element, configured to anchor the anchor and the tether to the tissue. The tissue-engaging element can be the same as or similar to other tissue-engaging elements described herein.

In some applications, the system/apparatus can further include a tubular spacer or divider defining a lumen along a spacer-axis and having (i) a primary region that is flexible in deflection; and (ii) at each end of the primary region, a secondary region that is less flexible in deflection than the primary region, the lumen extending through the primary region and both secondary regions. The tubular spacer can be threaded onto the tether between the first anchor and the second anchor, by the tether passing through the lumen.

In some applications, the primary region is elastically flexible in deflection.

In some applications, the primary region resists axial compression.

In some applications, each of the secondary regions are more resistant than the primary region to axial compression.

In some applications, each of the secondary regions is shorter than the primary region.

In some applications, a combined length of both of the secondary regions is shorter than the primary region.

In some applications, each of the secondary regions is less than 30 percent as long as the primary region. In some applications, each of the secondary regions is less than 20 percent as long as the primary region. In some applications, each of the secondary regions is less than percent as long as the primary region. In some applications, each of the secondary regions is at least 2 percent as long as the primary region. In some applications, each of the secondary regions is at least 5 percent as long as the primary region.

In some applications, the spacer or divider includes a helical coil that extends along the primary region.

In some applications, the helical coil includes a wire that is coiled to form the helical coil, and the wire has a core that includes a radiopaque material.

In some applications, the wire includes cobalt chrome, and the core includes platinum.

In some applications, the coil extends into the secondary regions.

In some applications, the helical coil includes a wire that is coiled to form the helical coil, the wire having a wire thickness, and, in a resting state of the helical coil, the helical coil has a pitch that is 1.4-2 times the wire thickness.

In some applications, in the resting state, the pitch of the helical coil is 1.6-1.8 times the wire thickness.

In some applications, the spacer includes, at each of the secondary regions, a rigid ring coupled to the end of the helical coil.

In some applications, the helical coil includes a wire that is coiled to form the helical coil, the wire having a wire thickness, and each of the rings has a length, along the spacer-axis, that is at least twice as great as the wire thickness.

In some applications, each of the rings is disposed at least partly inside of the helical coil.

In some applications, each of the rings has a flange disposed outside of the helical coil, the flange providing a bearing surface configured to facilitate sliding of the tether thereagainst.

There is provided, in accordance with some applications, a system and/or an apparatus, for use with a subject, the system and/or apparatus including a delivery tool and a stopper. The delivery tool can be percutaneously advanceable into the subject and can have a cavity. The stopper can include a first element including a first plate that defines a first passageway therethrough; a second element including a second plate that defines a second passageway therethrough; and a torsion bar.

In some applications, the torsion bar can connect the first plate to the second plate in a manner in which (i) the torsion bar biases the stopper toward a grip state in which the first passageway and the second passageway are offset with respect to each other, and (ii) the stopper is dimensioned such that, while the stopper is disposed in the cavity, the delivery tool retains the stopper in an open state, the stopper being transitionable into the open state by increasing stress on the torsion bar and alignment between the first passageway and the second passageway.

In some applications, in both the grip state and the open state, both the first passageway and the second passageway are parallel with the torsion bar.

In some applications, the cavity is defined by an inner surface of the delivery tool; and the stopper is dimensioned to be disposed within the cavity in a manner in which the first plate and the second plate are disposed within the cavity, with the inner surface retaining the stopper in the open state by pressing against the first plate and the second plate.

In some applications, while the stopper is disposed within the cavity, the inner surface pressing against the first plate and the second state inhibits torsional de-stressing of the torsion bar; and the stopper is configured to, in response to being ejected from the cavity, transition toward the grip state by torsional de-stressing of the torsion bar moving the first plate with respect to the second plate.

In some applications, in the open state of the stopper, the stopper defines a central longitudinal axis that passes through a center of the first plate and a center of the second plate; and transitioning of the stopper toward the grip state offsets the center of at least one of the first plate and the second plate with respect to the central longitudinal axis.

In some applications, in both the open state and the grip state, both the first passageway and the second passageway are parallel with the longitudinal axis.

In some applications, in the grip state, the first plate is nonaxial with the second plate.

In some applications, the delivery tool is a catheter.

In some applications, the system/apparatus further includes a tether (e.g., a line, wire, ribbon, rope, braid, contraction member, suture, etc.); while the stopper is in the open state, the alignment between the first passageway and the second passageway is sufficient for the tether to be slidable through the stopper; and while the tether is disposed through the stopper, transitioning of the stopper into the grip state grips the tether within the stopper, thereby inhibiting sliding of the tether through the stopper.

In some applications, the system/apparatus includes an implant that includes the tether, implant being contractable by applying tension to the tether, and, in the grip state of the stopper, the stopper is configured to lock the tension in the tether by gripping the tether.

In some applications, in the open state of the stopper, the first element and the second element are aligned with respect to each other such that the stopper is cylindrical.

In some applications, in the grip state, the first element is offset with respect to the second element such that the stopper is non-cylindrical.

The present invention will be more fully understood from the following detailed description of applications thereof, taken together with the drawings, in which:

BRIEF DESCRIPTION OF THE DRAWINGS

FIGS. 9A-C and 10A-C are schematic illustrations of an example anchor, in accordance with some applications;

FIGS. 36A-B, 37A-D, 38A-B, 39A-C, 40A-D, 41, and 42 are schematic illustrations of various tissue anchors and techniques for use therewith, in accordance with some applications;

FIGS. 49A-D are schematic illustrations of at least some steps in a technique for use with an implant that is coupled to the heart of a subject, in accordance with some applications;

DETAILED DESCRIPTION

Figure 1A:
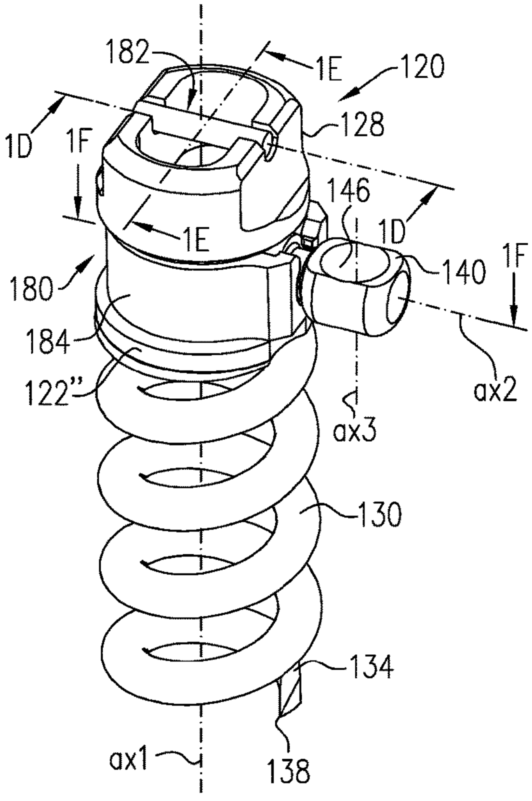
FIGS. 1A-I 2A-B, 3A-D, and 4A-B are schematic illustrations of examples of an anchor, an implant comprising the anchor, a system comprising the implant, and techniques for use therewith, in accordance with some applications.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure can be practiced without specific details being presented herein. Furthermore, well-known features can be omitted or simplified in order not to obscure the disclosure.

Throughout the specification, identical names are used to denote different implementations of an element. Unless stated otherwise, applications of the devices, systems, and techniques described herein can include any variant in which an element is substituted with another identically-named element. Furthermore, throughout the figures, the presence or absence of different suffixes for the same reference numerals are used to denote different implementations of the same elements. Unless stated otherwise, applications of the devices, systems, and techniques described herein can include any variant in which an element is substituted with another element having the same reference numeral, whether denoted with or without a suffix. In order to avoid undue clutter from having too many reference numbers and lead lines on a particular drawing, some elements are introduced via one or more drawings and not explicitly identified in every subsequent drawing that contains that element.

Reference is made to FIGS. 1A-I 2A-B, 3A-D, and 4A-B, which are schematic illustrations of examples of a tissue anchor 120, an implant 110 comprising the tissue anchor, a system 100 comprising the implant, and techniques for use therewith, in accordance with some applications. System 100 is a tissue-adjustment system and can be used for adjusting a dimension of a tissue structure (e.g., a soft tissue). For example, system 100 can be an annuloplasty system, and implant 110 can be an annuloplasty structure (e.g., an annuloplasty ring, annuloplasty implant, etc.).

Figure 1B:
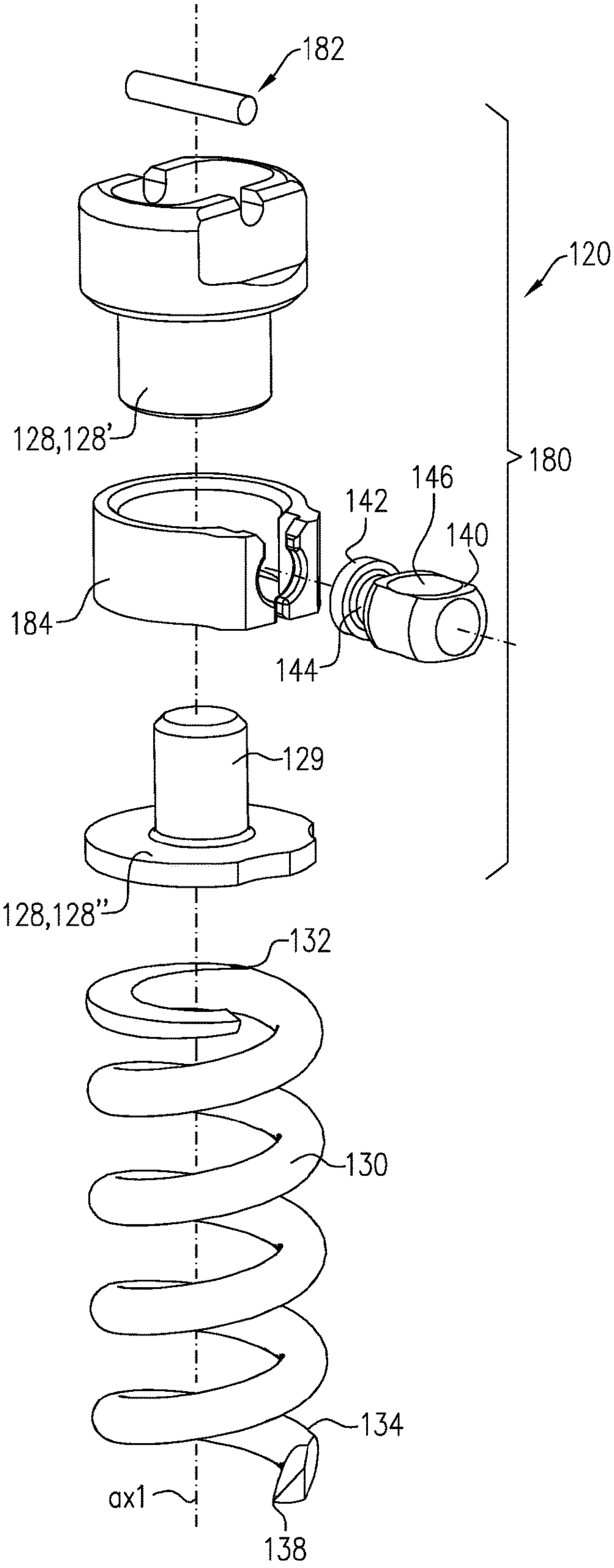
Figure 1C:
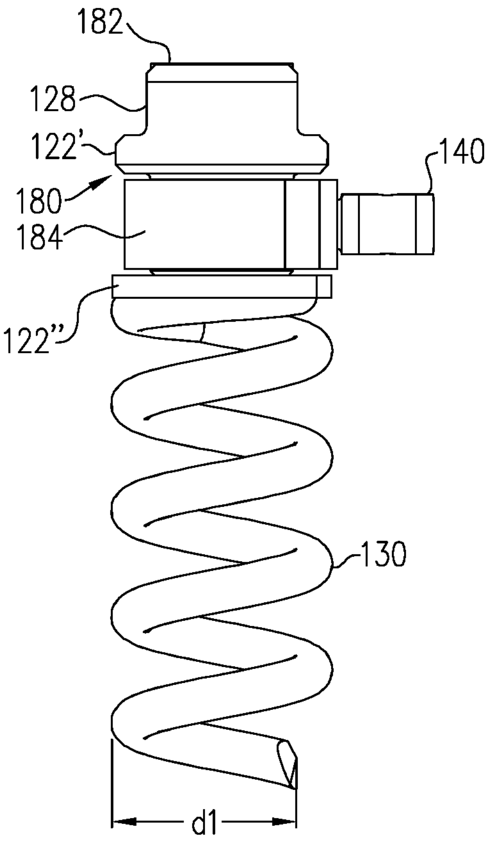
Figure 1D:
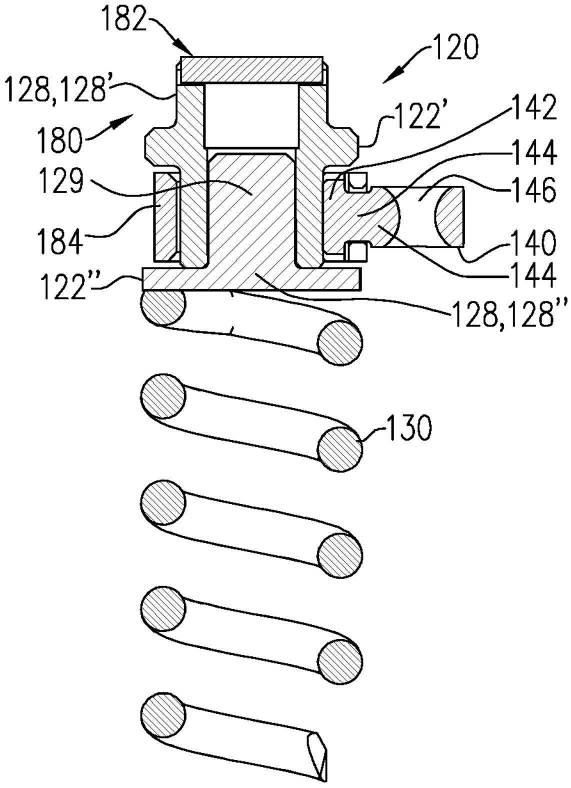
Figure 1E:
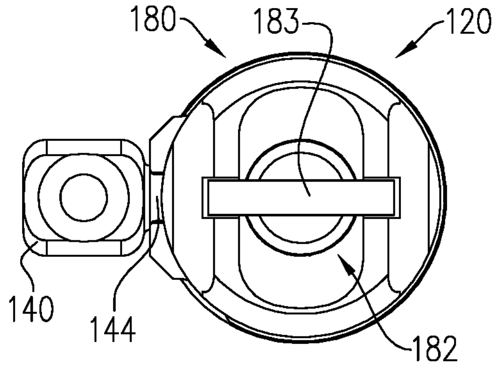
Figure 1F:
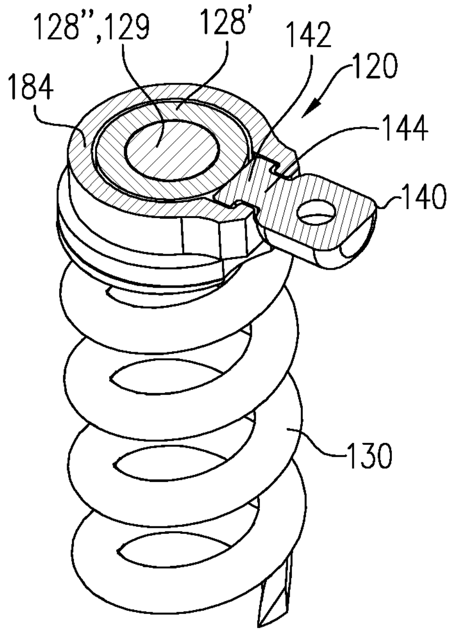

FIG. 1A shows an isometric view of anchor 120, FIG. 1B shows an exploded view, FIGS. 1C and 1E show side and top-down views, respectively, and FIGS. 1D and 1F show longitudinal and transverse cross-sections, respectively.

Anchor 120 comprises a tissue-engaging element 130 and a head 180. The tissue-engaging element can be configured in a variety of ways and can be the same as or similar to other tissue-engaging elements described herein. In some applications, as shown in FIGS. 1A-1F, the tissue-engaging element has a proximal end 132, a distal end 134, and defines central longitudinal axis ax1 of anchor 120. At distal end 134, tissue-engaging element 130 has a sharpened distal tip 138, and the tissue-engaging element is configured to be driven (e.g., screwed, pushed, etc.) into tissue (e.g., soft tissue) of the subject. In some applications, and as shown, tissue-engaging element 130 is helical and defines a central lumen along axis ax1. Optionally, tissue-engaging element 130 can be another type of tissue-engaging element, such as a dart, staple, hook, clip, clamp, pinching device, and/or as described hereinbelow with reference to FIGS. 13-17. In some applications, the tissue-engaging element can be hook-shaped, straight, angled, and/or another configuration. In some applications, the tissue-engaging element can include barbs or barbed portions to hold the tissue-engaging element in tissue.

Figures 3A, 3B:
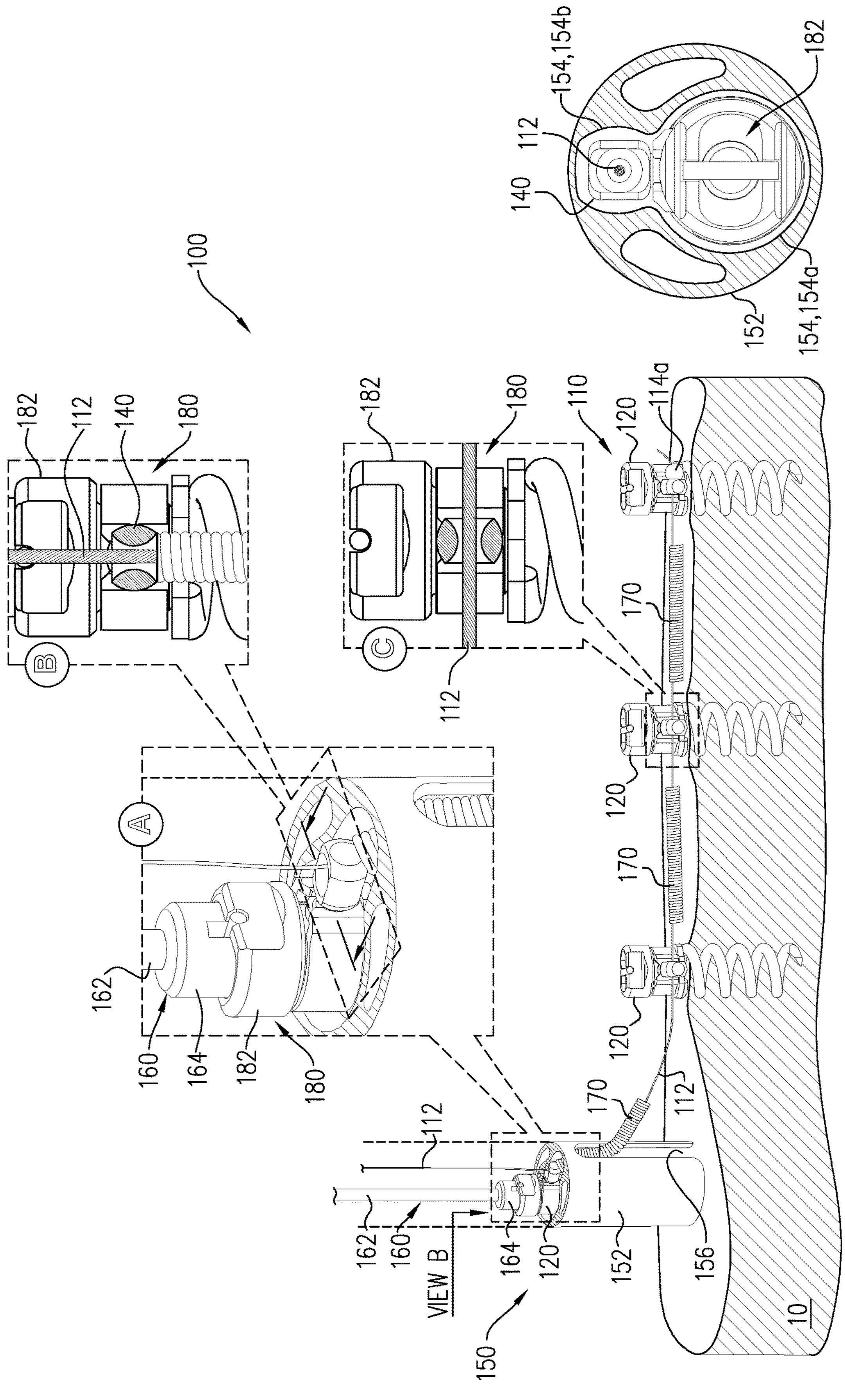

Tissue-engaging element 130 has a lateral width d1. For applications in which tissue-engaging element 130 is helical, width d1 is an outer diameter of the helix. Head 180 is coupled to proximal end 132 of tissue-engaging element 130 and comprises a driver interface 182 and an eyelet 140 (or other connector) that defines an aperture 146 therethrough. Driver interface 182 is configured to be reversibly engaged by an anchor driver 160 (FIG. 3A). Driver 160 often comprises an elongate and flexible shaft 162, and a driver head 164 coupled to a distal end of the shaft. Driver head 164 is the component of anchor driver 160 that reversibly engages driver interface 182. Driver interface 182 can be coupled (e.g., fixedly coupled) to tissue-engaging element 130. In some applications, and as shown, interface 182 comprises a bar 183 that can be transverse to axis ax1.

In some applications, and as shown, driver interface 182 is disposed or centered on central longitudinal axis ax1, and eyelet 140 is disposed laterally from axis ax1 (e.g., is eccentric), thereby defining an eyelet axis ax2 that is orthogonal to axis ax1. That is, eyelet axis ax2 is an axis that extends orthogonally laterally from axis ax1, through eyelet 140. Eyelet 140 is shaped to define a slide axis ax3 along which a tether (e.g., a line, wire, ribbon, rope, braid, contraction member, suture, etc.) is slidable through aperture 146. Often, slide axis ax3 is transverse to aperture 146. Often, slide axis ax3 is the axis that provides the least resistance through aperture 146.

Figure 1G:
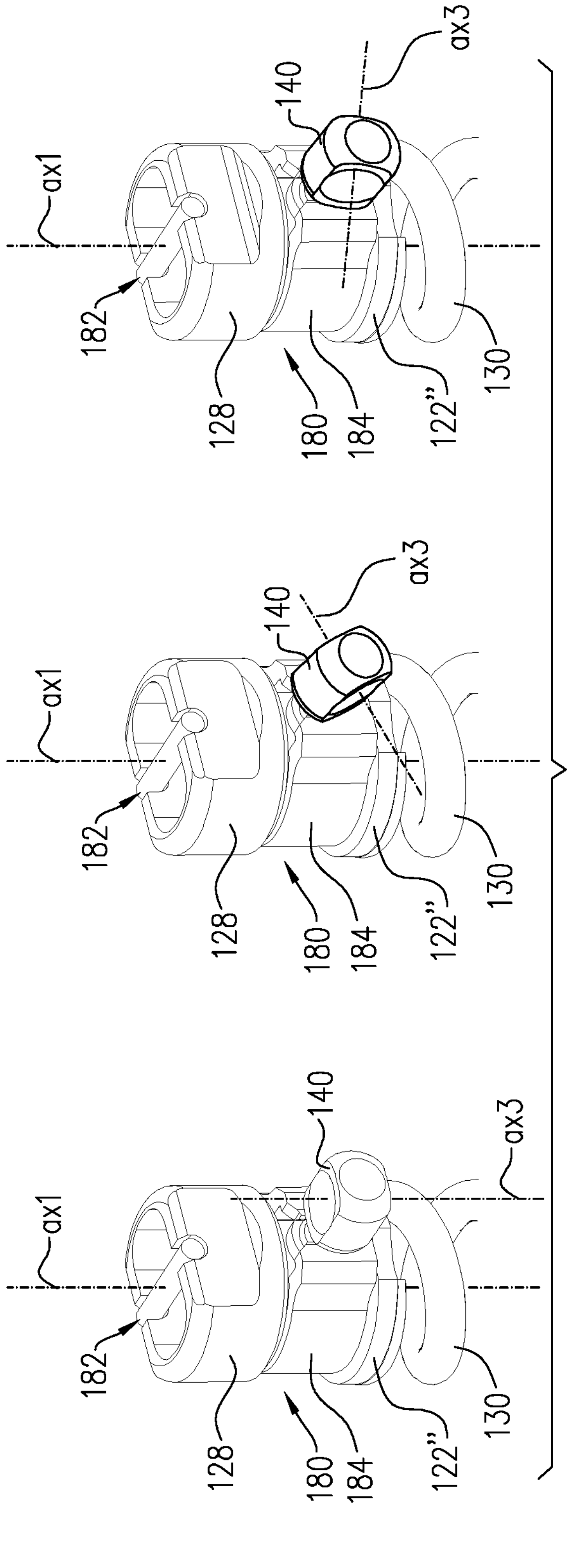
Figure 1H:
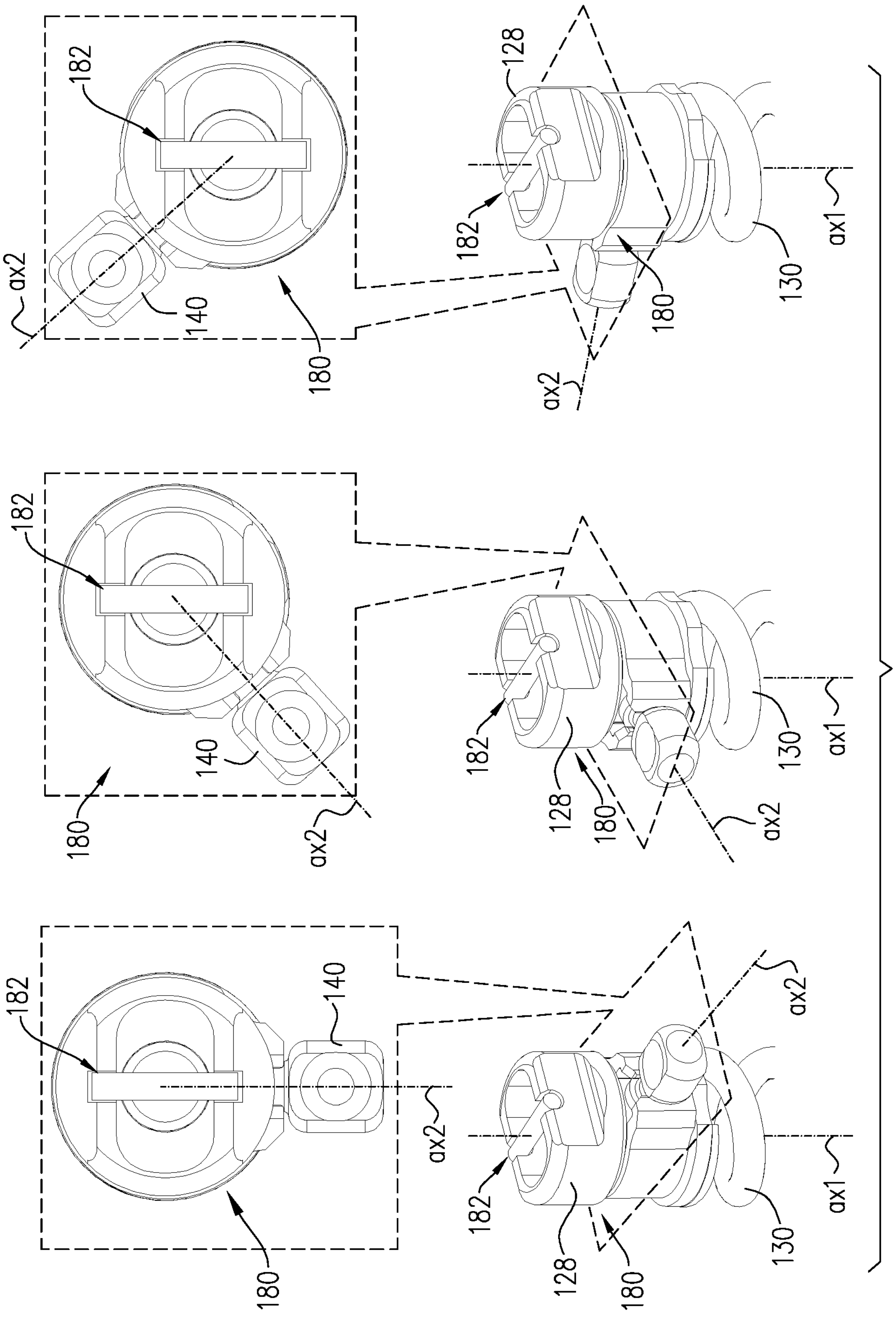
Figure 1I:
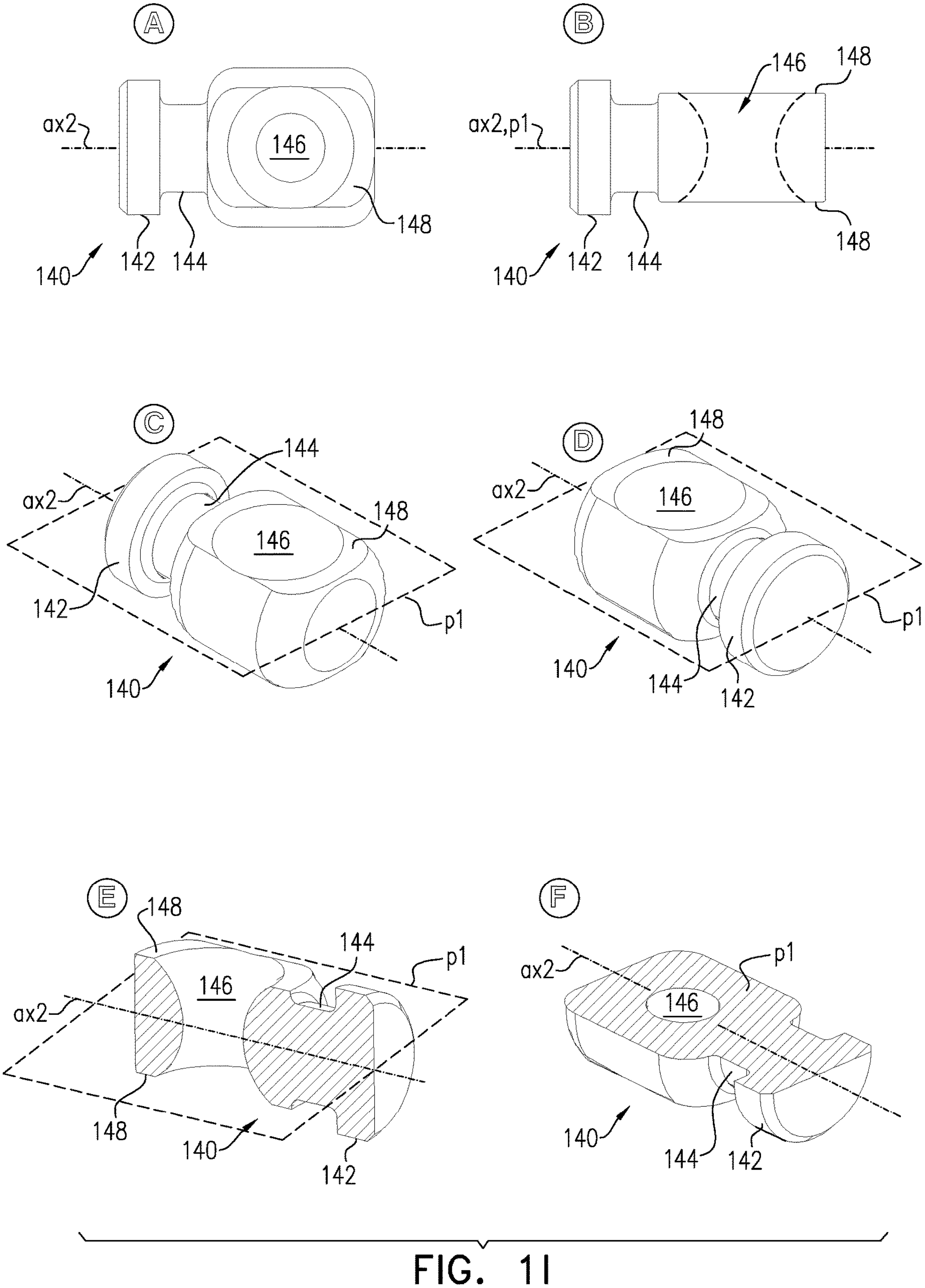

FIG. 1G shows eyelet 140 in different rotational orientations with respect to axis ax1. FIG. 1H shows eyelet 140 in different positions around axis ax1. FIG. 1I shows various views of eyelet 140.

In some applications, slide axis ax3 can be defined with respect to an aperture plane p1 of eyelet 140. For such applications, slide axis ax3 can be transverse to slide axis ax3. Aperture plane p1 is a cross-sectional plane through eyelet 140 in which aperture 146 appears enclosed (e.g., see frame F of FIG. 1I, which is a cross-section on aperture plane p1). Often, of all possible cross-sectional planes through eyelet 140 in which aperture 146 appears enclosed, aperture plane p1 is that in which aperture 146 has the smallest cross-sectional area (e.g., see frames B and E of FIG. 1I). In some applications, in cross-section on aperture plane p1, aperture 146 appears circular (e.g., see frame F of FIG. 1I). In some applications, aperture plane p1 is angled and positioned centrally with respect to eyelet 140 so as to divide the eyelet into two identical halves. In some applications, and as shown in FIG. 1I, eyelet axis ax2 lies on aperture plane p1.

In some applications, eyelet 140 is shaped to define two flat faces 148, aperture 146 extending through the eyelet between the faces, e.g., one of the faces being at each end of the aperture. In some applications, faces 148 are parallel with each other. In some applications, at least one of faces 148 is orthogonal to slide axis ax3 and/or parallel with eyelet axis ax2. As described in more detail hereinbelow, faces 148 are shaped to facilitate interaction with a tubular spacer or divider (e.g., tube, solid-wall tube, laser-cut tube, rod coil, spring, etc.).

In some applications, a narrowest part of aperture 146 is midway between flat faces 148. In some applications, aperture plane p1 is midway between, and parallel with, the flat faces. Frames B and F of FIG. 1I show the narrowest part of aperture 146 as being on plane p1, midway between flat faces 148.

In some applications, an inner surface of eyelet 140 is catenoid in shape. In some applications, an inner surface of eyelet 140 is hyperboloid in shape. See, for example, frames B and E of FIG. 1I.

As described in more detail hereinbelow, eyelet 140 is configured to facilitate sliding of anchor 120 along a tether (or sliding of the tether through the eyelet) while the anchor is aligned with the tether, i.e., while axis ax1 is parallel with the tether. As also described in more detail hereinbelow, eyelet 140 is also configured to facilitate sliding of the anchor along the tether (or sliding of the tether through the eyelet) while the anchor is oriented orthogonally to the tether—i.e., while axis ax1 is orthogonal to the tether. This is achieved at least partly due eyelet 140 being rotatable, e.g., such that slide axis ax3 can be oriented to be parallel with axis ax1 or orthogonal to axis ax1, and generally at any orientation therebetween. Eyelet 140 can be rotationally mounted in a manner that constrains slide axis ax3 to be orthogonal to eyelet axis ax2. The rotatability of eyelet 140 is illustrated by FIG. 1G, in which each of the frames shows the eyelet in a different rotational orientation with respect to axis ax1, the left-hand frame showing a rotational orientation in which axis ax3 is parallel with axis ax1.

In some applications, the mounting of eyelet 140 is also such that the eyelet is revolvable around axis ax1 while axis ax3 remains constrained to be orthogonal to axis ax2. This is illustrated by FIG. 1H, in which each frame shows eyelet 140 in a different position around axis ax1 (interface 182 and tissue-engaging element 130 being in the same position in each of the frames). It is hypothesized that such configuration of anchor 120, enabling rotation and revolution but not deflection of eyelet 140 advantageously increases predictability and reduces wear on the tether, compared to an anchor to which an eyelet is loosely coupled, e.g., like a link in a chain.

In some applications, the mounting of eyelet 140 is achieved by head 180 comprising a collar 184 (which can also be referred to as a ring) on which the eyelet is rotatably mounted. Collar 184 circumscribes and is rotatable about axis ax1, e.g., by being rotatably coupled to tissue-engaging element 130, such as by being rotatably coupled to another component of head 180 that is fixedly coupled to the tissue-engaging element. For example, collar 184 can be rotatably coupled to a stock 128 that is coupled (e.g., fixedly coupled) to tissue-engaging element 130, and that couples (e.g., fixedly couples) the tissue-engaging element to interface 182, e.g., in a manner that transfers torque from interface 182 to tissue-engaging element 130. Stock 128 can be considered to be, and/or can be referred to as, a mount. Stock 128 can be disposed on central longitudinal axis ax1.

As shown, stock 128 can be formed by two components being fixedly attached to each other: component 128', and component 128". Component 128" can be fixedly attached to tissue-engaging element 130 and to component 128'. For example, and as shown, component 128" can be shaped to define a core 129, and component 128" can serve as a cap that is fixed to (e.g., over) the core. Core 129 can be disposed on axis ax1. Component 128' can also define and/or serve as at least part of interface 182. Component 128' can be further from tissue-engaging element 130 than is component 128".

The rotatable coupling of collar 184 to stock 128 can be facilitated by the collar circumscribing the stock and being axially constrained by one or more flanges 122 defined by the stock, e.g., a proximal flange 122' defined by component 128', and/or a distal flange 122" defined by component 128".

Figure 2A:
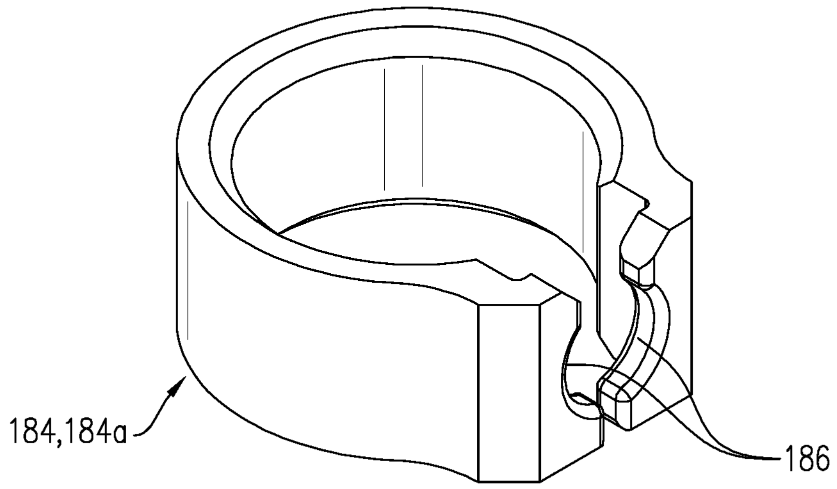
Figure 2B:
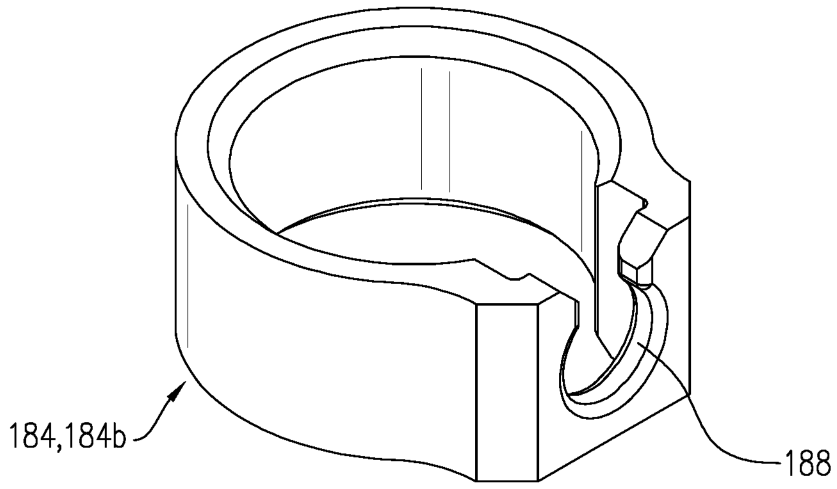

Alternatively or additionally, the rotatable coupling of eyelet 140 to collar 184 can be facilitated by the eyelet defining a flange 142 disposed medially to collar 184, and a stem 144 that extends laterally past the collar and couples flange 142 to the aperture of the eyelet. In some applications, these components thereby form a revolute joint between eyelet 140 and collar 184. FIGS. 2A-B illustrate two examples of this. FIG. 2A shows collar 184 as an open collar 184*a* that has free ends 186 that together support stem 144 (e.g., the free ends are bearing surfaces). FIG. 2B shows collar 184 as a closed collar 184*b* that defines a recess 188 that supports stem 144 (e.g., the collar defines a bearing surface that delineates at least part of the recess).

As described hereinabove, anchor 120 (e.g., eyelet 140 thereof) is configured to facilitate sliding of the anchor along a tether (or sliding of the tether through the anchor) while the anchor is aligned with the tether, e.g., while axis ax1 is parallel with the tether. This is hypothesized to facilitate transcatheter advancement of anchor 120 along the tether. As also described hereinabove, anchor 120 (e.g., eyelet 140 thereof) is configured to facilitate sliding of the anchor along the tether (or sliding of the tether through the anchor) while the anchor is oriented orthogonal to the tether, e.g., while axis ax1 is orthogonal to the tether. This is hypothesized to be useful, inter alia, for applications in which the tether is tensioned after implantation in order to adjust anatomical dimensions, such as annuloplasty. FIGS. 3A-D show such an application, in which tissue 10 represents tissue of the annulus of a native heart valve, such as the mitral or tricuspid valve, and implant 110 is an annuloplasty structure comprising a tether 112 (e.g., a line, wire, cord, ribbon, rope, braid, contraction member, suture, etc.) and multiple anchors 120.

FIGS. 3A-D show system 100, which comprises implant 110, and a delivery tool 150 for percutaneous (e.g., transluminal, such as transfemoral) implantation of the implant. Tool 150 comprises a flexible anchor driver 160 that is configured to reversibly engage driver interface 182 of anchor 120. Via this engagement, driver 160 is configured to drive (e.g., screw) tissue-engaging element 130 into tissue 10. In some applications, tool 150 further comprises a flexible tube 152 (e.g., a transluminal catheter) via which each anchor 120, engaged with driver 160, is advanceable to the tissue to which the anchor is to be anchored.

In FIG. 3A, three anchors 120 have already been anchored to tissue 10, and a fourth anchor is within a distal portion of tube 152. Sliding of tether 112 proximally through the first of the anchors to be anchored is inhibited by the presence of a stopper 114*a* locked to the tether. Each of these anchors was advanced through tube 152 a delivery state in which tether 112 extends through aperture 146 of eyelet 140 while generally parallel to axis ax1. This is illustrated by insets A and B.

After a given anchor 120 has been anchored to tissue 10, as a subsequent anchor is anchored to the same tissue, tether 112 becomes oriented orthogonally with respect to the given anchor, e.g., parallel with the tissue. Eyelet 140 rotates responsively, such that tether 112 can still take a clear straight path, along the now-rotated slide axis ax3, through aperture 146 of the eyelet. This is illustrated in inset C.

Figure 3C:
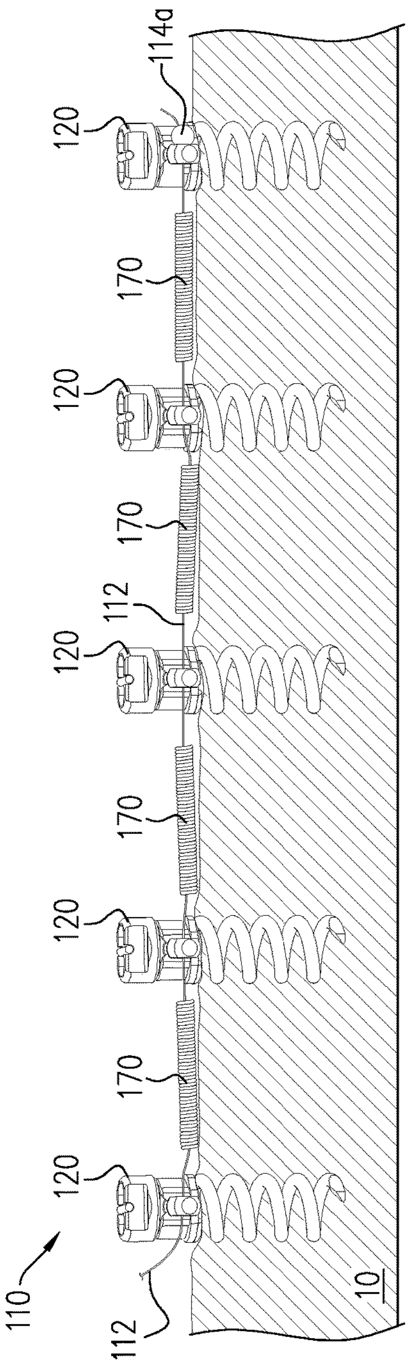
Figure 3D:
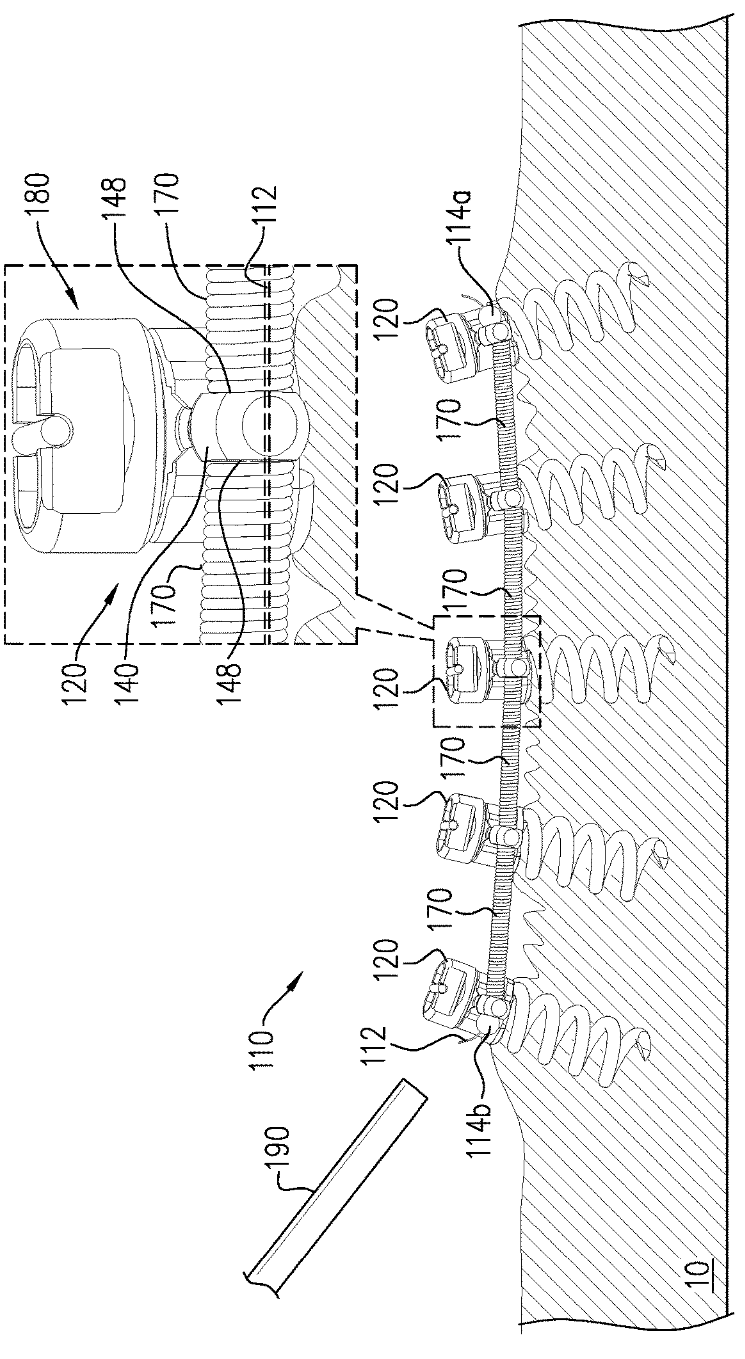

After a desired number of anchors 120 have been anchored (e.g., as shown in FIG. 3C), an adjustment tool 190 is introduced (e.g., over and along a proximal portion of tether 112) and is used to facilitate tensioning of the tether. A reference force is provided (e.g., against a last anchor to be anchored) by the tool and/or by tube 152, while tether 112 is pulled proximally. A distal end of tether 112 cannot slide out of the first anchor (e.g., is fixed to the first anchor), e.g., due to the presence of stopper 114*a*. Therefore, the tensioning of tether 112 draws anchors 120 closer to each other, thereby contracting the tissue to which the anchors are anchored (FIGS. 3C-D). This is facilitated by eyelets 140 providing smooth sliding of tether 112 through apertures 146 while the tether is orthogonal to the anchors, as described hereinabove. The tension is locked into implant 110, such as by fixing a second stopper 114*b* to tether 112 proximal to the last anchor. Excess tether 112 can then be cut and removed from the subject. FIG. 3D shows a state of implant 110 after stopper 114*b* has been fixed to tether 112, and excess tether has been cut and withdrawn into adjustment tool 190, which is shown as being retracted out of the subject.

In some applications, stopper 114*b* represents (or can be substituted with) a tether-handling device such as tether-handling device 410 or 460 described hereinbelow, mutatis mutandis, and/or a contracting-member-covering device and/or a fastener such as those described with reference to FIGS. 35A-46B of WO 2021/084407 to Kasher et al., mutatis mutandis, which is incorporated herein by reference.

Figure 4B:
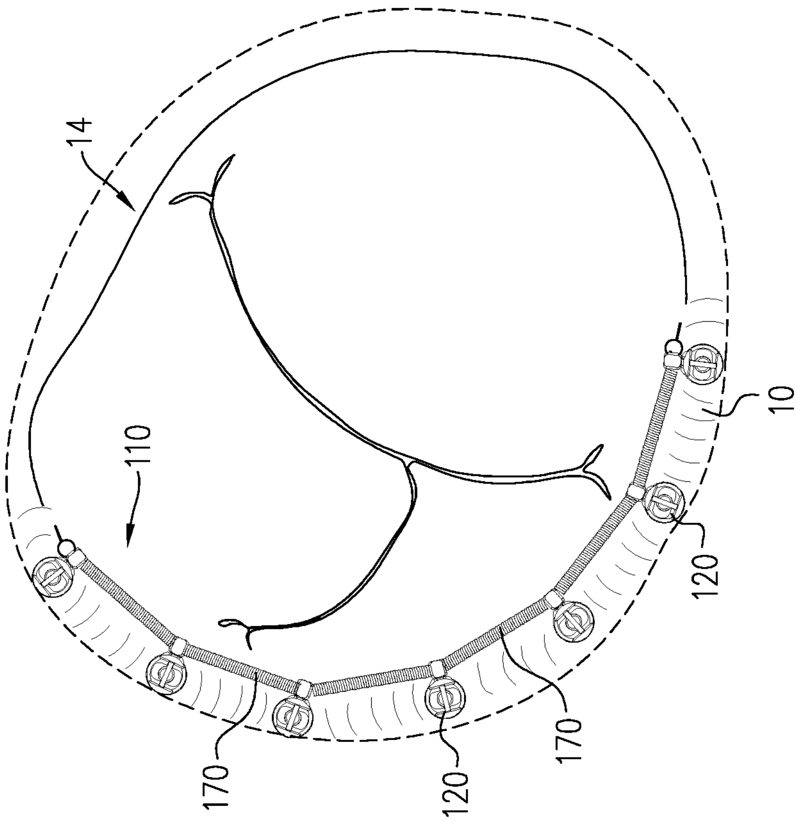
Figure 4A:
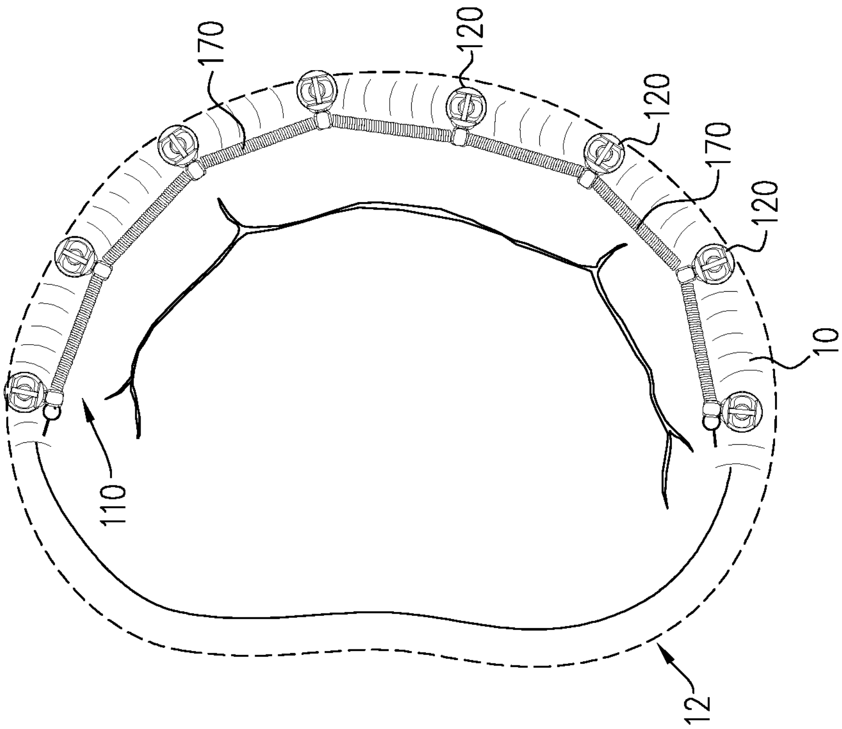

For simplicity, FIGS. 3A, 3C, and 3D show implant 110 in a linear configuration. However, for annuloplasty, implant 110 is often implanted in a curve (or even a complete ring) around the valve annulus, such that the contraction reduces the size of the valve annulus, improving coaptation of the valve leaflets. FIGS. 4A and 4B show implant 110 having been implanted partway around the annulus of the mitral valve 12 (FIG. 4A) and annulus of the tricuspid valve 14 (FIG. 4B), respectively.

As described hereinabove, in some applications, eyelet 140 is mounted to be revolvable around axis ax1. This therefore provides independence between the rotational position of the eyelet and that of tissue-engaging element 130. It is hypothesized that, for applications in which tissue-engaging element 130 is helical, this independence advantageously allows the tissue-engaging element to be screwed into tissue to the extent needed for optimal anchoring, without a requirement for the anchor to finish in a particular rotational orientation. It is further hypothesized that, irrespective of the type of tissue-engaging element 130 used, this independence allows eyelet 140 (and tether 112) to be in an optimal position, with respect to axis ax1 of each anchor 120, for a given application. For example, for an application in which implant 110 is used for annuloplasty, anchors 120 are often anchored in a curve around the valve annulus, and eyelets 140 and tether 112 are often disposed on the inside of the curve relative to axes ax1.

In some applications (e.g., as described hereinbelow with reference to FIGS. 29A-30B), driver head 164 has an introduction state and a locking state, anchor head 180 can be shaped to define a proximal opening via which interface 182 is accessible by the driver head while the driver head is in the introduction state (e.g., but not in the locking state), and anchor driver 160 can be configured to lock driver head 164 to interface 182 by transitioning the driver head into the locking state by moving a part of the driver head laterally.

In some applications, and as shown, tube 152 is shaped to control, during delivery and anchoring, a rotational position of eyelet 140 with respect to axis ax1 and/or tissue-engaging element 130. For some such applications, tube 152 defines an internal channel (e.g., a lumen) 154 that defines a major channel region 154*a* and a minor channel region 154*b* (FIG. 3B). Major channel-region 154*a* has a larger cross-sectional area than does minor channel region 154*b*. Anchor 120 is slidable through channel 154 with tissue-engaging element 130 sliding (typically snugly) through major channel region 154*a*, and eyelet 140 sliding (typically snugly) through minor channel region 154*b* and along tether 112. Rotational control of tube 152 thereby controls the position of eyelet 140, and therefore of tether 112, around axis ax1 of each anchor. While driver interface 182 and tissue-engaging element 130 are rotatable within tube 152 (e.g., during screwing of the tissue-engaging element into tissue 10), collar 184 and eyelet 140 (and thereby tether 112) are held still, thereby reducing a likelihood of the tether becoming wrapped around the anchor, twisted, or tangled. In some applications, and as shown, channel 154 has a keyhole-shaped orthogonal cross-section.

To anchor 120, the anchor is advanced out of a distal end of tube 152 while driver 160 rotates driver interface 182 (and thereby tissue-engaging element 130) with respect to the tube, and while minor channel region 154*b* often inhibits rotation of collar 184 with respect to the tube. In some applications, it is advantageous for the distal end of the tube to be disposed (or even pressed) against tissue 10 during anchoring of the anchor, e.g., as shown in FIG. 3A. In some applications, tube 152 defines a lateral slit 156 extending proximally from the distal end of the tube, such that the slit is continuous with the distal opening of the tube. In some applications, slit 156 is adjacent to (e.g., laterally outward from) minor channel region 154*b*, and allows tether 112, but not anchor 120, to exit tube 152 laterally, proximally from the distal end of the tube. It is believed that this facilitates implantation of implants such as implant 110, comprising multiple anchors coupled to (e.g., threaded on) a tether (e.g., a line, wire, cord, ribbon, rope, braid, contraction member, suture, etc.), e.g., by allowing tether 112 to exit tube 152 without being sandwiched against the tissue, and/or by reducing a likelihood of inadvertently ensnaring the tether while anchoring an anchor.

In some applications, a narrowest part of aperture 146 is no more than twice as wide as tether 112 is thick. For example, the narrowest part of aperture 146 may be no more than 50 percent wider, e.g., no more than 20 percent wider, e.g., no more than 5 percent wider than tether 112 is thick.

It is to be noted that anchors 120 remain threaded onto tether 112 throughout and after implantation, despite the change in orientation of the tether with respect to the anchor during implantation. It is hypothesized that this advantageously reduces a likelihood of an anchor embolizing.

In some applications, implant 110 comprises one or more spacers or dividers 170, threaded onto tether 112, often with each spacer disposed between two of anchors 120. Each spacer 170 can be tubular, defining two ends and a lumen therebetween, tether 112 passing through the lumen, and the ends of the spacer facing flat faces 148 of the anchors 120 between which the spacer is disposed.

Spacer 170 is flexible in deflection, and in some applications is elastically flexible—meaning that it can be deflected laterally by application of a force and will elastically return toward its resting shape upon removal of the force. In some applications, and as shown, the resting shape is that of an open cylinder. Despite being elastically flexible in deflection, spacer 170 resists axial compression. In some applications, spacer 170 is generally not axially compressible, meaning that, in its resting shape, the spacer is not compressible axially by forces having magnitudes that would be experienced by the spacer in its normal use.

In some applications, spacer 170 comprises (e.g., is defined by) a wire that is shaped as a helical coil that defines the lumen of the spacer. For some such applications, spacer 170 is initially axially compressible (typically while providing some degree of resistance to axial compression), and then once compressed to the extent that adjacent turns of the coil contact each other, becomes generally not axially compressible further. In some applications, in a resting state of the coil, the pitch of the coil is sufficiently small that the coil appears substantially closed, e.g., tubular. For example, the pitch of the coil can be less than twice the thickness of the wire (e.g., 1.4-2 times the thickness of the wire, such as 1.6-1.8 times the thickness of the wire, such as 1.7 times the thickness of the wire). In some applications, in the resting state of the coil, the coil is a closed coil, i.e., each turn of the coil is in contact with its adjacent coils.

In some applications, slit 156 is dimensioned to allow spacers 170, threaded on tether 112, to exit tube 152 laterally, proximally from the distal end of the tube.

Spacer 170 is configured to limit a proximity between the anchors 120 between which it is disposed. That is, as tether 112 is tensioned and anchors 120 become closer to each other, those of the anchors between which a spacer 170 is disposed are inhibited from further approaching each other once a limit, defined by the length of the spacer, has been reached.

In some applications, and as shown in the inset of FIG. 3D, the ends of spacer 170 are dimensioned to abut, flush against, the flat faces 148 of anchors 120. It is hypothesized that this results in a stable configuration when contraction of tether 112 presses flat faces 148 against the ends of spacer 170. For example, this flat and flush interface is hypothesized to provide tether 112 with a continuous lumen through spacers 170 and eyelets 140, while reducing a likelihood of tension on the tether causing lateral slipping of a spacer with respect to an adjacent eyelet.

In some applications, anchor 120 and/or implant 110 can be used in combination with apparatuses, systems, and/or implanted using methods/techniques, described in one or more of the following references, mutatis mutandis, each of which is incorporated herein by reference in its entirety for all purposes:

- U.S. patent application Ser. No. 14/437,373 to Sheps et al., filed Apr. 21, 2015, which published as US 2015/0272734 (now U.S. Pat. No. 9,949,828);
- U.S. patent application Ser. No. 15/782,687 to Iflah et al., filed Oct. 12, 2017, which published as US 2018/0049875 (now U.S. Pat. No. 10,765,514);
- U.S. patent application Ser. No. 16/534,875 to Brauon et al., filed Aug. 7, 2019, which published as US 2020/0015971 (now U.S. Pat. No. 11,123,191);
- International Patent Application PCT/IL2019/050777 to Brauon et al., which published as WO 2020/012481;
- International Patent Application PCT/IB2020/060044 to Kasher et al., which published as WO 2021/084407;
- U.S. patent application Ser. No. 17/145,258 to Kasher et al., filed Jan. 8, 2021, which published as US 2021/0145584; and
- International Patent Application PCT/IB2021/058665 to Halabi et al., filed Sep. 23, 2021, which published as WO 2022/064401.

Further, the techniques, methods, steps, etc. described or suggested in the references incorporated herein which can be used with the applications herein can be performed on a living animal or on a non-living simulation, such as on a cadaver, cadaver heart, simulator (e.g., with the body parts, tissue, etc. being simulated), etc.

Figure 5A:
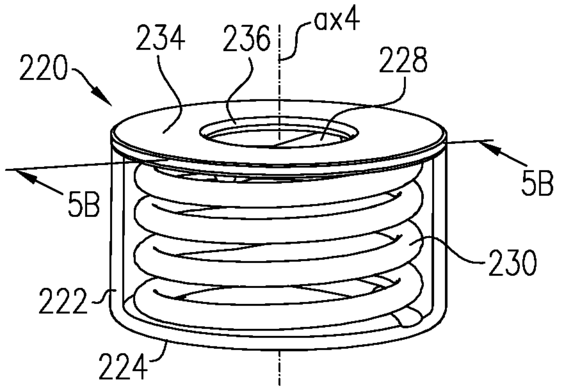
FIGS. 5A-D and 6A-C are schematic illustrations of an example anchor for use with tissue of a subject, in accordance with some applications.
Figure 5B:
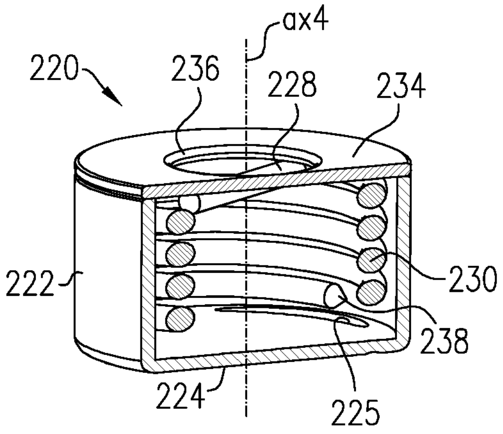
Figure 5C:
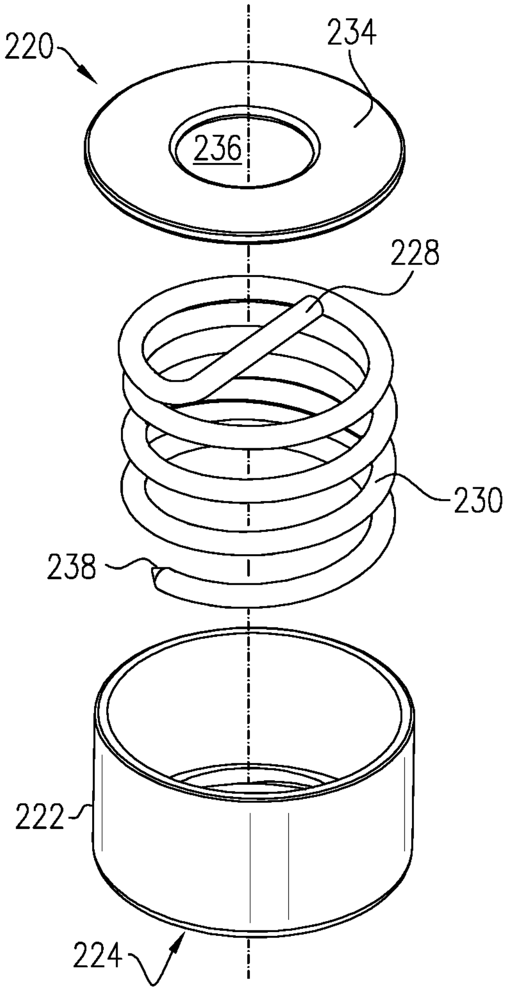
Figure 5D:
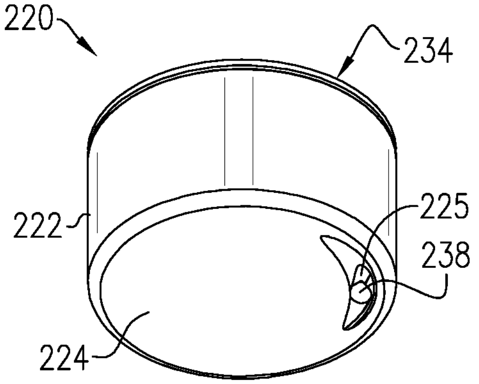

Reference is made to FIGS. 5A-D, and 6A-C, which are schematic illustrations of an anchor 220 for use with tissue (e.g., a soft tissue) of a subject, in accordance with some applications. FIG. 5A shows a cutaway view, FIG. 5B shows a cross-sectional view, FIG. 5C shows an exploded view, and FIG. 5D shows a projection. In some applications, anchor 220 can be used in place of other anchors described herein, mutatis mutandis. For example, in some applications anchor 220 can be used in place of anchor 120 of implant 110 described hereinabove, and although for simplicity anchor 220 is not described as having an eyelet, an eyelet such as eyelet 140 can be added to anchor 220 for use in implant 110.

Reference is also made to FIGS. 7A-C, and 8A-C, which are schematic illustrations of variants of anchor 220—anchors 220' and 220", respectively—in accordance with some applications. Mutatis mutandis, these variants can be used as described for anchor 220 and have the same components and functionality as anchor 220, except where noted.

Anchor 220 comprises a case 222 and a tissue-engaging element 230. Case 222 has a tissue-facing side 224 that defines a tissue-facing opening 225 from inside the case to outside the case. In some applications, tissue-engaging element 230 is shaped to define a helix that has multiple turns around an axis ax4 (e.g., a central longitudinal axis of anchor 220) and has distal tip 238 that can be sharpened.

Figures 6A, 6B, 6C:
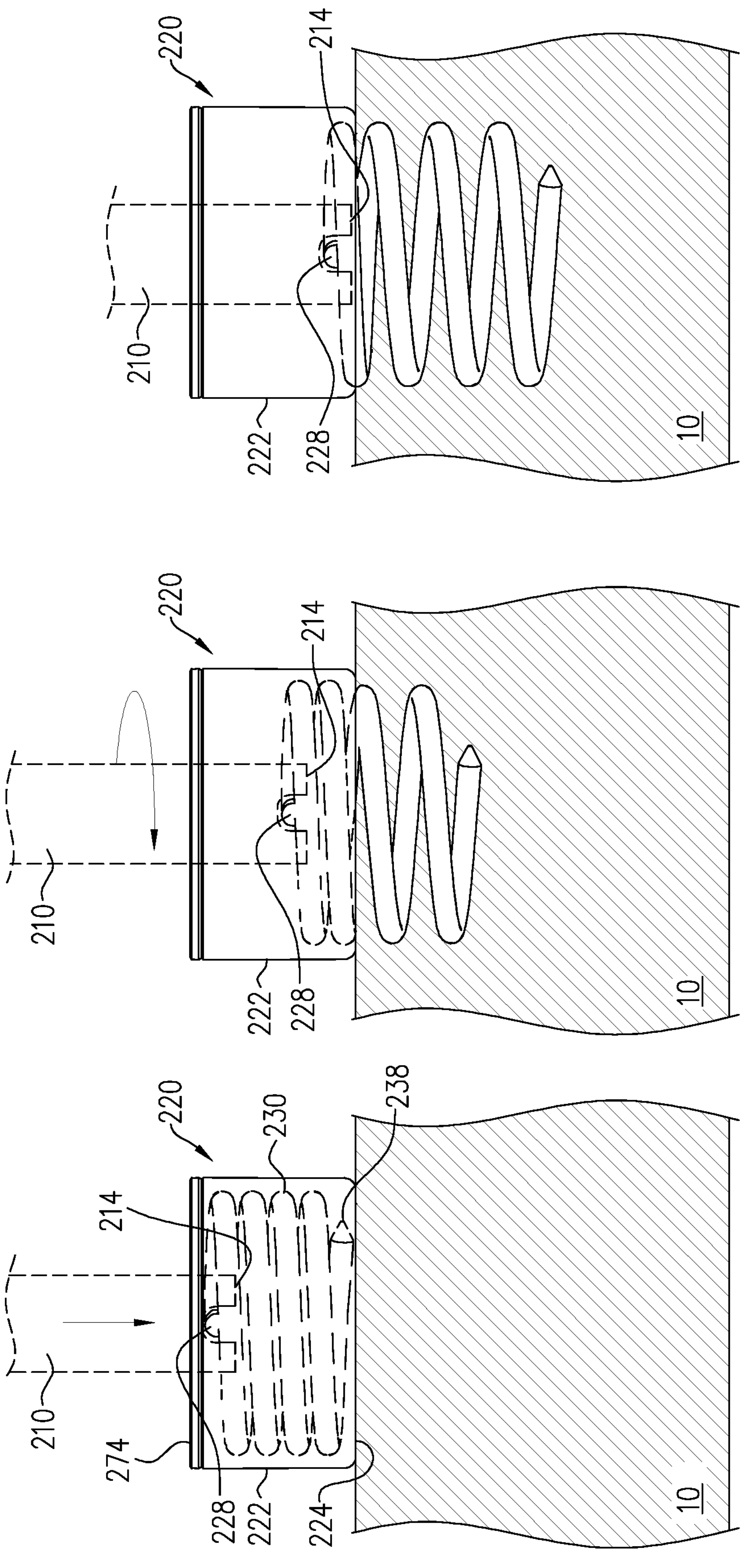
Figure 7C:
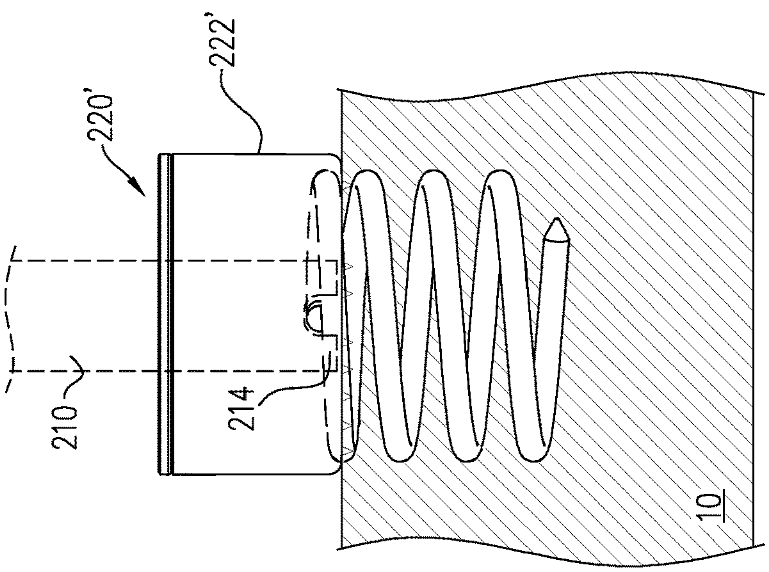
FIGS. 7A-C and 8A-C are schematic illustrations of example anchors, in accordance with some applications.
Figure 7B:
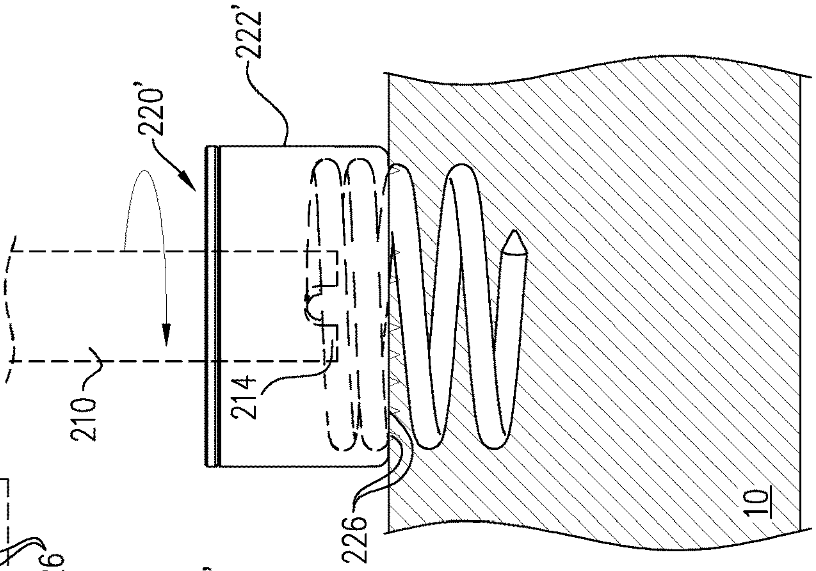
Figure 7A:
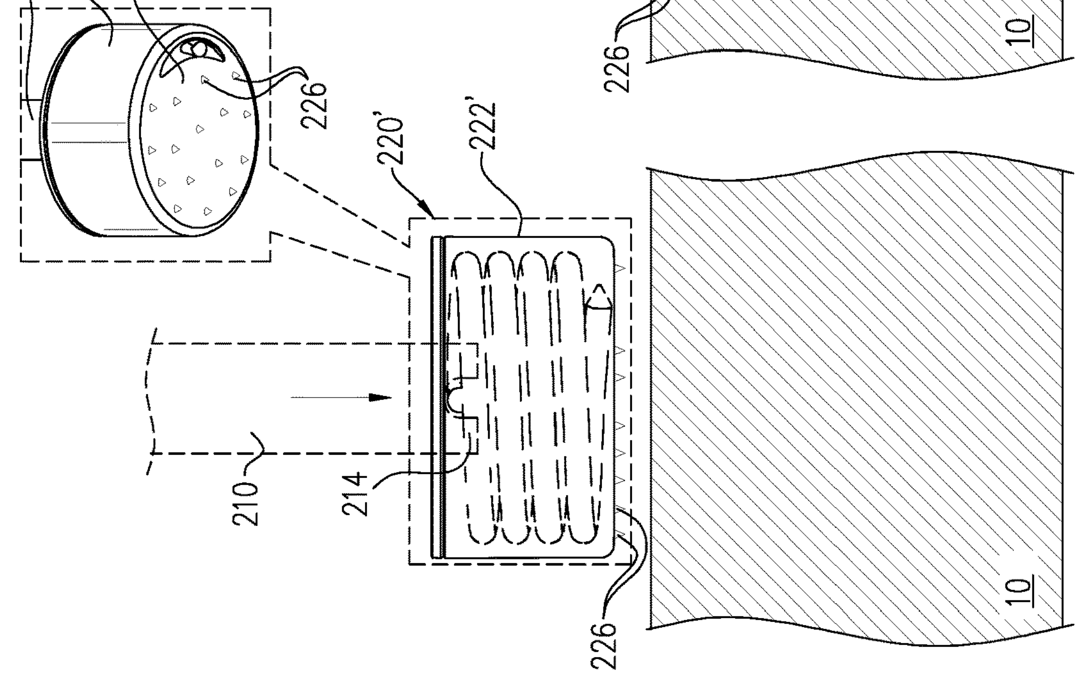
Figure 8A:
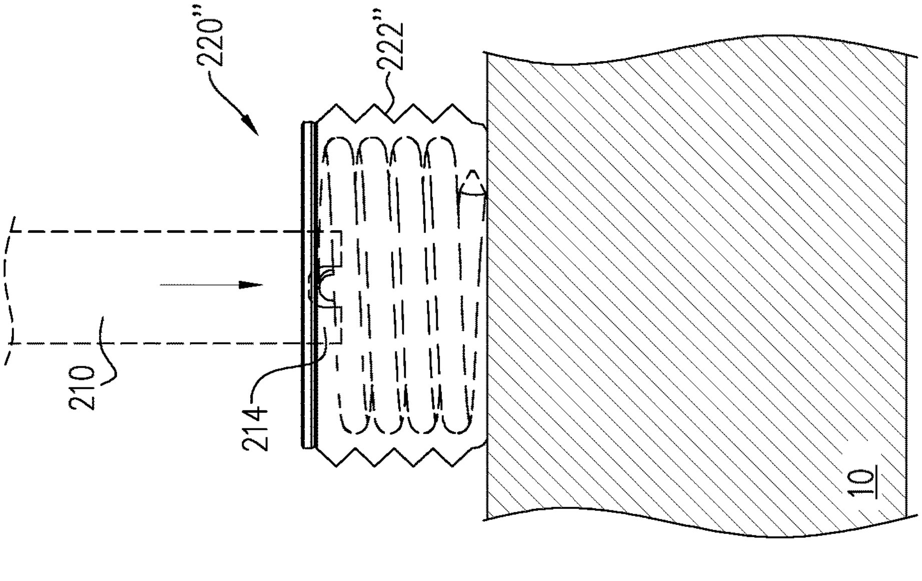
Figure 8B:
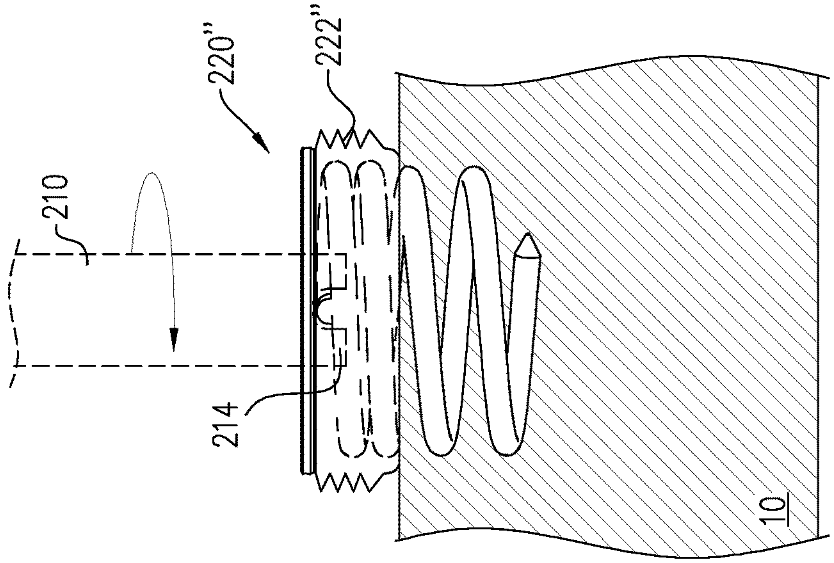
Figure 8C:
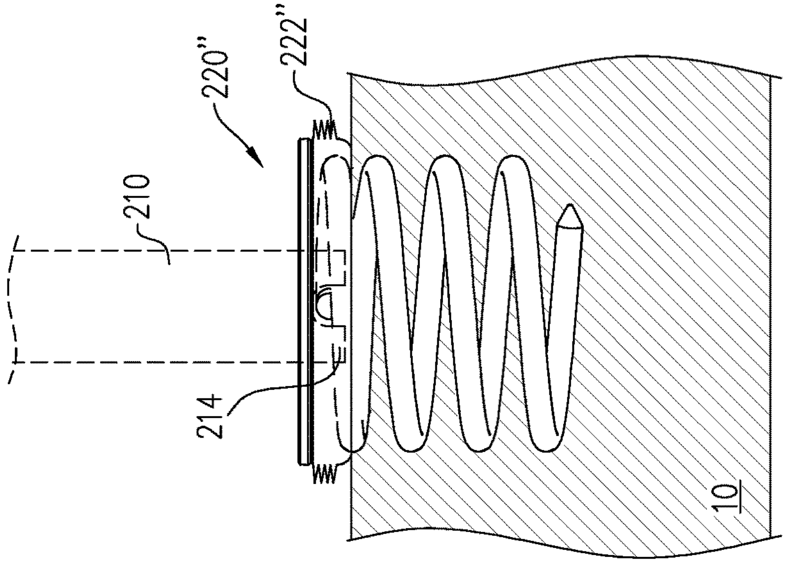

Anchor 220 can be provided with tissue-engaging element 230 disposed within case 222 and positioned such that rotation of the tissue-engaging element about axis ax4 feeds the helix distally out of opening 225. Tissue-engaging element 230 is configured to be screwed into tissue, and to anchor case 222 to the tissue, with tissue-facing side 224 serving as a head of anchor 220. FIGS. 6A-C show an example of the anchoring of anchor 220 to tissue 10, in accordance with some applications. It is hypothesized that anchor 220 advantageously conceals tissue-engaging element 230 until anchoring, thereby reducing a likelihood of inadvertently and/or prematurely engaging tissue or apparatus, e.g., during advancement and/or positioning of the anchor.

In some applications, and as shown, tissue-engaging element 230 is axially compressed within case 222. For such applications, as the helix is fed out of tissue-facing opening 225, progressively proximal portions of the helix automatically (e.g., elastically) axially expand as they become disposed outside of case 222 (FIGS. 6A-C), e.g., tissue-engaging element 230 is a compression spring. For some such applications, the portions of the helix disposed outside of the case have an expanded pitch that is at least twice as great as the original compressed pitch of the helix when the helix is entirely disposed within the case. It is hypothesized that this configuration of tissue-engaging element 230 advantageously (i) facilitates storing of a larger number of helical turns within a case 222 of a given size than would be possible with a rigid tissue-engaging element, and/or (ii) facilitates the exit of distal tip 238 from tissue-facing opening 225 upon rotation of the tissue-engaging element.

As shown in FIG. 6A, tissue-facing side 224 can be placed against the tissue prior to rotation of tissue-engaging element 230. In some applications, this placement facilitates screwing of tissue-engaging element 230 into the tissue by contact between the tissue and case 222 inhibiting rotation of the case with respect to the tissue, such that rotation of the tissue-engaging element (e.g., with respect to the tissue) is rotation also with respect to the case. Screwing of tissue-engaging element 230 into the tissue further presses tissue-facing side 224 against the tissue. Variant anchor 220' has a case 222' that defines grips 226 on a tissue-facing side 224' of the case, which when pressed against the tissue facilitate screwing of tissue-engaging element 230 into the tissue by further inhibiting rotation of the case with respect to the tissue.

Anchor 220 comprises a driver interface 228 at a proximal part of tissue-engaging element 230. By interfacing with interface 228, an anchor driver 210 (which can be the same as or different to driver 160) can rotate tissue-engaging element 230 and drive the tissue-engaging element into tissue. In some applications, and as shown, interface 228 is rotationally locked with the helix of tissue-engaging element 230. In the example shown, interface 228 comprises a bar that can be transverse to axis ax4, and that can be defined by the proximal part of tissue-engaging element 230. For example, a single piece of stock (e.g., a wire) can be shaped to define both the helix of tissue-engaging element 230, and interface 228. However, other configurations of drivers and driver interfaces can be used, including those described elsewhere herein.

Case 222 can have a driver side 234 that, in some applications, defines a driver opening 236 from inside the case to outside the case, thereby providing access to interface 228. In some applications, and as shown, driver opening 236 is disposed in front of interface 228, and/or the interface is visible via the driver opening. For applications in which interface 228 comprises a bar, the bar can be parallel to driver opening 236 (i.e., to a plane in which the opening lies).

In some applications, and as shown, driver side 234 is opposite tissue-facing side 224 (e.g., is parallel with the tissue-facing side).

At a distal portion of anchor driver 210, the driver has a driver head 214 that is configured to engage interface 228, and to rotate the tissue-engaging element by applying torque to the interface, e.g., as described for anchor 120, mutatis mutandis. In some applications, driver head 214 is dimensioned to access interface 228 from outside case 222 via driver opening 236.

As shown, anchor 220 can be configured such that screwing of tissue-engaging element 230 into the tissue moves interface 228 and/or a proximal part of the tissue-engaging element toward tissue-facing side 224. As shown, this can eventually result in sandwiching of tissue-facing side 224 between the tissue and the interface/proximal part of the tissue-engaging element. In some applications, and as shown, this movement of interface 228 and/or the proximal part of the tissue-engaging element is also movement away from driver side 234. However, in variant anchor 220", shown in FIGS. 8A-C, the case 222" of the anchor is elastic, and is configured to automatically contract as the helix is fed distally out of tissue-facing opening 225, such that driver side 234 follows the interface/proximal part of the tissue-engaging element toward tissue-facing side 224.

Reference is made to FIGS. 9A-C and 10A-C, which are schematic illustrations of a tissue anchor 240, in accordance with some applications. In some applications, anchor 240 can be used as a component of an implant, such as an implant comprising multiple anchors connected by a tether (e.g., a line, wire, cord, ribbon, rope, braid, contraction member, suture, etc.). For example, anchor 240 can be used in implant 110 in place of anchor 120, mutatis mutandis. For this reason, anchor 240 is shown as comprising an eyelet 242, which in some applications can be, mutatis mutandis, similar to (or identical to) eyelet 140 described hereinabove, or to an eyelet described in WO 2021/084407 to Kasher et al., which is incorporated herein by reference. In some applications, anchor 240 can be used for other purposes, and may not comprise an eyelet.

Anchor 240 comprises a tissue-engaging element 241 that has a sharpened distal tip 244, and a hollow body 246 proximal from tip 244. Hollow body 246 is shaped to define a chamber 254, and a lateral wall 256 around the chamber. A central longitudinal axis ax5 of anchor 240 generally passes through chamber 254 and tip 244. One or more (e.g., two) ports 258 are defined in lateral wall 256.

Anchor 240 (e.g., tissue-engaging element 241 thereof) further comprises a spring 260 that often comprises an elongate element 261 that has two ends 262 and defines a loop 264 therebetween. Loop 264 can be disposed within chamber 254. In some applications, spring 260 is a helical torsion spring. In some applications, and as shown, ends 262 are sharpened, e.g., to facilitate their piercing of tissue 10.

In a first state of anchor 240, spring 260 is constrained (e.g., medially) by lateral wall 256, e.g., as shown in FIGS. 9A, 9C, 10A, and 10B. As described in more detail hereinbelow, anchor 240 is transitionable from the first state into a second state in which, relative to the first state, spring 260 (e.g., elongate element 261 thereof) is under less strain, and ends 262 are disposed further apart from each other (e.g., as shown in FIG. 10C). In the second state each of ends 262 protrudes laterally from hollow body 246 via a respective port 258. Often, in the first state the ends do not protrude laterally from the hollow body.

In some applications, anchor 240 has an anchor head 250 that can comprise a driver interface 252 configured to be reversibly engaged by an anchor driver 280. In some applications, driver 280 can be identical to driver 160 described hereinabove, mutatis mutandis.

Figure 10A:
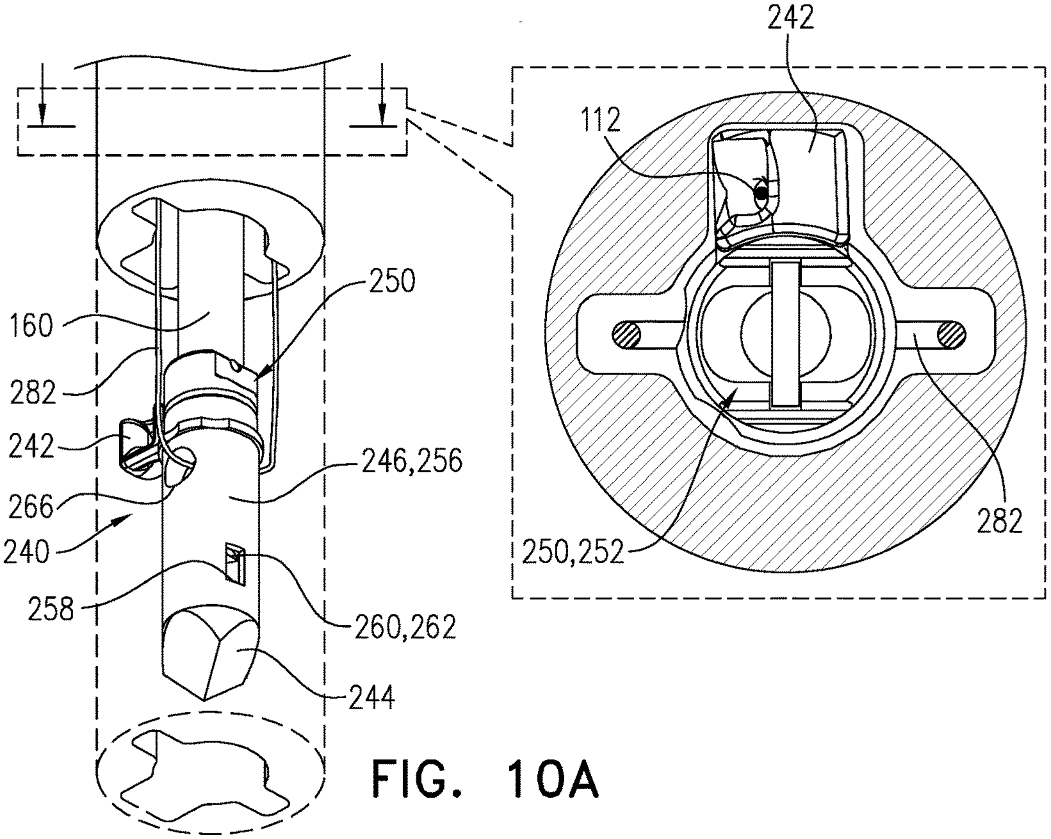
Figure 10B:
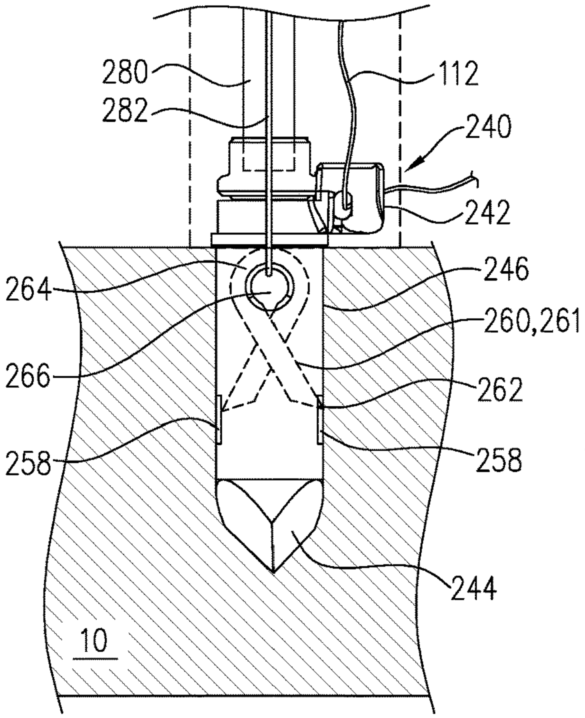
Figure 10C:
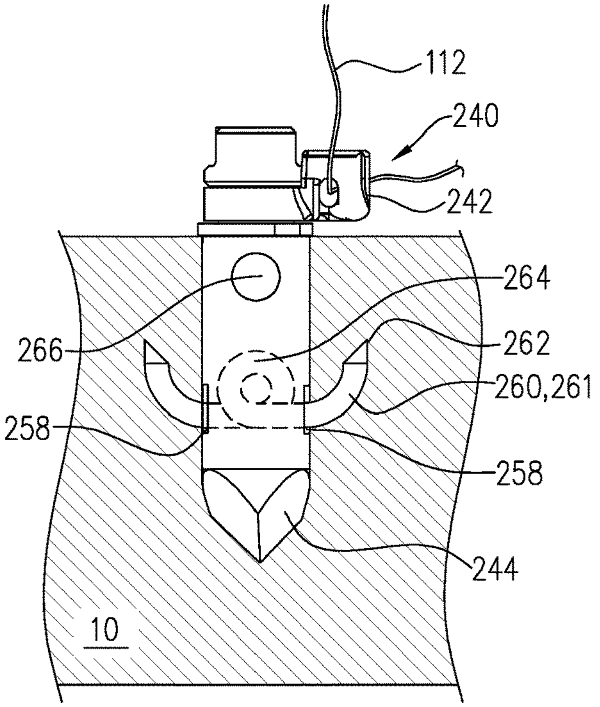

FIGS. 10A-C show a typical use of anchor 240. Anchor 240 can be delivered into the subject while the anchor is in its first state (FIG. 10A), and is advanced distally into tissue 10, often with tip 244 piercing the tissue (FIG. 10B). This advancement can be primarily axial, e.g., with little or no rotation. Once hollow body 246 is (or at least ports 258 are) disposed within tissue 10, the anchor is transitioned into its second state, such that ends 262 protrude laterally from hollow body 246 via ports 258, and into tissue 10, thereby securing the anchor in the tissue (FIG. 10C).

Due to the nature of spring 260, in some applications, when anchor 240 transitions from its first state to its second state, loop 264 becomes smaller.

In some applications, when anchor 240 transitions from its first state to its second state, loop 264 moves axially (e.g., distally) within chamber 254, e.g., as shown by the transition from FIG. 10B to FIG. 10C.

In some applications, and as shown, in the first state ends 262 are disposed distally from loop 264. Optionally, ends 262 can be disposed proximally from loop 264 in the first state. In some applications, and as shown, in the second state ends 262 are disposed proximally from loop 264 (but outside of body 246). Optionally, ends 262 can be disposed distally from loop 264 in the second state.

In some applications, and as shown, spring 260 is biased to automatically transition the anchor into the second state. For such applications, in order to retain anchor 240 in its first state (e.g., for transluminal delivery and/or insertion into the tissue), a retainer 282 can be used. Retainer 282 can be coupled to spring 260 in a manner that inhibits spring 260 from moving. In the example shown, to transition anchor 240 from its first state to its second state, loop 264 moves distally within chamber 254. Retainer 282 retains anchor 240 in its first state by inhibiting spring 260 (e.g., loop 264 thereof) from moving distally within the chamber, thereby preventing ends 262 from sliding out of ports 258.

In some applications, at least one window 266 is defined in lateral wall 256, and retainer 282 is configured to retain anchor 240 in the first state by extending through the window and into loop 264. For example, and as shown, two windows 266 can be defined in lateral wall 256, and the retainer can extend through one of the windows, through the loop, and out of the other of the windows. For some such applications, the two windows can be opposite each other and rotationally offset from the two ports 258. For example, a port axis ax6 that passes through ports 258 can be orthogonal to a window axis ax7 that passes through the windows 266. Axis ax6 and/or axis ax7 can intersect axis ax5. In some applications, and as shown, windows 266 are axially offset from ports 258.

Reference is made to FIGS. 11A-D, and 12A-E, which are schematic illustrations of respective systems 300 and 320, in accordance with some applications. System 300 comprises a tissue anchor 302 and a tool 310, and system 320 comprises a tissue anchor 322 and a tool 330. In some applications, anchor 302 and/or anchor 322 can each be used as a component of an implant, such as an implant comprising multiple anchors connected by a tether (e.g., a line, wire, cord, ribbon, rope, braid, contraction member, suture, etc.). For example, anchor 302 and/or anchor 322 can be used in implant 110 in place of anchor 120, mutatis mutandis. In such cases, anchor 302 and/or anchor 322 (e.g., a head thereof) can comprise an eyelet. Anchor 302 is shown with a head 303 that comprises an eyelet 304, and anchor 322 is shown without an eyelet. In some applications, anchor 302 and/or anchor 322 can have an eyelet that is, mutatis mutandis, similar to (or identical to) eyelet 140 described hereinabove, or to an eyelet described in WO 2021/084407 to Kasher et al., which is incorporated herein by reference. Optionally, anchor 240 can be used for other purposes, and may not comprise an eyelet, as shown.

Tool 310 is advanceable to the heart, and comprises a tube 312, and a driver 314 that extends through at least part of the tube. Driver 314 reversibly engages head 303 of anchor 302. For simplicity, this engagement is not described in detail here, but in some applications, it is as described for one or more of the other anchors and drivers described herein. Tube 312 has a distal end that defines an opening 316. Anchor 302 comprises a tissue-engaging element 306 and is configured to be anchored to tissue 10 by the tissue-engaging element being driven into the tissue.

Tool 330 is advanceable to the heart and comprises a tube 332 and a driver 334. Driver 334 reversibly engages a head 323 of anchor 322. For simplicity, this engagement is not described in detail here, but in some applications, it is as described for one or more of the other anchors and drivers described herein. Tube 332 has a distal end that defines an opening 336. Anchor 322 comprises a tissue-engaging element 326 and is configured to be anchored to tissue by the tissue-engaging element being driven into the tissue.

For each of systems 300 and 320, during transluminal advancement, and/or immediately prior to anchoring the anchor, the anchor is disposed at least partly within the tube. As shown, for system 300 anchor 302 can be disposed entirely within tube 312, and for system 320 at least a distal tip of anchor 322 (e.g., of tissue-engaging element 326) can be exposed out of opening 336.

Figure 11A:
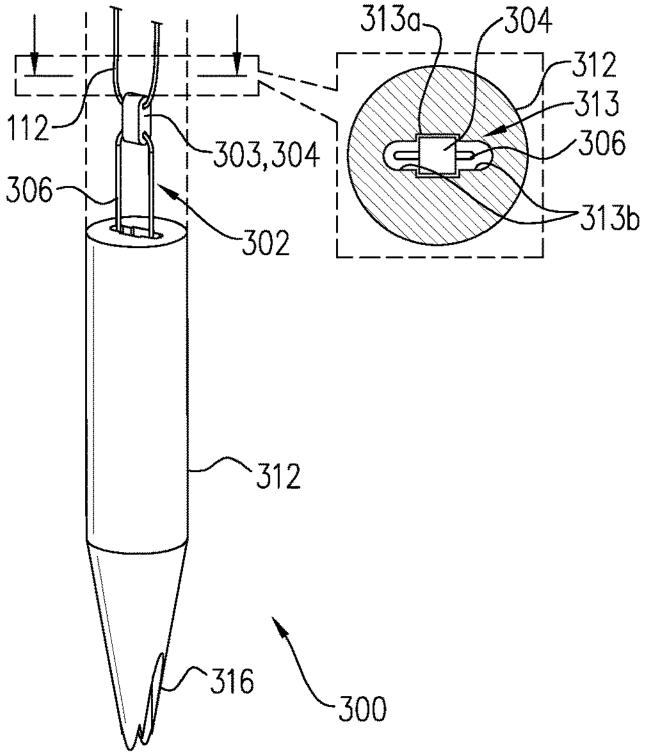
FIGS. 11A-D and 12A-E are schematic illustrations of respective example systems, in accordance with some applications.
Figure 11B:
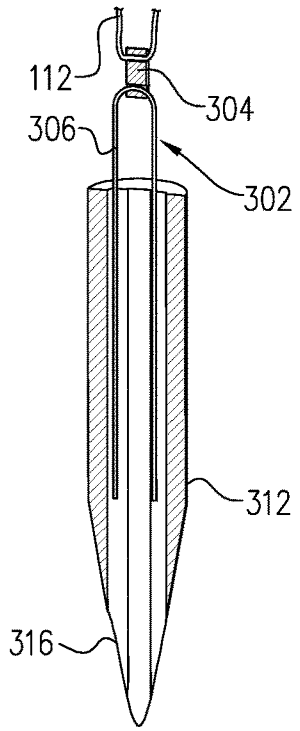
Figure 11C:
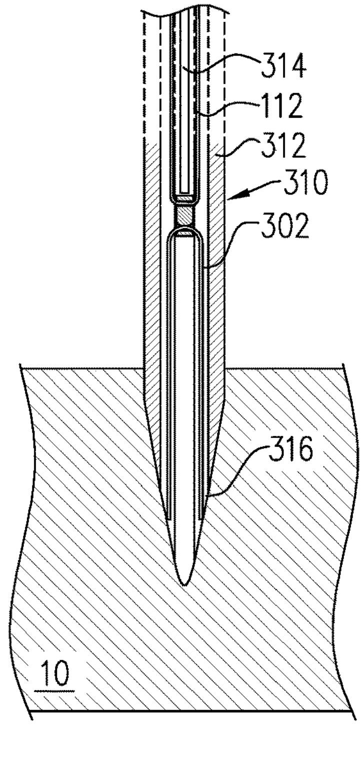
Figure 11D:
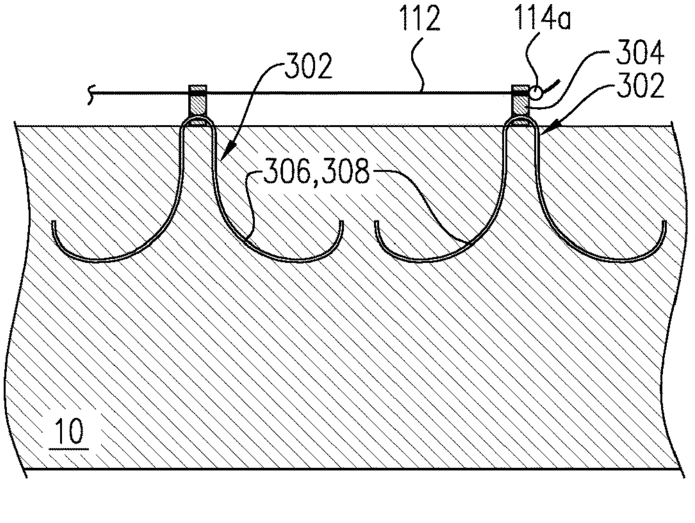
Figure 12A:
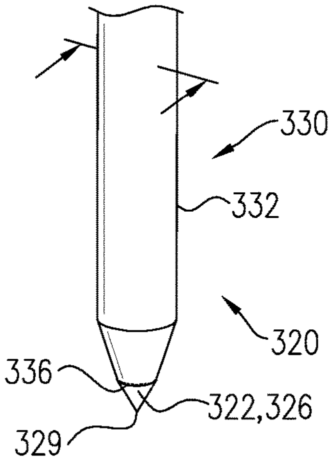
Figure 12B:
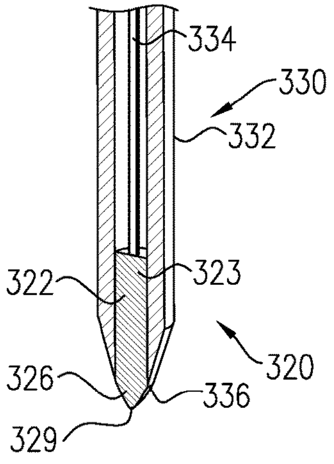
Figure 12C:
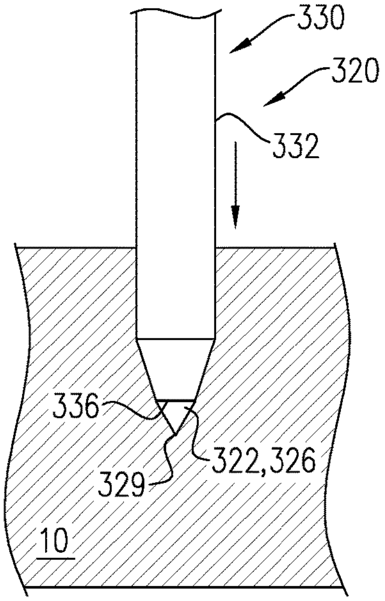
Figure 12D:
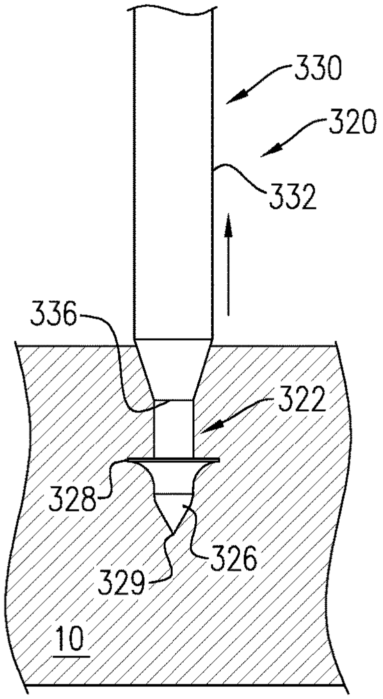
Figure 12E:
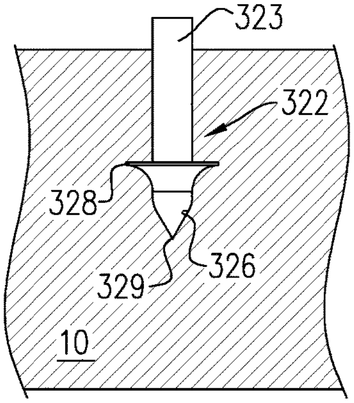

Each of tools 310 and 330 is configured to, while the respective anchor remains disposed at least partly within the respective tube, penetrate the distal end of the respective tube into tissue 10 such that the opening becomes submerged within the tissue (FIGS. 11C and 12C).

Each of drivers 314 and 334 extends through at least part of its respective tube, a distal end of the driver being reversibly engaged with the respective anchor within the tube. The driver is configured to drive the tissue-engaging element of the respective anchor out of the opening of the respective tube and into tissue 10, while the opening remains disposed within the tissue.

In some applications, and as shown, the distal end of tubes 312 and 332 is tapered and/or sharpened.

In some applications, for each of systems 300 and 320, at least a part of the tissue-engaging element is constrained by the tube (e.g., during transluminal advancement and/or immediately prior to anchoring the anchor) and is configured to automatically change shape within the tissue upon exiting the opening. For example, tissue-engaging element 306 of anchor 302 comprises one or more tines 308 easy that automatically deflect and/or curves (e.g., laterally) upon exiting opening 316, and tissue-engaging element 326 of anchor 322 comprises one or more flanges that automatically deflects, expands, and/or curves (e.g., laterally) upon exiting opening 336.

In some applications, tines 308 are metallic, e.g., comprising a superelastic and/or shape-memory material such as Nitinol. In some applications, flange 328 comprises a sheet and a self-expanding frame supporting the sheet. In some applications, flange 328 (e.g., the sheet thereof) comprises a polymer.

In some applications, and as shown (e.g., in FIGS. 11A-B), tube 312 defines a channel 313 that has a central channel region 313*a* and lateral channel regions 313*b*, and houses anchor 302 with a head of the anchor (in the example shown, the head of the anchor comprises eyelet 304) disposed in the central channel region, and each of tines 308 disposed in a respective one of the lateral channel regions, such that, within the channel, the anchor is slidable axially but is inhibited from rotating. It is hypothesized that this provides similar advantages to those described as being provided by the configuration of the channel of system 100, mutatis mutandis.

In some applications, and as shown, channel 313 is wider at central channel region 313*a* than at lateral channel regions 313*b*.

Opening 316 can be defined by channel 313 reaching the distal end of tube 312. In some applications, and as shown, the shape of opening 316 (e.g., along with tapering of the distal end of tube 312) shapes the distal end of tube 312 to resemble a beak.

In some applications, system 320 is configured such that, during transluminal advancement and/or immediately prior to anchoring, a distal tip 329 of tissue-engaging element 326 of anchor 322 is disposed outside of (e.g., distal from) opening 336, and tool 330 is configured to, while the distal tip is disposed outside of the opening, penetrate the distal end of tube 332 into tissue 10 such that the opening becomes submerged within the tissue (FIG. 12C). For such applications, anchor 322 (e.g., tissue-engaging element 326 thereof) is shaped to fit snugly within opening 336 such that, while tool 330 penetrates the distal end of tube 332 into tissue 10, the anchor (e.g., the tissue-engaging element thereof) blocks the opening. It is hypothesized that this configuration advantageously facilitates piercing of the tissue without tissue 10 entering tube 332. For some such applications, and as shown, distal tip 329 and the distal end of 332 tube together define a tapered point, the distal tip being a distal portion of the tapered point and the distal end of the tube being a proximal portion of the tapered point. It is hypothesized that this configuration advantageously facilitates smooth entry into tissue 10.

Reference is made to FIGS. 13-17, which are schematic illustrations of respective tissue anchors, in accordance with some applications. In some applications, these anchors can each be used as a component of an implant, such as an implant comprising multiple anchors connected by a tether (e.g., a line, wire, cord, ribbon, rope, braid, contraction member, suture, etc.). For example, these anchors can be used in implant 110 in place of anchor 120, mutatis mutandis. Each of these anchors has eyelet, which in FIGS. 13-17 is shown as a simple ring, but can optionally be, mutatis mutandis, similar to (or identical to) eyelet 140 described hereinabove, or to an eyelet described in WO 2021/084407 to Kasher et al., which is incorporated herein by reference for all purposes. Optionally, these anchors can be used for other purposes, and may not comprise an eyelet, as shown.

Figure 13:
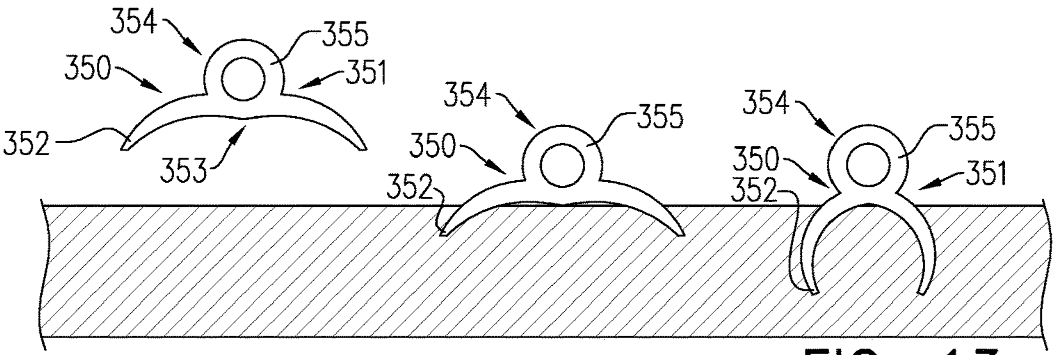
FIGS. 13-17 are schematic illustrations of respective example anchors, in accordance with some applications.

FIG. 13 shows a tissue anchor 350 that comprises a head 351, and multiple tissue-engaging elements 352. Head 351 has a tissue-facing side 353, and an opposing side 354 that defines an eyelet 355. Tissue-engaging elements 352 are disposed laterally from head 351, and each has a sharpened tip. In a delivery state of anchor 350 (left frame), tissue-engaging elements 352 are configured to be driven linearly into tissue 10 (middle frame). While tissue-engaging elements 352 are disposed within the tissue, transitioning of anchor 350 (e.g., the tissue-engaging elements thereof) toward a gripping state brings the tips toward each other and presses tissue-facing side 353 of head 351 against the tissue (right frame).

Each of FIGS. 14-17 shows a respective tissue anchor that is similar to anchor 350, with the additional feature of the tissue-facing side of the head of the anchor defining grips. For these tissue anchors, the transitioning of the anchor toward its gripping state presses the grips against the tissue.

Figure 14:
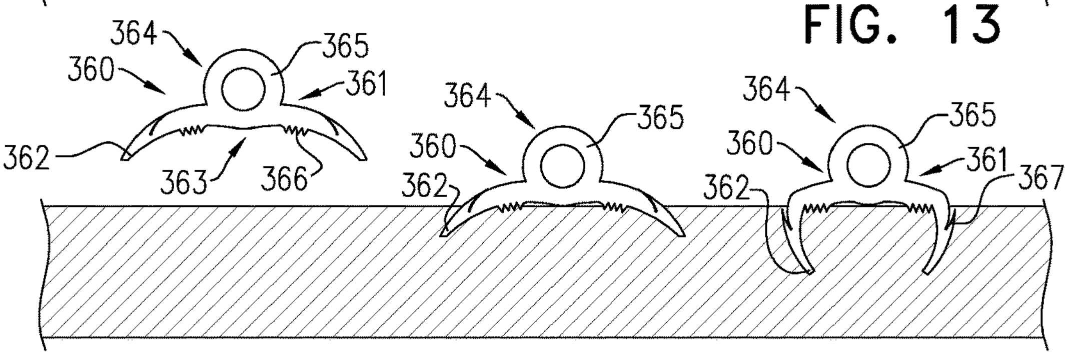

FIG. 14 shows a tissue anchor 360 that comprises a head 361 and tissue-engaging elements 362. Head 361 has a tissue-facing side 363 shaped to define grips 366, and an opposing side 364 that defines an eyelet 365. Tissue-engaging elements 362 are disposed laterally from head 361, and each has a sharpened tip. In a delivery state of anchor 360 (left frame), tissue-engaging elements 362 are configured to be driven linearly into tissue 10, e.g., such that grips 366 contact the tissue (middle frame). While tissue-engaging elements 362 are disposed within the tissue, transitioning of anchor 360 (e.g., the tissue-engaging elements thereof) toward a gripping state brings the tips toward each other and presses grips 366 against the tissue (right frame).

Figure 15:
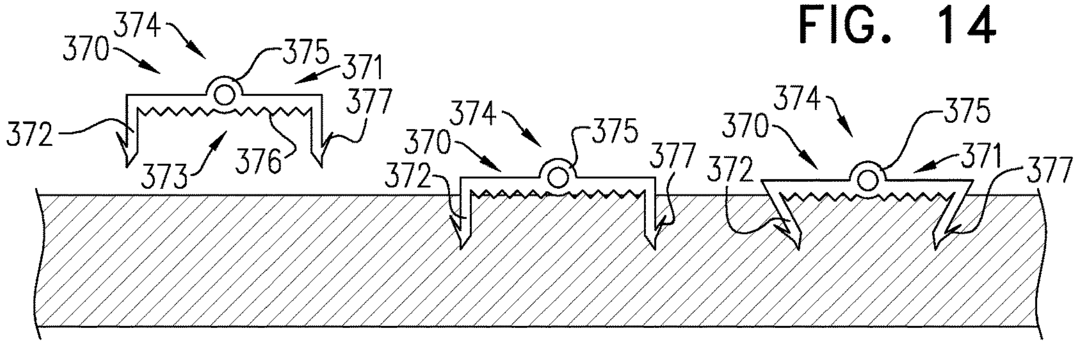

FIG. 15 shows a tissue anchor 370 that comprises a head 371 and tissue-engaging elements 372. Head 371 has a tissue-facing side 373 shaped to define grips 376, and an opposing side 374 that defines an eyelet 375. Tissue-engaging elements 372 are disposed laterally from head 371, and each has a sharpened tip. In a delivery state of anchor 370 (left frame), tissue-engaging elements 372 are configured to be driven linearly into tissue 10, e.g., such that grips 376 contact the tissue (middle frame). While tissue-engaging elements 372 are disposed within the tissue, transitioning of anchor 370 (e.g., the tissue-engaging elements thereof) toward a gripping state brings the tips toward each other and presses grips 376 against the tissue (right frame).

Figure 16:
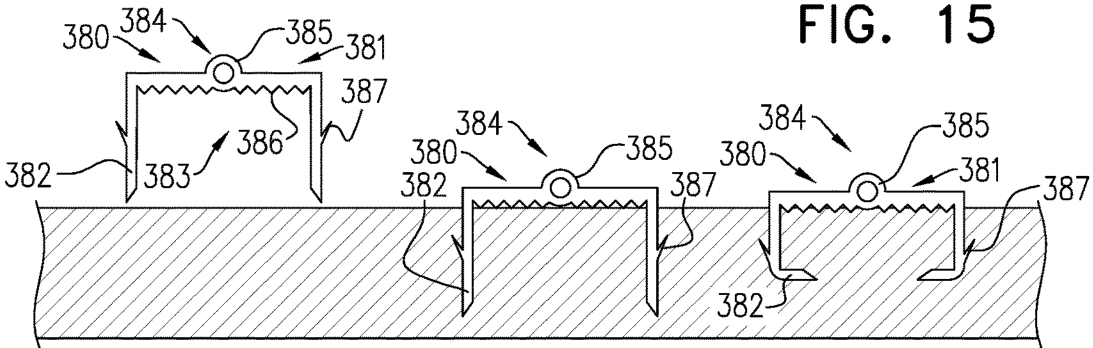

FIG. 16 shows a tissue anchor 380 that comprises a head 381 and tissue-engaging elements 382. Head 381 has a tissue-facing side 383 shaped to define grips 386, and an opposing side 384 that defines an eyelet 385. Tissue-engaging elements 382 are disposed laterally from head 381, and each has a sharpened tip. In a delivery state of anchor 380 (left frame), tissue-engaging elements 382 are configured to be driven linearly into tissue 10, e.g., such that grips 386 contact the tissue (middle frame). While tissue-engaging elements 382 are disposed within the tissue, transitioning of anchor 380 (e.g., the tissue-engaging elements thereof) toward a gripping state brings the tips toward each other and presses grips 386 against the tissue (right frame).

Figure 17:
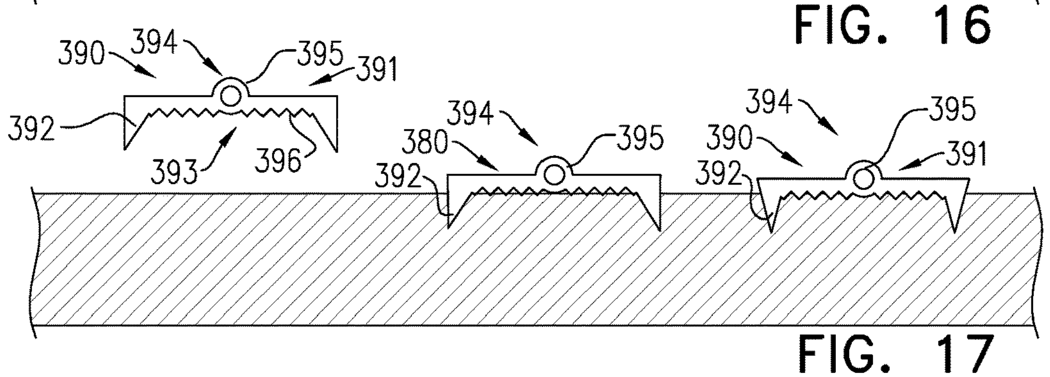

FIG. 17 shows a tissue anchor 390 that comprises a head 391 and tissue-engaging elements 392. Head 391 has a tissue-facing side 393 shaped to define grips 396, and an opposing side 394 that defines an eyelet 395. Tissue-engaging elements 392 are disposed laterally from head 391, and each has a sharpened tip. In a delivery state of anchor 390 (left frame), tissue-engaging elements 392 are configured to be driven linearly into tissue 10, e.g., such that grips 396 contact the tissue (middle frame). While tissue-engaging elements 392 are disposed within the tissue, transitioning of anchor 390 (e.g., the tissue-engaging elements thereof) toward a gripping state brings the tips toward each other and presses grips 396 against the tissue (right frame).

Reference is again made to FIGS. 13-17. In some applications, transitioning of the tissue-engaging elements toward the gripping state squeezes the tissue between the multiple tissue-engaging elements.

Reference is again made to FIGS. 13-17. In some applications (e.g., as shown for anchor 380), each of the tissue-engaging elements has a deflecting portion, and a static portion that connects the deflecting portion to the head, both the deflecting portion and the static portion being configured to be driven linearly into the tissue while the tissue-engaging element is in the delivery state. For such applications, the tissue-engaging element can be configured such that, when the tissue-engaging element transitions toward the gripping state (i) the static portion remains static with respect to the head, and (ii) the deflecting portion deflects with respect to the static portion and with respect to the head.

Reference is again made to FIGS. 13-17. In some applications (e.g., as shown for anchors 360, 370, and 380), each of the tissue-engaging elements has a medial side and a lateral side, the medial side being closer than the lateral side to the other tissue-engaging elements (at least in the delivery state), and each of the tissue-engaging elements is shaped to define a barb (367, 377, 387) on the lateral side. For some such applications (e.g., as shown for anchor 360), in the delivery state the barb is obscured (e.g., by another part of the tissue-engaging element), and in the gripping state the barb is exposed. For some such applications in which, additionally, the tissue-engaging element has a static portion and a deflecting portion, the barb can be defined by the static portion. For other such applications, the barb can be defined by the deflecting portion.

Reference is now made to FIGS. 18A-C, 19A-D, 20A-C, and 21A-E, which are schematic illustrations of tether-handling systems 400 and 450, in accordance with some applications, each comprising a respective tether-handling device 410, 460. Tethers are used in various medical procedures, including as sutures and/or as components of implants. It is commonly necessary to lock or secure such a tether at a certain point in the procedure. In the above example of tether 112 of implant 110, a stopper (e.g., stopper 114*b*) is used for this purpose. Each of tether handling devices 410 and 460 can be used to secure a tether such as tether 112, e.g., in place of stopper 114*b*, and/or for a similar purpose in the implants described in WO 2021/084407 to Kasher et al., which is incorporated herein by reference for all purposes.

Additionally, each of tether handling devices 410 and 460 can also be useful for applications in which the tether is to be cut (e.g., as described for system 100), by being configured to manage a vestigial piece of the tether, e.g., by moving, confining, covering, and/or obscuring it. It is hypothesized that this is particularly advantageous for applications in which the cut end of the tether is hard and/or sharp, in order to reduce a likelihood of the hard and/or sharp cut end injuring adjacent tissue.

In some applications, for system 100 described hereinabove (and other similar systems), this locking and handling of tether 112 is performed after the final anchor of the implant has been implanted. In FIGS. 19A-D and 21A-E, this final anchor is represented by a block that is indicated by reference numeral 120*f*. The block can schematically represent the head of the final anchor, or a component of the head such as an eyelet.

Figure 18A:
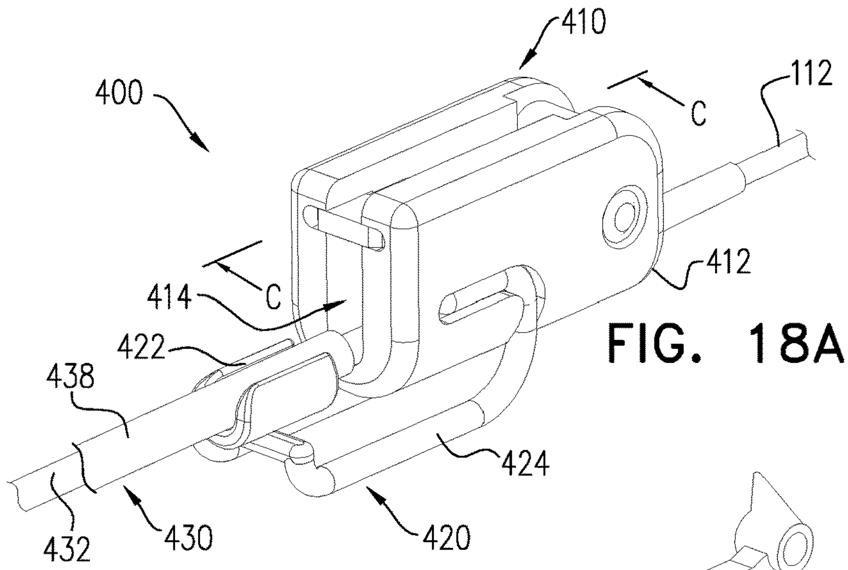
FIGS. 18A-C, 19A-D, 20A-C, and 21A-E are schematic illustrations of example tether-handling systems, each comprising a respective tether-handling device, in accordance with some applications.
Figure 18B:
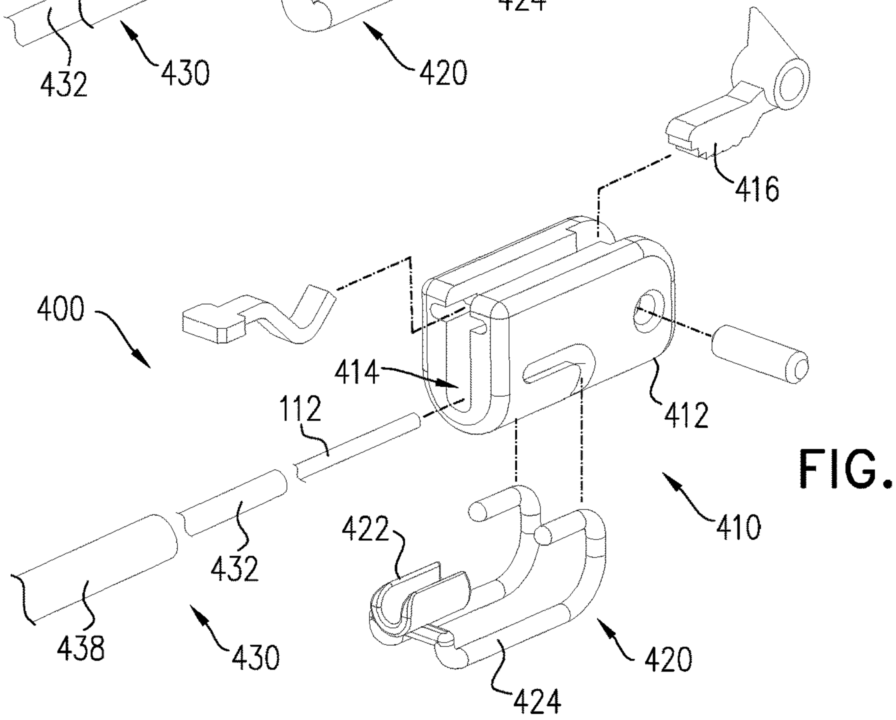
Figure 18C:
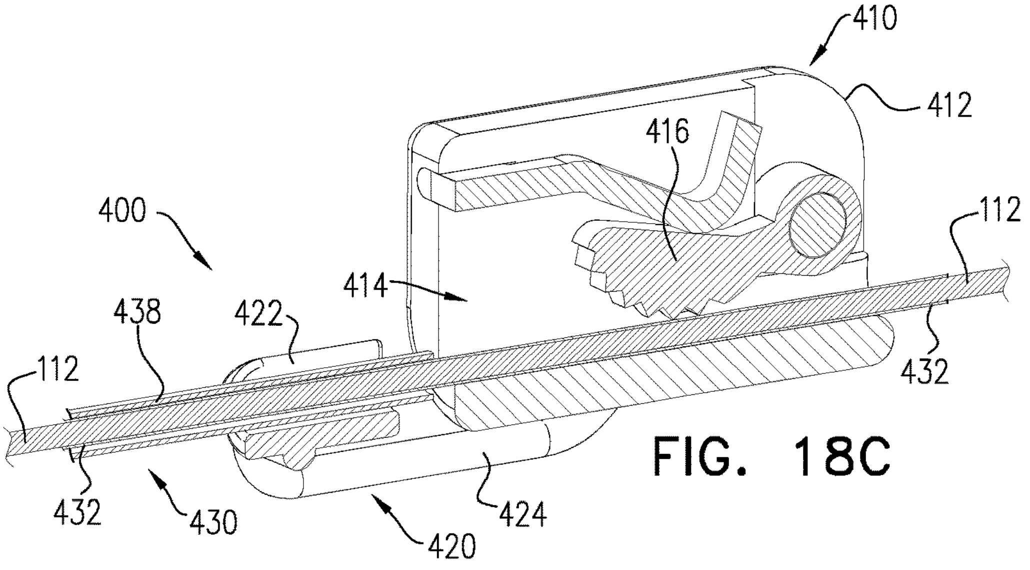

FIGS. 18A-C and 19A-D show system 400 comprising tether-handling device 410, e.g., for use with system 100 in place of stopper 114*b*. FIG. 18A shows a projection, FIG. 18B shows an exploded view, and FIG. 18C shows a cross-section.

Device 410 comprises a housing 412, shaped to define a passage 414 therethrough. Device 410 further comprises a clamp 416, coupled to housing 412, and biased to clamp onto tether 112 within passage 414 in a manner that inhibits sliding of the housing (and the locking device as a whole) with respect to the tether.

Figure 19A:
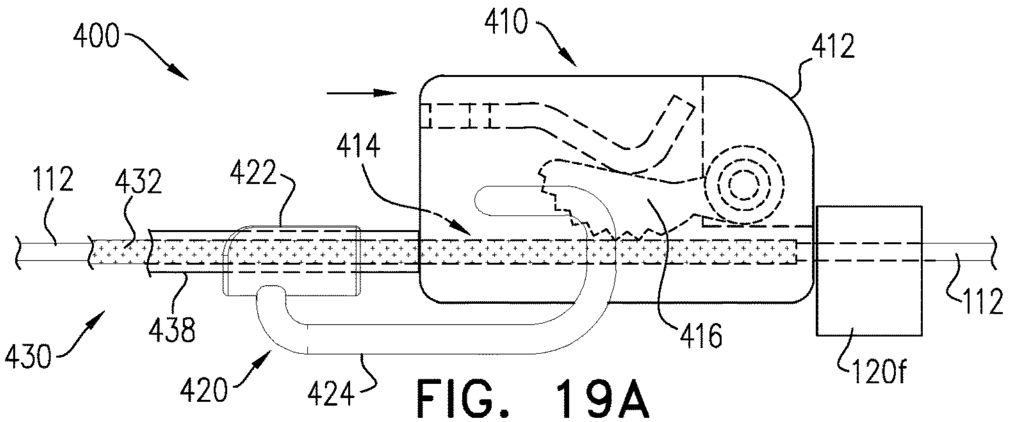
Figure 19B:
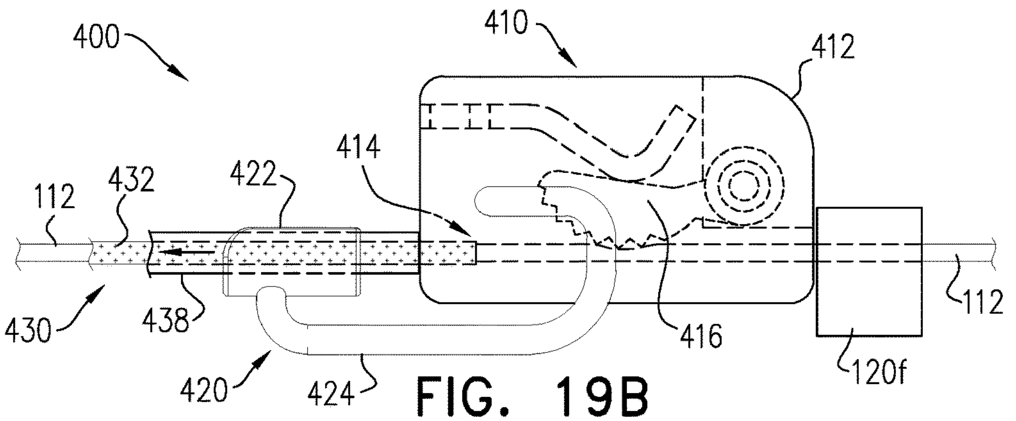

In some applications, device 410 further comprises an arm 420, extending proximally from housing 412. Arm 420 can comprise a conduit 422, shaped to receive a portion of the tether proximally from the housing. Conduit 422 can be circumferentially closed, or as shown, can have an open lateral side. Arm 420 can also comprise a lever 424, coupling conduit 422 to housing 412, and biased to place the conduit in an offset position with respect to passage 414. An example of this offset position is shown in FIG. 19D, described hereinbelow.

System 400 further comprises a tool 430 that comprises a tube 432. FIGS. 18A and 19A show a delivery state of system 400, in which tool 430 is coupled to device 410. In the delivery state, tube 432 is disposed (i) within passage 414 in a manner that inhibits clamp 416 from clamping, and (ii) within conduit 422 in a manner that constrains the conduit in an in-line position with respect to the passage (i.e., despite the bias of lever 424). For example, and as shown, tube 432 can extend distally through conduit 422 and into passage 414.

It is to be noted that, in this context, the term "in-line" (including the specification and the claims) means that tether 112 can extend between passage 414 and conduit 422 while remaining generally straight.

After final anchor 120*f* has been anchored, tether 112 remains extending proximally from the final anchor. In the delivery state, device 410 is transluminally slid distally over and along tether 112 toward anchor 120*f*, with the tether extending through passage 414 (FIG. 19A). In some applications, tether 112 is threaded through passage 414 after final anchor 120*f* has been implanted, and the anchor driver that was used to anchor the final anchor has been withdrawn. In some applications, tool 430 comprises an advancement member (e.g., a pusher) 438 that reversibly engages device 410 (e.g., housing 412 thereof), and is used to transluminally slide device 410 over and along tether 112 toward anchor 120*f*. Tube 432 can be disposed laterally from advancement member 438, or through the advancement member (as shown).

In some applications, once device 410 is disposed at anchor 120*f*, in order to contract the tissue to which implant 110 is anchored tension can be applied to tether 112 by pulling on the tether (e.g., from outside of the subject) while a reference force is provided against anchor 120*f* by device 410 (e.g., by advancement member 438 pushing device 410 against anchor 120*f*). The tension is then locked into implant 110 by fixing device 410 to tether 112 by retracting tube 432 out of passage 414 until it no longer inhibits clamp 416, and the clamp thereby automatically clamps onto the tether (FIG. 19B).

Figure 19C:
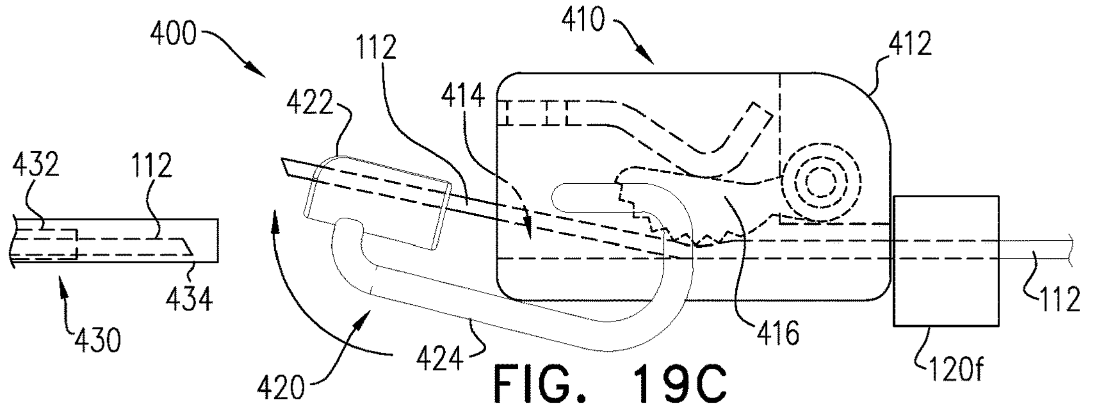
Figure 19D:
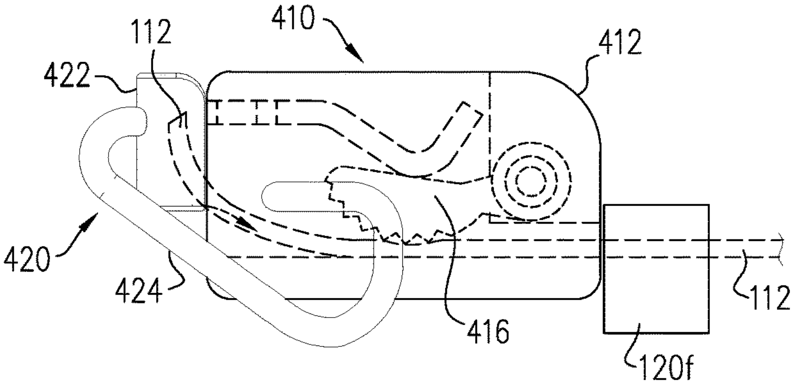

Once tube 432 has been retracted sufficiently (e.g., out of conduit 422), tether 112 is cut, often in a position that is proximal from conduit 422 (FIG. 19C). The resulting release of arm 420 triggers lever 424 to move conduit 422 into an offset position with respect to passage 414 (FIGS. 19C-D). It is to be noted that, in this context, the term "offset" (including the specification and the claims) means that, in order for tether 112 to extend between passage 414 and conduit 422, the tether must bend. In some applications, and as shown, lever 424 is biased to place conduit 422 against the proximal side of housing 412.

The cutting of tether 112 can be performed using a cutter 434, which can be a component of tool 430. Cutter 434 can be advanceable over and along tether 112, and axially moveable with respect to (e.g., advanceable over and along) tube 432, e.g., the tube is slidable within the cutter. Advancement member 438 is shown as having been removed prior to advancement of cutter 434 (or at least prior to cutting of tether 112), but in some applications cutter 434 can be advanced through advancement member 438.

In some applications, system 400 is configured to have an intermediate state in which tube 432 has been retracted out of passage 414 but not out of conduit 422. For some such applications, in the intermediate state, a distal part of tube 432 remains disposed within housing 412, e.g., proximally from passage 414 and/or from clamp 416. In the intermediate state, tube 432 no longer inhibits clamp 416, and the clamp thereby automatically clamps onto tether 112. FIG. 19B shows an example of such an intermediate state.

In some applications, tether 112 has sufficient tensile strength relative to the bias of lever 424 that, even in the absence of tube 432, tension on tether 112 proximally from clamp 416 can inhibit the lever from moving conduit 422 into the offset position. Nonetheless, this tension is eliminated upon the cutting of tether 112, triggering lever 424 to move conduit 422 into the offset position as described hereinabove.

Cutting of tether 112 often can leave behind a vestigial piece of the tether. For example, and as shown, cutting of tether 112 proximally from conduit 422 may leave a vestigial piece of the tether protruding proximally from the conduit. Arm 420 is configured such that the movement of conduit 422 into the offset position moves the vestigial piece of tether 112 toward the housing 412, e.g., confining the vestigial piece close to the housing. In some applications, the resulting curved shape of the vestigial piece of tether 112 means that the vestigial piece is drawn into conduit 422, such that the end of the tether is within the conduit.

Figure 20A:
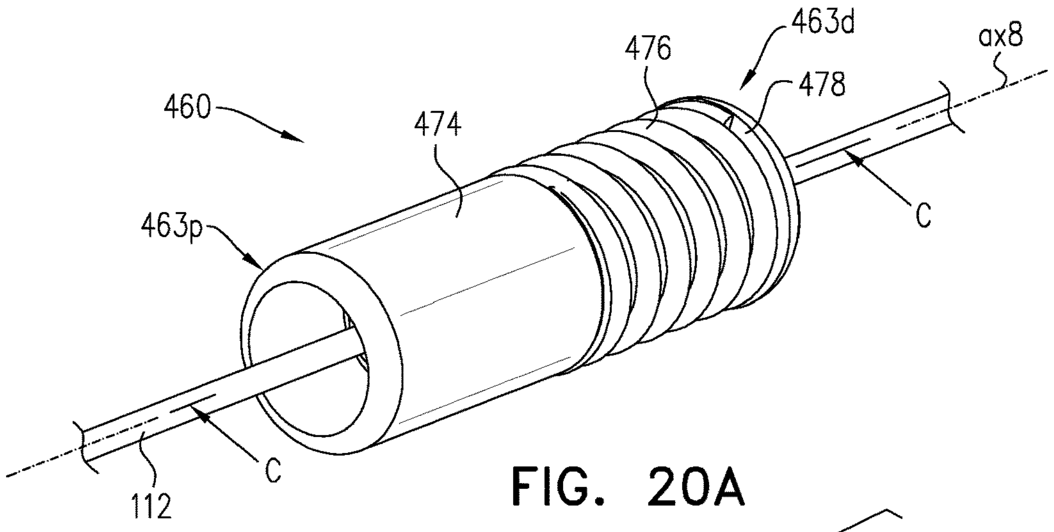
Figure 20B:
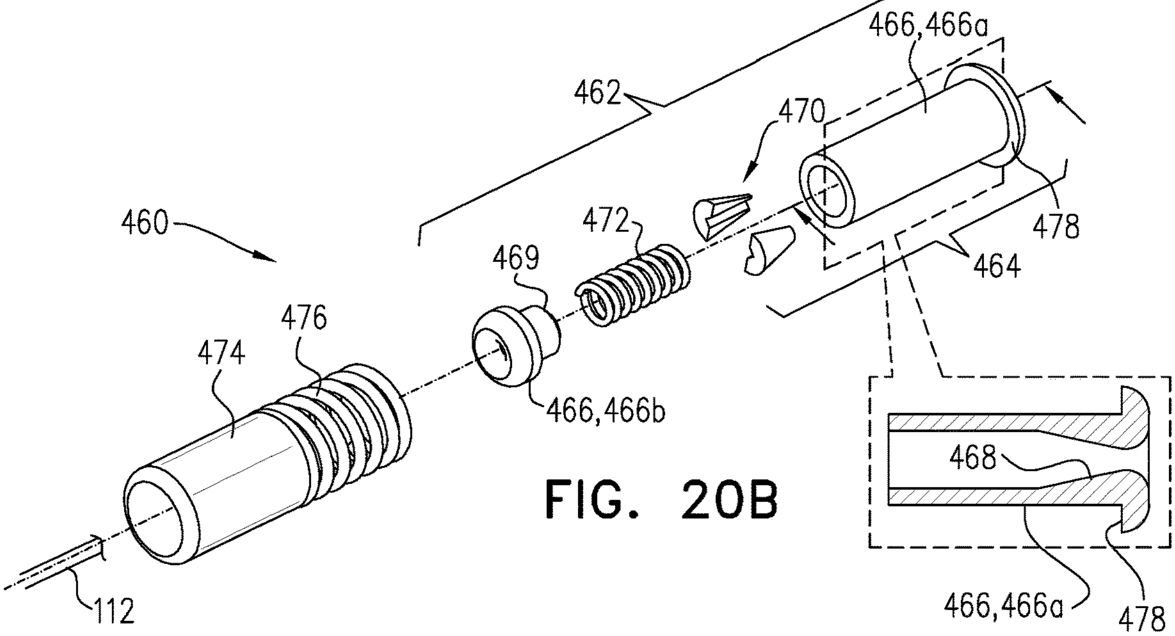
Figure 20C:
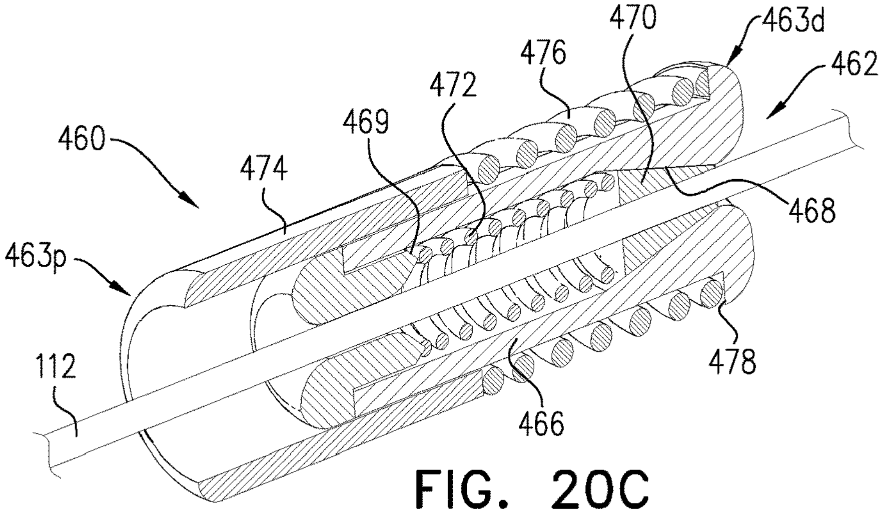

FIGS. 20A-C and 21A-E show system 450 comprising tether-handling device 460, e.g., for use with system 100 in place of stopper 114*b*. System 450 can be used for similar purposes to system 400, mutatis mutandis. FIG. 20A shows a projection of device 460, FIG. 20B shows an exploded view, and FIG. 20C shows a cross-section. System 450 often further comprises a tool 480, described hereinbelow.

Device 460 comprises a clamp 462 that comprises a chuck 464 and a spring 472. Chuck 464 has a longitudinal axis ax8 and comprises a sleeve 466 and a collet 470. Sleeve 466 is shown as comprising two discrete subcomponents that are fixed together. In FIG. 20B alone these subcomponents are labeled 466*a* and 466*b*. In some applications, the entirety of sleeve 466 is made from a single unified member, e.g., a single piece of stock. Collet 470 is shown as comprising two discrete subcomponents. However, collet 470 can optionally comprise three or more subcomponents. Furthermore, the subcomponents of collet 470 may not be discrete, e.g., they can be movable (e.g., flexible) parts integrated in a unified member, e.g., made from a single piece of stock.

In some applications, sleeve 466 circumscribes axis ax8 (e.g., thereby defining axis ax8 as the longitudinal axis of chuck 464) and has a tapered inner surface 468. Collet 470 can be disposed within sleeve 466, and is dimensioned to receive a tether, such as tether 112, therethrough (e.g., dimensioned to define a passage therethrough). Spring 472 axially pushes collet 470 against surface 468 such that the collet is squeezed medially by sleeve 466 (e.g., by surface 468 thereof). When tether 112 is present within collet 470, this squeezing of the collet causes the collet to clamp onto the tether, thereby inhibiting sliding of the tether through the collet in at least one axial direction. This axial direction can be distally (in FIGS. 21A-E, this is a rightward direction with respect to collet 470). Often, this axial direction is the same axial direction in which spring 472 axially pushes collet 470 against surface 468 (in FIGS. 21A-E this is a rightward direction with respect to sleeve 466).

In some applications, the inner surface of collet 470 is roughened or knurled to facilitate gripping of tether 112.

In some applications, and as shown, sleeve 466 and collet 470 are concentric with axis ax8. As shown, spring 472 can also be concentric with axis ax8.

In some applications, spring 472 is a compression spring, such as a helical compression spring, as shown. For some such applications, and as shown, spring 472 circumscribes axis ax8, and device 460 is configured to be threaded onto the tether such that sleeve 466, collet 470, and the spring circumscribe the tether.

In some applications, and as shown, sleeve 466 has an opposing surface 469, and spring 472 is maintained under compression between the opposing surface and collet 470 (e.g., in a relaxed state of the spring, the spring is longer than the distance between the opposing surface and the collet). That is, for such applications, spring 472 applies an opposing force against surface 469 while axially pushing collet 470 against surface 468.

Figure 21A:
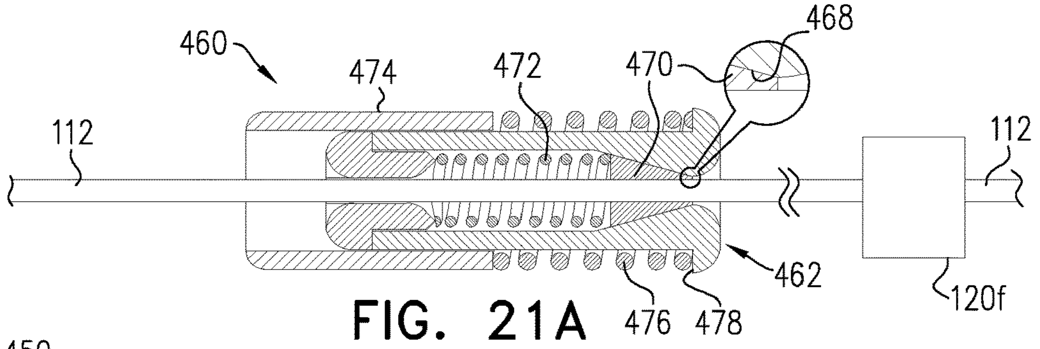
Figure 21B:
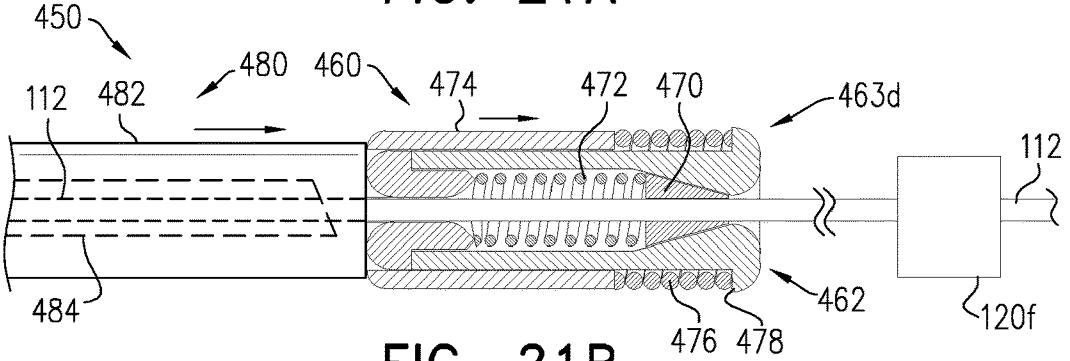
Figure 21C:
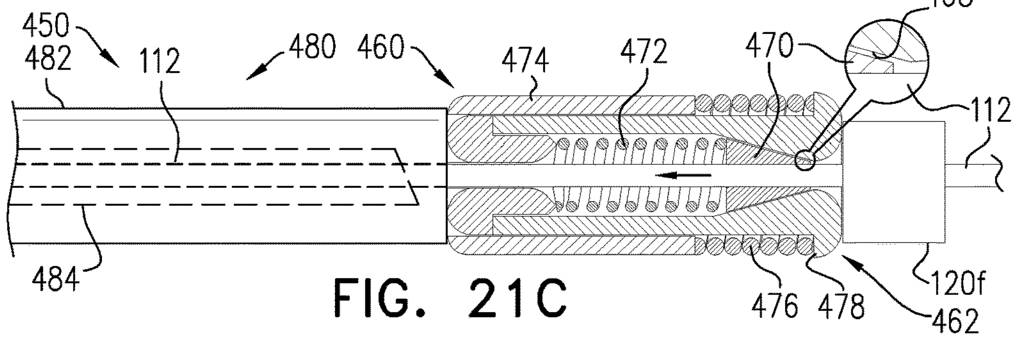
Figure 21D:
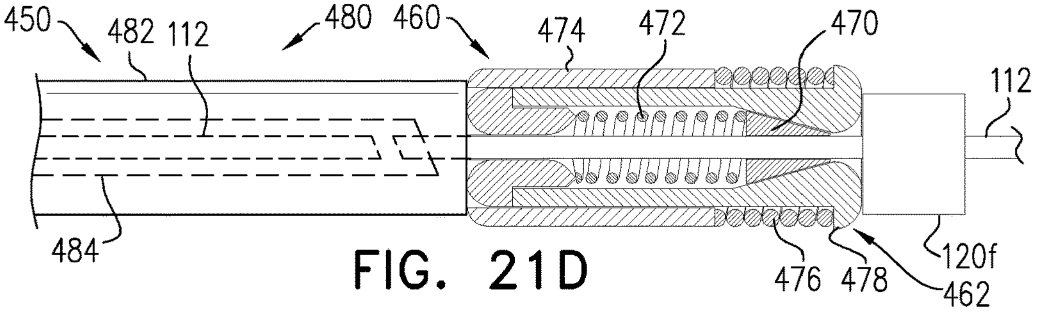
Figure 21E:
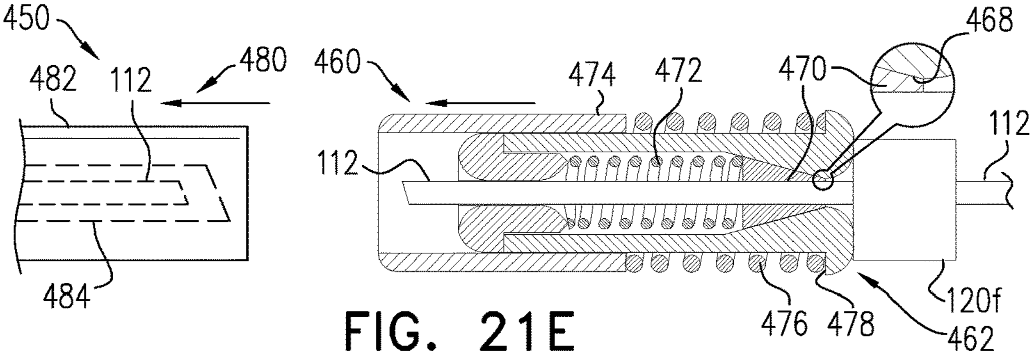

FIGS. 21A-E show steps in an example procedure using system 450, in accordance with some applications. Device 460 is threaded onto tether 112 (FIG. 21A). This can be performed after final anchor 120*f* has been anchored to the tissue. Tool 480 (e.g., a tubular member 482 thereof) is used to push device 460 distally over and along tether 112, toward final anchor 120*f* (FIGS. 21B-C). Once device 460 is in contact with final anchor 120*f*, tool 480 provides a reference force, via device 460, against the final anchor, to facilitate tensioning of tether 112 as the tether is pulled proximally (FIG. 21C). Once a desired degree of tension (or a desired degree of contraction of the tissue) has been achieved, a cutter 484 is used to cut tether 112 proximally from clamp 462, and tool 480 is removed from the subject (FIGS. 21D-E). Clamp 462 maintains the tension on tether 112 by inhibiting movement of the tether with respect to the clamp. Cutter 484 can be a component of tool 480, e.g., disposed within tubular member 482. Cutter 484 can be fixedly axially positioned with respect to tubular member 482 (e.g., as shown) or can be axially movable within the tubular member.

In some applications, and as shown, clamp 462 is configured to inhibit sliding of tether 112 through collet 470 only in a first axial direction, and to facilitate sliding of the tether through the collet 470 in a second, opposite, axial direction (leftward in FIGS. 21A-E). It is hypothesized that this advantageously obviates the need clamp 462 to be actively unlocked and/or locked. For example, and as shown in FIGS. 21B-C, pushing clamp 462 distally along tether 112 moves the tether proximally through the clamp (e.g., through sleeve 466 thereof), such that the tether pushes collet 470 axially away from surface 468 (and against spring 472), thereby relieving/reducing clamping of the tether by the collet, and allowing the tether to slide proximally through the clamp. This pushing of collet 470 is represented by a small gap between the collet and surface 468 in the inset of FIG. 21C, in which tether 112 is moving proximally with respect to clamp 462 (e.g., compared with the inset of FIG. 21A, in which the tether is stationary with respect to the clamp).

As described hereinabove, clamp 462 (e.g., chuck 464 thereof) facilitates one-way sliding of device 460 along tether 112. To facilitate the techniques described hereinabove, the device 460 can be threaded onto tether 112 in an orientation in which this one-way is distally, i.e., such that clamp 462 (e.g., device 460 as a whole) is slidable distally along the tether but is inhibited from sliding proximally along the tether. This orientation thereby defines clamp 462 as having a proximal end 463*p* and a distal end 463*d*, the clamp being slidable distally along tether 112 with the distal end leading the proximal end. Surface 468 often tapers toward distal end 463*d*.

As described with reference to system 400, mutatis mutandis, cutting of tether 112 can leave behind a vestigial piece of the tether, e.g., protruding proximally from chuck 464. As also described hereinabove, it is hypothesized that it is advantageous to move, confine, cover, and/or obscure the vestigial piece of the tether. In some applications, device 460 comprises a sheath 474 that is elastically coupled to sleeve 466. In a resting state, sheath 474 extends proximally from sleeve 466 (FIG. 21A). The elastic coupling of sheath 474 to sleeve 466 is such that (i) the sheath is retractable distally over the sleeve by application of a distally-directed force to the sheath, and (ii) in response to removal of the distally-directed force, the sheath automatically re-extends proximally. In some applications, the sheath is rigid at least with respect to deflection.

In some applications, tool 480 is configured to provide this distally-directed force, e.g., when pushing device 460 distally along tether 112. For example, at least a distal part of tool 480 (e.g., tubular member 482 thereof) can be dimensioned to contact sheath 474 in a manner in which the pushing of device 460 distally by the tool distally retracts the sheath (FIGS. 21B—C). For some such applications, and as shown, sheath 474 becomes retracted sufficiently that tool 480 (e.g., tubular member 482 thereof) contacts sleeve 466.

In some applications, and as shown, cutter 484 cuts tether 112 while sheath 474 is distally retracted (FIG. 21D), such that upon withdrawal of tool 480 (and thereby removal of the distally-directed force that the tool applies to the sheath), the sheath automatically re-extends proximally and ensheathes the vestigial piece of the tether (FIG. 21E).

In some applications, the elastic coupling of sheath 474 to sleeve 466 is provided by a spring 476, e.g., spring 472 being a collet-spring, and spring 476 being a sheath-spring. Spring 476 can be disposed laterally from sleeve 466, e.g., circumscribing the sleeve. Spring 476 can be a helical spring, as shown. Spring 476 can be a compression spring, mounted such that, when the distally-directed force is applied to sheath 474, and the sheath responsively retracts over sleeve 466, spring 476 becomes compressed against a flange 478 that extends laterally from sleeve 466.

As shown, spring 476 can be sufficiently weak (e.g., to have a sufficiently low spring constant) relative to spring 472 that sheath 474 becomes fully retracted (e.g., tool 480 contacts sleeve 466) during distal pushing of device 460 along tether 112. Optionally, spring 476 can be sufficiently strong relative to spring 472 (e.g., to have a sufficiently high spring constant) that device 460 becomes pushed along tether 112 without sheath 474 being fully retracted. For example, sheath 474 can become further retracted when anchor **120*f* resists further distal advancement of device 460**.

Figure 22A:
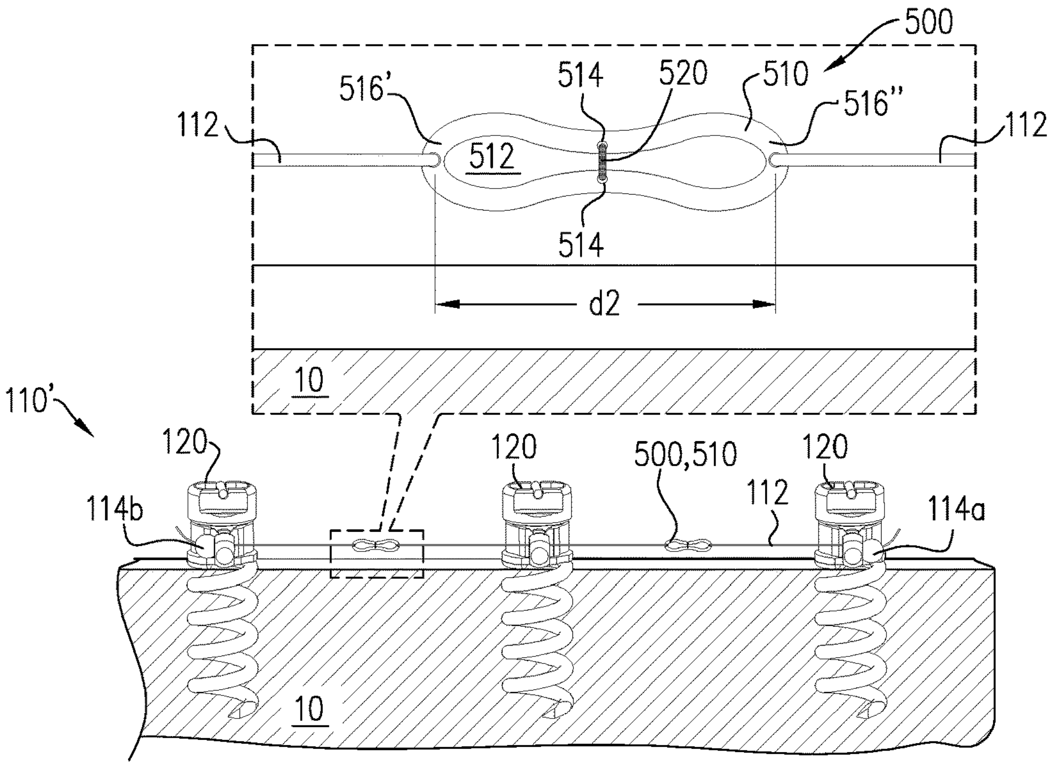
FIGS. 22A-B, 23A-B, and 24A-D are schematic illustrations of various example tensioners, in accordance with some applications.
Figure 22B:
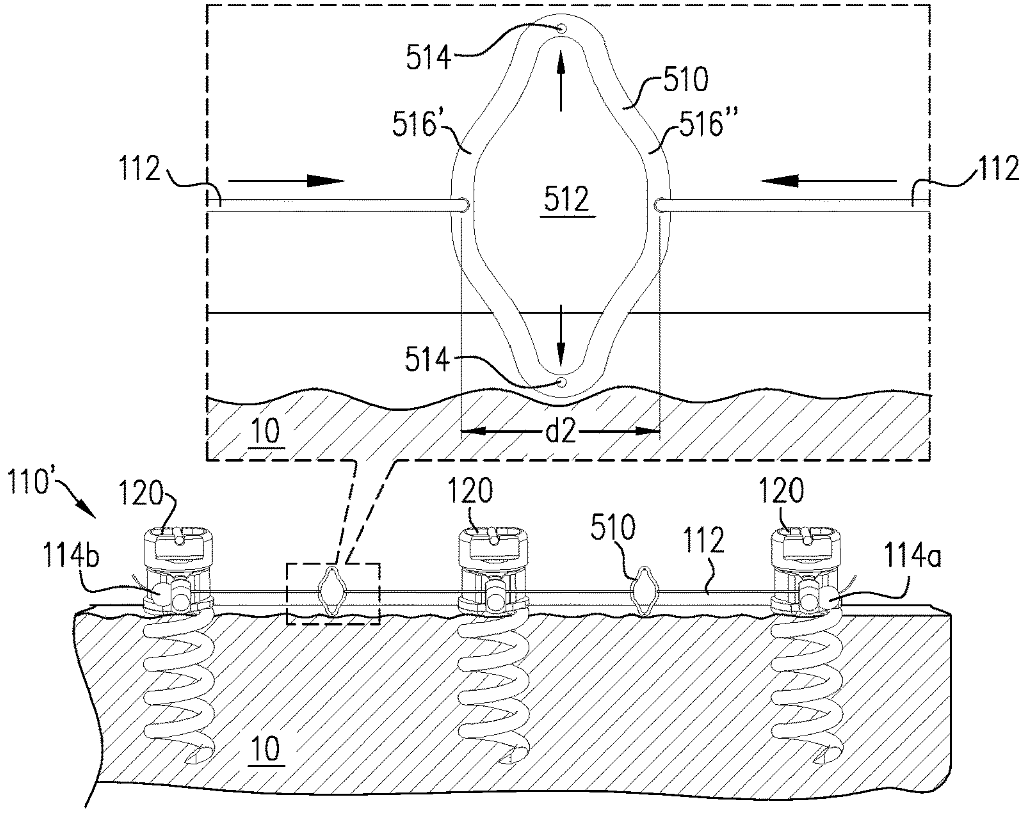
Figure 23A:
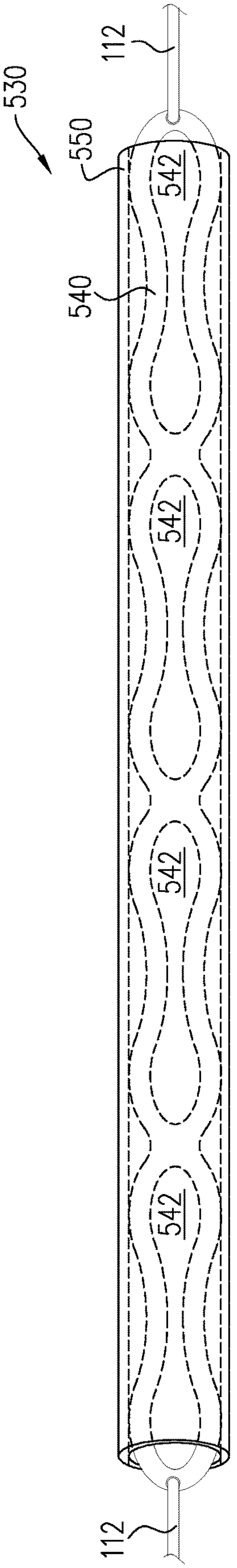
Figure 23B:
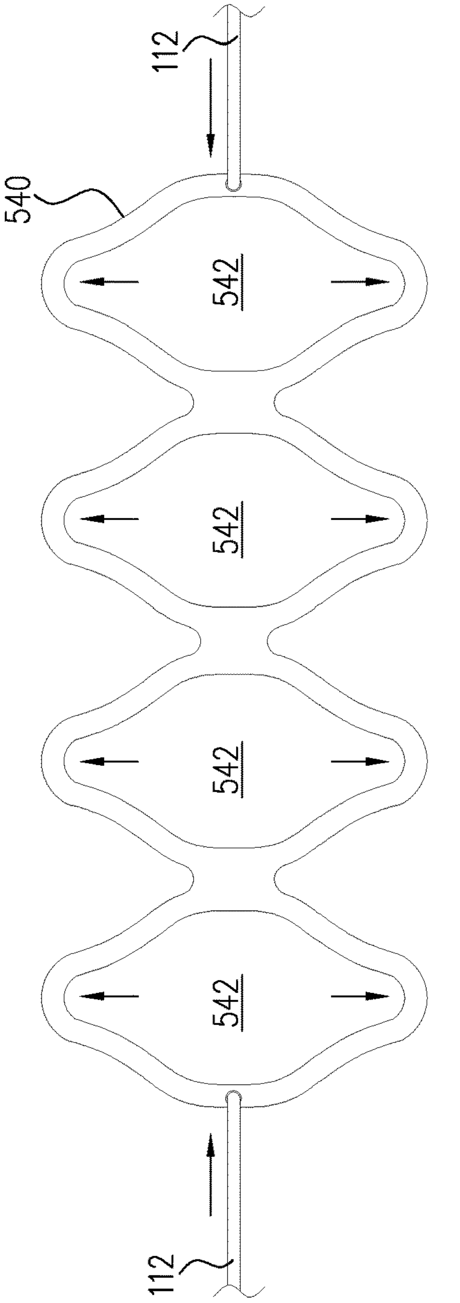

Reference is made to FIGS. 22A-B, 23A-B, and 24A-D, which are schematic illustrations of various tensioners, in accordance with some applications. FIGS. 22A-B show a tensioner 500, FIGS. 23A-B show a tensioner 530, and FIGS. 24A-D show a tensioner 560.

Tissue-adjustment implants that comprise a tether (e.g., a line, wire, cord, ribbon, rope, braid, contraction member, suture, etc.) whose tensioning causes contraction of tissue (such as implant 110 described hereinabove) can exert forces on the tissue at the sites at which the tether is anchored to the tissue, e.g., at the sites at which tissue anchors are anchored. It is hypothesized that, in some applications, it is advantageous to delay the application of at least some of the tension to the tether, e.g., such that post-anchoring tissue recovery and/or growth can enhance anchoring, thereby reducing a likelihood of de-anchoring or another deleterious event occurring before (or after) the desired final amount of tether-tension and tissue-contraction has been achieved.

Although tensioners 500, 530, and 560 are described herein for use with implant 110, it is to be noted that the scope of the present disclosure includes the use of these tensioners in other contexts, such as with other tissue-adjusting implants, mutatis mutandis. Similarly, although the tensioners are shown as being used with anchors 120, which are tissue-piercing anchors, it is to be noted that the tensioners can alternatively or additionally be used with clips, or other types of anchor, mutatis mutandis.

Each of tensioners 500, 530, and 560 is configured to be coupled to at least one tether (e.g., tether 112) between two anchors (e.g., anchors 120) and comprises a spring and a restraint that restrains the spring in an elastically-deformed shape. The restraint is bioresorbable, such that after implantation of the implant within the heart, disintegration of the restraint releases the spring from the restraint. The spring is configured to, upon release from the restraint, automatically move away from the elastically-deformed state toward a second shape (e.g., a relaxed or resting shape). The coupling of the spring to the tether is such that the movement of the spring away from the elastically-deformed state toward the second shape pulls, via the tether, the two anchors toward each other. That is, the disintegration of the restraint allows the spring to apply tension to the tether, thereby drawing the anchors toward each other. Tensioners 500, 530, and 560 can therefore be considered delayed-tensioning devices. Often, when the implant is implanted (e.g., during the same procedure), a certain degree of tension is applied to the tether, and additional tension is applied by the spring upon disintegration of the restraint. It is to be noted that, due to the tension on tether 112, the spring may not actually reach its second shape.

There is provided, in accordance with some applications, an implant comprising: a first anchor; a second anchor; and at least one tether coupling the first anchor to the second anchor. A tensioner can also be coupled to the at least one tether between the first anchor and the second anchor, and can comprise a spring and a restraint, restraining the spring in an elastically-deformed shape of the spring.

In some applications, the restraint is bioresorbable, such that after implantation of the implant within the heart, disintegration of the restraint releases the spring from the restraint. In some applications, the spring is configured to, upon release from the restraint, automatically move away from the elastically-deformed state toward a second shape. In some applications, the coupling of the spring to the at least one tether being such that the movement of the spring away from the elastically-deformed state toward the second shape pulls, via the at least one tether, the first anchor and the second anchor toward each other.

In some applications, there is provided an implant comprising: a tether, anchors slidably coupled to the tether, and configured to anchor the tether to tissue of the heart, a spring, having a resting state, and coupled to the tether in a manner in which movement of the spring toward the resting state applies tension to the tether, and a restraint.

In some applications, the restraint is coupled to the spring in a manner that inhibits the spring from moving toward the resting state. In some applications, the restraint comprises a material that is configured to disintegration within the heart and is configured such that disintegration of the material reduces the inhibition of the spring by the restraint.

FIGS. 22A-B show an example of a tensioner, in the form of tensioner 500, in accordance with some applications. Tensioner 500 is shown as a component of a modified implant 110, which has been assigned the reference numeral 110'. Tensioner 500 comprises a spring 510 and a restraint 520. FIG. 22A shows implant 110' immediately after implantation, with spring 510 in its elastically-deformed state. FIG. 22B shows implant 110' at a subsequent time, after disintegration of restraint 520 and movement of spring 510 toward its second shape.

Spring 510 is a foreshortening spring and can have a cellular structure, i.e., defining one or more cells 512. When spring 510 moves away from its elastically-deformed state toward its second shape (i.e., foreshortens), cell 512 can become smaller in a first dimension (horizontally, in FIGS. 22A-B) and larger in a second direction (vertically, in FIGS. 22A-B). In some applications, while in its elastically-deformed state, spring 510 is longer in the first dimension than in the second dimension. For some such applications, in its second state, spring 510 is shorter in the first dimension than in the second dimension. It is to be noted that spring 510 is (or serves as) a tension spring.

In FIGS. 22A-B, tether 112 is shown as actually comprising multiple discrete tethers connected to each other via tensioners 500. For each tensioner 500, one of these discrete tethers is coupled to a first part 516' of spring 510, and another of these discrete tethers is coupled to a second part 516" of the spring. An inter-part distance d2, between first part 516' and second part 516", is smaller in the second state than in the elastically-deformed state. Therefore, in some applications, a first tether tethers a first anchor to a first part of the spring; a second tether that is distinct from the first tether tethers the second anchor to a second part of the spring; and the first and second tethers thereby couple the first anchor to the second anchor via the spring.

In some applications, restraint 520 restrains spring 510 by holding portions of the spring together. It is to be noted that, in this context, the term "together" (including the specification and the claims) means inhibiting the portions of the spring from moving away from each other including variants in which the portions of the spring are held in contact with each other, and variants in which they are held together but not in contact with each other. Restraint 520 can be extension-resistant and can comprise a tether (e.g., a line, wire, cord, ribbon, rope, braid, contraction member, suture, etc.), a band, or a ring, e.g., an element that has tensile strength. In some applications, and as shown, spring 510 can have eyelets 514, or other similar features such as notches, via which restraint 520 is coupled to the spring, and/or is inhibited from moving with respect to the spring. For example, and as shown, restraint 520 can be threaded through eyelets 514. Other eyelets, or similar features, can be present on parts 516' and 516" in order to facilitate coupling of tether 112 thereto.

FIGS. 23A-B show an example of a tensioner, in the form of tensioner 530, in accordance with some applications. Tensioner 530 comprises a spring 540 and a restraint 550. FIG. 23A shows tensioner 530 with spring 540 in its elastically-deformed state. FIG. 23B shows tensioner 530 after disintegration of restraint 550 and movement of spring 540 toward its second shape.

Spring 540 is similar to spring 510, but often defines at least two cells 542, e.g., three or more cells.

In some applications, restraint 550 restrains spring 540 by holding portions of the spring together. For example, and as shown, restraint 520 can comprise a tube. However, restraint 550 can optionally comprise a suture, a band, or a ring, e.g., as described for tensioner 500.

In FIGS. 23A-B, tether 112 is shown as actually comprising multiple discrete tethers connected to respective parts of springs 540, e.g., as described hereinabove for tensioner 500, mutatis mutandis.

Figures 24A, 24B, 24C, 24D:
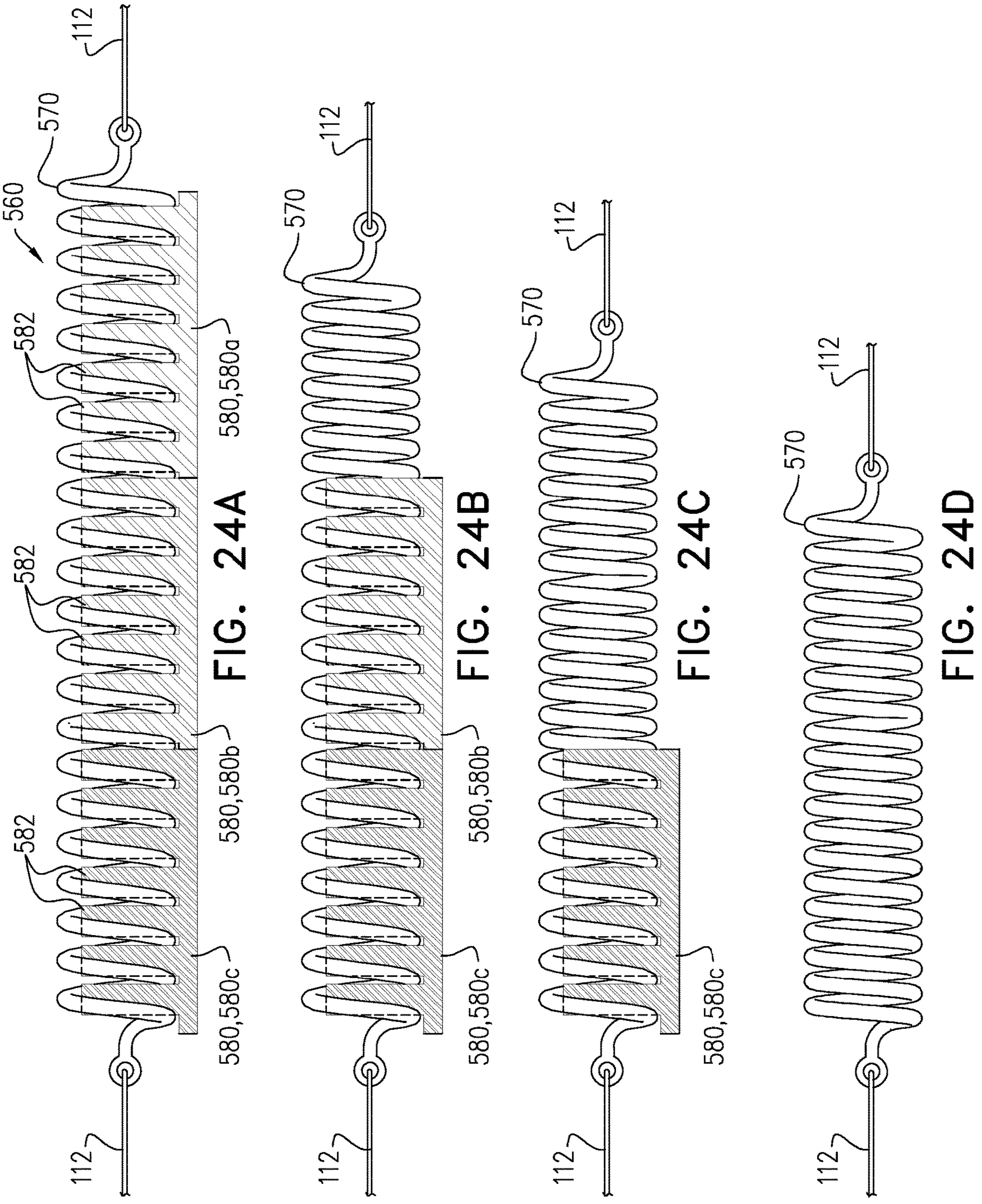

FIGS. 24A-B show an example of a tensioner, in the form of tensioner 560, in accordance with some applications. Tensioner 560 comprises a spring 570 and multiple restraints 580*a*, 580*b*, and 580*c*. FIG. 24A shows tensioner 560 with spring 570 in its elastically-deformed state. FIGS. 24B-C shows tensioner 560 progressively moving toward its second shape after disintegration, successively, of restraints 580*a*, 580*b*, and 580*c*.

Spring 570 can be a tension spring. For example, and as shown, spring 570 can have a coiled structure, such as a helical coil.

In some applications, restraints 580 restrain spring 570 by holding portions of the spring apart from each other. For example, and as shown, each of restraints 580 can comprise one or more spacers or dividers 582. Each spacer 582 can be compression-resistant and can hold adjacent portions (e.g., turns) of spring 570 apart from each other. Restraints 580 are shown as having a comb-like structure, with spacers 582 connected to each other in a series. However, restraint 580 and/or spacers 582 thereof can be shaped differently, e.g., according to the shape and type of spring 570, mutatis mutandis.

For each of tensioners 500, 530, and 560, the lifespan of at least one of the restraints of the tensioner (which is dependent on a rate of biosorption/disintegration of the restraint) is between 1 day and 2 years (e.g., between 15 days and 2 years, e.g., between 15 days and 1 year, e.g., between 15 days and 6 months, e.g., between 1 and 3 months, e.g., between 1 and 2 months) after implantation of the implant in the heart.

For each of tensioners 500, 530, and 560, the lifespan of at least one of the restraints of the tensioner can be between 1 day and 2 years (e.g., between 15 days and 2 years, e.g., between 15 days and 1 year, e.g., between 15 days and 6 months, e.g., between 1 and 3 months, e.g., between 1 and 2 months) after implantation of the implant in the heart.

Each of restraints 580, is configured to reach a threshold amount of disintegration after a respective period of time after implantation in the heart, and once the threshold has been reached, the restraint no longer inhibits its respective spring. This is, in effect, the lifespan of a given restraint. Restraints 580 can be configured to have different lifespans, in order to gradually release spring 570 (e.g., release respective portions of the spring in a staggered manner), thereby gradually (e.g., in a staggered manner) increasing tension on the tether over time. That is, upon expiry of each lifespan, spring 570 moves partway toward the resting state, but remains inhibited by the remaining restraint(s) 580. This is represented in FIGS. 24A-D as restraint 580*a* having the shortest lifespan (the expiry of which is represented in FIG. 24B), restraint 580*b* having the next shortest lifespan (the expiry of which is represented in FIG. 24C), and restraint 580*c* having the longest lifespan (the expiry of which is represented in FIG. 24D).

Similar effects can be achieved by using multiple tensioners 500 or 530, mutatis mutandis. For example, the restraint of each tensioner 500 or 530 used can have a different lifespan. Alternatively or additionally, a given tensioner can have multiple restraints, each with a different lifespan. For example, tensioner 530 can comprise one restraint 550 per cell 542 of spring 540, or tensioners 500 and 530 can comprise multiple restraints per cell.

For tensioners that have multiple restraints, the restraint with the shortest lifespan can be referred to as a first restraint of the tensioner, and a restraint with a longer lifespan can be referred to as a second restraint of the tensioner. In some applications, the lifespan of the second restraint is at least twice as great (e.g., at least three times as great) as the lifespan of the first restraint. In some applications, the lifespan of the first restraint is between 1 and 3 months (e.g., between 1 and 2 months), and the lifespan of the second restraint is between 3 months and 1 year (e.g., between 3 and 6 months).

As described hereinabove, each of tensioners 500, 530, and 560 is described as being used with a tether by the tether actually comprising multiple discrete tethers connected to each other via the tensioners. However, optionally, in some applications each of the tensioners can be used with an unbroken, continuous tether. For such applications, the tensioner is coupled to the tether such that the movement of the spring away from the elastically-deformed state toward the second shape introduces tortuosity to the path that the tether takes. For some such applications, the tether can be threaded through part of the tensioner. It is hypothesized that such a configuration may advantageously facilitate sliding of the tensioner along the tether, e.g., during implantation and/or during initial contraction of the implant.

In some applications, one or more of the tensioners described herein are mounted on the head of a tissue anchor.

Reference is now made to FIGS. 25A-F and 26A-B which are schematic illustrations of an anchor-handling assembly 600, in accordance with some applications. Assembly 600 can be used, inter alia, to de-anchor and remove an anchor

120 during implantation of implant 110, e.g., upon identifying that a given anchor has been anchored suboptimally. Assembly 600 is described as being used with anchors 120 of implant 110, but it is to be noted that the scope includes using assembly 600 with other anchors, mutatis mutandis.

Anchor-handling assembly 600 comprises a sleeve 610 and a tool 620. Sleeve 610 has a distal portion 612 that includes a distal end 614 of the sleeve.

Figure 25A:
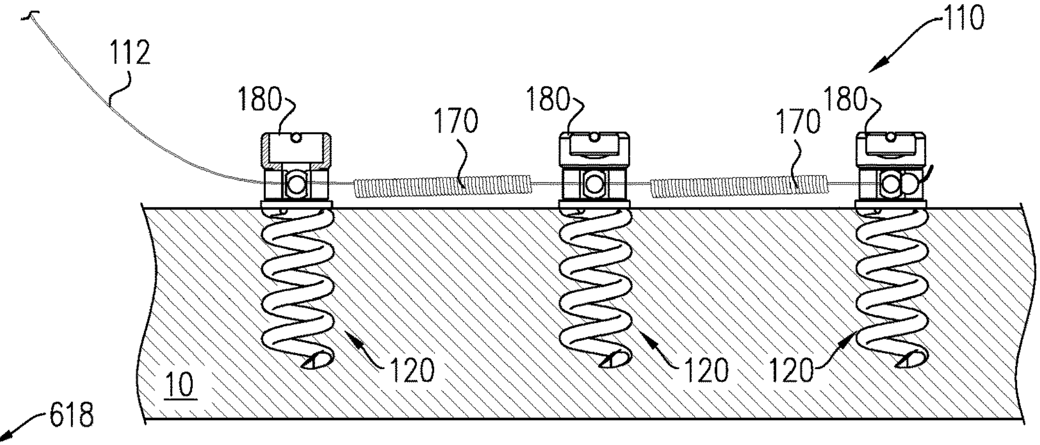
FIGS. 25A-F and 26A-B are schematic illustrations of an example anchor-handling assembly, in accordance with some applications.
Figure 25B:
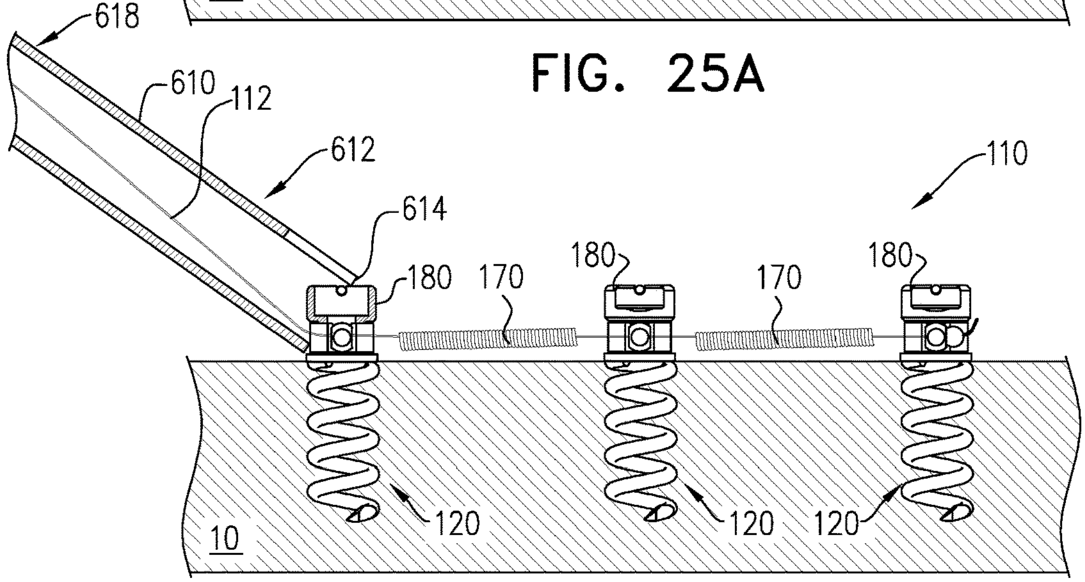
Figure 25C:
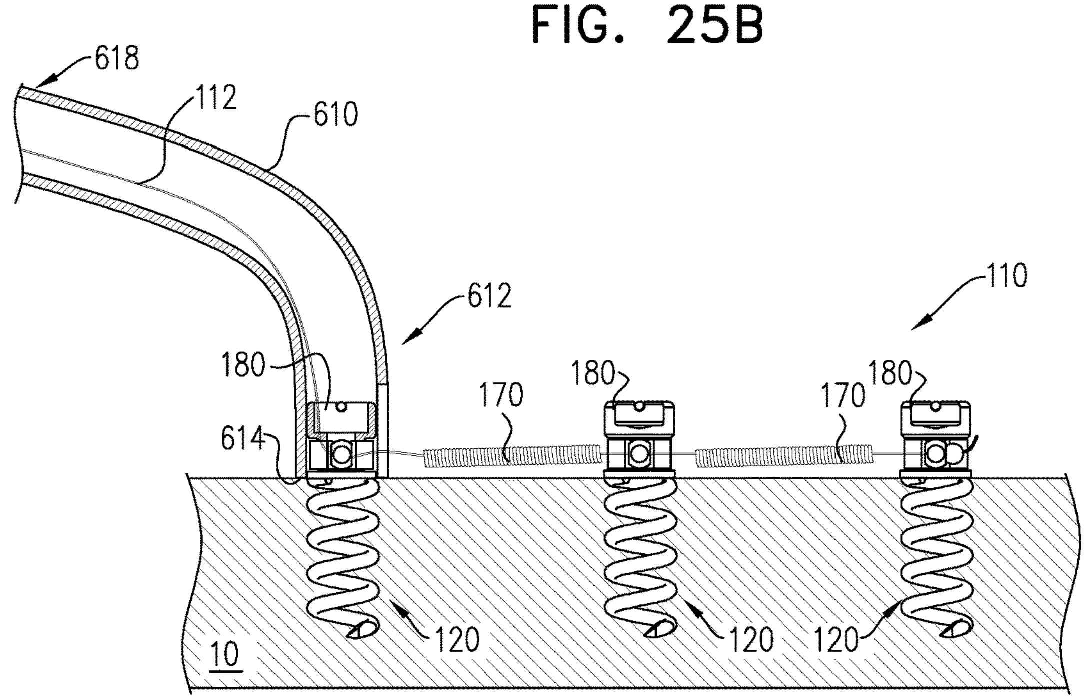

FIG. 25A shows implant 110 during implantation thereof, with three anchors 120 having been anchored to tissue 10. Should it be determined that the left-most anchor (which is the most recently-anchored anchor) should be de-anchored and removed, distal portion 612 of sleeve 610 is transluminally advanced to the anchor, and over anchor head 180 of the anchor (FIGS. 25B-C). Distal end 614 of sleeve 610 can be dimensioned to fit snugly over anchor head 180.

Tool 620 comprises a flexible shaft 622, and a tool head 624 that is coupled to a distal end of the shaft and comprises jaws 626. Jaws 626 are biased to assume an open state and are reversibly squeezable into a closed state.

Figure 25D:
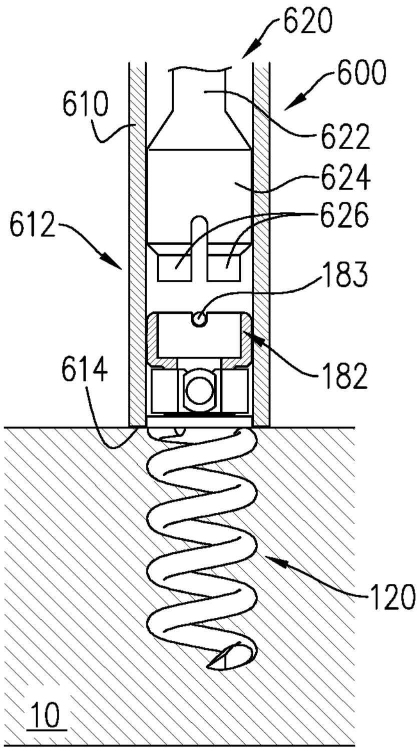
Figure 25E:
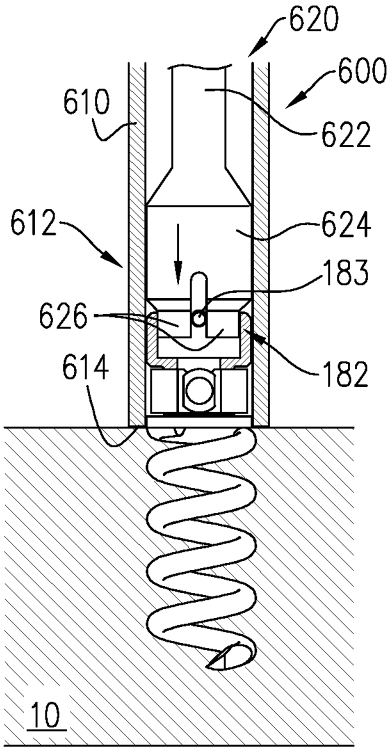

While distal end 614 remains disposed over anchor head 180, tool head 624 is advanced distally through sleeve 610 to distal portion 612 (FIG. 25D). Jaws 626 are dimensioned, relative to an inner dimension of distal portion 612 of sleeve 610, such that disposition of the tool head 624 in the distal portion of the sleeve squeezes the jaws into the closed state. While jaws 626 remain in the closed state, they are locked to interface 182 (e.g., bar 183 thereof), e.g., by advancing tool head 624 further distally, thereby pushing tool head 624 against anchor head 180 (FIG. 25E), e.g., such that the interface (e.g., bar 183 thereof) is received into a gap between the jaws.

In some applications, jaws 626 and interface 182 are configured to define a snap-fitting, and assembly 600 (e.g., tool 620 thereof) is configured to lock the jaws to the interface while the jaws remain in the closed state by snap-fitting the jaws to the interface.

In some applications, assembly 600 is configured such that, while tool head 624 is disposed in distal portion 612, jaws 626 resist becoming unlocked from interface 182, e.g., such that a pulling force required to remove the driver head from the interface is greater than that the pushing force that was required to lock the jaws to the interface (e.g., the jaws are unlockable from the interface). That is, while remaining in the closed state, the jaws are configured (i) to become locked to the interface by receiving the interface into the gap in response to the jaws being pushed onto the interface with a distally-directed force having a magnitude, by the interface deflecting the jaws apart (e.g., transiently); and (ii) to resist becoming unlocked from the interface by the interface leaving the gap, wherein pulling of the jaws with a proximally-directed force having the magnitude is insufficient to pull the jaws off of the interface.

Figure 25F:
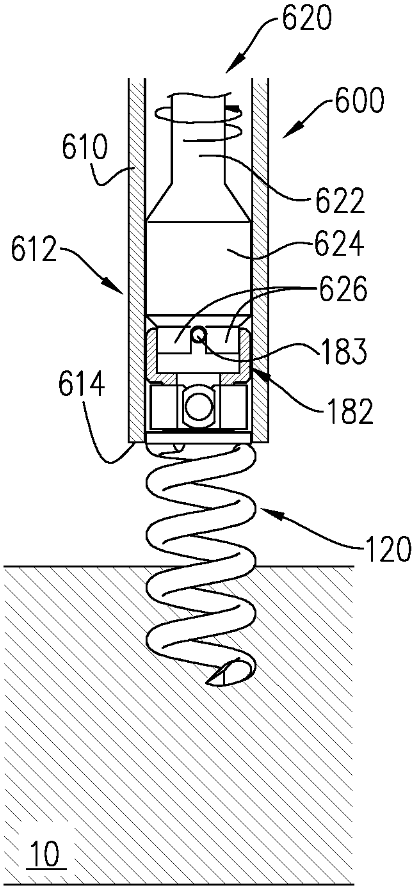

While jaws 626 remain locked to interface 182, tool 620 is used to apply a de-anchoring force to anchor head 180, e.g., torque in the opposite rotational direction to that which was previously used to implant the anchor (FIG. 25F). In some applications, and as shown, as anchor 120 becomes de-anchored tool 620 and sleeve 610 are retracted proximally in concert, thereby maintaining jaws 626 in the closed state.

Figure 26A:
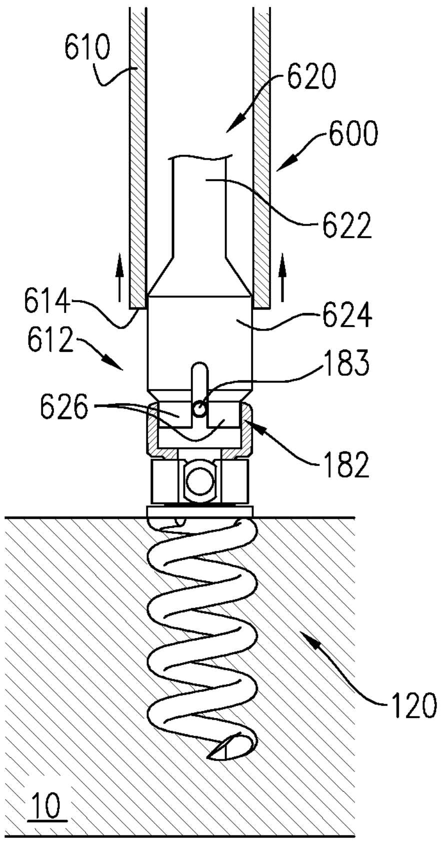
Figure 26B:
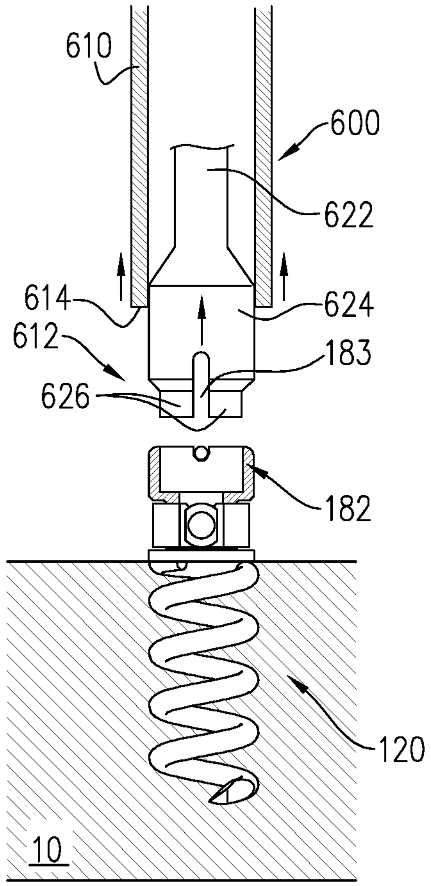

Tool 620 (e.g., jaws 626 thereof) can be unlockable from interface 182 by retracting sleeve 610 proximally with respect to anchor head 180 and tool head 624, such that the distal portion of the sleeve ceases to squeeze the jaws into the closed state, and the jaws (which can become exposed from the sleeve) automatically move apart (FIG. 26A). Tool 620 (or assembly 600 as a whole) can then be retracted (FIG. 26B). In some applications, this unlocking can be performed upon determining that the anchor should not, in fact, be de-anchored, or that a suboptimal condition exists for de-anchoring. In some applications, the unlocking can be performed if assembly 600 is used for the initial anchoring of the anchor, rather than for de-anchoring.

In some applications, sleeve 610 has an intermediate portion 618 that is proximal from distal portion 612, and that is internally dimensioned such that disposition of tool head 624 therein does not squeeze jaws 626 into the closed state. Therefore, in some applications, jaws 626 are squeezed into their closed state by advancing tool head 624 from intermediate portion 618 distally into distal portion 612.

Figure 27A:
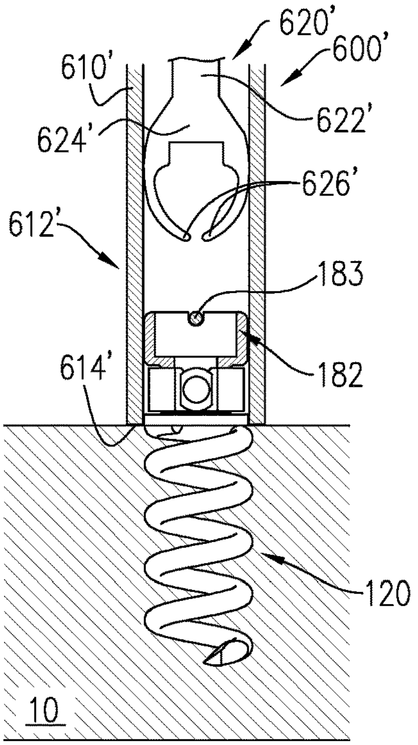
FIGS. 27A-C and 28A-B are schematic illustrations of an example anchor-handling assembly, in accordance with some applications.
Figure 27B:
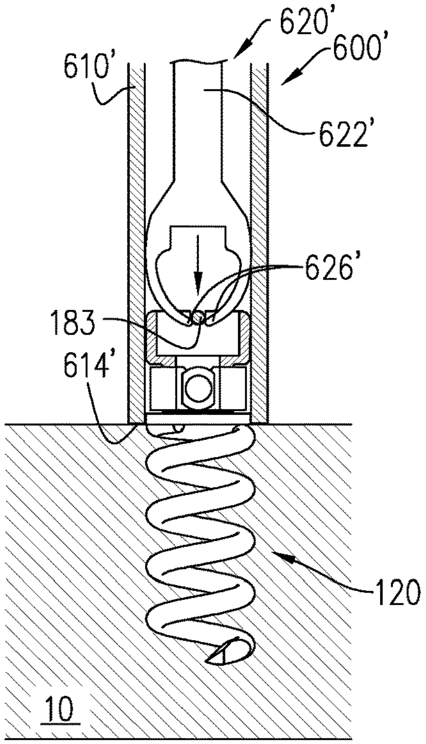
Figure 27C:
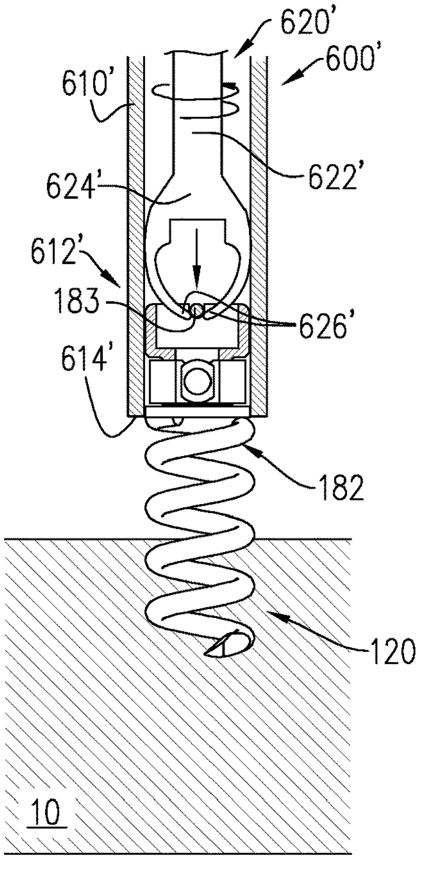
Figure 28A:
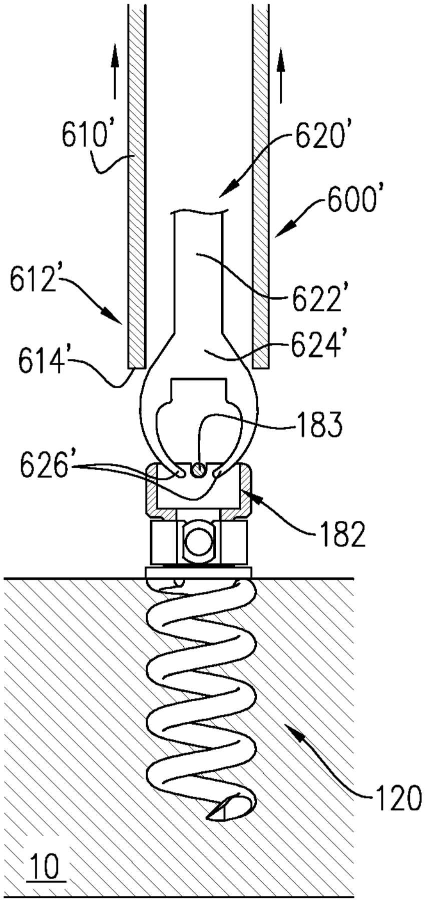
Figure 28B:
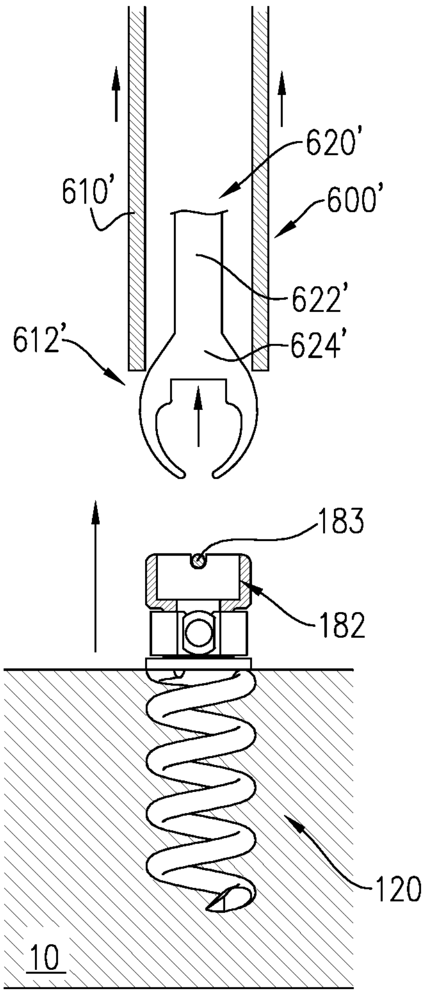

Reference is now made to FIGS. 27A-C and 28A-B, which are schematic illustrations of an anchor-handling assembly 600', in accordance with some applications. Anchor-handling assembly 600' includes similar corresponding components as assembly 600, and has the same overall functionality, but is structured slightly differently. For example, jaws 626' of assembly 600' are longer, curved, and can be more flexible than jaws 626 of assembly 600. FIGS. 27A-C show steps in the use of assembly 600' that are equivalent to those shown in FIGS. 25D-F for assembly 600, mutatis mutandis. FIGS. 28A-B show steps in the use of assembly 600' that are equivalent to those shown in FIGS. 26A-B for assembly 600, mutatis mutandis.

Figure 29B:
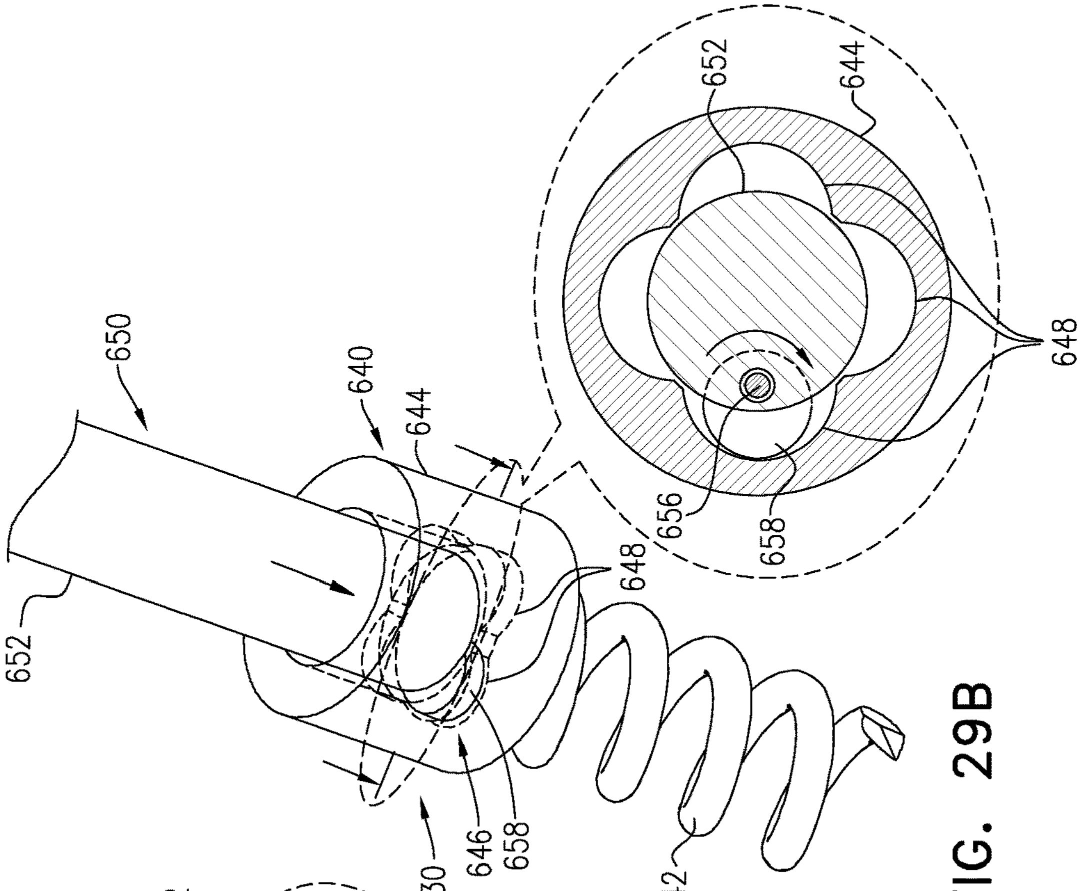
FIGS. 29A-B and 30A-B are schematic illustrations of respective anchor systems, in accordance with some applications.
Figure 29A:
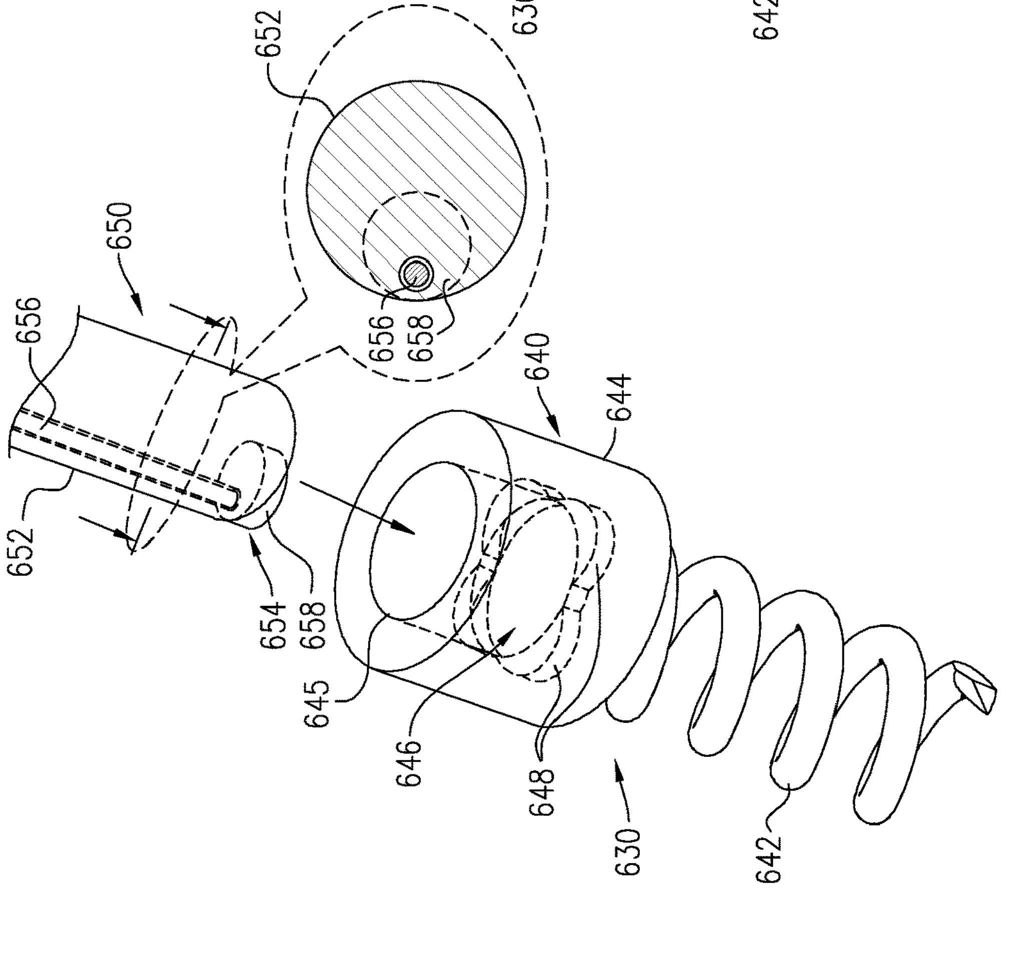
Figure 30A:
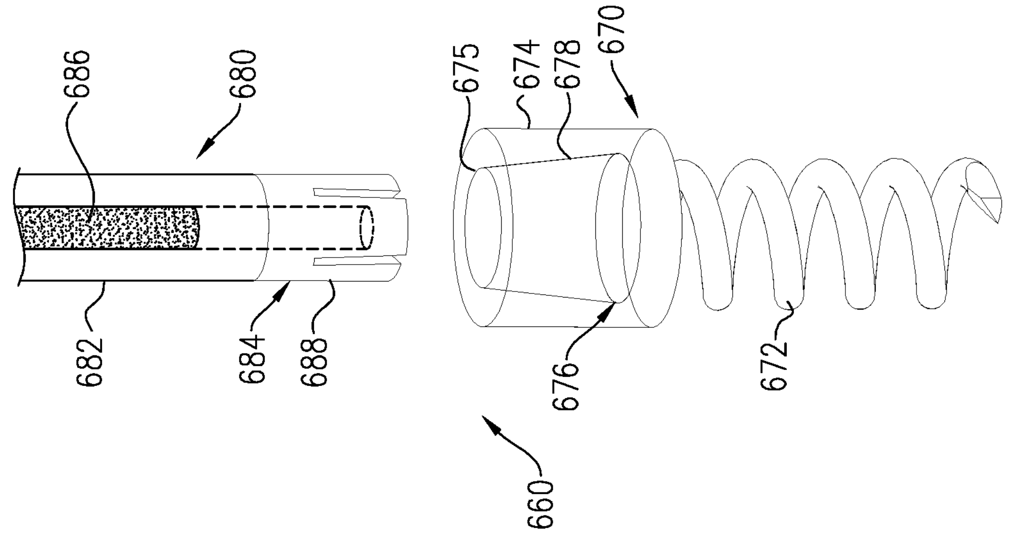
Figure 30B:
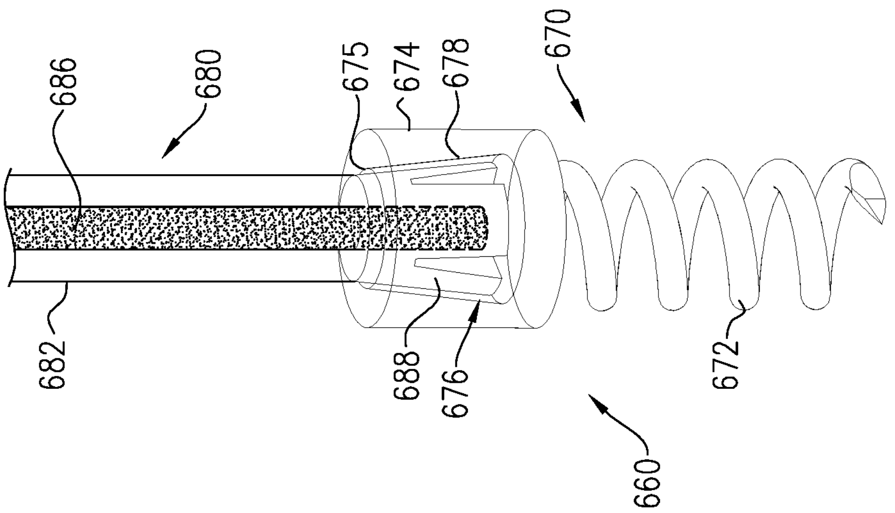

Reference is made to FIGS. 29A-B and 30A-B, which are schematic illustrations of anchor systems 630 and 660, in accordance with some applications. FIGS. 29A-B show anchor system 630, which comprises a tissue anchor 640 and an anchor driver 650 for use therewith, and FIGS. 30A-B show anchor system 660, which comprises a tissue anchor 670 and an anchor driver 680 for use therewith. Systems 630 and 660 can be used with systems, apparatuses, and techniques described elsewhere herein, e.g., by substituting the anchor (or the anchor head thereof) and the anchor driver (or the driver head thereof), mutatis mutandis. For example, anchor drivers 650 and 680 can be used to de-anchor and remove anchors 640 and 670, respectively, and/or to deliver and anchor the anchors.

Anchor 640 comprises a tissue-engaging element 642 and an anchor head 644. Anchor driver 650 comprises a flexible shaft 652, and a driver head 654 disposed at the distal end of the shaft. Anchor 670 comprises a tissue-engaging element 672 and an anchor head 674. Anchor driver 680 comprises a flexible shaft 682 and a driver head 684 disposed at the distal end of the shaft.

In some applications, for each of systems 630 and 660: the anchor head has a driver interface 646 or 676; the driver head has an introduction state (FIGS. 29A and 30A) and a locking state (FIGS. 29B and 30B); the anchor head is shaped to define a proximal opening 645 or 675 via which the driver interface is accessible by the driver head while the driver head is in the introduction state; and the anchor driver is configured to lock the driver head to the interface by transitioning the driver head into the locking state by moving a part of the driver head laterally.

In some applications, for each of systems 630 and 660, the anchor driver comprises a rod 656 or 686 extending through the shaft, and the rod is configured to transition the driver head into the locking state by applying a force to the driver head.

For system 630, driver head 654 comprises a cam 658 coupled to rod 656, and the rod is configured to transition driver head 654 into its locking state by rotating the cam such that at least part of the cam protrudes laterally. In some applications, and as shown, this is achieved by rod 656 being eccentric with respect to shaft 652 and/or with respect to cam 658.

In some applications, cam 658 does not protrude laterally at all in the introduction state (e.g., the cam is flush with shaft 652).

In some applications, in transverse cross section with respect to the longitudinal axis of shaft 652, shaft 652 and/or and cam 658 are circular.

In some applications, and as shown, interface 646 is shaped to define multiple recesses 648, each dimensioned to receive cam 658 as it protrudes laterally. This enables driver 650 to engage anchor 640 in multiple rotational orientations of the driver with respect to the anchor.

For system 660, driver head 684 comprises fins 688, and rod 686 is configured to transition driver head 684 into its locking state by being advanced distally between the fins such that the rod pushes the fins radially outward such that the fins lock to interface 676. Fins 688 can be configured to, when pushed radially outward by rod 686, lock to interface 676 via a friction fit. In some applications, and as shown, interface 676 can be shaped to define a frustoconical chamber 678 (e.g., with its wider base further than its narrower base from opening 675). Driver 680 can generally engage anchor 670 in any rotational orientation of the driver with respect to the anchor.

Reference is now made to FIGS. 31A-B, 32A-B, 33A-B, 34A-C, and 35A-C, which are schematic illustrations of systems, apparatuses, and techniques for use at a heart valve, in accordance with some applications. Described hereinabove (e.g., with reference to FIGS. 25A-27C) is the de-anchoring/removal of an anchor. It is to be noted that, for a tissue-adjusting implant that comprises multiple anchors coupled to (e.g., threaded on) a tether, such as implant 110, it may be possible to de-anchor/remove only the most recently-anchored anchor. For example, if it is desired to leave the most recently-anchored anchor in place, the most recently-anchored anchor may obstruct the de-anchored anchor (e.g., a more distal anchor) from being removed (e.g., from being slid proximally along the tether). A similar challenge may exist in delivering/anchoring an additional anchor. That is, the nature of such implants may limit the addition of anchors to a distal-to-proximal order, and/or may limit the subtraction of anchors to a proximal-to-distal order.

Figure 31A:
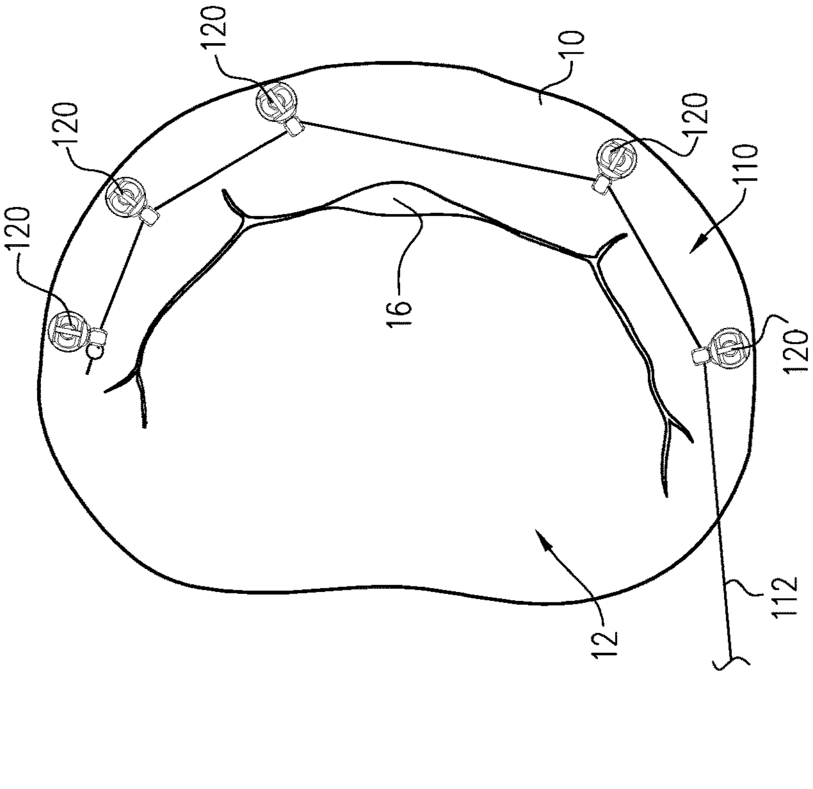
FIGS. 31A-B, 32A-B, 33A-B, 34A-C, and 35A-C are schematic illustrations of systems, apparatuses, and techniques for adding anchors to an implant and/or removing anchors from an implant, in accordance with some applications.
Figure 31B:
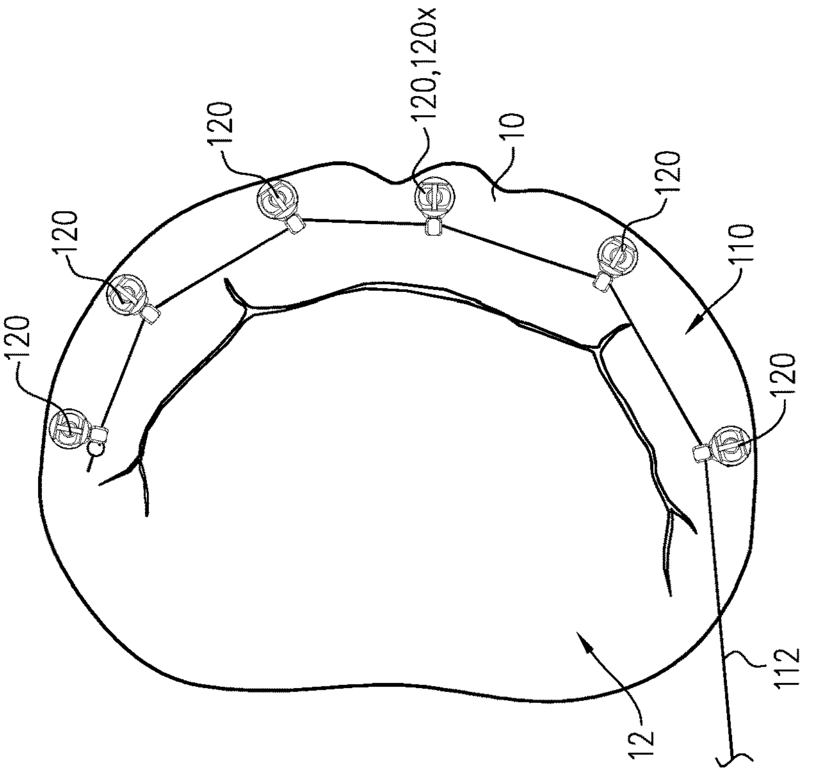

FIG. 31A shows a scenario in which 5 anchors 120 of implant 110 have been anchored to tissue 10 of the annulus of mitral valve 12, but in which tensioning of tether 112 reshapes the annulus, suboptimally leaving a regurgitation site 16 at which the leaflets of the valve do not coapt. FIG. 31B shows an additional anchor 120*x* having been coupled (e.g., slidably coupled) to tether 112 between previously-anchored anchors, and anchored to the tissue, further reshaping the annulus such that regurgitation site is reduced (e.g., eliminated). That is, FIGS. 31A-B show addition of anchor 120*x* independently of a distal-to-proximal order.

Figure 32B:
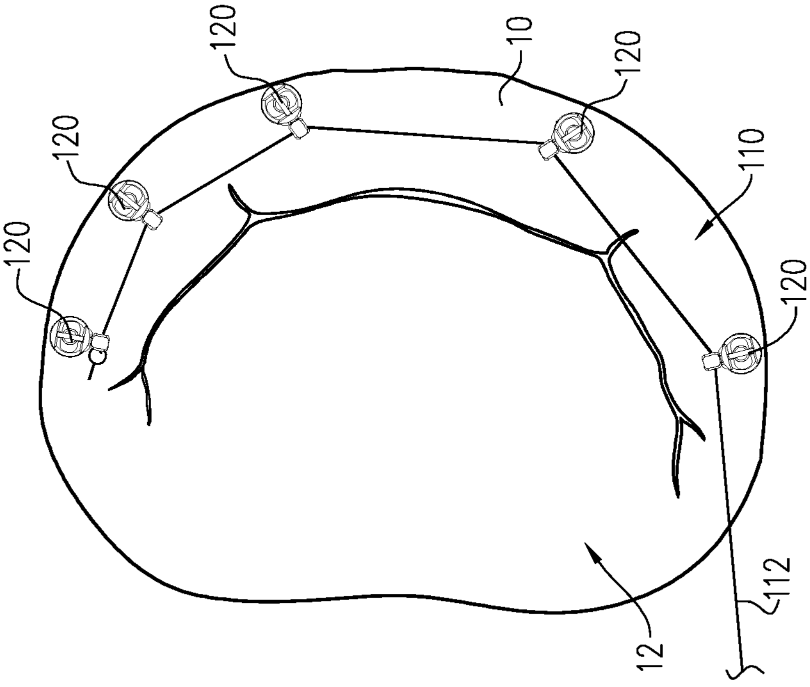
Figure 32A:
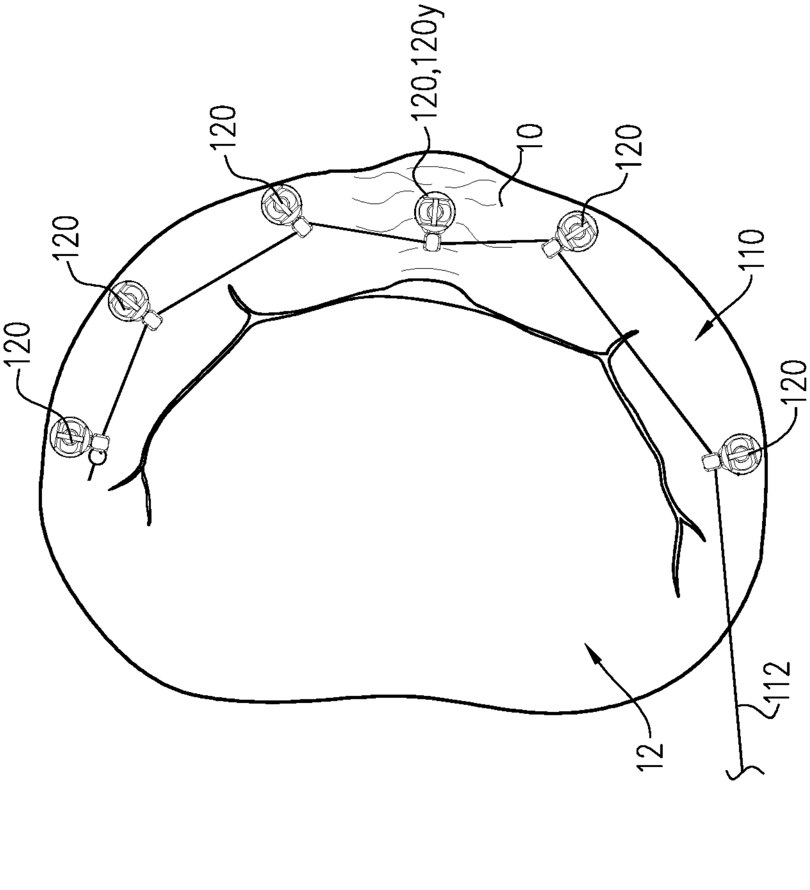

FIG. 32A shows a scenario in which several anchors 120 of implant 110 have been anchored to tissue 10 of the annulus of mitral valve 12, but in which tensioning of tether 112 reshapes the annulus in a manner that results in an undesirable deformation of the valve. FIG. 32B shows one of these anchors (labeled 120*y* in FIG. 32A) having been de-anchored and decoupled from tether 112, from between previously-anchored anchors, thereby relieving (e.g., eliminating) the deformation. That is, FIGS. 32A-B show subtraction of anchor 120*y* independently of a proximal-to-distal order.

FIGS. 33A-B, 34A-C, and 35A-C show a system and/or apparatus configured to facilitate such order-independent techniques. One of the challenges in adding or subtracting anchors in an order-independent manner is navigating a tool to the correct position. For example, in order to access the most recently-anchored anchor it is possible to advance a tool along tether 112, e.g., as shown in FIGS. 25A-F. However, it may be difficult to use such a technique in order to access a more distal anchor, e.g., because the most recently-anchored anchor would obstruct advancement of the tool along the tether. Each of the anchors described with reference to FIGS. 33A-35C can be used in place of one or more of the anchors described with reference to FIGS. 31A-32B, mutatis mutandis.

Figure 33A:
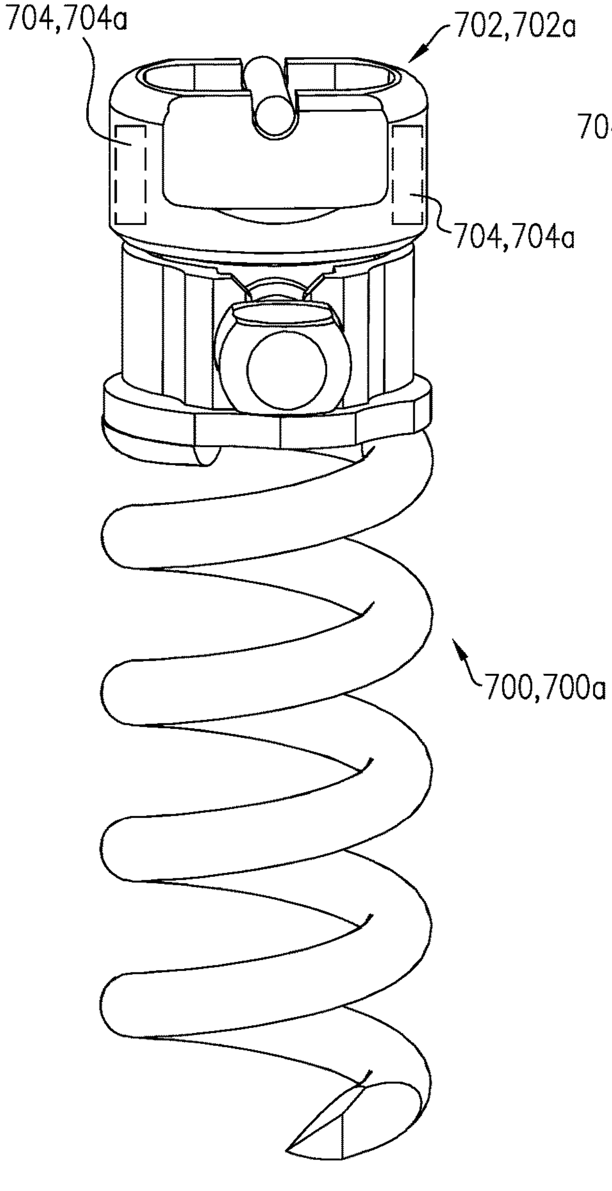
Figure 33B:
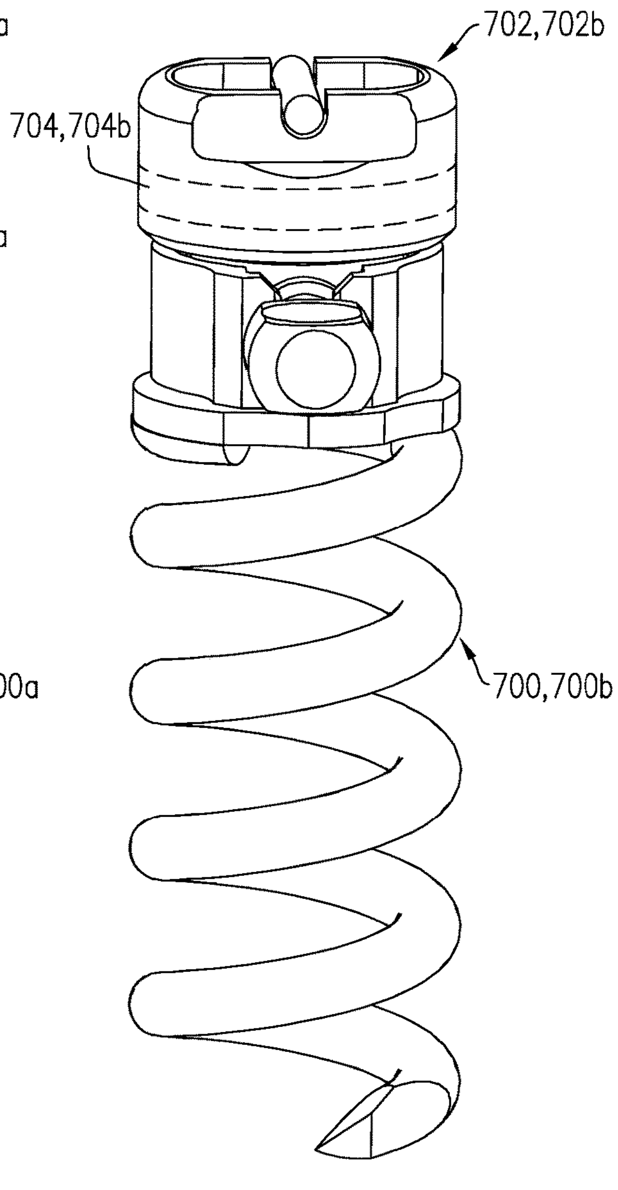

FIGS. 33A and 33B show, respectively, implementations 700*a* and 700*b* of a tissue anchor 700 that has an anchor head 702 that comprises one or more magnets 704. Anchor head 702*a* of anchor 700*a* comprises a plurality of magnets 704*a*, e.g., distributed circumferentially around the anchor head. Anchor head 702*b* of anchor 700*b* comprises a magnet 704*b* that can be centrally positioned, e.g., being disc-shaped or ring-shaped. Anchor 700 is configured to facilitate navigation of a tool to an anchor (e.g., to an anchor other than the most recently-anchored anchor) without advancement of the tool along the tether. Magnet(s) 704 may reduce the navigation accuracy required, e.g., by 704 drawing the tool toward into engagement with anchor 702 once the tool has been navigated to within a threshold proximity of the anchor.

Figure 34C:
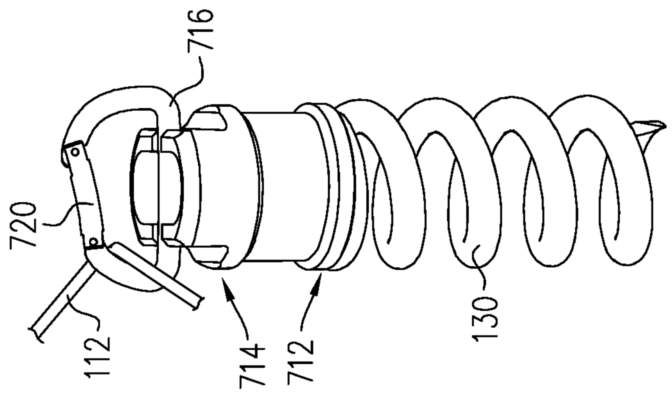
Figure 34B:
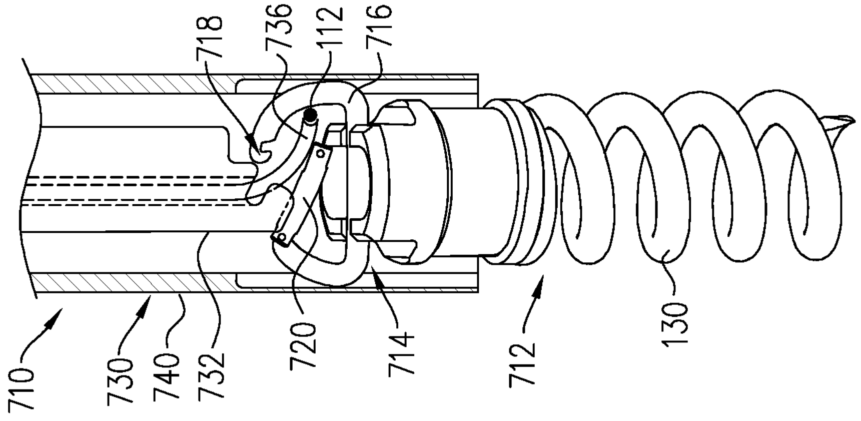
Figure 34A:
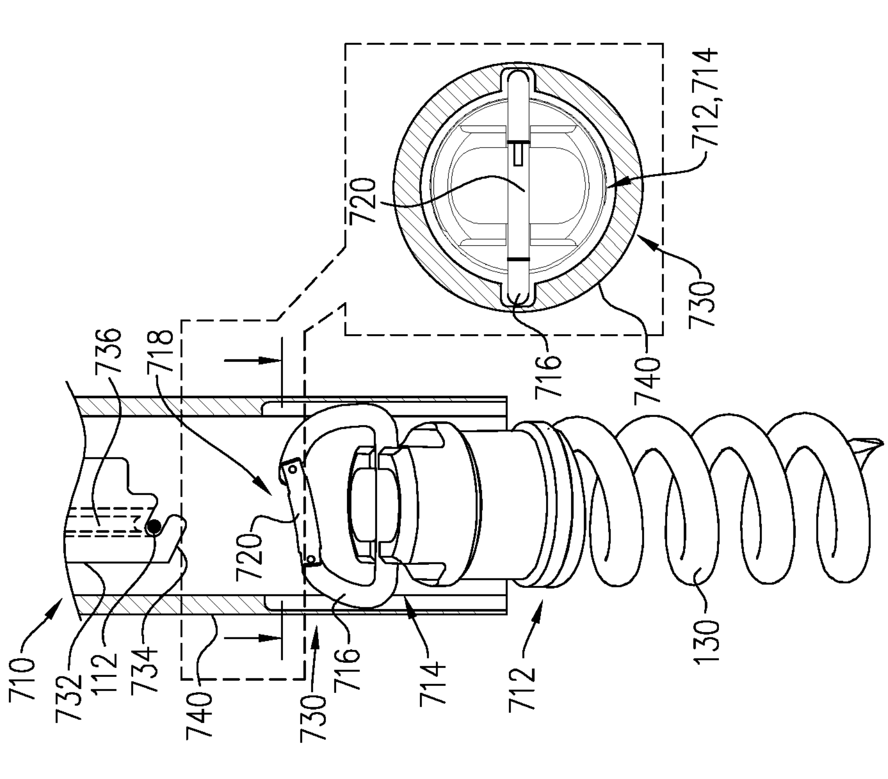

FIGS. 34A-C show a system 710 that comprises a tissue anchor 712 and an anchor-handling assembly 730, in accordance with some applications. Anchor 712 has an anchor head 714 that comprises a shackle 716, in accordance with some applications. Shackle 716 has a reversibly openable opening 718 via which a tether (e.g., tether 112) is passable laterally by temporarily opening the opening (FIGS. 34A-B), e.g., thereby slidably coupling the anchor to the tether (FIG. 34C). Alternatively or additionally, shackle 716 can be configured to facilitate decoupling of the tether from the anchor, mutatis mutandis. It is to be noted that, in this context, the term "laterally" (including the specification and the claims) is intended to distinguish between this passage of the tether into the shackle (which can, and often does, occur without access to an end of the tether), and the threading of a tether into a regular eyelet, which may be regarded as being axial movement.

In some applications, at opening 718, shackle 716 comprises a spring-loaded gate 720 (e.g., shackle 716 is a snap shackle). Gate 720 is shown as being a single gate, but can optionally be a double gate. In some applications, gate 720 is configured to open inwardly but not outwardly.

Anchor-handling assembly 730 often further comprises a link tool 732.

In some applications, tool 732 is configured to, within the heart, temporarily open opening 718 and pass tether 112 laterally through the opening and into shackle 716, thereby slidably coupling tether 112 to anchor 712 (e.g., to achieve the result described with reference to FIGS. 31A-B). For example, tool 732 can comprise (i) an actuator 734, configured to actuate gate 720 to open it (e.g., by pushing against the gate), and/or (ii) a limb 736, configured to move tether 112 through open gate 720 and into shackle 716. In some applications, anchor-handling assembly 730 also comprises a driver 740, configured to anchor the anchor by driving the tissue-engaging element into the tissue, e.g., by applying torque to head 714 (e.g., to shackle 716). For simplicity, FIGS. 34A-C do not show the tissue, but are nonetheless drawn as though immediately after anchor 712 has been anchored, i.e., the coupling of tether 112 to the anchor is performed immediately after the anchor has been anchored. However, it is to be understood that the scope includes coupling of tether 112 to the anchor prior to anchoring the anchor, mutatis mutandis. Furthermore, although driver 740 is shown as coaxial with link tool 732, the driver and the link tool can be parallel with each other or can be independent of each other.

In some applications, tool 732 is configured to, within the heart, temporarily open opening 718 and pass tether 112 laterally through the opening and out of shackle 716, thereby decoupling tether 112 from anchor 712 (e.g., to achieve the result described with reference to FIGS. 32A-B). For example, limb 736 can be configured to move tether 112 through open gate 718 and out of shackle 716. In some applications, driver 740 is configured to de-anchor (e.g., unscrew) the anchor, e.g., by applying torque to head 714 (e.g., to shackle 716). It is to be understood that the scope includes decoupling of tether 112 from the anchor prior to, or subsequently to, de-anchoring the anchor, mutatis mutandis.

It is to be noted that, for the sake of clarity, FIGS. 34A-B and 35A-B show tether 112 as a single dot, similar to a cross-section through the tether.

There is provided, in accordance with some applications, a method comprising: (i) transluminally securing a tether along the tissue by anchoring a plurality of anchors to respective sites of the tissue such that the tether extends between the anchors of the plurality and along the tissue, each anchor of the plurality having a respective eyelet through which the tether passes; and (ii) while the plurality of anchors remains anchored to the tissue, transluminally slidably coupling an additional anchor to the tether between two of the anchors of the plurality, and anchoring the additional anchor to the tissue.

There is also therefore provided, in accordance with some applications, a method comprising: (i) transluminally securing a tether along the tissue by anchoring a plurality of anchors to respective sites of the tissue such that the tether extends between the anchors of the plurality and along the tissue, each anchor of the plurality having a respective eyelet through which the tether passes; and (ii) transluminally decoupling from the tether one anchor of the plurality from between two other anchors of the plurality.

The above method(s) and steps can be performed on a living animal or on a simulation, such as on a cadaver, cadaver heart, simulator (e.g., with the body parts, heart, tissue, etc. being simulated), etc.

Figure 35C:
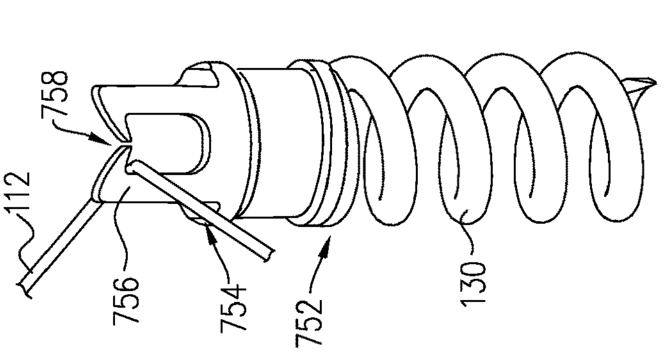
Figure 35B:
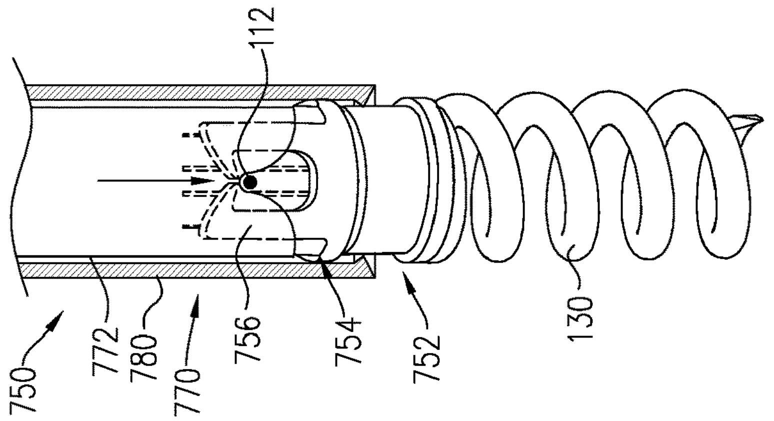
Figure 35A:
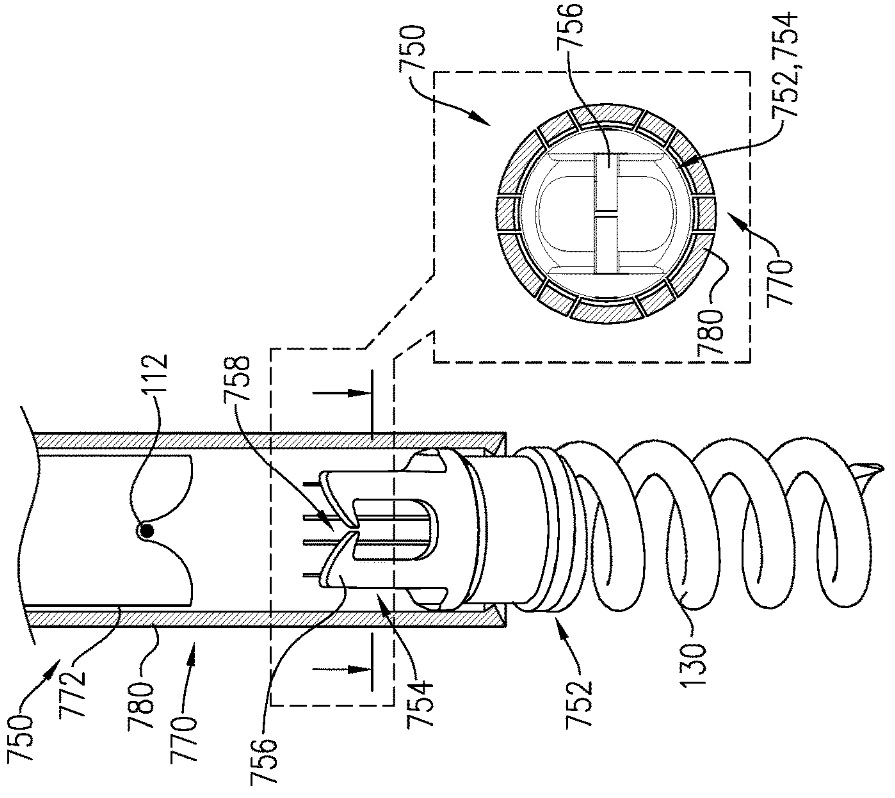

FIGS. 35A-C show a system 750 that comprises a tissue anchor 752 and an anchor-handling assembly 770, in accordance with some applications. Anchor 752 has an anchor head 754 that comprises a shackle 756, in accordance with some applications. Shackle 756 has a reversibly openable opening 758 via which a tether (e.g., tether 112) is passable laterally by temporarily opening the opening (FIGS. 34A-B), e.g., thereby slidably coupling the anchor to the tether (FIG. 34C). Alternatively or additionally, shackle 756 can be configured to facilitate decoupling of the tether from the anchor, mutatis mutandis.

In some applications, shackle 756 is configured to facilitate clipping of the tether into and/or out of the shackle. For example, shackle 756 can be a snap shackle that transiently opens as the tether is pressed laterally into, and passes through, opening 758, thereby snapping into the shackle.

Anchor-handling assembly 770 often further comprises a link tool 772.

In some applications, tool 772 is configured to, within the heart, temporarily open opening 758 and pass tether 112 laterally through the opening and into shackle 756, thereby slidably coupling tether 112 to anchor 752 (e.g., to achieve the result described with reference to FIGS. 31A-B). For example, and as shown, tool 772 can press tether 112 laterally into and through opening 758, with the opening transiently opening as the tether passes through. In some applications, anchor-handling assembly 770 also comprises a driver 780, configured to anchor the anchor by driving the tissue-engaging element into the tissue, e.g., by applying torque to head 754 (e.g., to shackle 756). For simplicity, FIGS. 35A-C do not show the tissue, but are nonetheless drawn as though immediately after anchor 712 has been anchored, i.e., the coupling of tether 112 to the anchor is performed immediately after the anchor has been anchored. However, it is to be understood that the scope includes coupling of tether 112 to the anchor prior to anchoring the anchor, mutatis mutandis. Furthermore, although driver 780 is shown as coaxial with link tool 772, the driver and the link tool can be parallel with each other or can be independent of each other.

In some applications, tool 772 is configured to, within the heart, temporarily open opening 758 and pass tether 112 laterally through the opening and out of shackle 756, thereby decoupling tether 112 from anchor 752 (e.g., to achieve the result described with reference to FIGS. 32A-B). For example, tool 772 can pull tether 112 laterally into and through opening 758, with the opening transiently opening as the tether passes through on its way out of shackle 756. In some applications, driver 780 is configured to de-anchor (e.g., unscrew) the anchor, e.g., by applying torque to head 754 (e.g., to shackle 756). It is to be understood that the scope includes decoupling of tether 112 from the anchor prior to, or subsequently to, de-anchoring the anchor, mutatis mutandis.

Reference is again made to FIGS. 31A-B. In some applications, tether 112 is tensioned prior to adding additional anchor 120*x*, e.g., because the need to add the anchor is identified only upon tensioning of the tether. For some such applications, tether 112 is relaxed subsequently to being tensioned (e.g., after identifying the need for the additional anchor) and prior to anchor 120*x* being added. Tether 112 can then be re-tensioned subsequently to adding the additional anchor.

Reference is again made to FIGS. 32A-B. In some applications, tether 112 is tensioned prior to removing anchor 120*y*, e.g., because the need to remove the anchor is identified only upon tensioning of the tether. For some such applications, tether 112 is relaxed subsequently to being tensioned (e.g., after identifying the need to remove the anchor) and prior to anchor 120*y* being removed. Tether 112 can then be re-tensioned subsequently to removing anchor 120*y*.

Reference is now made to FIGS. 36A-B, 37A-D, 38A-B, 39A-C, 40A-D, 41, and 42, which are schematic illustrations of various tissue anchors and techniques for use therewith, in accordance with some applications. Except where noted, each of these anchors and its components can be as described for anchor 120 and its identically-named components, mutatis mutandis. Furthermore, each of these anchors can be used as a component of an implant that further comprises a tether, e.g., as described hereinabove, mutatis mutandis. For example, each of these anchors can comprise a tissue-engaging element and a head that comprises an eyelet, and a driver interface that is coupled (e.g., fixedly coupled) to the tissue-engaging element. The tissue-engaging element can be the same as or similar to other tissue-engaging elements described herein.

Similarly to anchor 120, each of these anchors can be configured to facilitate smooth sliding of a tether through the aperture of the eyelet both (i) while the tether is parallel with the central longitudinal axis of the anchor (e.g., during delivery to the heart), and (ii) while the tether is oriented orthogonal to the central longitudinal axis (e.g., after the anchor has been anchored to tissue of the heart). In some applications, the eyelet is revolvable or rotatable about the central longitudinal axis of the anchor, e.g., due to being mounted on a rotatable collar, e.g., similarly to as described for anchor 120, mutatis mutandis. The eyelet can be deflectable with respect to the central longitudinal axis of the anchor, as described in more detail hereinbelow.

For each of these anchors, the head of the anchor can comprise a driver interface, configured to be reversibly engaged by an anchor driver that advances and anchors the anchor, e.g., as described hereinabove for other anchors. The driver interface can be disposed on, or concentric with, the central longitudinal axis of the anchor.

Figure 36A:
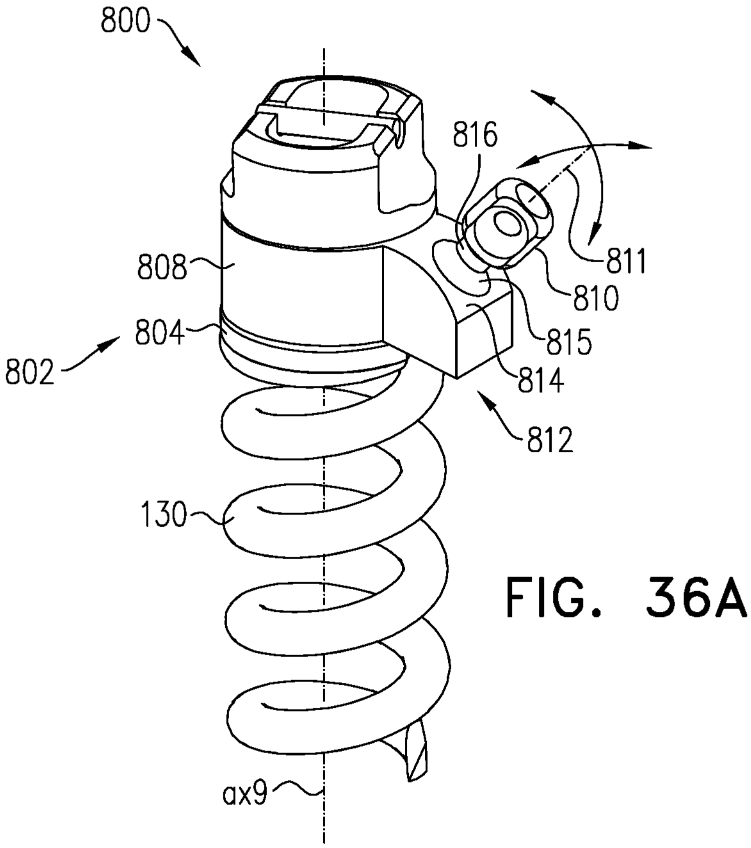
Figure 36B:
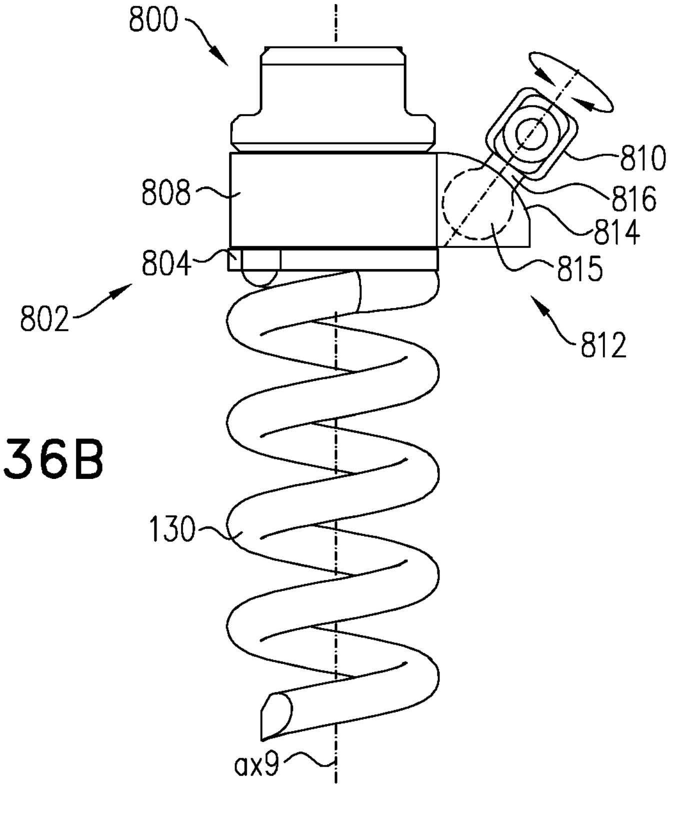

FIGS. 36A-B show a tissue anchor 800 that comprises an anchor head 802 that comprises an eyelet 810, which, similarly to eyelet 140 of anchor 120, is disposed laterally from central longitudinal axis ax9 of anchor 800, i.e., is eccentric. However, whereas eyelet 140 of anchor 120 is solely rotatably coupled to collar 184 (e.g., by a revolute joint therebetween), eyelet 810 is coupled to a collar 808 of anchor 800 via a ball joint 812. In addition to allowing rotation of eyelet 810 (e.g., similarly to the revolute joint between eyelet 140 and collar 184), ball joint 812 also allows deflection of the eyelet with respect to collar 808 and with respect to axis ax9 of the anchor. It is hypothesized that the extra freedom that this configuration provides to eyelet 810 advantageously allows the eyelet to assume an optimal orientation upon tensioning of tether 112, e.g., according to relative positions of other anchors of the implant, thereby facilitating smooth sliding of the tether through the eyelet. It is further hypothesized that this configuration increases predictability of the implant and reduces wear on the tether, compared to an anchor to which an eyelet is loosely coupled, e.g., like a link in a chain.

FIGS. 37A-D show a tissue anchor 820 that, similarly to anchor 800, comprises an anchor head 822 that comprises an eyelet 830 that is coupled via a ball joint 832. However, whereas ball joint 812 of anchor 800 is disposed laterally from the central longitudinal axis of the anchor (i.e., is eccentric), ball joint 832 (e.g., a ball 835 thereof) is disposed on central longitudinal axis ax10 of anchor 820. FIGS. 38A-B show anchor 820 being used as a component of an implant, e.g., similarly to as described hereinabove, with reference to FIGS. 3A-D, for anchor 120 of implant 110, mutatis mutandis.

Anchor 800 is shown as comprising tissue-engaging element 130, described hereinabove, and anchor 820 is shown as comprising tissue-engaging element 241, described hereinabove. However, it is to be understood that throughout this patent application, other combinations of anchor heads and tissue-engaging elements are possible and contemplated. For example, tissue-engaging element 130 of anchor 800 can be replaced with tissue-engaging element 241, mutatis mutandis.

Therefore, each of anchors 800 and 820 comprises (i) a tissue-engaging element defining a central longitudinal axis of the anchor, having a sharpened distal tip, and configured to be driven into tissue of a subject; and (ii) an anchor head, coupled to a proximal end of the tissue-engaging element. The anchor head comprises a stock (e.g., a stock 804 of anchor 800, and a stock 824 of anchor 820, each of which can be as described for other anchors hereinabove, mutatis mutandis), a ball joint, and an eyelet, coupled to the stock via the ball joint.

For the anchor head of each of anchors 800 and 820, an eyelet axis (eyelet axis 811 for head 802 of anchor 800, and eyelet axis 831 for head 822 of anchor 820) passes through a center of the ball of the ball joint and a center of the eyelet, and the ball joint generally allows the eyelet to be moved laterally from the central longitudinal axis of the anchor, e.g., into a position in which the eyelet axis is orthogonal to the central longitudinal axis, e.g., for transluminal delivery. For example, in such a configuration, the anchor can be advanced through tube 152, with the tissue-engaging element of the anchor sliding through major channel region 154*a*, and the eyelet of the anchor sliding through minor channel region 154*b*, e.g., similarly to as described hereinabove for anchor 120, mutatis mutandis.

Ball joint 812 comprises a socket 814, and a bearing stud 816 that defines a ball 815 at a first end of the bearing stud, the ball being disposed within the socket. The other end of bearing stud 816 defines (or is coupled to) eyelet 810. Similarly, ball joint 832 comprises a socket 834, and a bearing stud 836 that defines a ball 835 at a first end of the bearing stud, the ball being disposed within the socket. The other end of bearing stud 836 defines (or is coupled to) eyelet 830.

Similarly to ball joints that are known in the art, each of ball joints 812 and 832 allows, within a given spherical-sector of deflection, deflection of its bearing stud into any angular disposition. The spherical-sector of deflection can be delimited by the bearing stud being obstructed by a rim of the socket, e.g., at a given magnitude of angular deflection from a midpoint of the spherical-sector of deflection. In some applications, the spherical-sector of deflection has a solid angle of at least one steradian (e.g., at least two steradians, e.g., 2-5 steradians, such as 3-5 steradians). In some applications, in order to retain the ball in the socket, the socket is greater than hemispherical, such that the solid angle of the spherical-sector of deflection is less than a steradians (e.g., less than 6 steradians, such as less than 5 steradians).

Figure 37A:
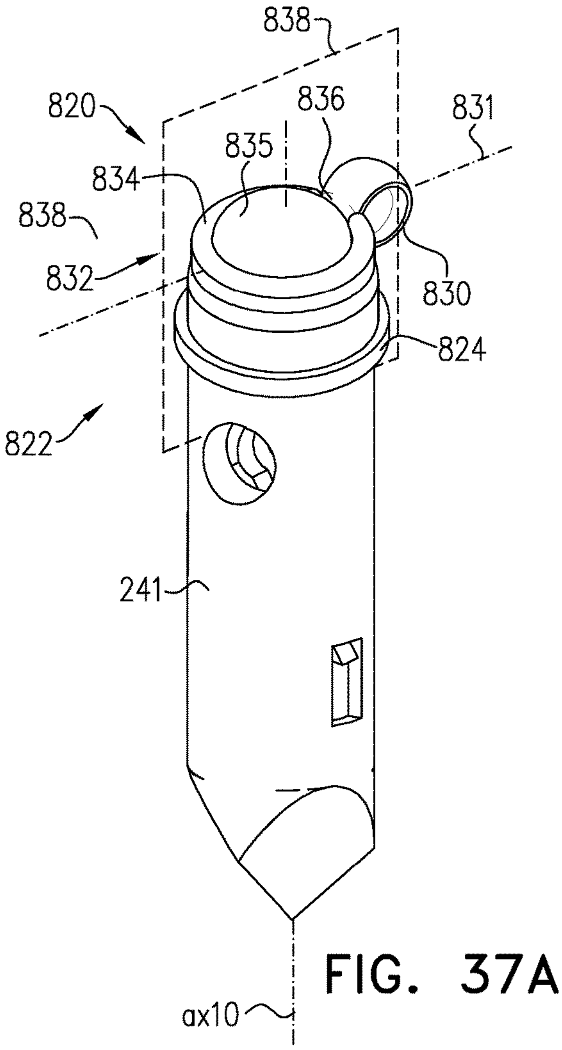
Figure 37B:
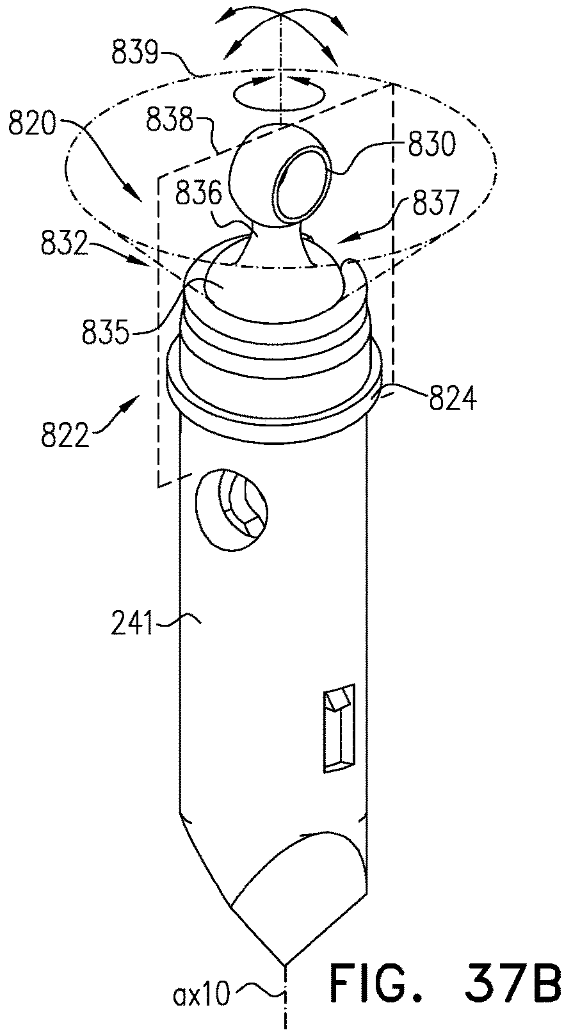
Figure 37C:
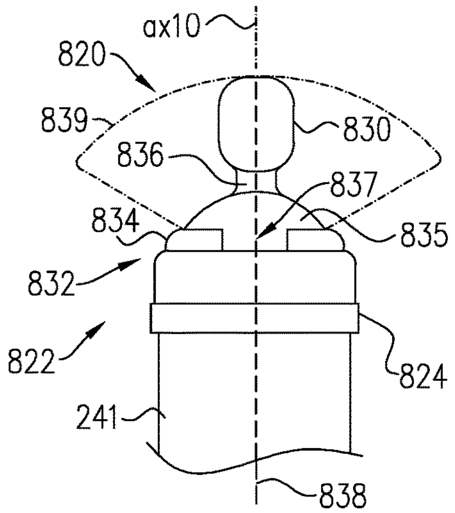
Figure 37D:
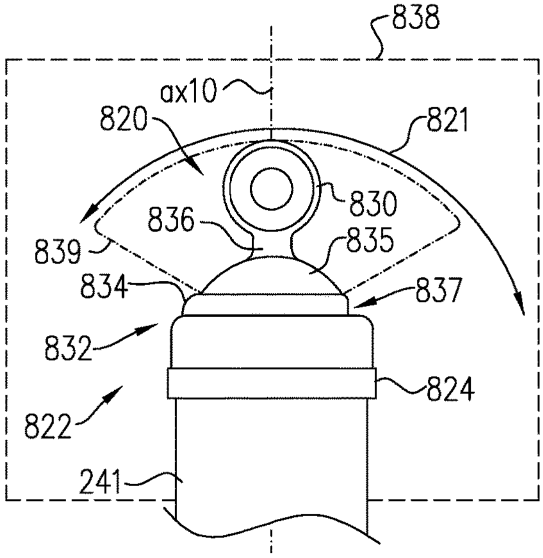
Figure 38B:
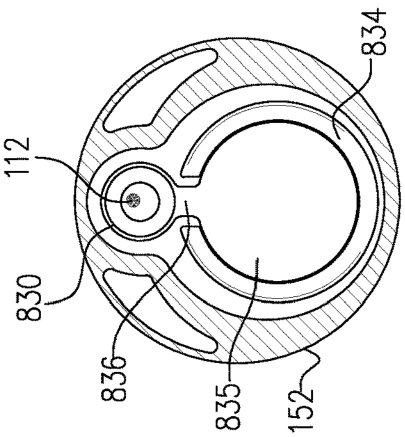
Figure 38A:
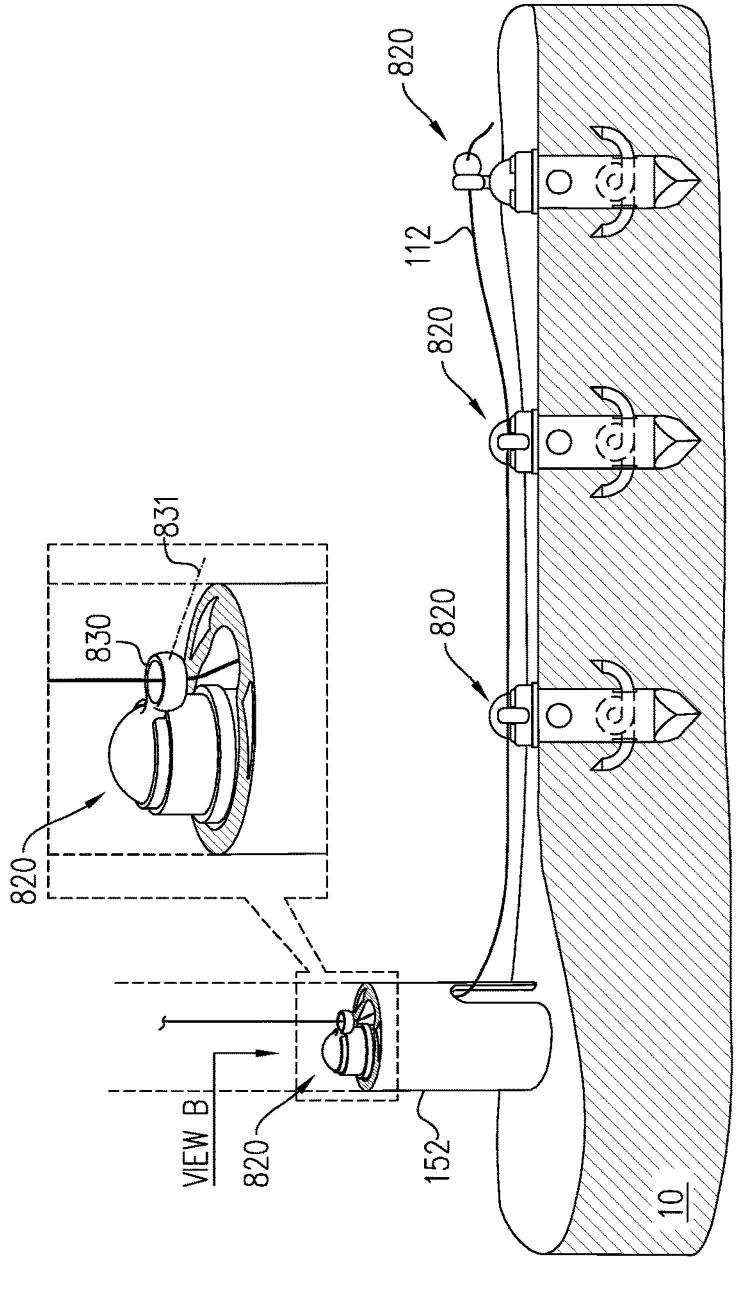

FIGS. 37B and 37D show the spherical-sector of deflection 839 of ball joint 832. In some applications, and as shown, a midpoint of spherical-sector of deflection 839 lies on central longitudinal axis ax10 of anchor 820.

In some applications, and as shown, ball joint 832 (e.g., socket 834 thereof) allows, on a particular deflection plane 838, deflection of bearing stud 836 beyond the limits of spherical-sector of deflection 839 (e.g., to a greater magnitude of angular deflection from the midpoint of spherical-sector of deflection 839). This can be provided by the rim of socket 834 defining a notch 837 into which bearing stud 836 may pass. On deflection plane 838, ball joint 832 thereby defines a planar angular arc of deflection 821, within which bearing stud 836 may deflect planarly, and which extends beyond the limits of the spherical-sector of deflection. In some applications, planar angular arc of deflection 821 is at least 110 degrees (e.g., at least 120 degrees, e.g., at least 140 degrees, e.g., at least 160 degrees, e.g., at least 180 degrees, such as at least 200 degrees). In some applications, planar angular arc of deflection 821 is no greater than 200 degrees (e.g., no greater than 180 degrees, e.g., no greater than 160 degrees, such as no greater than 140 degrees).

Similarly to as described hereinabove for eyelet 140, a narrowest part of the aperture of eyelet 810 and/or eyelet 830 can be midway between opposite faces of the eyelet. In some applications, the inner surface of eyelet 810 and/or eyelet 830 is hyperboloid in shape. In some applications, the inner surface of eyelet 810 and/or eyelet 830 is catenoid in shape.

Figures 40A, 40B:
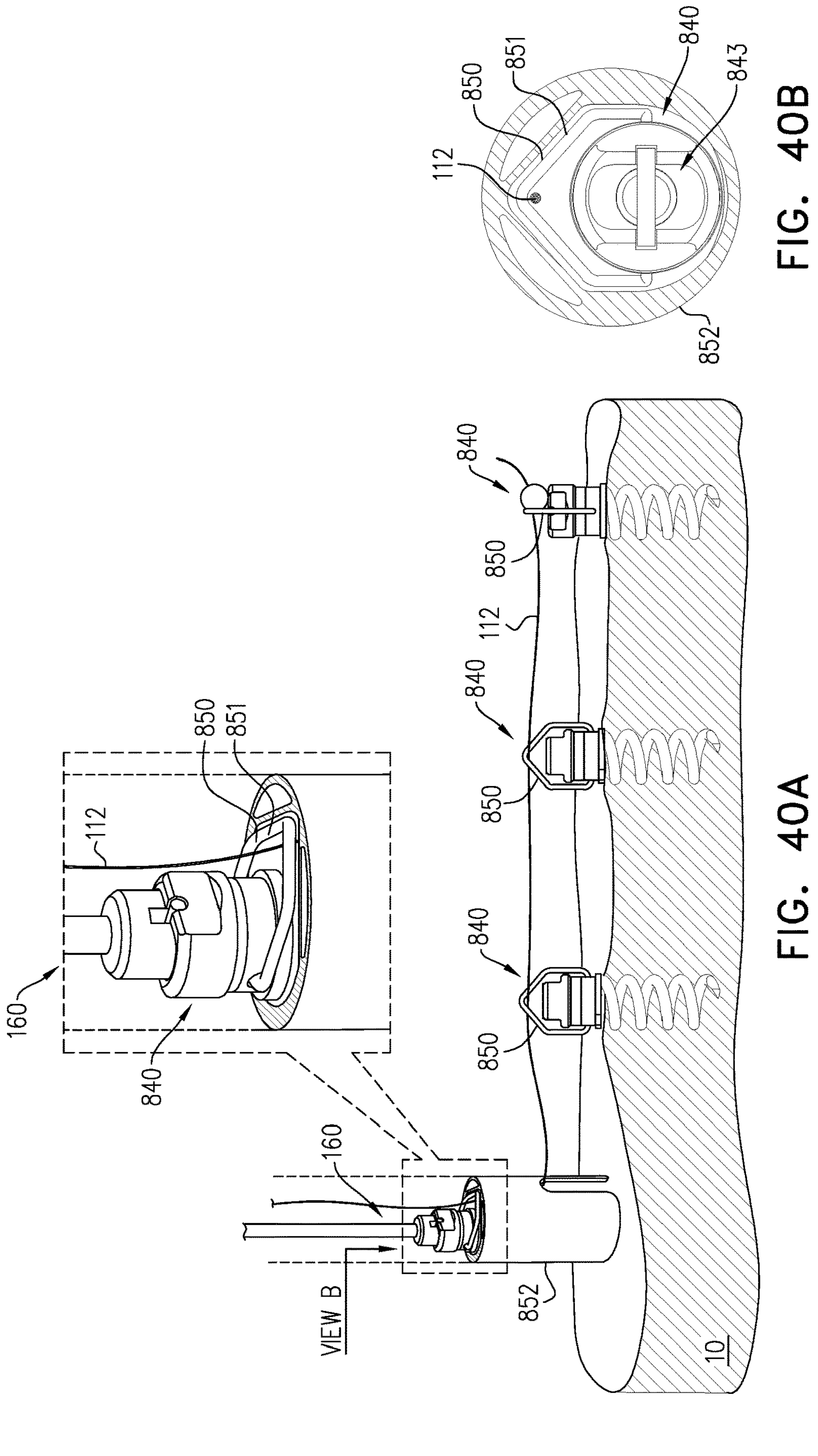

FIGS. 38A-B show a step in the implantation of an implant that comprises multiple tissue anchors 820 slidably coupled to (e.g., threaded onto) tether 112, in accordance with some applications. This implant is analogous to implant 110 described hereinabove, but comprising multiple anchors 820 instead of anchors 120, and FIGS. 40A-B are analogous to FIGS. 3A-B, mutatis mutandis. Although FIGS. 38A-B show an implant that does not comprise spacers threaded onto tether 112 between anchors 820, spacers or dividers such as those described elsewhere herein can be used. Anchor 800 can be used in the same manner, mutatis mutandis.

As shown in FIGS. 38A-B, eyelet is deflectable laterally from axis ax10 such that anchor 820 is transluminally advanceable along tether 112, e.g., through a tube such as tube 152. For example, eyelet axis 831 can be orthogonal to axis ax10.

In some applications, and similarly to the aperture of eyelet 140 of anchor 120, the aperture of eyelets 810 and 830 may be no more than twice as wide as the thickness of the tether (e.g., no more than 50 percent wider than the thickness of the tether, such as no more than 20 percent wider than the thickness of the tether).

FIGS. 39A-C show various views of a tissue anchor 840, and FIGS. 40A-D show at least some steps in the implantation of an implant that comprises multiple such tissue anchors slidably coupled to (e.g., threaded onto) tether 112, in accordance with some applications. This implant is analogous to implant 110 described hereinabove, but comprising multiple anchors 840 instead of anchors 120, and FIGS. 40A-D are analogous to FIGS. 3A-D, mutatis mutandis. Anchor 840 comprises an anchor head 842 that comprises a stock 844, a driver interface 843, and an eyelet 850. Stock 844 is coupled (e.g., fixedly coupled) to a proximal end of the tissue-engaging element of anchor 840 (tissue-engaging element 130, in the example shown), and is coupled (e.g., fixedly coupled) to driver interface 843, e.g., in a manner that transfers torque from interface 843 to the tissue-engaging element.

Eyelet 850 is hingedly coupled to stock 844 such that the eyelet is pivotable over interface 843, e.g., such that the eyelet is positionable on a first side of the driver interface and is pivotable over the driver interface to a second, opposite side of the driver interface, the second side being opposite the first side. The pivoting can also allow eyelet 850 to be positioned on a central longitudinal axis ax11 of anchor 840. Pivoting of eyelet 850 is illustrated in FIGS. 39B-C. Although FIGS. 39B-C show roughly 100 degrees of pivoting, the hinged coupling can be such that eyelet 850 is pivotable in an arc of up to 180 degrees, or even greater than 180 degrees.

In some applications, eyelet 850 is also rotatably coupled to stock 844, e.g., by the eyelet being coupled to a collar 848 of head 842, and the collar being rotatably coupled to the stock, and thereby being rotatable about axis ax11.

In some applications, and as shown, head 842 comprises an arch 851, and that has two base termini 855. For some such applications, arch 851 defines at least part of eyelet 850. The hinged coupling of eyelet 850 to stock 844 can be achieved by base termini 855 being hingedly coupled to stock 844 at respective hinge points opposite each other. For applications in which head 842 comprises collar 808, and as shown, the hinged coupling of eyelet 850 to stock 844 can be achieved by base termini 855 being hingedly coupled to the collar at the hinge points. For example, and as shown, collar 808 can define a recess at each of the hinge points, and the respective base terminus is hingedly coupled to the collar by protruding into the recess.

Thus, the coupling of eyelet 850 allows the eyelet both (i) to deflect with respect to axis ax11, and (ii) rotate/revolve about axis ax11.

Figure 41:
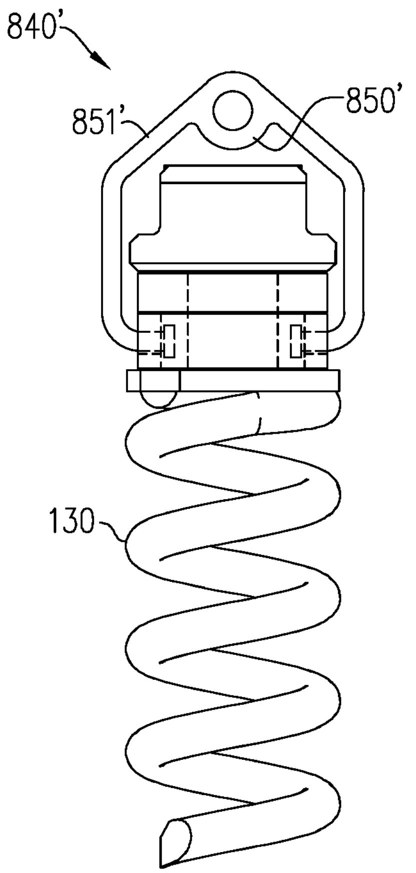
Figure 42:
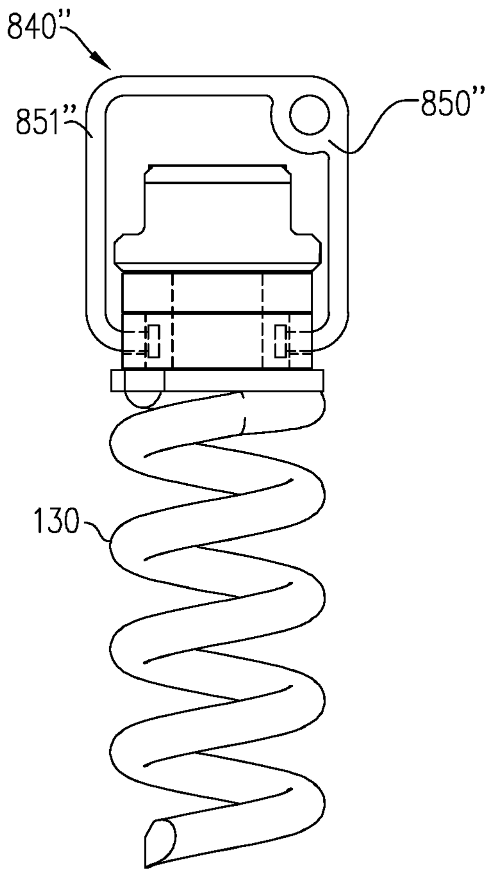

Anchor 840 is shown with most of arch 851 being part of eyelet 850, such that in at least some orientations of the eyelet interface 843 is disposed within eyelet 850. FIGS. 41 and 42 show variants of anchor 840 in which the eyelet is disposed on the arch in a manner that spaces the eyelet from the anchor interface of the anchor. FIG. 41 shows a variant 840' of anchor 840 that comprises an eyelet 850' that is disposed centrally on an arch 851', e.g., such that in at least one orientation the eyelet is positionable on the central longitudinal axis of the anchor. FIG. 42 shows a variant 840" of anchor 840 that comprises an eyelet 850" that is disposed eccentrically on an arch 851", e.g., such that in any possible orientation of the eyelet the eyelet is lateral from central longitudinal axis of the anchor.

As shown in FIGS. 40A-B, eyelet 850 is deflectable laterally from axis ax11 such that anchor 840 is transluminally advanceable along tether 112, e.g., through a tube 852, such as by using driver 160 or another driver. For example, arch 851 can be orthogonal to axis ax11, and/or an eyelet axis passing through eyelet 850 and the hinge points can be orthogonal to axis ax11. Tube 852 can be similar or identical to tube 152, described hereinabove.

Figure 40C:
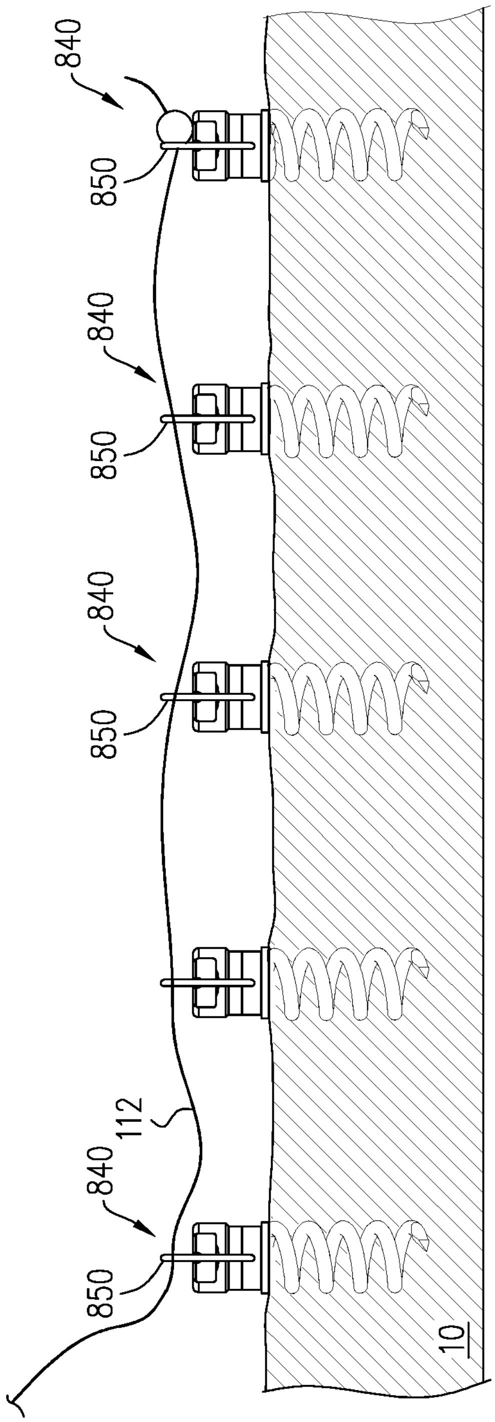
Figure 40D:
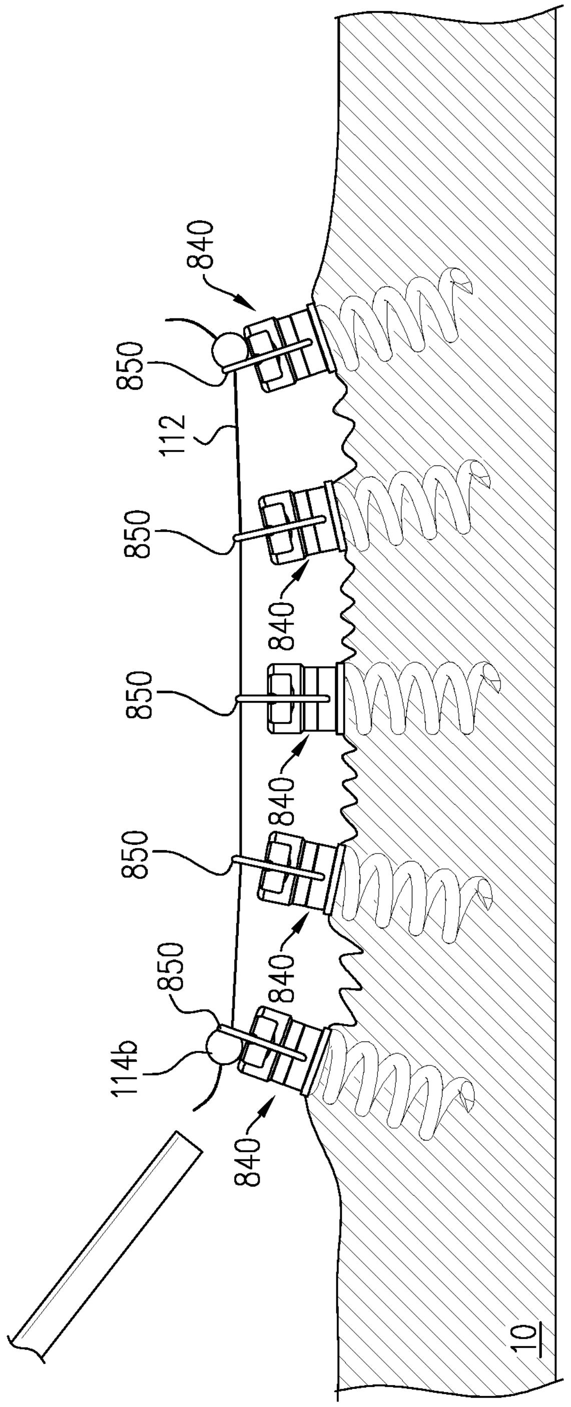

FIG. 40C shows five anchors 840 having been anchored, with tether 112 extending through the eyelet 850 of each anchor, and proximally out of the subject. FIG. 40D shows tether 112 having been tensioned, and stopper 114*b* having been advanced and locked to the tether to lock the tension in the tether, e.g., as described for implant 110, mutatis mutandis.

Head 842 allows the eyelet to be moved laterally from the central longitudinal axis of the anchor, e.g., into a position in which the eyelet axis is orthogonal to the central longitudinal axis, such as for transluminal delivery. For example, in such a configuration, the anchor can be advanced through tube 852, with the tissue-engaging element of the anchor sliding through a major channel region of the tube, and the eyelet of the anchor sliding through a minor channel region of the tube, e.g., similarly to as described hereinabove for anchor 120, mutatis mutandis.

Although FIGS. 40A-D show an implant that does not comprise spacers threaded onto tether 112 between anchors 840, spacers or dividers such as those described elsewhere herein can be used.

Figure 43A:
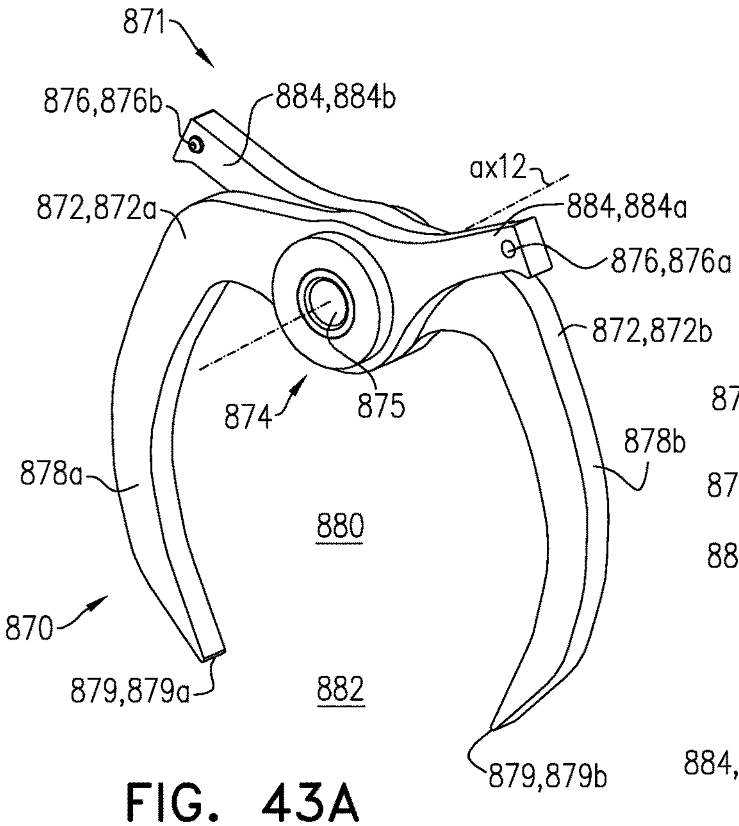
FIGS. 43A-C, which are schematic illustrations of a tissue anchor and a variant thereof, in accordance with some applications.
Figure 43B:
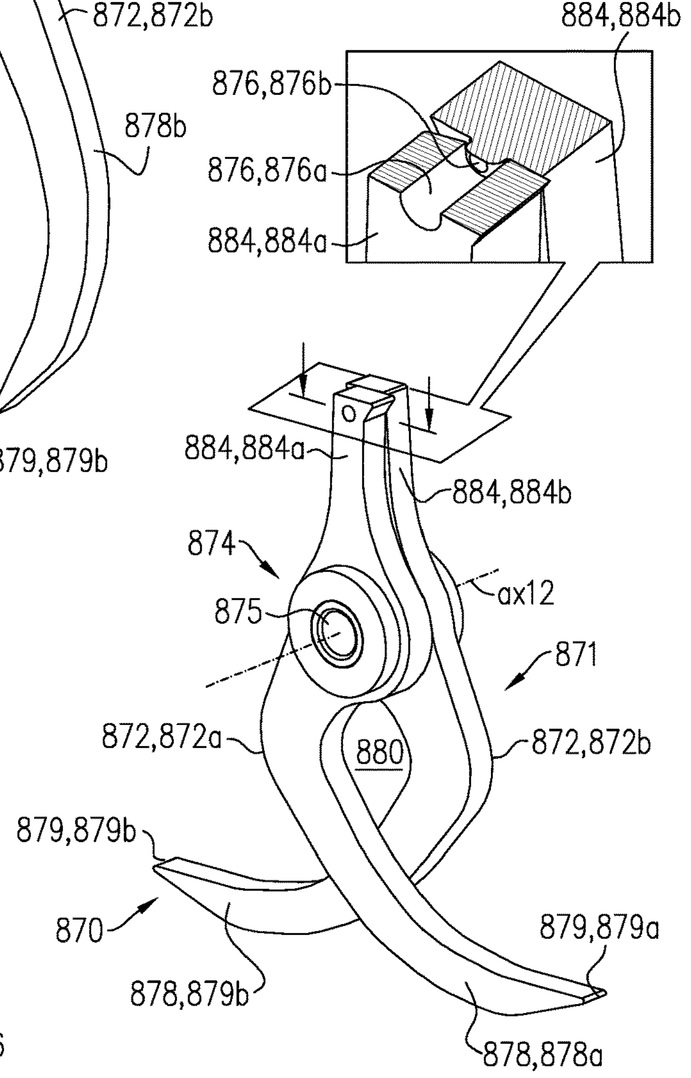
Figure 43C:
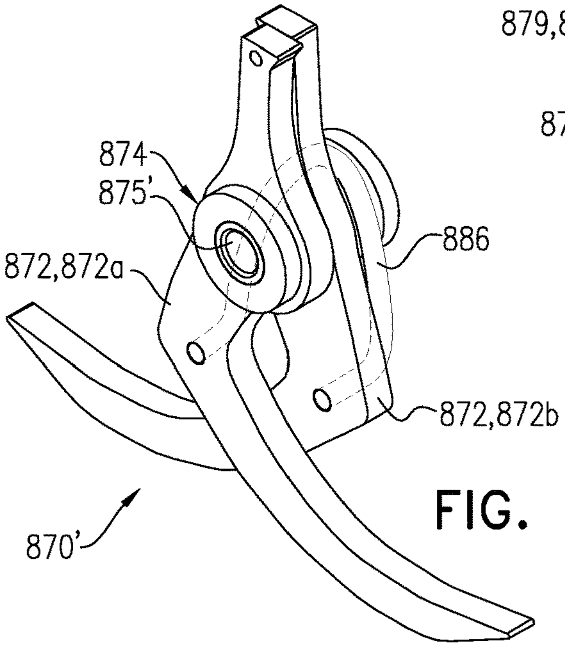

Reference is made to FIGS. 43A-C, which are schematic illustrations of a tissue anchor 870, and a variant 870' thereof, in accordance with some applications. Anchor 870 can be used as an anchor of an implant that comprises a tether, e.g., as described for other anchors hereinabove, mutatis mutandis. Alternatively, anchor 870 can be employed in other manners.

Like the other anchors described herein, anchor 870 is transluminally deliverable, e.g., to a heart of a subject. Anchor 870 comprises two arms 872 (e.g., a first arm 872*a* and a second arm 872*b*) that are hingedly coupled to each other at a revolute joint 874 that defines a hinge axis ax12. Revolute joint 874 often comprises a pin 875 that extends through each arm 872. Each of arms 872 can be rigid. Each arm 872 defines a coupling 876 and a hook 878, e.g., arm 872*a* defines a first coupling 876*a* and a first hook 878*a*, and arm 872*b* defines a second coupling 876*b* and a second hook 878*b*. Each hook 878 curves about and away from hinge axis ax12, terminating in a respective tip 879 (i.e., a first tip 879*a* and a second tip 879*b*), which can be sharpened. Hooks 878 curve in opposite directions about hinge axis ax12. In some applications, hooks 878 lie on respective planes, the planes being parallel with each other and orthogonal to hinge axis ax12.

Anchor 870 is transitionable between an open state (e.g., as shown in FIG. 43A), and a closed state (e.g., as shown in FIG. 43B). In the open state, arm 872*a* is in a first rotational position about hinge axis ax12, and hooks 878*a* and 878*b* define a space 880 therebetween, tips 879*a* and 879*b* define therebetween a gap 882 into the space. For example, hooks 878 can define respective concavities that face each other, space 880 including both concavities. In the closed state, arm 872*a* is in a second rotational position about hinge axis ax12, and gap 882 is smaller than in the open state. For example, and as shown in FIG. 43B, there may be effectively no gap between hooks 878 into space 880, thereby forming space 880 into an aperture of an eyelet defined by hooks 878.

Although the preceding paragraph describes the open and closed states with respect to rotational positions of arm 872*a* about hinge axis ax12, these positions are relative to arm 872*b*. That is, in the open state arms 872*a* and 872*b* are in a first rotational juxtaposition about hinge axis ax12, and in the closed state arms 872*a* and 872*b* are in a second rotational juxtaposition about the hinge axis. In some applications, transitioning of anchor 870 toward the closed state involves rotating both arms 872 about hinge axis ax12 (e.g., relative to another component, such as an anchor driver used to advance and actuate the anchor). However, in some applications, transitioning of anchor 870 toward the closed state involves rotating only one of arms 872.

In the open state tips 879 may face in generally the same direction as each other, e.g., so as to facilitate penetration of hooks 878 into the tissue. Anchor 870 can be transitioned toward the closed state after tips 879 have been penetrated into the tissue, and the transition typically advances hooks 878 further into the tissue. Collectively, hooks 878 thereby serve as a tissue-engaging element 871 of anchor 870.

In some applications, and as shown, in the closed state, tips 879 face away from each other.

In the open state, couplings 876*a* and 876*b* are disengaged from each other, whereas in the closed state the couplings are engaged with each other. The engagement inhibits anchor 870 from transitioning out of the closed state, thereby inhibiting de-anchoring of the anchor from the tissue. In some applications, one of couplings 876 (coupling 876*b* in the example shown) comprises a protrusion, and the other (coupling 876*a* in the example shown) comprises a recess, the couplings engaging each other by the protrusion protruding into the recess. In some applications, couplings 876 are configured to automatically engage each to each other when brought into alignment with each other. For example, and as shown, arms 872 may be sufficiently close to each other along axis ax12 that the protrusion of coupling 876*b* snaps into the recess of coupling 876*a* upon the couplings becoming aligned.

In some applications, each arm 872 defines a respective beam 884 (e.g., arm 872*a* defines a beam 884*a*, and arm 872*b* defines a beam 884*b*). For some such applications, and as shown, revolute joint 874 is disposed between the beam and the hook of each arm 872 (e.g., pin 875 extends through each arm between the beam and the hook), such that each arm is a class I lever whose fulcrum is the revolute joint, and therefore such that anchor 870 is therefore a class I double-lever whose fulcrum is the revolute joint. For some such applications, anchor 870 is transitionable from the open state toward the closed state by driving one or both beams 884 about hinge axis ax12. That is, for some such applications, anchor 870 is actuatable (e.g., by an anchor driver that engages beams 884) by applying a force to one or both beams 884.

For applications in which each arm 872 defines a respective beam 884, transitioning anchor 870 toward its closed state can be achieved by increasing an alignment between the beams. For example, and as shown, couplings 876 can be disposed on beams 884, and the hinged coupling between arms 872 can be such that anchor 870 is transitionable into the closed state by bringing the beams into alignment with each other such that the couplings responsively engage each other.

In some applications, and as shown, a radius of curvature of each hook 878 increases with distance from revolute joint 874. Thus, in some applications, the curving of each hook 878 can be considered to be generally spiral, despite having less than one (e.g., less than half of a) full turn. It is hypothesized that such a shape is advantageous compared to a hook that has a more circular curve, e.g., by improving anchoring, such as by reducing conversion of a pulling force applied to the anchor into rotation of arms 872 about revolute joint 874.

Variant 870' (FIG. 43C) can be identical to anchor 870, except where noted. Compared to anchor 870, variant 870' further comprises a spring 886 that is configured to bias at least one of arms 872 toward a respective given rotational position about hinge axis ax12. In the example shown, spring 886 is configured to bias the anchor toward the closed state. In some applications, spring 886 and couplings 876 synergize such that, in order to return the anchor toward its open state, sufficient force must be applied to overcome both the spring and the engagement of the couplings. Spring 886 can be coupled to both arms 872, e.g., by each end of the spring being connected to a respective one of the arms, such as by protruding through a hole in the arm, e.g., as shown. In some applications, and as shown, spring 886 is connected to the hook 878 of each arm, e.g., as shown. Optionally, spring 886 can be connected to the beam 884 of each arm.

In some applications, spring 886 is a torsion spring. For some such applications, and as shown, spring 886 is mounted on a pin 875', which may be identical to pin 875 except to accommodate the spring, e.g., by pin 875' being longer and/or comping an additional flange to retain the spring.

Reference is made to FIGS. 44A-E and 45A-E, which are schematic illustrations of tissue anchors 900 and 920, and techniques for use thereof, in accordance with some applications. Each of tissue anchors 900 and 920 comprises a stem (902 for anchor 900, and 922 for anchor 920), an arm (904 for anchor 900, and 924 for anchor 920), and a hinge (906 for anchor 900, and 926 for anchor 920) via which the arm is coupled to the stem—often at a distal part (e.g., a distal end) of the stem. The stem also has a proximal part, and an intermediate part between the proximal part and the distal part. Each of arms 904 and 924 has a first side (904*a* for arm 904, and 924*a* for arm 924) and a second side (904*b* for arm 904, and 924*b* for arm 924). The arm can be coupled to the hinge such that the hinge is disposed between the first side and the second side of the arm, e.g., the position of the hinge delimiting the first side and the second side of the arm.

Figures 44A, 44B, 44C, 44D:
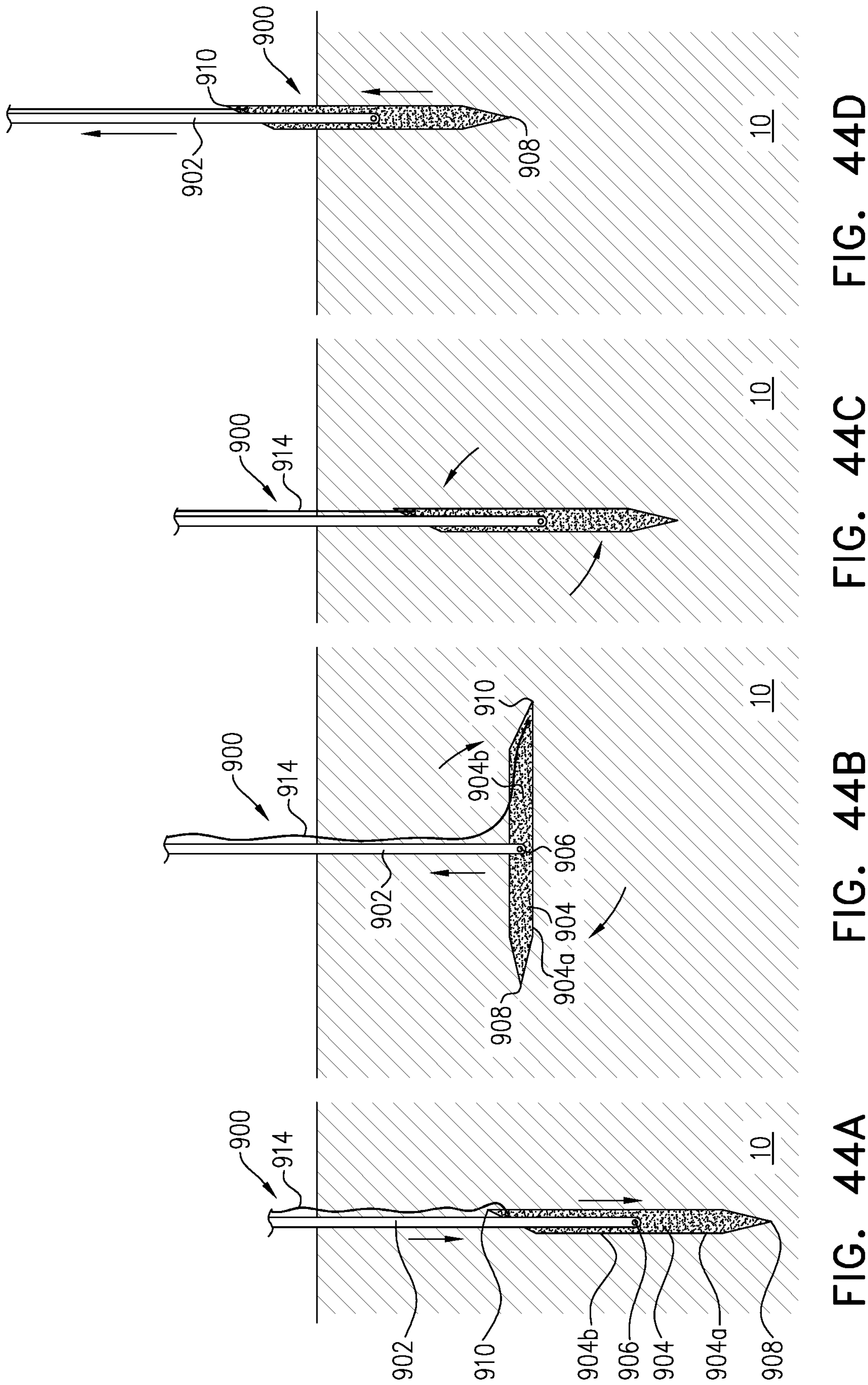
FIGS. 44A-E and 45A-E are schematic illustrations of tissue anchors and techniques for use thereof, in accordance with some applications.
Figure 45A:
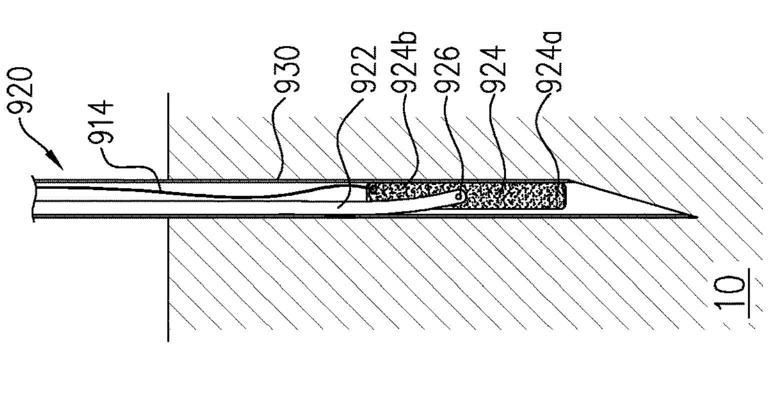

For each of anchors 900 and 920, the anchor is anchorable into the tissue (e.g., tissue by advancing into the tissue, in succession, the first side of the arm (i.e., the first side of the arm serving as a leading arm), the hinge, and the intermediate part of the stem, such that stem extends, from the distal end of the stem and the hinge (which are within the tissue), to the proximal part of the stem above the tissue, e.g., as shown in FIG. 44A (for anchor 900) and FIG. 45A (for anchor 920). Anchor 920 (e.g., arm 924 thereof) can be advanced into the tissue within a hollow needle 930 that has a sharpened tip that is configured to be penetrated into the tissue. Anchor 900 (e.g., arm 904 thereof) can be configured to be driven into the tissue directly, e.g., exposed, without a hollow needle. To facilitate this, first side 904*a* of arm 904 can therefore have a sharpened tip 908. Tip 908 can be centralized, to facilitate straight advancement of arm 904 through the tissue. In some applications, second side 904*b* is longer (e.g., 5-50 percent longer, e.g., 5-30 percent longer, such as 10-30 percent longer) than first side 904*a* which can alternatively or additionally facilitate straight advancement of arm 904 through the tissue, e.g., by conferring positive longitudinal stability on arm 904 in a distal direction.

Figure 45B:
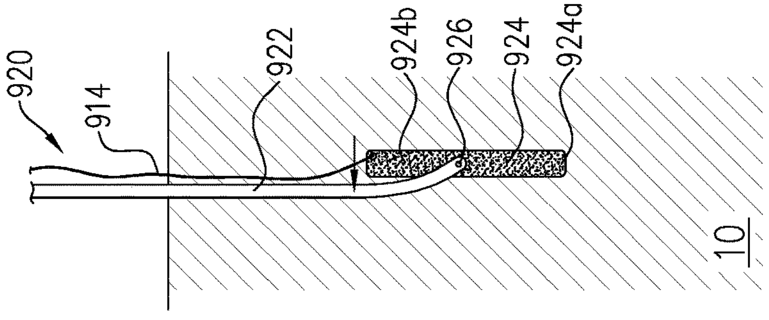
Figure 45C:
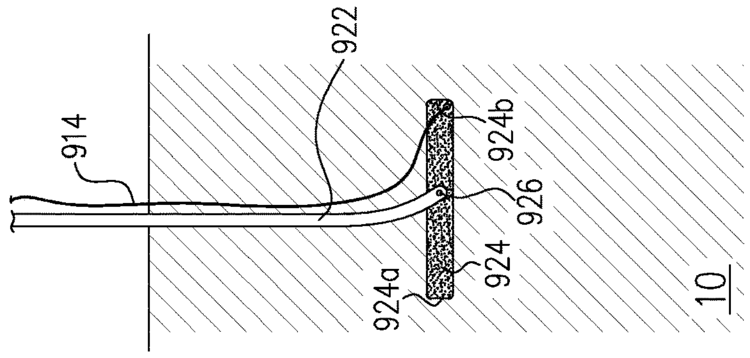
Figure 45D:
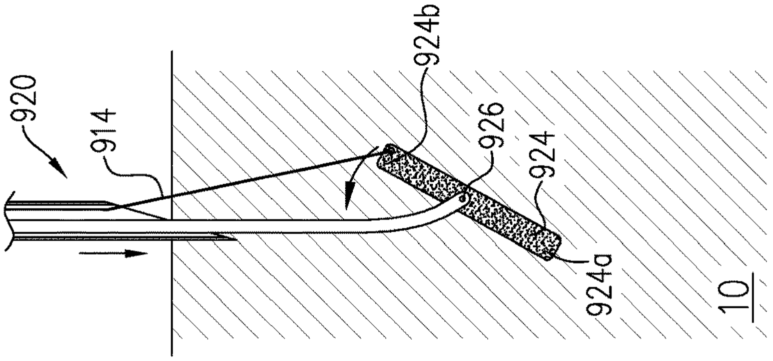

Within the tissue, each of arms 904 and 924 is pivotable about the respective hinge such that the respective anchor is transitionable toward a restraining state in which the arm extends transversally across the stem, e.g., as shown in FIG. 44B (for anchor 900) and FIG. 45B (for anchor 920). In the restraining state, the arm inhibits withdrawal of the anchor from the tissue. Thus, each of anchors 900 and 920 can be considered to comprise a tissue-engaging element that comprises the arm and often also at least part of the stem. During the pivoting of the arm, the first side of the arm moves proximally with respect to the stem, and the second side of the arm moves distally with respect to the stem. This pivoting can be achieved by pulling proximally on (i.e., applying a proximal pulling force to) the stem of the anchor, e.g., as though to extract the anchor from the tissue, with the arm automatically deflecting in response to the pulling. To facilitate this behavior in anchor 900, second side 904*b* of arm 904 can have a sharpened tip 910, which can be eccentric (as shown), such that in response to initial movement of anchor 900 proximally through the tissue, tip 910 pulls to one side, causing pivoting of arm 904 (FIG. 44B). For applications in which second side 904*b* is longer than first side 904*a*, this can alternatively or additionally facilitate pivoting of arm 904 in response to initial proximal movement of anchor 900 through the tissue, e.g., by conferring negative longitudinal stability on arm 904 in a proximal direction.

Anchor 920 is shown with another feature that facilitates pivoting of the arm (arm 924) in response to initial movement of the anchor proximally through the tissue. Stem 922 is biased to automatically curve, upon deployment from needle 930 within the tissue (FIG. 45B), with the needle being configured to inhibit curving of the stem while the stem is disposed within the needle. For example, stem 922 can comprise an elastic or shape memory material. The curving of stem 922 upon deployment can move the stem laterally with respect to arm 924, thereby creating a gap between the stem and second side 924*b* of the arm. Upon initial movement of anchor 920 proximally through the tissue, the tissue resists second side 624*b* such that arm 924 responsively pivots.

Figure 44E:
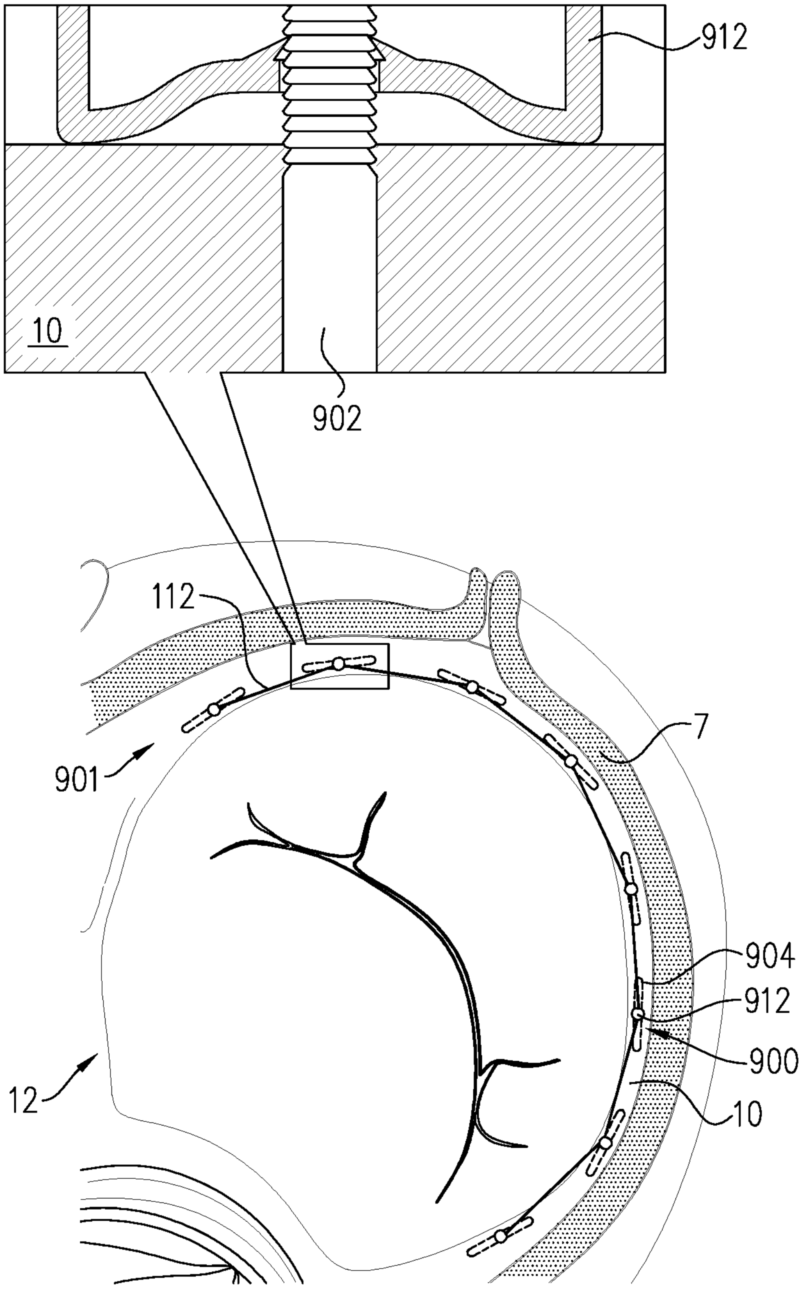

In some applications, each of anchors 900 and 920 further comprises a head, coupled to the stem of the anchor (e.g., to a proximal part of the stem). A head 912 of anchor 900 is shown in FIG. 44E, and it is to be understood that a similar arrangement is possible for anchor 920, mutatis mutandis. Head 912 can represent, or include features of, the head of one or more of the other anchors described herein. Optionally, the head of one or more of the other anchors described herein can be modified to include features of head 912.

FIG. 44E shows an application in which anchor 900 is used as a component of an implant 901 that is similar to implant 110. For such applications, head 912 can be slidably coupled to (e.g., threaded onto) tether 112. Head 912 is configured be moved distally along stem 902 toward hinge 906, such that tissue 10 becomes sandwiched between the head and arm 904. It is hypothesized that this advantageously stabilizes the anchor within the tissue and improves anchoring. It is further hypothesized that the movability of head 912 along stem 902 can be hemodynamically advantageous, e.g., due to the head and tether 112 being closer to the surface of tissue 10.

Although FIG. 44E shows implant 901 being used at mitral valve 12, it is to be noted that the implant can be used at other sites, such as other heart valves, e.g., the tricuspid valve.

In some applications, and as shown, a retrieval line 914 is coupled to the second side of the arm in a manner in which proximal pulling of the retrieval line transitions the anchor away from the restraining state by pivoting the arm with respect to the stem such that the first side of the arm moves distally with respect to the stem, and the second side of the arm moves proximally with respect to the stem, i.e., toward the state in which the anchor originally entered the tissue. Retrieval line 914 often provides the operator with the option to de-anchor anchor 900 or anchor 920, e.g., if it is determined that the position or anchoring of the anchor is suboptimal.

FIGS. 44C-D show retrieval line 914, coupled to second side 904*b* of arm 904, being used to facilitate de-anchoring of anchor 900. Proximal pulling (i.e., tensioning) of retrieval line 914 transitions anchor 900 away from its restraining state by pivoting arm 904 with respect to stem 902 such that first side 904*a* moves distally with respect to the stem, and second side 904*b* moves proximally with respect to the stem (FIG. 44C). Subsequently, and typically while tension is maintained on retrieval line 914, anchor 900 is withdrawn from the tissue, e.g., by proximal pulling of stem 902 (FIG. 44D). FIGS. 44D-E show a similar process for anchor 920, except that needle 930 (or another tube) can be advanced distally over and along retrieval line 914 and stem 922, and withdrawal of the anchor can include pulling the retrieval line, the stem, and at least second side 924*b* of arm 924, into the needle (or the other tube). In some applications, advancement of needle 930 (or the other tube) over and along stem 922 re-straightens the stem.

Upon determining that the anchor has been anchored optimally, retrieval line 914 can be decoupled from the anchor and withdrawn from the subject, leaving the anchor disposed in the tissue. For example, retrieval line 914 can be looped through an eyelet in the second side of the arm and can be decoupled from the anchor by being unlooped. However, it is to be understood that the other reversible couplings can be used.

There is provided, in accordance with some applications, a method for implanting an implant into tissue of a heart of a subject, the method comprising: (i) into the subject, introducing a tissue anchor including a stem, a head coupled to a proximal part of the stem, an arm, and a hinge via which the arm is coupled to the stem, the stem having an intermediate part between the distal end and the proximal part, and (ii) toward the heart, transluminally advancing the anchor along a tether with the head sliding over the tether.

In some applications, the method includes advancing into the tissue, in succession, a first side of the arm, the hinge, and the intermediate part of the stem, such that a proximal part of the stem extends above the tissue In some applications, the method includes, within the tissue, transitioning the anchor toward a restraining state thereof by pivoting the arm about the hinge such that the arm extends transversally across the distal end of the stem.

In some applications, the method includes, subsequently, sandwiching the tissue between the arm and the head by moving the head distally along the stem toward the hinge.

Figure 45E:
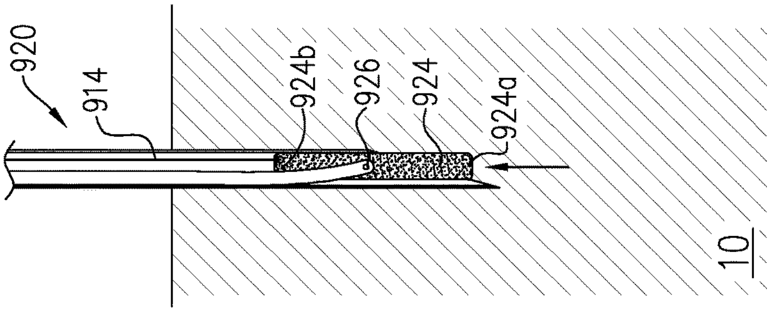
Figure 46C:
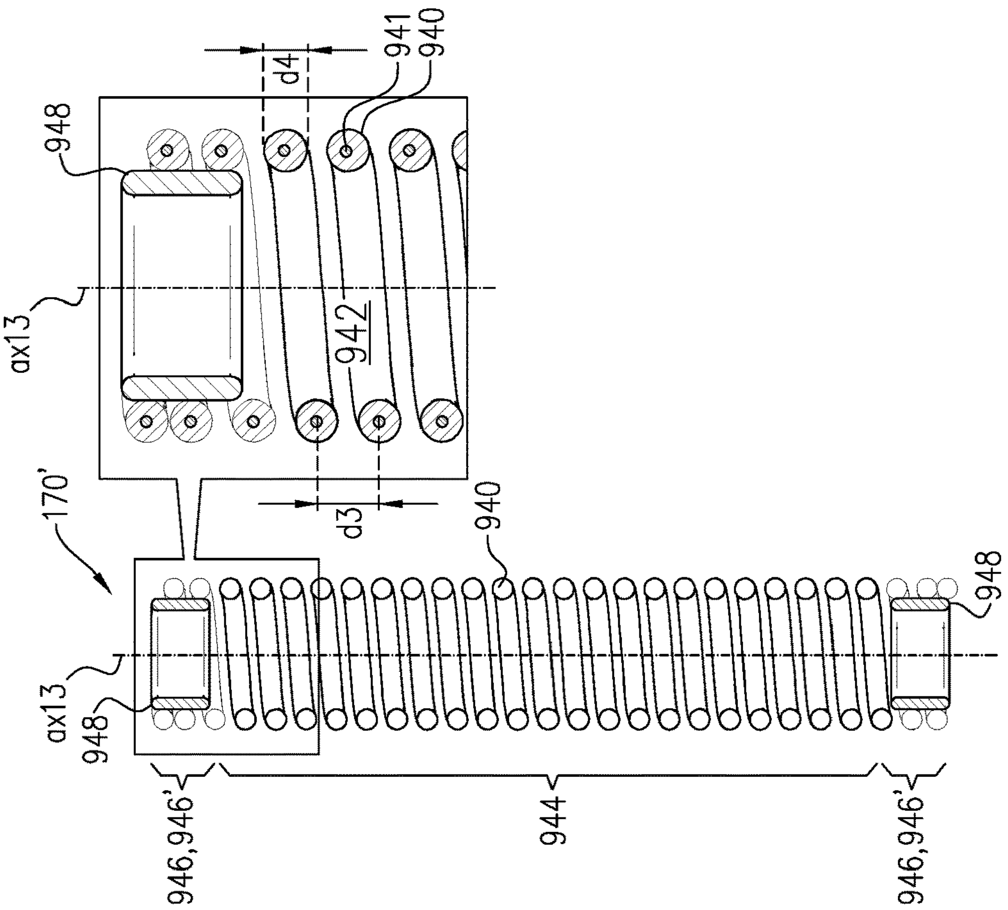
FIGS. 46A-C and 47A-C are schematic illustrations of example spacers, in accordance with some applications.
Figure 46B:
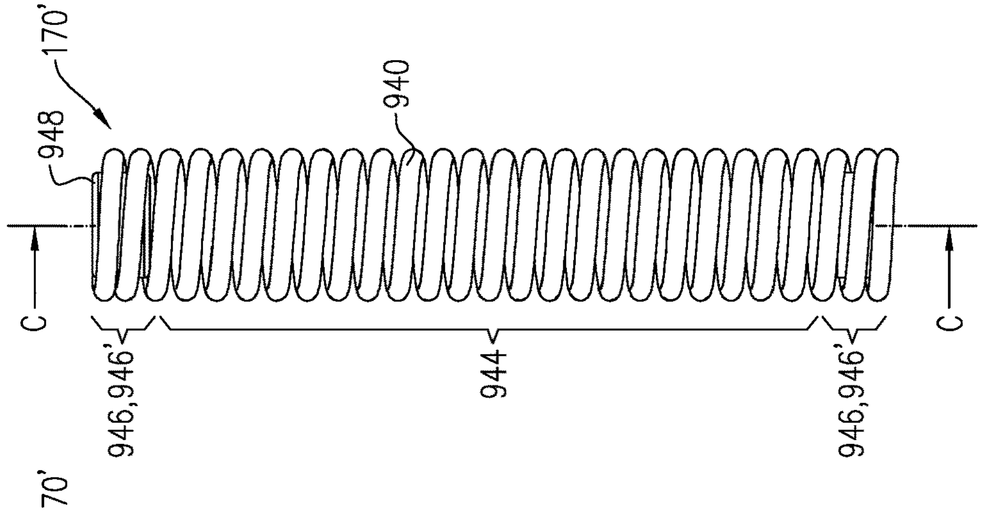
Figure 46A:
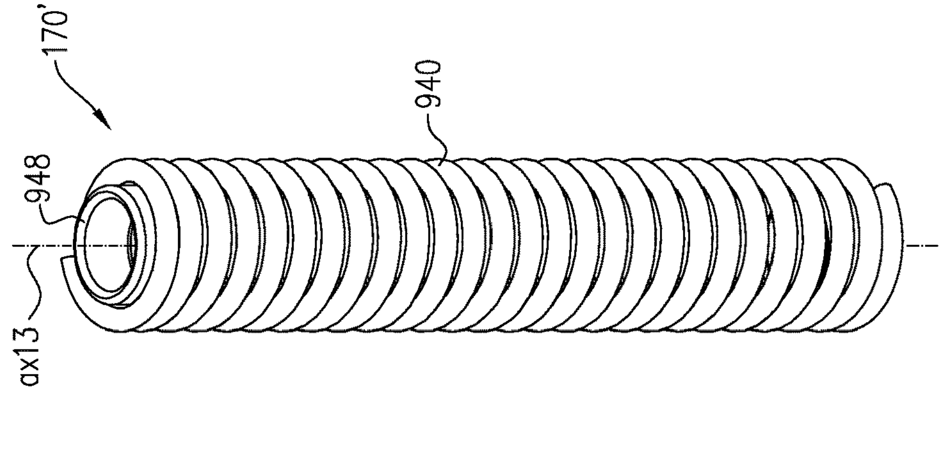
Figures 47A, 47B, 47C:
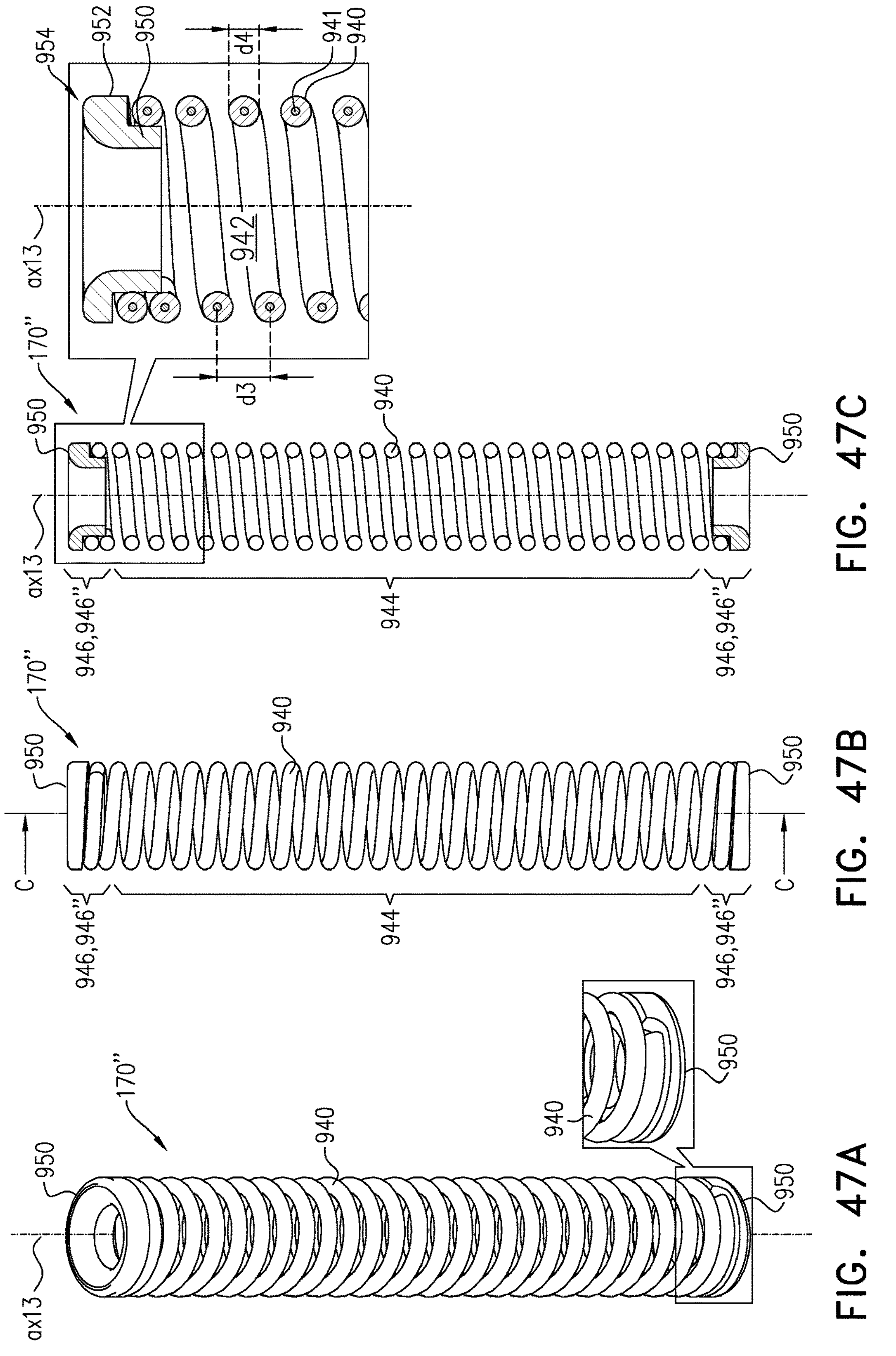

For applications in which anchor 900 or 920 is used as a component of an annuloplasty implant (e.g., an implant similar to implant 110), the anchor can be driven into the annulus of the heart valve being treated. For both the mitral valve and the tricuspid valve, a coronary artery is disposed close to the annulus of the valve, within the wall of the atrium upstream of the valve, e.g., disposed alongside at least part of the atrium. It is desirable to avoid the coronary artery when anchoring anchors (e.g., anchors of an annuloplasty implant) to the annulus. Anchors 900 and 920 are hypothesized to be advantageously advanceable into the annulus while the arm of the anchor is generally orthogonal to the coronary artery, with the narrowness of the anchor in this state facilitating avoidance of the coronary artery. In some applications, the anchor is oriented rotationally such that, when transitioned into the restraining state, the arm becomes generally parallel with the coronary artery. Thereby even when the anchor is thus widened, it avoids the coronary artery. This is shown in FIG. 45E, in which anchors 900 of implant 901 are anchored to the annulus (tissue 10) of mitral valve 12, with arm 904 of each anchor being generally parallel with the left coronary artery 7.

Reference is now made to FIGS. 46A-C and 47A-C, which are schematic illustrations of spacers or dividers 170' and 170", in accordance with some applications. Spacers or dividers 170' and 170" are variants of spacer or divider 170, described hereinabove, and can be used as described hereinabove for spacer or divider 170. Each of spacers or dividers 170' and 170" comprises a wire 940 that is shaped as a helical coil that defines a lumen 942 of the spacer or divider. In some applications, and as shown, in a resting state of the coil, a pitch d3 of the coil is sufficiently small that the coil appears substantially closed, e.g., tubular. For example, pitch d3 can be less than twice a thickness d4 of the wire (e.g., 1.4-2 times the thickness of the wire, such as 1.6-1.8 times the thickness of the wire, such as 1.7 times the thickness of the wire). In some applications, in the resting state of the coil the coil is a closed coil, i.e., each turn of the coil is in contact with its adjacent coils.

Spacers or dividers 170' and 170" are flexible in deflection, and generally are elastically flexible, i.e., they can be deflected laterally by application of a force and will elastically return toward its resting shape upon removal of the force. In some applications, starting in their resting state, spacers or dividers 170' and 170" are initially axially compressible (e.g., while providing some degree of resistance to axial compression), and then once compressed to the extent that adjacent turns of the coil contact each other, become generally not axially compressible further.

Each of spacers or dividers 170' and 170" has a primary region 944 and, at each end of the primary region, a secondary region 946. The primary regions of spacers or dividers 170' and 170" can be identical to each other and are therefore provided the common reference numeral 944. The secondary regions of spacer or divider 170' are not necessarily identical to those of spacer or divider 170", and therefore the secondary regions of spacers or dividers 170' and 170" have been further provided the respective reference numerals 946' and 946".

In some applications, and as shown, the pitch, flexibility, and compressibility characteristics described hereinabove for spacers or dividers 170' and 170" apply only to primary region 944, and secondary regions 946 have one or more different characteristics from the primary region. For example, secondary regions 946 can be less flexible in deflection and/or less axially compressible than primary region 946. In some applications, this reduced flexibility and/or compressibility is at least in part due to the pitch of the coil of wire 940 being smaller in secondary regions 946 than in primary region 944, e.g., as shown. Alternatively or additionally, the reduced flexibility and/or compressibility is at least in part due to the spacer or divider comprising, coupled to wire 940 at each secondary region, a ring 948 (for spacer or divider 170') or 950 (for spacer or divider 170").

Primary and secondary regions 944 and 946 are axial regions, i.e., the length of a given region refers to the region's length along axis ax13. In some applications, for a given spacer or divider 170' or 170", each secondary region 946 can be shorter than primary region 944. Further, for a given spacer or divider 170' or 170", a combined length of both secondary regions 946 can be shorter than primary region 944. In some applications, for a given spacer or divider 170' or 170", each secondary region 946 is less than 30 percent as long (e.g., less than 20 percent as long, e.g., less than 10 percent as long) as primary region 944, and/or is at least 2 percent as long (e.g., at least 5 percent as long) as the primary region. For example, each secondary region 946 can be 5-10 percent as long as primary region 944.

Rings 948 and 950 can be rigid and can be formed from a single piece of stock material. Rings 948 and 950 can be disposed inside of the coil of wire 940 (e.g., as shown), although in some applications can be disposed around the outside of the coil. Rings 948 and 950 can be coupled to wire 940 by welding, brazing, adhering, and/or interference fit.

In some applications, each of rings 948 and 950 has a length, along axis ax13, that is greater than (e.g., at least twice as great as) wire thickness d4. In some applications, the ring extends past at least two turns of the coil of wire 940. In some applications, for a given spacer or divider 170' or 170", each ring 948 or 950 can be shorter than primary region 944. Further in some applications, for a given spacer or divider 170' or 170", a combined length of both rings 948 or 950 can be shorter than primary region 944. In some applications, for a given spacer or divider 170' or 170", each ring 948 or 950 is less than 30 percent as long (e.g., less than 20 percent as long, e.g., less than 10 percent as long) as primary region 944, and/or is more than 2 percent as long (e.g., more than 5 percent as long) as the primary region. For example, each ring 948 or 950 can be 5-10 percent as long as primary region 944.

Rings 948 and 950 are hypothesized to improve the interaction of spacers or dividers 170' and 170" with the anchors of the implant with which they are used. For example, when used with implant 110 comprising anchors 120, upon contraction of the implant rings 948 and 950 can stably abut, flush against, the flat faces 148 of eyelets 140 of anchors 120. It is further hypothesized that rings 948 and 950 may reduce a likelihood of part of the spacer or divider (e.g., part of the helical coil) becoming medially compressed and drawn into the eyelet of an anchor of the implant upon contraction of the implant.

In some applications, rings 948 and 950 obscure the end of the coil of wire 940, thereby reducing a likelihood of tether 112 entering between turns of the coil.

Whereas ring 948 can be a simple ring, ring 950 often has a flange 952 at its end. In some applications, flange 952 facilitates coupling of ring 950 to the coil of wire 940. In some applications, flange 952 provides spacer or divider 170'' with a rim 954 that has a greater radius of curvature than that which would be provided in the absence of ring 950 (e.g., than that which might be provided by wire 940 alone). It is hypothesized that this greater radius of curvature confers an advantage on rim 954 as a bearing surface against which tether 112 may slide, e.g., by reducing a likelihood of the rim engaging with and/or damaging the tether.

In some applications, ring 950 can be shaped asymmetrically in order that its shape matches that of the coil of wire 940, e.g., so as to facilitate coupling therebetween. This is visible in the insets of FIGS. 47A and 47C, in which the height of flange 952 differs at different circumferential positions around axis ax13, in order to accommodate the terminal turn of the coil of wire 940.

In some applications, the position of rings 948 and 950 inside the coil of wire 940 reduces the diameter of lumen 942 at secondary regions 946. It is hypothesized that, in some applications, this reduced diameter advantageously biases tether 112 toward a central longitudinal axis ax13 of the spacer or divider, thereby reducing a likelihood of undesirable interactions between the tether and the coil of wire 940.

It is to be noted that, although rings 948 and 950 have been named "rings," they can have a greater length than shown in the figures, and therefore in some applications can be described as tubes.

Rings 948 and 950 can comprise a cobalt chrome alloy. Wire 940 can comprise a cobalt chrome alloy. In some applications, and as shown, wire 940 has a core 941 that comprises a radiopaque material such as platinum. For example, wire 940 can comprise a drawn filled tube. The resulting radiopacity of core 941 is hypothesized to facilitate fluoroscopic guidance of implantation and/or contraction of the implant (e.g., implant 110). For example, the fluoroscopically-visible length of spacers or dividers 170' or 170'' can be used as a reference for spacing apart anchors during anchoring, and/or an indication of a degree of contraction of the implant.

Reference is now made to FIGS. 48A-E, which are schematic illustrations of a tether-handling system 970, in accordance with some applications. System 970 comprises a stopper 971, and often further comprises a tool 976 for use with the stopper. Tethers are used in various medical procedures, including as sutures and/or as components of implants. It is commonly necessary to lock or secure such a tether at a certain point in the procedure. In the above example of tether 112 of implant 110, a stopper (e.g., stopper 114*b*) is used for this purpose. Stopper 971 can be used to secure a tether such as tether 112, e.g., in place of stopper 114*b*, and/or for a similar purpose in the implants described in WO 2021/084407 to Kasher et al., which is incorporated herein by reference for all purposes.

In some applications, for system 100 described hereinabove (and other similar systems), this locking of tether 112 is performed after the final anchor of the implant has been implanted. In FIGS. 48D-E, this final anchor is represented by a portion of a tissue anchor that is indicated by reference numeral 978.

Figure 48A:
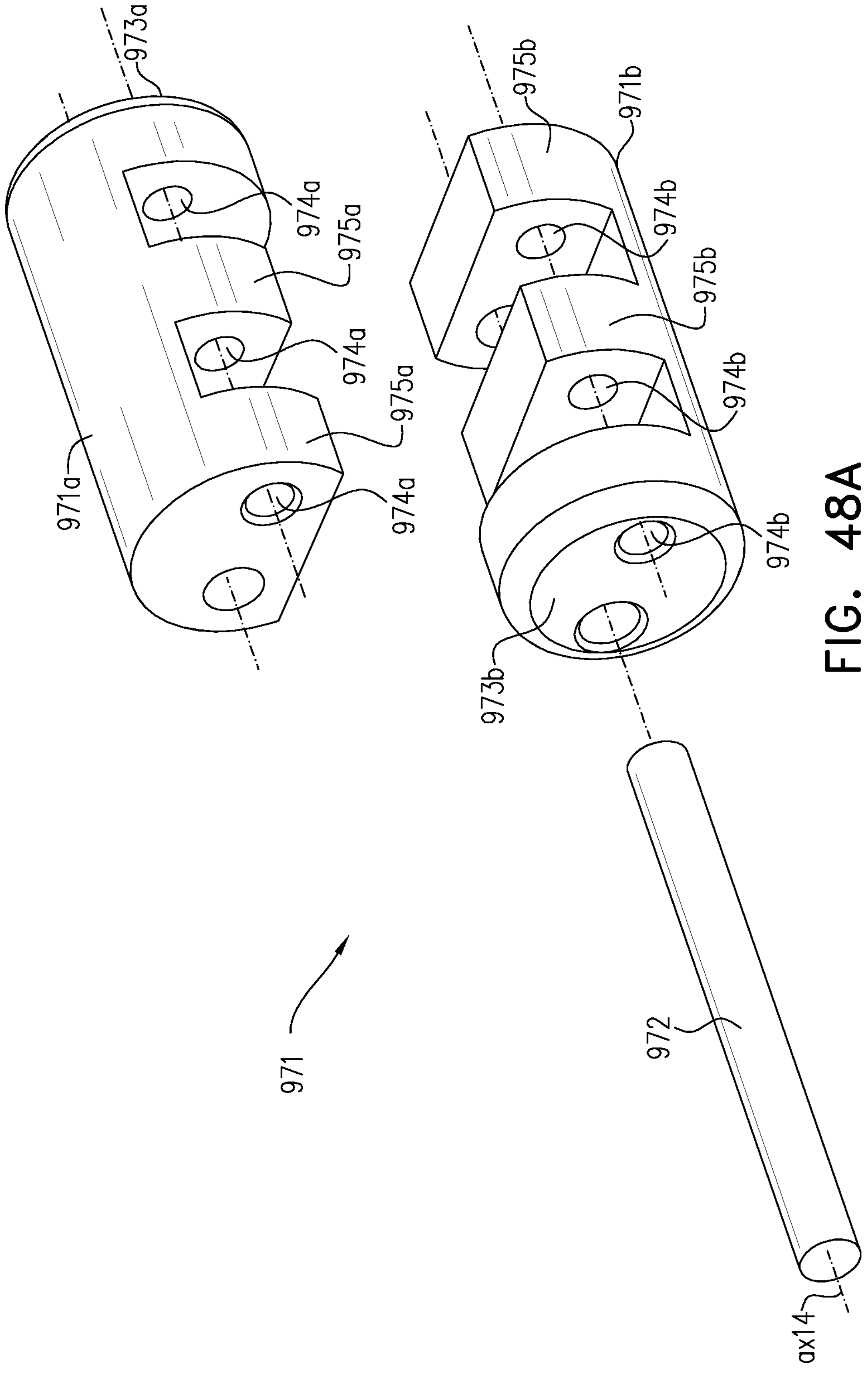
FIGS. 48A-E are schematic illustrations of a tether-handling system, in accordance with some applications.
Figure 48B:
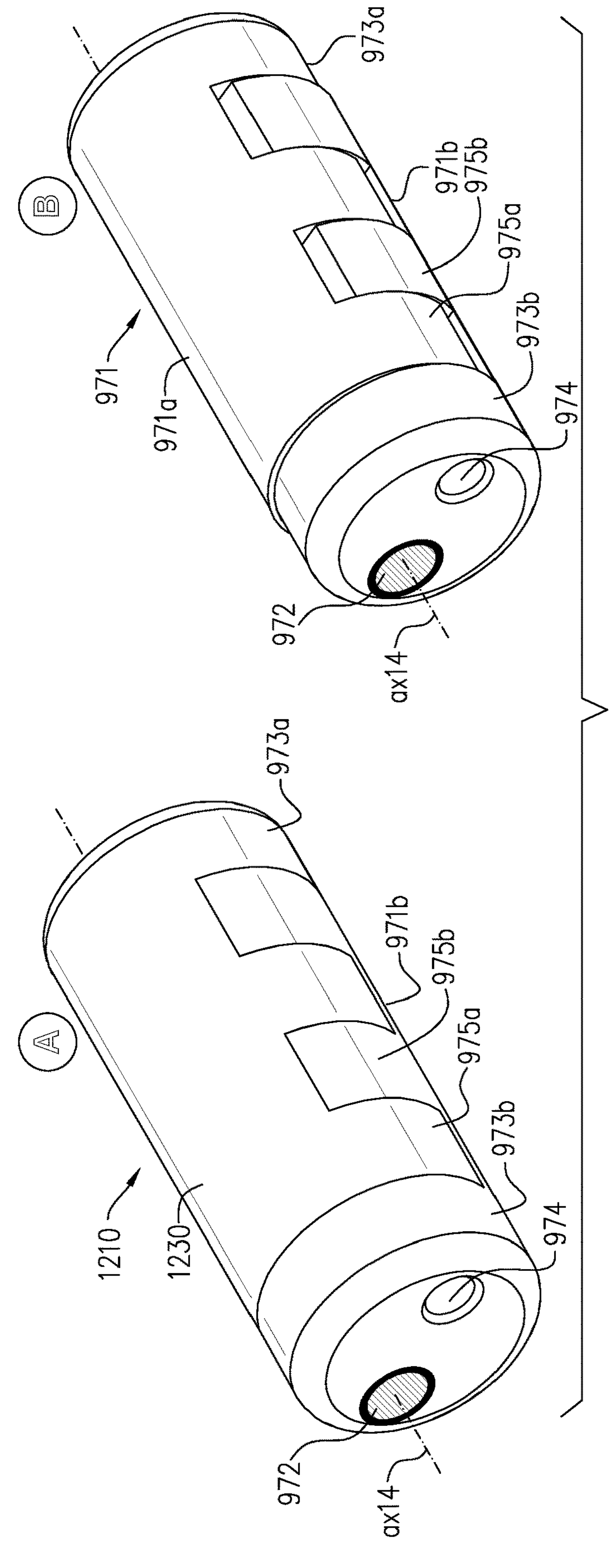
Figure 48C:
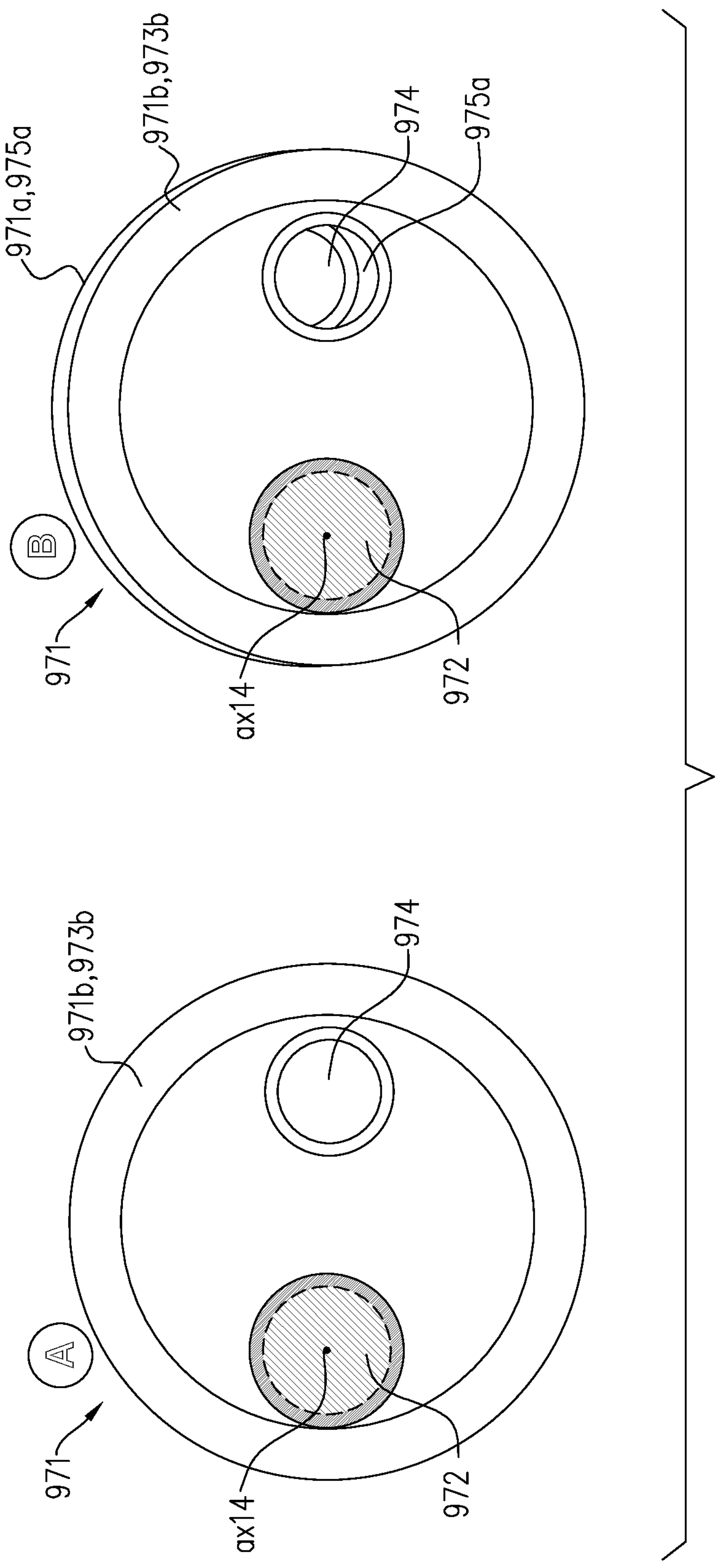
Figure 48E:
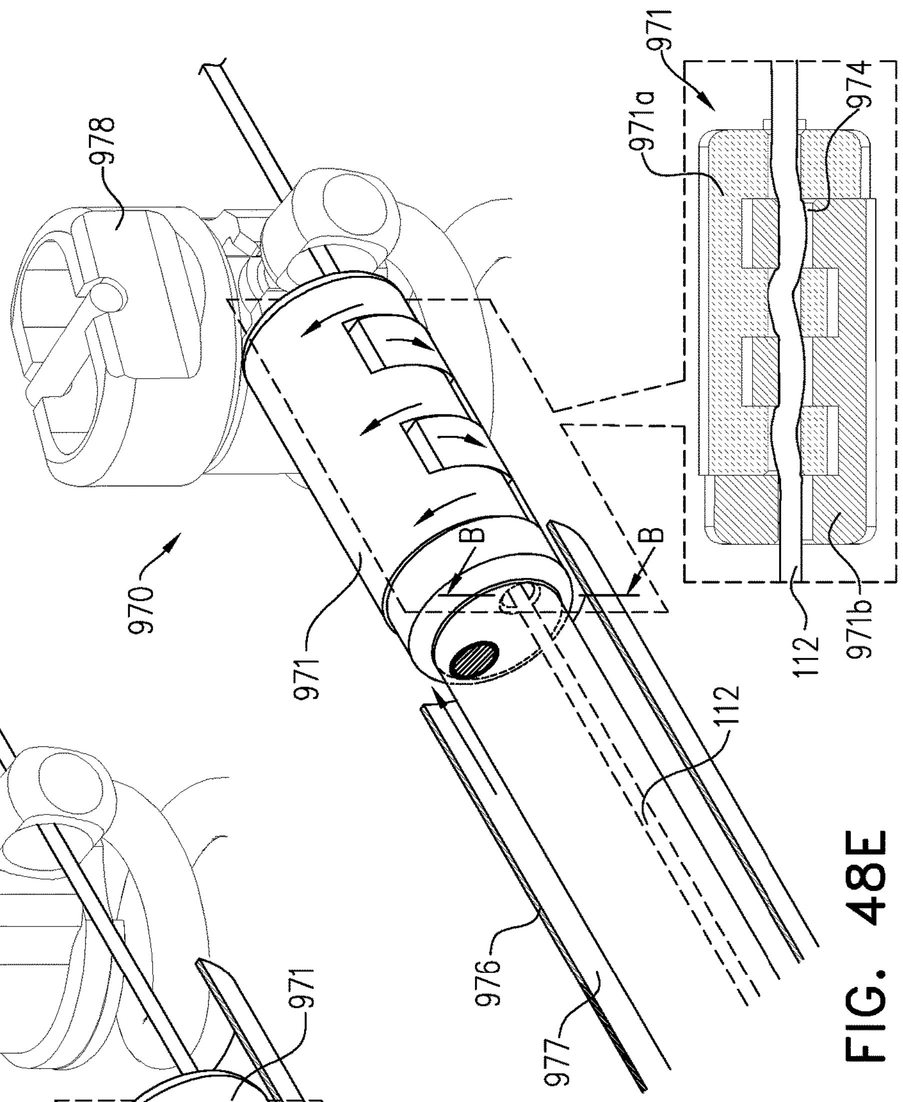
Figure 48D:
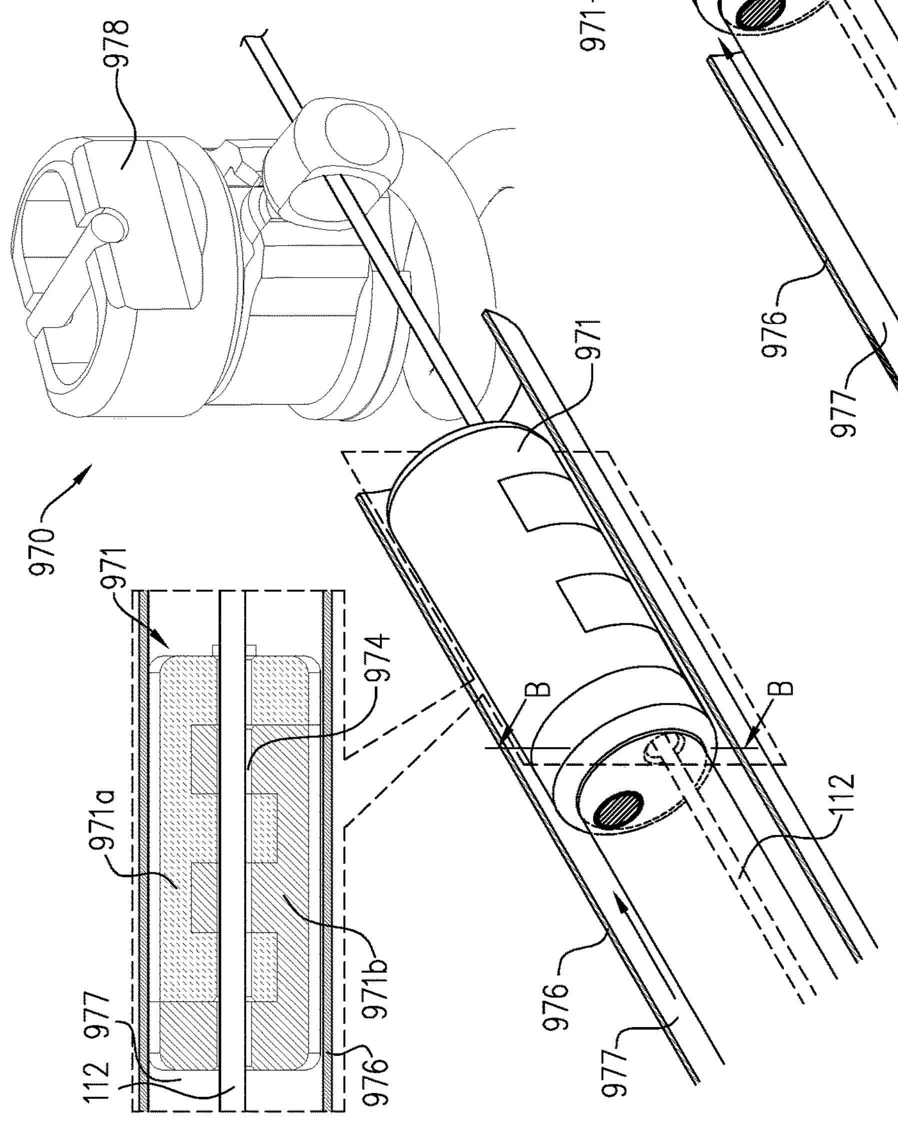

FIGS. 48A-E show system 970 comprising stopper 971, e.g., for use with system 100 in place of stopper 114*b*. FIG. 48A shows an exploded view of the stopper, FIG. 48B shows a perspective view of the stopper in both an open state ("A") and a grip state ("B"), FIG. 48C shows an end-view of the stopper in the open state ("A"), and the grip state ("B"), and FIGS. 48D-E show the stopper being delivered using tool 976 in the open state (FIG. 48D), and transitioning to the grip state upon being delivered out of the delivery tool (FIG. 48E).

Stopper 971 comprises a first element 971*a* and a second element 971*b*. Each of these elements comprises at least one plate, and often comprises multiple plates rigidly coupled to each other. For example, first element 971*a* comprises a primary plate 973*a*, and one or more auxiliary plates 975*a*, and second element 971*b* comprises a primary plate 973*b*, and one or more auxiliary plates 975*b*.

Each plate of element 971*a* defines a respective passageway 974*a* therethrough. For applications in which element 971*a* comprises multiple plates, each defining a respective passageway 974*a*, the multiple passageways 974*a* can be aligned with each other, e.g., as shown. Similarly, each plate of element 971*b* defines a respective passageway 974*b* therethrough. For applications in which element 971*b* comprises multiple plates, each defining a respective passageway 974*b*, the multiple passageways 974*b* can be aligned with each other, e.g., as shown.

In at least some states of stopper 971, the two elements are arranged such that passageways 974*a* and 974*b* collectively define a channel 974 through the stopper. Stopper 971 can be configured to be threaded onto tether 112, with the tether extending through channel 974.

For applications in which each of elements 971*a* and 971*b* comprise multiple plates, they can be coupled with the auxiliary plates intercalating with each other, e.g., as shown.

First element 971*a* can be coupled to second element 971*b* via a torsion bar 972, in a manner in which the torsion bar biases the stopper towards a grip state of the stopper (the term "grip state" is explained hereinbelow). In the grip state, first passageway 974*a* and second passageway 974*b* are offset with respect to each other. This bias can be achieved by torsion bar 972 being fixedly attached (e.g., welded, brazed, or adhered) both to primary plate 973*a* of first element 971*a*, and to primary plate 973*b* of second element 971*b*, e.g., in a manner in which the two plates are biased to being positioned offset with each other.

Although torsion bar 972 biases stopper 971 toward the grip state of the stopper, the stopper can be transitioned into an "open state" (the term "open state" is explained hereinbelow) by increasing stress on the torsion bar, such that the torsion bar twists about itself (i.e., about a central longitudinal axis ax14 of the torsion bar), such that alignment between passageways 974*a* and 974*b* is increased. In the open state of stopper 971, tether 112 is slidable through channel 974.

In some applications, tool 976 defines a cavity 977, for holding stopper 971 in the open state. In some applications, tool 976 is a delivery tool, e.g., a catheter or sheath, for delivering stopper 971 towards the heart of the subject, and at least a portion of the delivery tool defines the cavity. In some applications, stopper 971 is dimensioned such that while the stopper is disposed within the cavity, the tool maintains the stopper in the open state. This can be achieved by the cavity being sufficiently narrow such that the walls of cavity 977 press against first element 971*a* (e.g., at least primary plate 973*a* thereof), and second element 971*b* (e.g., at least primary plate 973*b* thereof), thus forcing the alignment of the two elements with respect to each other. Transitioning of stopper 971 into its open state twists (i.e., increases torsional stress on) torsion bar 972. In some applications, stopper 971 is transitioned into its open state by introducing the stopper into cavity 977.

In some applications, tether 112 is adapted to extend, from within the heart where it can be a component of an implant (e.g., implant 110), through the delivery tool, and out of the subject. For some such applications, stopper 971 is transluminally advanceable, within tool 976, over and along tether 112 towards the heart of the subject, whilst the stopper is threaded on the tether and is maintained in the open state.

In some applications, cavity 977 is a lumen that extends through the delivery tool, and stopper 971 is slidable, through the lumen and over and along the tether towards the heart. Optionally, tool 976 advances cavity 977 toward the heart with stopper 971 disposed therein (e.g., stationary within the cavity).

The torsional stress of torsion bar 972 in the open state of is such that ejecting stopper 971 from the cavity 977 of tool 976, such as out of a distal part of the delivery tool and into the heart of the subject, transitions the stopper towards the grip state, by torsional de-stressing of the torsion bar (i.e., the torsion bar twisting about central longitudinal axis ax14). This causes passageways 974*a* and 974*b* to become less aligned with each other, and thus gripping the tether within channel 974, as is shown in the enlarged view of the stopper in FIG. 48E. That is, the offset between passageways 974*a* and 974*b* is such that the tether is no longer slidable through the stopper, and thus the tether is essentially trapped within the stopper.

In some applications, the torsional de-stressing of torsion bar 972 upon ejection from tool 976 is induced by the removal of the pressing on elements 971*a* and 971*b* by the walls of cavity 977, such that torsion bar 972 becomes free to torsionally de-stress (at least in part), moving at least primary plates 973*a* and 973*b* with respect to each other.

In some applications, and as shown, the first element 971*a* and the second element 971*b* are adapted to fit conformably together, with the auxiliary plates intercalating with each other. In some applications, first element 971*a* is identical to second element 971*b*. In some applications, first element 971*a* is a mirror image of second element 971*b*.

In some applications, in the open state of stopper 971, the two elements assume a cylindrical configuration, as is shown by FIGS. 48B-C. In some applications, cavity 977 has a generally circular cross-section, such that stopper 971, held in the open state, is slidable snugly therethrough.

In some applications, in the grip state of stopper 971, the auxiliary plates 975*a* of first element are offset with auxiliary plates 975*b* of second element 971*b*, such that, in the grip state of the stopper, the first element and the second are less conformably fitted together. For applications in which stopper 971 is cylindrical in its open state, the stopper can become less cylindrical in its grip state, e.g., as illustrated by state "B" of FIGS. 48B-C.

Reference is made to FIGS. 49A-D, which are schematic illustrations of at least some steps in a technique for use with an implant that is coupled to the heart of a subject, in accordance with some applications. In some applications, the technique is used with an implant that includes a tether that is locked under tension and can also include multiple anchors that are coupled to tissue of the heart and slidably coupled to the tether. For example, and as shown in FIGS. 49A-D, the technique can be used with implant 110. The technique can be performed on a living animal or a non-living simulation. Other examples of implants with which the technique can be used include implants or annuloplasty structures described in one or more of the following, each of which is incorporated herein by reference:

- U.S. patent application Ser. No. 14/437,373 to Sheps et al., filed Apr. 21, 2015, which published as US 2015/0272734 (now U.S. Pat. No. 9,949,828);
- U.S. patent application Ser. No. 15/782,687 to Iflah et al., filed Oct. 12, 2017, which published as US 2018/0049875 (now U.S. Pat. No. 10,765,514);
- U.S. patent application Ser. No. 16/534,875 to Brauon et al., filed Aug. 7, 2019, which published as US 2020/0015971 (now U.S. Pat. No. 11,123,191);
- International Patent Application PC T/IL2019/050777 to Brauon et al., which published as WO 2020/012481;
- International Patent Application PCT/IB2020/060044 to Kasher et al., which published as WO 2021/084407;
- U.S. patent application Ser. No. 17/145,258 to Kasher et al., filed Jan. 8, 2021, which published as US 2021/0145584; and
- International Patent Application PCT/IB2021/058665 to Halabi et al., filed Sep. 23, 2021, which published as WO 2022/064401.

The technique can be for relieving the tension on the tether of the implant. For example, for applications in which the implant is an annuloplasty structure, at some time after implantation of the implant (e.g., after several months, or several years) it may be determined that it has become advantageous or necessary to implant a prosthetic valve at the native heart valve, e.g., due to further deterioration of the native heart valve. For some such applications the annuloplasty structure and/or the contracted annulus that is contracted by the annuloplasty structure may impede the implantation of a prosthetic valve, and/or may be detrimental to the implanted prosthetic valve. It is therefore hypothesized that, in some applications, it is advantageous to relieve the tension on the tether of the implant, e.g., in order to allow the native heart valve to relax and/or re-expand, prior to implanting the prosthetic valve.

FIG. 49A shows implant 110 implanted at mitral valve 12, e.g., as described hereinabove. In implant 110, the tension can be locked in tether 112 by stopper 114*b*, often by the stopper being locked to a first portion 112' of the tether, e.g., inhibiting the first portion of the tether from sliding with respect to at least one anchor 120, such as by the stopper abutting the anchor.

As described hereinabove, implant 110 may or may not comprise spacers or dividers 170. For the sake of clarity, implant 110 is shown in FIGS. 49A-D without spacers or dividers. The technique described with reference to FIGS. 49A-D can be used with implants that include spacers or dividers such as those described herein, as well as implants that do not include spacers or dividers.

FIG. 49A shows implant 110 having been implanted at valve 12, e.g., as described hereinabove. FIG. 49 may be analogous to FIG. 4A. At some time after implantation of implant 110 (e.g., upon determining that it has become advantageous or necessary to implant a prosthetic valve), an elongate tool 960 that comprises a holder 961 and a cutter 962 is advanced to the implant (FIG. 49B). The stopper that is locking the tension in the tether—in this case stopper 114*b*—is secured to holder 961. For example, and as shown, holder 961 can include a chamber 966, and the stopper can be secured to the holder by advancing the stopper through an opening (e.g., a distal opening) of the holder and into the chamber, e.g., by advancing the opening over the stopper (inset A of FIG. 49B). Furthermore, cutter 962 can be disposed at the opening, and the stopper be passed through the opening and past the cutter into chamber 966, e.g., as shown. Cutter 962 (e.g., a blade thereof) may obstruct stopper 114*b* from re-exiting the chamber via the opening, especially after the cutter has been actuated (inset B of FIG. 49B). In the example shown, cutter 962 is actuated by pulling on one or more pull-wires 963 such that sliding of tapered surfaces with respect to each other causes the cutter to move. For example, tapered surfaces 964 can be fixed to pull-wires 963, and tapered surfaces 965 can be fixed to cutter 962 (e.g., blades thereof), and upon pulling of pull-wires 963, surfaces 965 can slide, with respect to surfaces 964, and toward tether 112. However, other cutters and actuation mechanisms thereof can be used.

Sufficient actuation of cutter 962 cuts tether 112, thereby relieving the tension on the tether (inset B of FIG. 49B). In some applications, and as shown, the tether is cut between stopper 114*b* and the anchor 120 against which the stopper abuts. For some such applications, this is achieved by advancing tool 960 until a distal part of the tool abuts anchor 120 (e.g., an eyelet thereof), e.g., as shown in inset A of FIG. 49B. The cutting forms a first cut end 116' and a second cut end 116" of the tether, the first cut end belonging to first portion 112' of the tether, and the second cut end belonging to a second portion 112" of the tether. In some applications, upon cutting, second portion 112" of the tether pulls second cut end 116" away from cutter 962 and past anchor 120 (e.g., out of an eyelet of the anchor, through which tether 112 had been threaded), thereby relieving tension on the tether. In some applications, second cut end 116" is pulled past only a subset of anchors 120 (e.g., past only the first anchor, i.e., the anchor against which the stopper abutted), and not past another subset of anchors (e.g., a second anchor), thereby remaining coupled to the other subset of anchors.

Figure 49C:
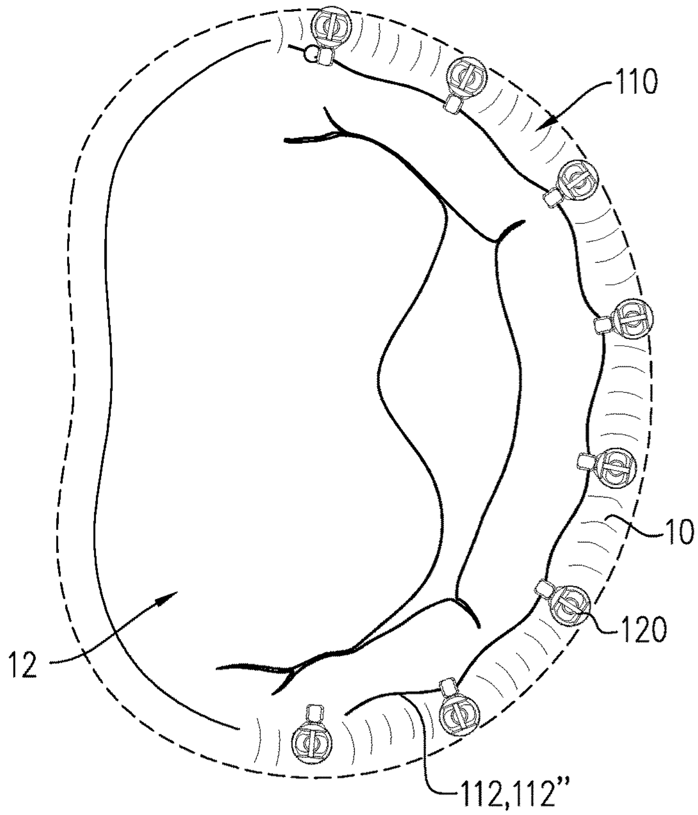
Figure 49D:
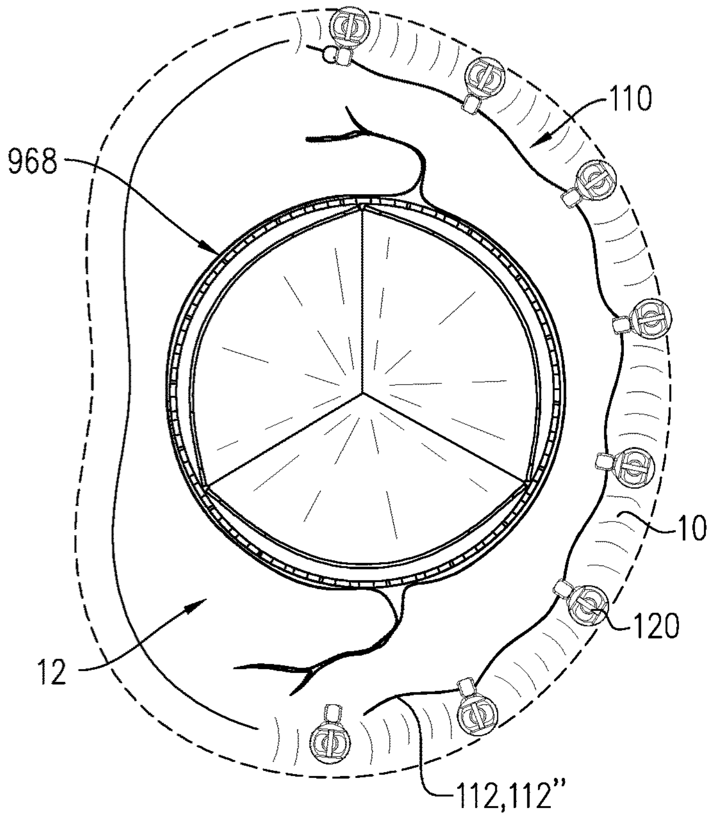

Tool 960, stopper 114*b*, and first portion 112' can then be withdrawn from the subject, leaving second portion 112" of the tether coupled to the heart (inset C of FIG. 49B). FIG. 49C shows the tether (e.g., second portion 112" thereof) having responsively become slack, and mitral valve 12 having relaxed and expanded. FIG. 49D shows a prosthetic valve 968 having been subsequently implanted at (e.g., in) the mitral valve.

There is provided, in accordance with some applications, a method, comprising: to an implant that is coupled to a heart of a subject, transluminally advancing an elongate tool that includes a holder and a cutter, the implant including: (i) a tether under tension, and (ii) a stopper locking the tension in the tether by being locked to a first portion of the tether. The method also includes securing the stopper to the holder.

In some applications, the method includes, while the stopper remains secured to the holder and locked to the first portion of the tether: (a) relieving the tension on the tether by cutting the tether with the cutter; and (b) withdrawing the tool, the stopper, and the first portion of the tether from the subject while leaving a second portion of the tether coupled to the heart.

Although in the example described hereinabove the tension is locked in the tether of the implant by a stopper, it is to be noted that the technique is applicable to implants in which tension is locked in a tether by other means, such as by a knot. Irrespective of whether the tension is locked in the tether by a stopper or by other means, the technique can include removing one portion of the cut tether from the subject, e.g., while leaving the other portion of the tether coupled to the heart. For example, for stopper-locked implants the portion of the cut tether to which the stopper is locked (e.g., first portion 112', described hereinabove) can be removed from the subject; and for knot-locked implants the portion of the tether that includes the knot can be removed from the subject.

There is provided, in accordance with some applications, a method, comprising: (i) transluminally advancing an elongate tool to a tether that is under tension and disposed within a heart of a subject, the elongate tool including a holder and a cutter, (ii) securing a first portion of the tether to the holder, and (iii) while the first portion of the tether remains secured to the holder, (a) relieving the tension on the tether by cutting the tether with the cutter, thereby separating the first portion of the tether from a second portion of the tether; and (b) withdrawing the tool and the first portion of the tether from the subject while leaving the second portion of the tether coupled to the heart.

It is to be noted that, although the technique of FIGS. 49A-D is described being used with an implant that was previously implanted transluminally, in some applications the technique can be used with an implant that was previously implanted surgically.

Figure 50:
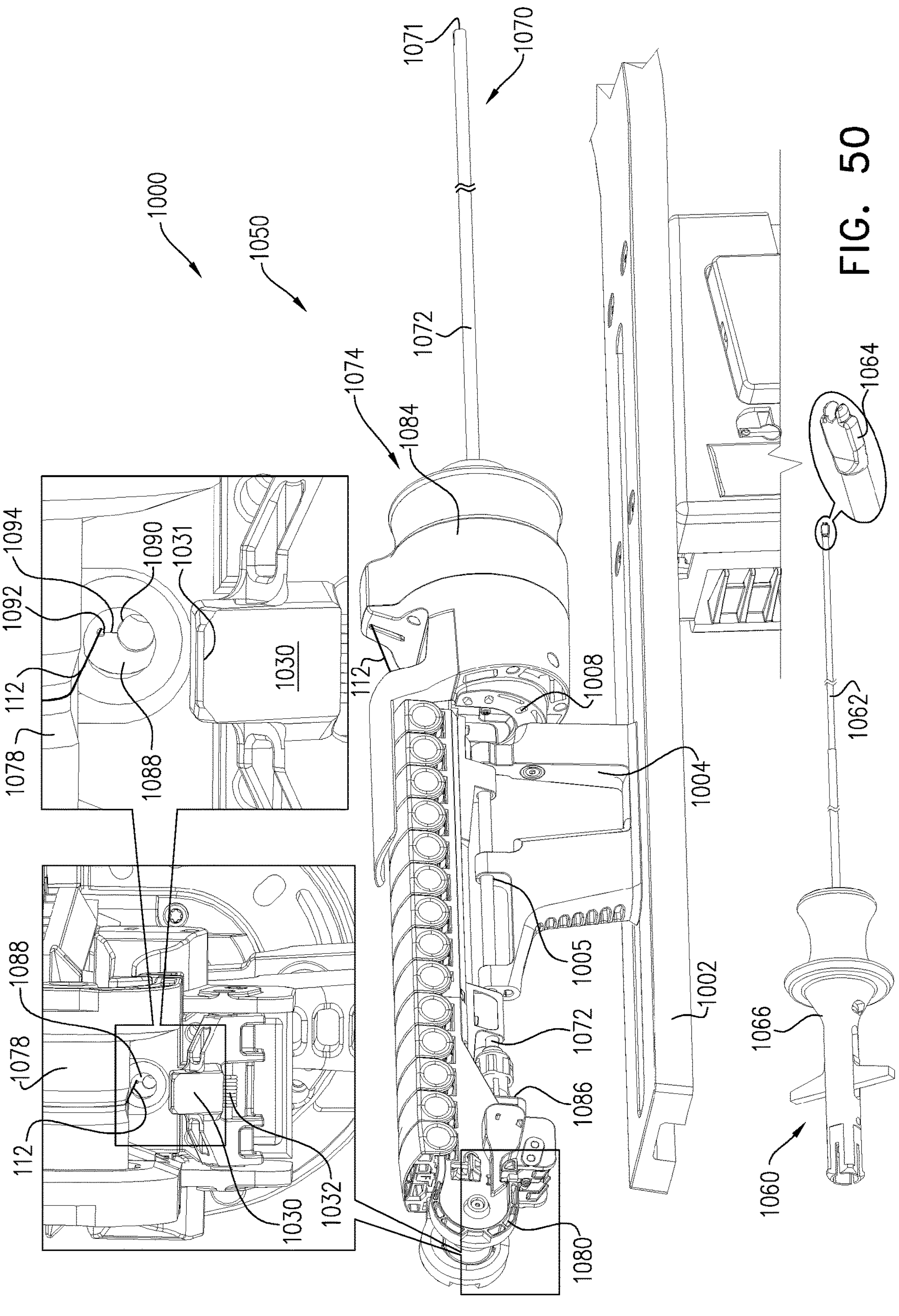
FIGS. 50, 51, 52A-F, and 53A-E are schematic illustrations of a system for use with a subject, in accordance with some applications.

Reference is made to FIGS. 50, 51, 52A-F, and 53A-E, which are schematic illustrations of a system 1000 for use with a subject, in accordance with some applications. FIG. 50 shows an overview of system 1000, which comprises an implant and a delivery tool 1050.

In the description of system 1000, the implant of the system is described and shown as implant 110, which is described in more detail hereinabove e.g., with reference to FIGS. 1A-4B. However, it is to be understood that system 1000 may comprise other implants, mutatis mutandis, e.g., delivery tool 1050 can be used to implant other implants, mutatis mutandis. For example, system 1000 can comprise other implants that comprise, or are anchored with, multiple anchors such as, but not limited to, implants and/or anchors described herein, and/or implants and/or anchors described in WO 2021/084407 to Kasher et al., which is incorporated herein by reference (e.g., implants that comprise multiple anchors slidably coupled to, e.g., threaded onto—a tether). Alternatively or additionally, delivery tool 1050 and/or components thereof can be used, mutatis mutandis, to facilitate implantation of an implant (e.g., an annuloplasty structure) described in WO 2014/064694 to Sheps et al., and/or WO 2016/174669 to Iflah et al., each of which is incorporated herein by reference. Furthermore, and more generally, system 1000 and/or techniques described for use therewith can be used in combination with one or more of the systems and/or techniques described in the references referenced in this paragraph.

As described hereinabove, implant 110 comprises multiple tissue anchors 120 and a tether 112 on which the tissue anchors are threaded. As described in more detail hereinbelow, during implantation only a distal portion of tether 112 remains implanted in the subject, while a proximal portion of the tether remains attached to delivery tool 1050. Nonetheless, for the sake of simplicity, implant 110 is described herein as comprising the tether.

Tissue anchors 120 are distributed in a series along tether 112, and delivery tool 1050 can be used to implant 110 by an anchor driver 1060 being used, for each of anchors 120 consecutively, to advance the anchor distally into the subject and to anchor the anchor to internal tissue of the subject, e.g., as described hereinabove with reference to FIGS. 1A-4B. For example, and as shown, implant 110 can be an annuloplasty implant, implanted by distributing anchors 120 around at least a portion of an annulus of a native heart valve of the subject, such as the mitral or tricuspid valve. Further in some applications, a distal end of tether 112 can be advanced distally into the subject along with the first anchor, and subsequent anchors can be advanced by sliding them distally along the tether.

Delivery tool 1050 comprises an anchor driver 1060, and a catheter device 1070 that comprises a flexible tube (e.g., a catheter) 1072, configured to be advanced into the subject. In some applications, delivery tool 1050 can serve as delivery tool 150, described hereinabove (e.g., with reference to FIGS. 1A-4B). In some applications, tube 1072 can serve as, correspond to, and/or be substituted with tube 152, described hereinabove (e.g., with reference to FIGS. 1A-4B). In some applications, driver 1060 can serve as, correspond to, and/or be substituted with driver 160 or any of the other anchor drivers described hereinabove.

Figure 51:
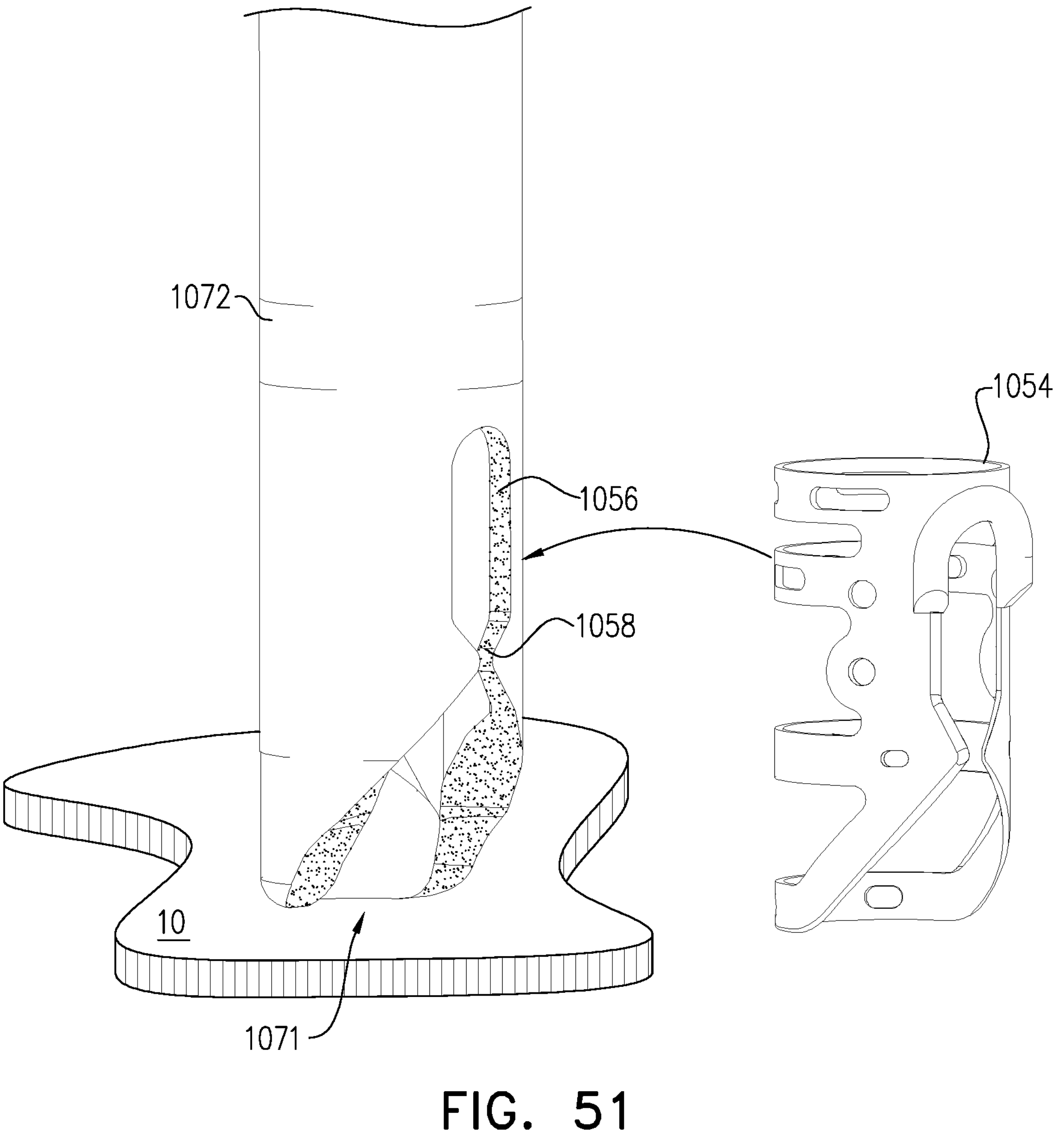

For applications in which implant 110 is an annuloplasty implant, and as shown, tube 1072 can be a transluminally (e.g., transfemorally) advanceable catheter. In some applications, at a distal portion of tube 1072, the tube defines a lateral slit 1056 extending proximally from the distal end of the tube, such that the slit is continuous with distal opening 1071 of the tube (FIG. 51). In some applications, slit 1056 is similar in structure and/or function to slit 156, described hereinabove. For example, slit 1056 allows tether 112 and typically spacers or dividers 170, but not anchors 120, to exit tube 1072 laterally, proximally from the distal end of the tube. However, slit 1056 is shaped to define a narrowed inlet 1058 into the lateral slit, configured to inhibit (although not preclude) the tether from distally exiting the lateral slit, e.g., prematurely and/or inadvertently. In some applications, tube 1072 comprises a tip frame 1054 that maintains (e.g., supports) lateral slit 1056, narrowed inlet 1058, and/or distal opening 1071. For some such applications, tip frame 1054 is resilient, e.g., in order to deform responsively to being pressed against the tissue, so as to reduce a likelihood of injury to the tissue.

Device 1070 further comprises an extracorporeal unit (e.g., an extracorporeal control unit) 1074, configured to remain outside the body of the subject. In some applications, extracorporeal unit 1074 defines, or is coupled to, a handle of device 1070. In some applications, extracorporeal unit 1074 shares one or more features with one or more of extracorporeal units 1074, 1074, and 1474 described in International Patent Application PCT/IB2021/058665 to Halabi et al., filed Sep. 23, 2021, which published as WO 2022/064401, and which is incorporated herein by reference. Furthermore, device 1070 can be used, mutatis mutandis, to facilitate implantation of any of the implants described in US 2021/0145584 to Kasher et al., which is incorporated herein by reference.

Figure 52A:
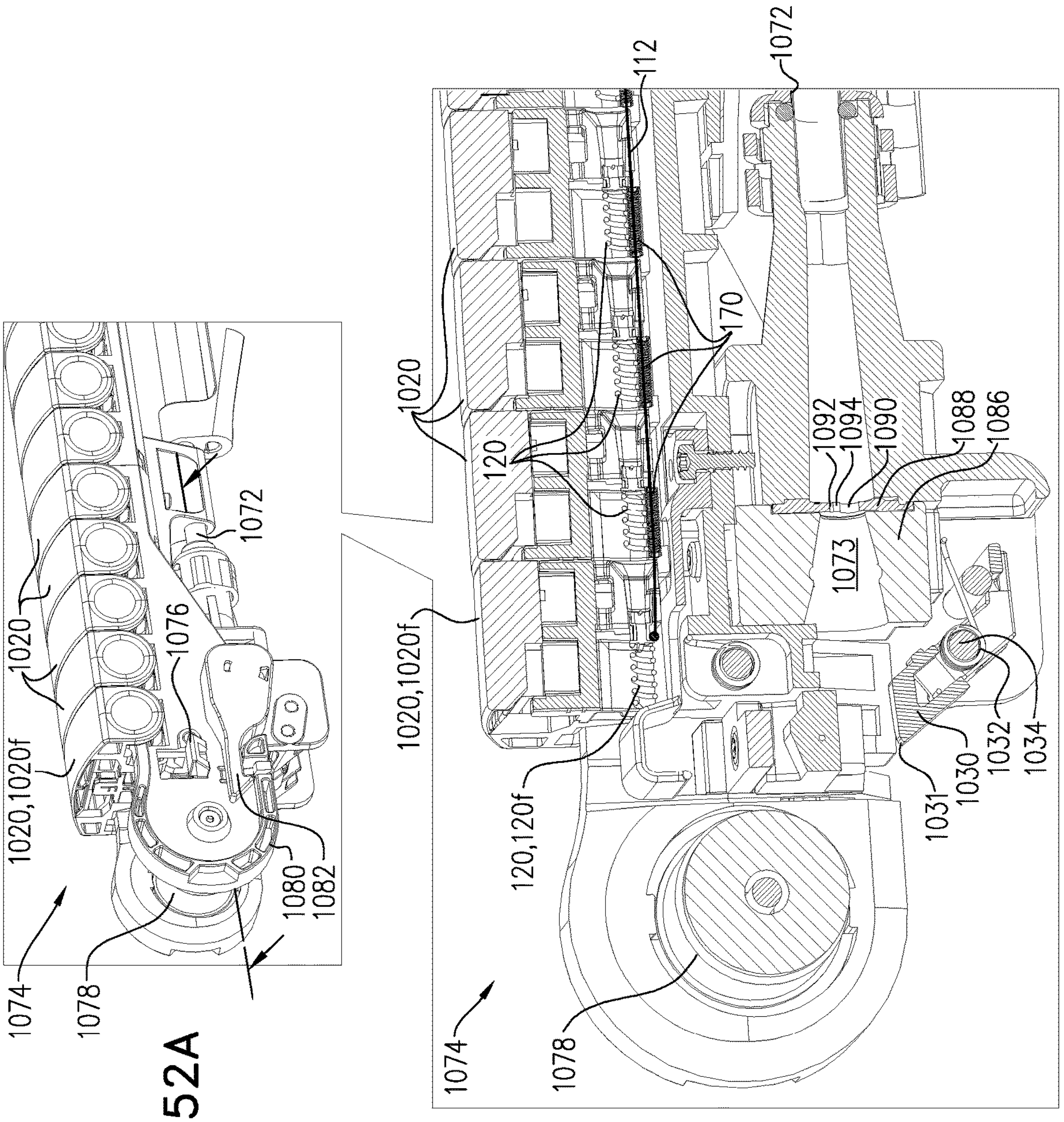
Figure 52B:
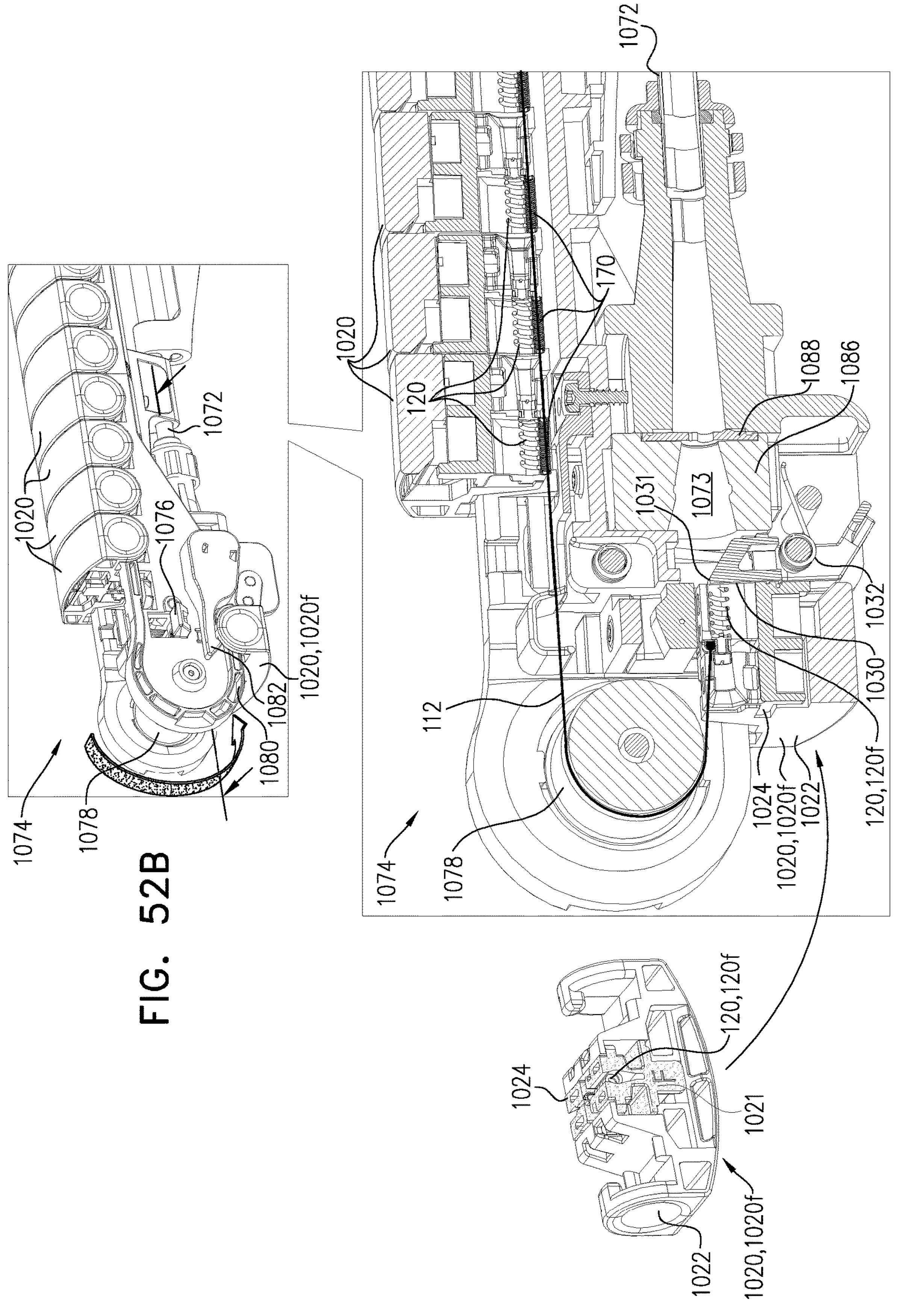

The system/apparatus, e.g., catheter device 1070, comprises a series of cartridges 1020, each holding (e.g., cradling) a respective anchor 120. FIGS. 50 and 52A show an initial state of device 1070, with each of cartridges 1020 coupled to extracorporeal unit 1074 in a respective initial position. In some applications, extracorporeal unit 1074 comprises or defines one or more tracks 1080 (e.g., a groove, as shown, a rail, slots, etc.) along which each cartridge 1020 is moveable (e.g., slidable, etc.), while remaining coupled to the extracorporeal unit, from the respective initial position of the cartridge to a deployment position in which the cartridge holds its tissue anchor 120 opposite a proximal opening 1073 of tube 1072. An example of such movement is shown in the transition between FIG. 52A and FIG. 52B, in which a first cartridge 1020*f* (which holds a first anchor 1200, is moved (e.g., slid) from its initial position (FIG. 52A), into the deployment position (FIG. 52B). This can be performed manually by the operator, who grasps the cartridge by hand. In some applications, a track is not used and the cartridge can be moved into position by other means, e.g., separately attached into position by hand, rotated into position, etc.

As shown, the movement from the initial position to the deployment position can include cartridge 1020 turning around (e.g., around a proximal end of catheter device 1070), e.g., performing a U-turn. Thus, each anchor 120 can be initially oriented with its tissue-engaging element 130 pointing proximally with respect to catheter device 1070 (FIG. 52A), and subsequently becomes oriented with its tissue-engaging element pointing distally with respect to the catheter device (FIG. 52B). Furthermore, cartridges 1020 are therefore typically initially arranged in “reverse” order, with first cartridge 1020*f* being the most proximal of the cartridges with respect to delivery tool 1050 overall (FIGS. 50 and 52A). Similarly, the distal end of tether 112 can be initially the most proximally-positioned part of the tether.

As described hereinabove, first anchor 120*f* is inhibited from sliding off of tether 112, e.g., by stopper 114*a*, or by being fixedly attached to the tether. Therefore, first cartridge 1020*f*, carrying first anchor 120*f*, brings the distal end of tether 112 with it to the deployment position (FIG. 52B). In some applications, and as shown, this arrangement is facilitated by device by extracorporeal unit 1074 comprising a bearing (e.g., a sheave, or pulley wheel) 1078 (e.g., a proximal bearing) around which tether 112 turns. Track 1080 guides each cartridge from its initial position, around bearing 1078 where it performs the U-turn, and to the deployment position.

It is hypothesized that configuring device 1070 as described hereinabove, with tether 112 extending proximally and then distally, advantageously positions cartridges 1020 in a manner that is particularly accessible to the operator. For example, it allows each cartridge 1020 (and the anchor 120 within), in turn, to be accessible at a proximal end of catheter device 1070 without obstruction by a subsequent cartridge.

In some applications, each cartridge 1020 is configured to lock to extracorporeal unit 1074 upon arriving at the deployment position. Such a configuration can be achieved, for example, using a latch mechanism, e.g., with extracorporeal unit 1074 comprising one or more latches 1082, and each cartridge 1020 being correspondingly shaped to be locked to by the one or more latches. Latches 1082 can be elastic or spring-loaded, such that they transiently flex (e.g., outward) responsively to the arrival of cartridge 1020, and then automatically lock to the cartridge upon the cartridge becoming fully positioned at the deployment position (e.g., a snap fit).

System 1000 is configured for anchor driver 1060 to, for each anchor 120 in turn, engage the anchor while its cartridge 1020 is in the deployment position, advance the anchor distally out of the cartridge and through tube 1072, and drive the anchor into tissue (e.g., tissue of the heart). This is represented in FIG. 52E. However, in some applications, and as shown, extracorporeal unit 1074 comprises a barrier 1030 that, in a closed state thereof, obstructs proximal opening 1073. In this context, “obstruct” does not necessarily mean that barrier 1030 covers opening 1073 completely. Rather, as shown, “obstruct” may mean that the barrier is an obstacle to anchor 120 exiting cartridge 1020 and/or entering tube 1072 via proximal opening 1073, e.g., by the barrier being disposed directly between the anchor in the cartridge and the proximal opening of the catheter. However, in some applications, barrier 1030 can be configured to cover opening 1073 completely.

Each cartridge 1020 is movable along track 1080 from its initial position to the deployment position such that, in the deployment position, the cartridge holds the respective anchor opposite the proximal opening, and barrier 1030 is in its closed state. In some applications, barrier 1030 can be closed (e.g., manually, and/or via a separate step) prior to movement of the cartridge into the deployment position. In some applications, and as shown, barrier 1030 is configured to transition into its closed state responsively to movement of the cartridge toward the deployment position, e.g., responsively to arrival of the cartridge at the deployment position (FIG. 52B). In the particular example shown, cartridge 1020 (e.g., a face 1021 defined thereby) is configured to push barrier 1030 into its closed state upon arrival of the cartridge at the deployment position.

Figure 52C:
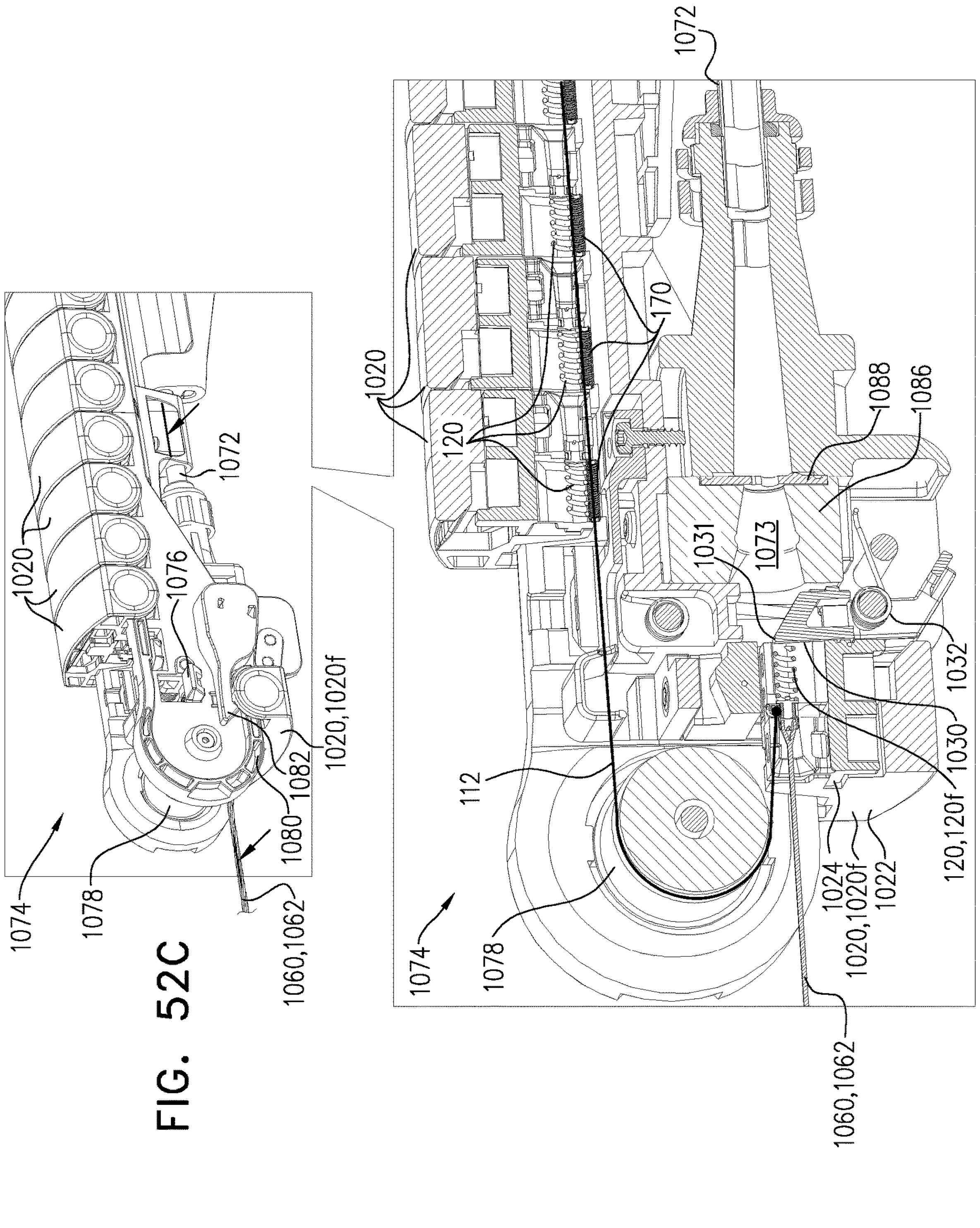
Figure 52D:
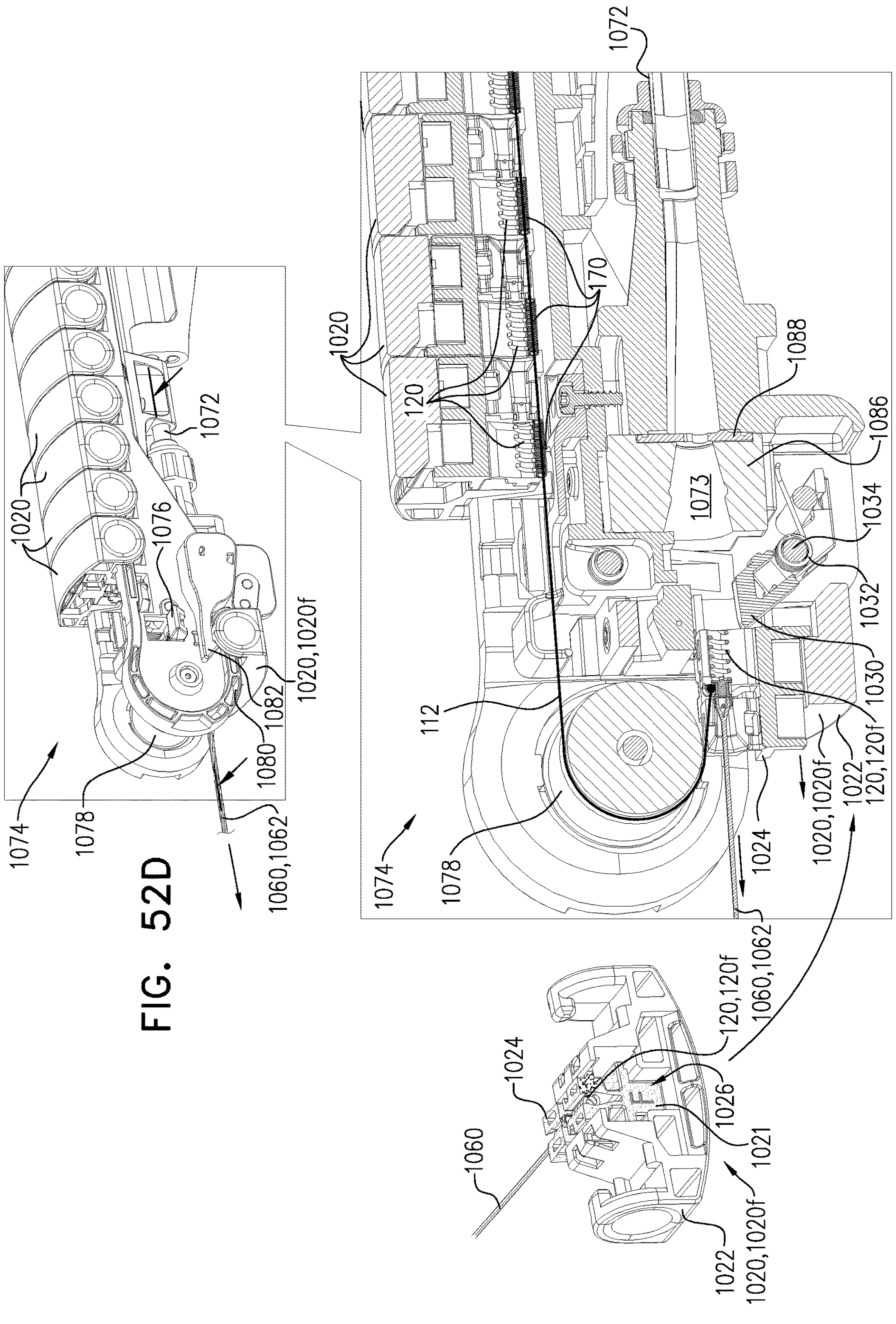
Figure 52E:
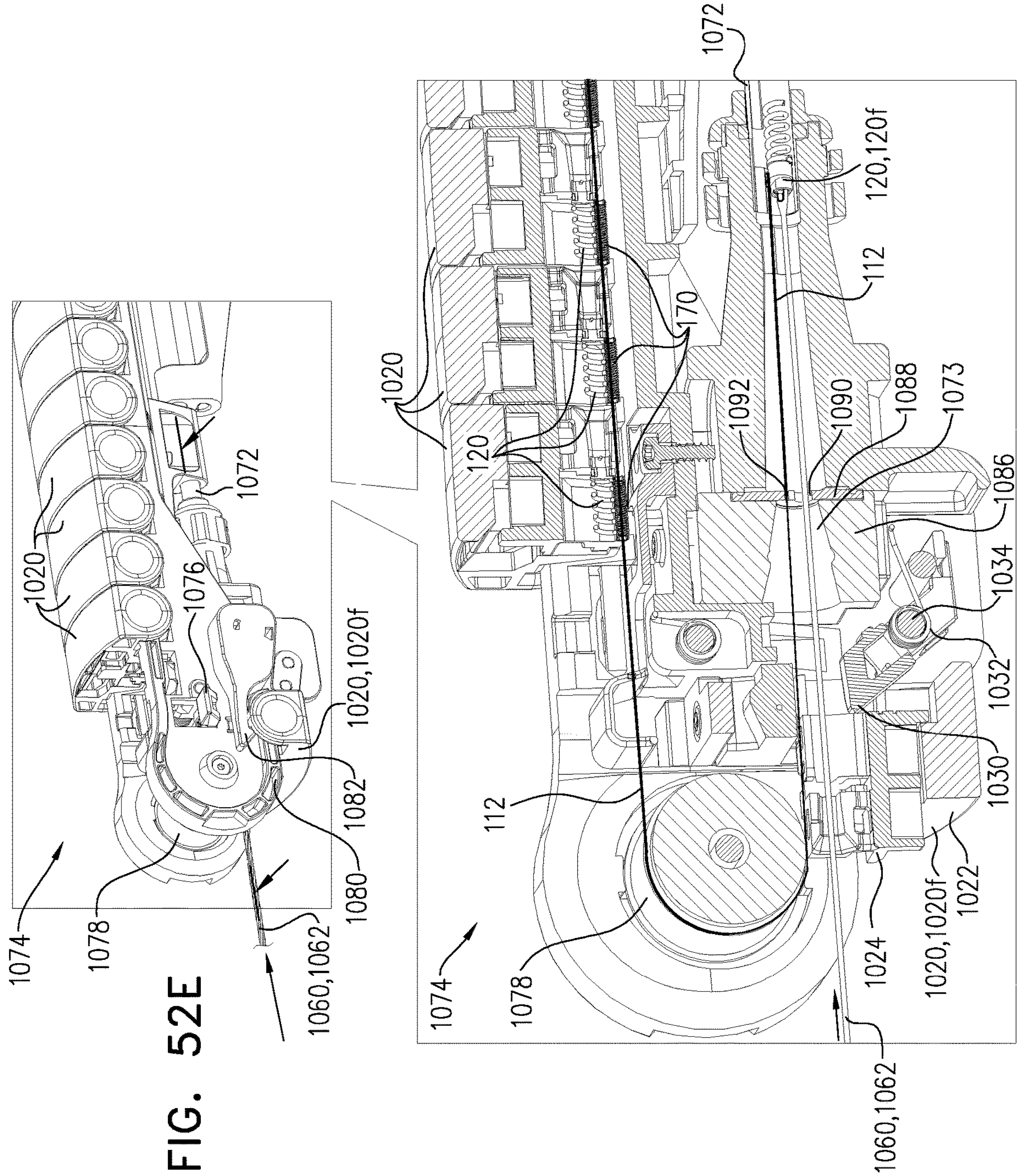

Once cartridge 1020 is in the deployment position, holding anchor 120 opposite proximal opening 1073 of tube 1072, the operator engages anchor driver 1060 with the anchor—e.g., to interface 182 of head 180 of the anchor (FIG. 52C). Anchor driver 1060 can comprise an elongate and flexible shaft 1062, a driver head 1064 coupled to the distal end of the shaft, and an actuating handle 1066 configured to reversibly engage the driver head with anchor 120, e.g., via a control rod extending from the handle to the driver head. While driver 1060 is engaged with anchor 120, a force can be applied by the driver to the anchor that transitions barrier 1030 into its open state (FIG. 52D). This force can be an engagement-verification force that challenges the engagement of the anchor by the anchor driver. System 1000 is configured to define a threshold magnitude of the force, such that the barrier transitions into the open state responsively to the force only upon the force exceeding the threshold magnitude. In the example shown, this threshold magnitude can be defined primarily by the configuration of each cartridge 1020. However, it is to be noted that the scope of the disclosure includes other components of system 1000 contributing to the defining of the threshold magnitude. Should anchor driver 1060 be suboptimally engaged with anchor 120, it becomes disengaged from the anchor upon application of the force below the threshold magnitude, and barrier 1030 remains closed. To proceed further, the driver (or a new driver) must be re-engaged with the anchor. Only upon successful application of the force to the anchor at or above the threshold magnitude, thereby verifying engagement of the anchor, does barrier 1030 open, allowing driver 1060 to advance anchor 120 distally beyond the barrier and into and through tube 1072. It is hypothesized that such a configuration reduces a likelihood of a suboptimally-engaged anchor being inadvertently prematurely released from driver 1060 within tube 1072 or the body of the subject (e.g., prior to anchoring in the tissue), and/or an inability of the driver to apply the force required to drive the anchor into the tissue.

In the example shown, the force (e.g., the engagement-verification force) is a proximal pulling force. However, it is to be understood that the scope of the disclosure includes the use of other forces, such as torque, mutatis mutandis.

In some applications, and as shown, the force (e.g., the engagement-verification force) applied by driver 1060 to anchor 120 transitions barrier 1030 into its open state by inducing a conformational change in cartridge 1020, e.g., barrier 1030 can be configured to transition into its open state responsively to the conformational change.

In some applications, and as shown, barrier 1030 can be biased (e.g., by a spring-loaded displacement mechanism, such as a spring 1032) toward being in its open state.

In some applications in which (i) barrier 1030 opens responsively to a conformational change in cartridge 1020, and (ii) the barrier is biased toward being open, arrival of cartridge 1020 at the deployment position while in a first conformation applies a closing force to barrier 1030 (FIG. 52B), and the conformational change in the cartridge caused by the engagement-verification force relieves (e.g., removes) the closing force from the barrier, thereby allowing the barrier to open (FIG. 52D). In the example shown, barrier 1030 is pivotably mounted (e.g., on a pin 1034), and opens and closes by pivoting. In some applications, and as shown, the closing force is a distally-directed pushing force applied by cartridge 1020 (e.g., face 1021 thereof) pressing against barrier 1030, e.g., a leading edge 1031 thereof.

In some applications, and as shown, each cartridge 1020 comprises a first piece 1022 and a second piece 1024, e.g., each of the pieces being a respective monolithic structure made from a single piece of material.

In some applications, and as shown, cartridge 1020 is coupled to extracorporeal unit 1074 via coupling between first piece 1022 and the extracorporeal unit, e.g., by the first piece being slidably engaged with track 1080. In some applications, and as shown, first piece 1022 is shaped and/or positioned to be grasped by hand by a human operator.

In some applications, and as shown, second piece 1024 holds (e.g., cradles) anchor 120. In some applications, and as shown, second piece 1024 is mounted inside first piece 1022.

In some applications, the conformational change described hereinabove includes relative movement between pieces 1022 and 1024, such that face 1021 becomes displaced, thereby relieving the closing force. For example, and as shown, the conformational change can include second piece 1024 sliding proximally with respect to first piece 1022, e.g., being pulled proximally by the proximally-directed engagement-verification force applied to anchor 120 by driver 1060, thereby displacing face 1021 proximally (FIG. 52D). For such applications, face 1021 can be defined by second piece 1024. For applications in which second piece 1024 is mounted inside first piece 1022 and holds anchor 120, this proximal movement/displacement creates a distal-facing recess 1026 in cartridge 1020 (e.g., within the first piece, where the second piece previously resided), into which barrier 1030 can move (e.g., pivot) as it returns toward its open state.

For applications in which opening of the barrier is achieved by inducing a conformational change in cartridge 1020, the threshold magnitude can be defined at least partly by the configuration of each cartridge, e.g., a resistance to the conformational change. For example, for applications in which the conformational change includes relative movement between pieces of the cartridge (e.g., between pieces 1022 and 1024), the threshold magnitude can be defined at least partly by resistance of the cartridge to the movement between its pieces. For example, the pieces can be fitted to have a particular degree of friction between them, and/or the cartridge can define a ridge or catch that is only overcome by the force exceeding the threshold magnitude.

Figure 52F:
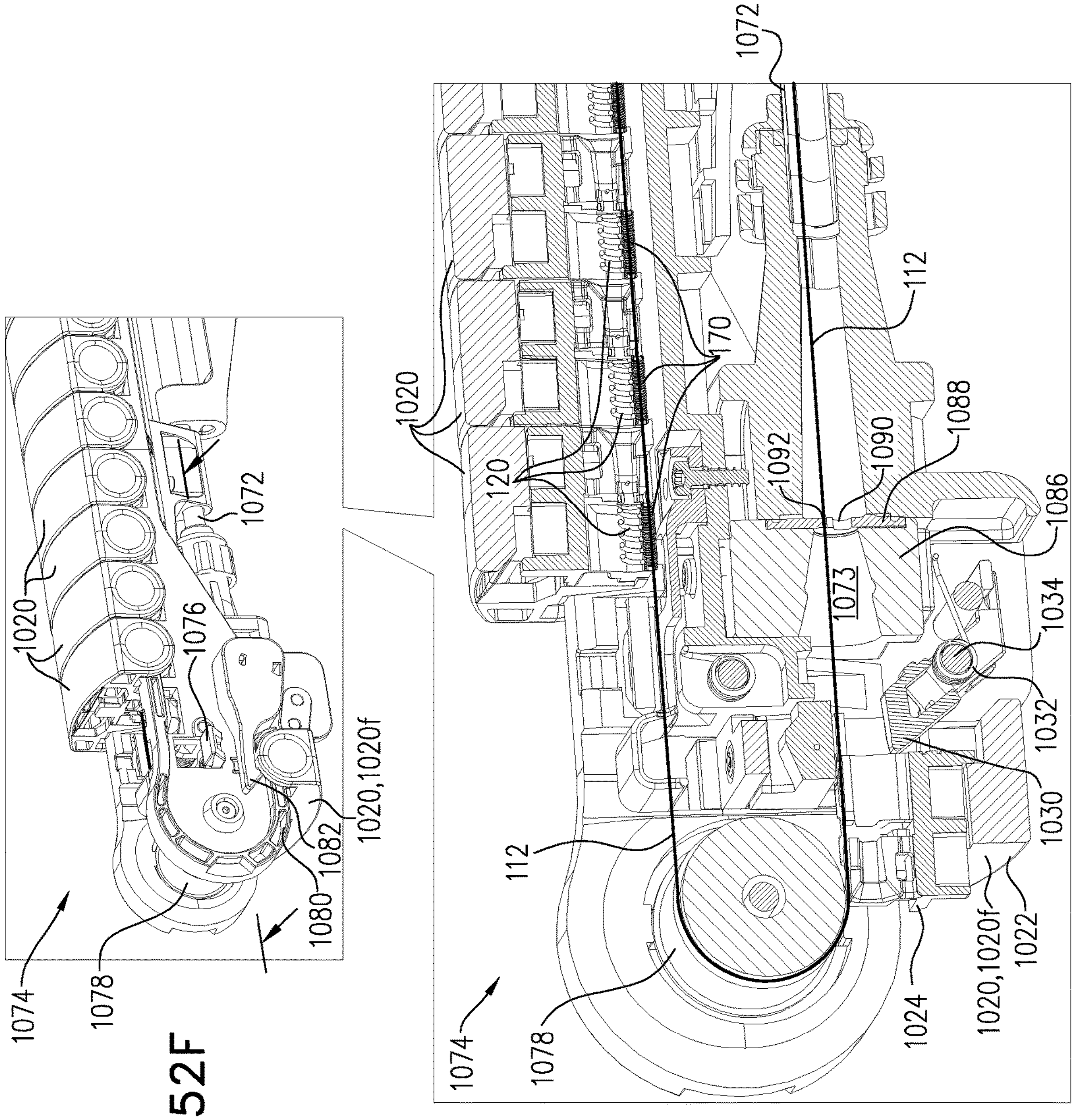

Once barrier 1030 is open, driver 1060 can be used to advance anchor 120 distally beyond the barrier, through opening 1073 into tube 1072 (FIG. 52E), and through the catheter to the tissue (e.g., to tissue of the heart), and to anchor the anchor to the tissue. As shown, this can be performed while cartridge 1020 remains in the deployment position, e.g., with driver 1060 (e.g., shaft 1062 thereof)

extending through the cartridge. After anchoring, driver 1060 can be disengaged from anchor 120 and withdrawn (FIG. 52F).

As described hereinabove, because first anchor 120*f* is inhibited from sliding off of tether 112 first cartridge 1020*f*, carrying first anchor 120*f*, brings the distal end of tether 112 to the deployment position (FIG. 52B). Similarly, advancement of first anchor 120*f* advances the distal end of tether 112 through tube 1072 to the tissue, and anchoring the first anchor anchors the distal end of the tether to the tissue. Upon withdrawal of driver 1060, tether 112 remains extended through tube 1072 (FIG. 52F), such that advancement of subsequent anchors 120 through the catheter includes sliding the subsequent anchors over and along the tether toward the previously-anchored anchors.

For each cartridge 1020, once its anchor 120 has been anchored, the cartridge is removable from the deployment position such that the deployment position becomes vacant for a successive cartridge. In some applications, removal of cartridge 1020 is facilitated by actuating a release latch 1076 on extracorporeal unit 1074. In some applications, removal of the cartridge from the deployment position involves removal of the cartridge from extracorporeal unit 1074 entirely. This can be facilitated by cartridge 1020 being slidably coupled to tether 112 only via anchor 120, and thereby becoming decoupled from the tether upon the anchor exiting the cartridge. In some applications, removal of the cartridge is performed after driver 1060 has been withdrawn, and in some applications the driver (e.g., its presence within the cartridge) may inhibit removal of the cartridge.

In some applications, extracorporeal unit 1074 comprises a tensioner 1084 (e.g., comprising a spring-loaded winch) that, during implantation of implant 110, reduces slack on tether 112 and/or generally manages the tether. It is hypothesized that advantageously reduces a likelihood of tether 112 becoming twisted or entangled, or of inadvertent engagement of the tether with the anchor being delivered. It is further hypothesized that reducing slack using a winch, rather than by a human operator manually pulling on a proximal end of the tether, advantageously provides greater control over the magnitude and consistency of tension applied to the tether, and may further advantageously reduce the number of human operators required. In some applications, tensioner 1084 is as described in International Patent Application PCT/IB2021/058665 to Halabi et al., filed Sep. 23, 2021, which published as WO 2022/064401, and which is incorporated herein by reference. It is to be noted, however, that aspects of system 1000 (such as, but not limited to, cartridges 1020 and barrier 1030) can be used independently of tensioner 1084 (or of any tensioner). Thus, the scope of the present disclosure includes variants of system 1000 that do not comprise tensioner 1084, and variants that do not comprise any tensioner.

As shown, for applications in which spacers or dividers 170 (or variants thereof) are used (i.e., for applications in which implant 110 comprises the spacers or dividers), prior to implantation they can be disposed at extracorporeal unit 1074, threaded on tether 112 alternatingly with anchors 120. In some applications, each cartridge 1020 can hold one of the spacers, such as the spacer that will precede the anchor housed by the cartridge (as shown), or the spacer that will follow the anchor housed by the cartridge.

In some applications, a port 1086 is disposed at proximal opening 1073 of tube 1072. Port 1086 can have a tapered lumen that facilitates smooth advancement of anchors 120 into tube 1072.

Port 1086 can comprise a membrane 1088 that provides hemostatic sealing during the implantation procedure. Membrane 1088 can be formed from a silicone. The material (e.g., the silicone) from which membrane 1088 is formed can have a hardness of 38-42 (e.g., 40) Shore A. Membrane 1088 can be about 1 mm thick. Membrane 1088 can be oriented substantially transversely to the proximal end of tube 1072.

Membrane 1088 can be shaped to define a first aperture 1090 and a second aperture 1092, connected by a closed slit 1094. In some applications, first aperture 1090 is larger (e.g., at least twice as large, e.g., at least three times larger, e.g., 3-10 times larger, such as at least 4 times larger) in diameter than second aperture 1092. For example, first aperture 1090 can be 1.5-2.5 mm (e.g., 1.7-2.2 mm, e.g., 1.8-2.0 mm, such as 1.9 mm) in diameter, whereas second aperture 1092 can be 0.2-0.7 mm (e.g., 0.2-0.6 mm, e.g., 0.3-0.5 mm, such as 0.4 mm) in diameter.

As shown, port 1086 (e.g., membrane 1088 thereof) can be oriented such that first aperture 1090 lies on the axis along which driver 1060 and the tissue-engaging element of anchor 120 is advanced. While a cartridge 1020 is in the deployment position (FIG. 52B), the tissue-engaging element of its tissue anchor 120 can be aligned with first aperture 1090, thereby defining the anchor-advancement axis from the tissue anchor, through the first aperture, and through tube 1072.

As also shown, second aperture 1092 typically lies on the axis along which tether 112 is advanced. Each anchor can be advanced through membrane 1088 with (i) its central longitudinal axis and/or tissue-engaging element aligned with first aperture 1090, and (ii) its eyelet, which is threaded onto tether 112, aligned with second aperture 1092.

It is to be noted that typically neither aperture 1090 (and thereby the anchor-advancement axis) nor aperture 1092 is aligned centrally with respect to tube 1072. Rather, the center of first aperture 1090 can be disposed on one side of the central axis of the catheter, and the center of second aperture 1092 can be disposed on the opposite side of the central axis of the catheter. However, for applications in which first aperture 1090 is sufficiently large, the first aperture can overlap the central axis of the catheter (despite nonetheless not being centered on the central axis of the catheter).

As each anchor 120 passes membrane 1088 distally, slit 1094, and typically also apertures 1090 and 1092, responsively open or widen transiently and then close or re-narrow behind the anchor.

In some applications, aperture 1090 is dimensioned to seal around driver 1060 (e.g., shaft 1062 thereof), which can be narrower than the head of anchor 120. For example, in some applications the diameter of aperture 1090 is 80-120 percent (e.g., 90-110 percent) the thickness of shaft 1062.

In some applications, aperture 1092 is dimensioned to seal around tether 112, which is narrower than the eyelet of anchor 120. For example, in some applications the diameter of aperture 1092 is 50-200 (e.g., 80-120 percent, such as 90-110 percent) the thickness of tether 112.

When driver 1060 is withdrawn proximally through membrane 1088, tether 112 typically remains extended through second aperture 1092 (FIG. 52F).

It is hypothesized that the double-aperture configuration of membrane 1088 advantageously provides better hemostatic sealing for the implantation procedure compared to other configurations, such as single larger aperture or slit. For example, during anchoring of an anchor 120 (at which time tether 112 and shaft 1062 extend through membrane 1088) slit 1094, disposed between the tether and the driver, can be closed.

Figure 56A:
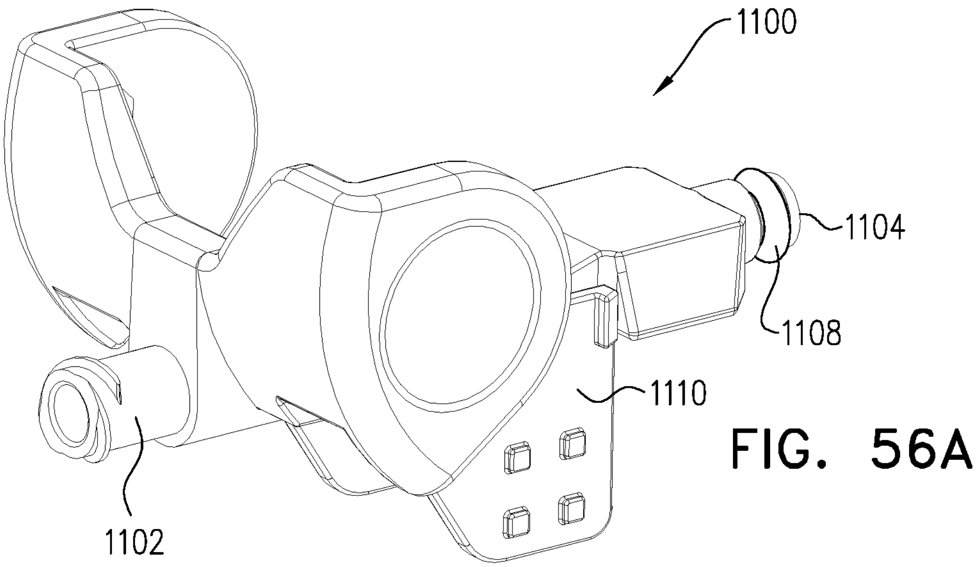
FIGS. 56A-B and 57A-B are schematic illustrations of a flushing adapter, in accordance with some applications.
Figure 56B:
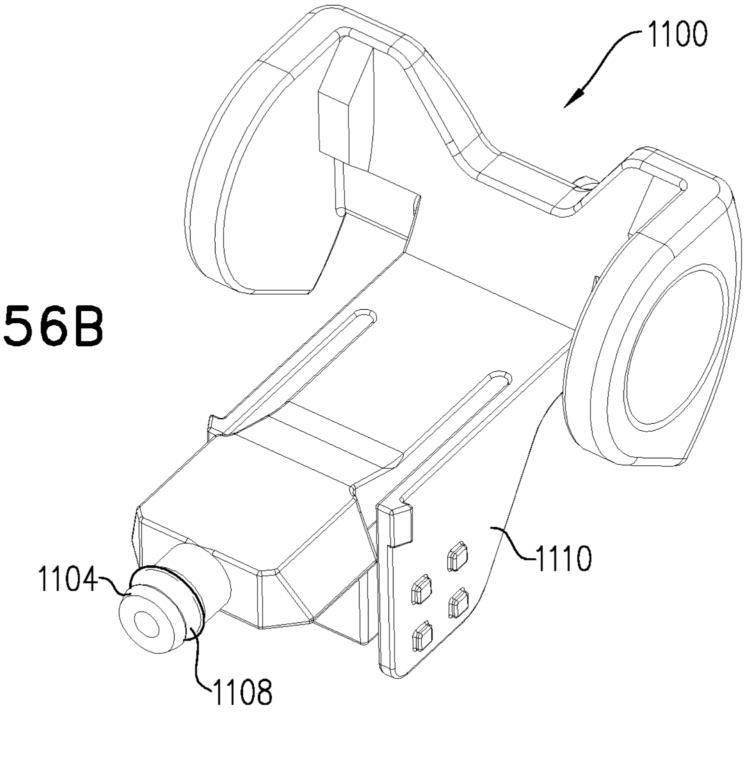
Figure 57A:
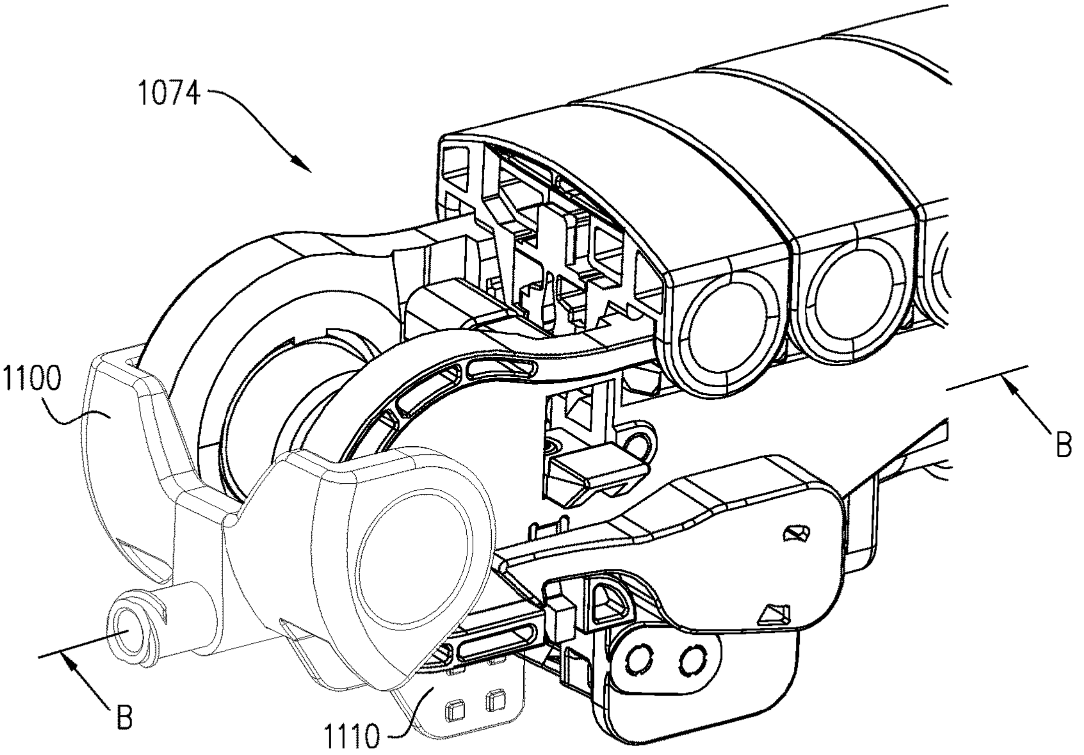
Figure 57B:
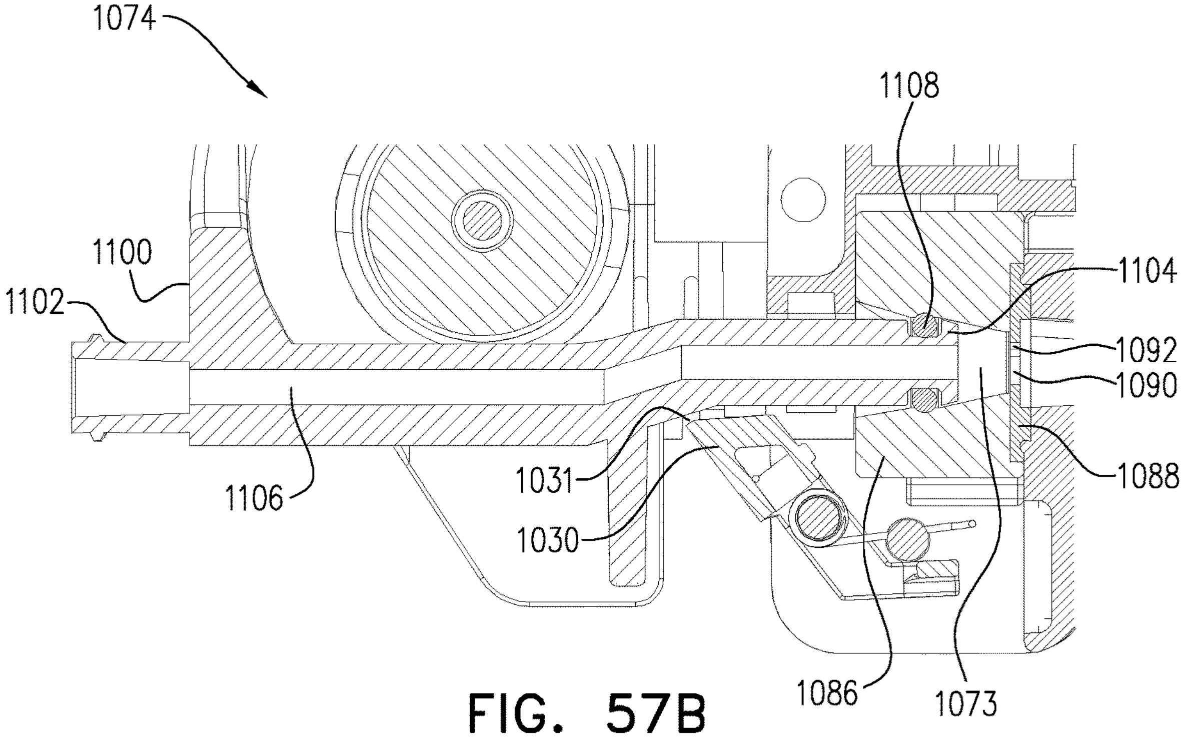

Reference is further made to FIGS. 56A-B and 57A-B, which are schematic illustrations of a flushing adapter 1100, in accordance with some applications. Flushing adapter 1100 is an optional component of system 1000. FIGS. 56A-B are perspective views of flushing adapter 1100, and FIGS. 57A-B are perspective and cross-sectional views, respectively, of the flushing adapter locked to extracorporeal unit 1074 of catheter device 1070 of system 1000, in accordance with some applications.

Flushing adapter 1100 can comprise a fluid fitting 1102 (which serves as an inlet), a nozzle 1104 (which serves as an outlet), and a channel 1106 therebetween. In some applications, flushing adapter 1100 is reversibly lockable to extracorporeal unit 1074 in a flushing position in which (i) fitting 1102 is accessible from outside of catheter device 1070, and (ii) nozzle 1104 is in fluid communication (e.g., sealed fluid communication) with port 1086 such that fluid driven into the flushing adapter via the fitting is directed distally through tube 1072.

In general, flushing of catheter devices with a liquid such as saline can be performed prior to and/or during a transcatheter procedure, e.g., in order to ensure that the catheter device is clear (e.g., of air or blood). However, in existing catheter devices the flushing liquid can be introduced laterally, e.g., at a point that is distal to the proximal end of the catheter. In contrast, flushing adapter 1100 is positioned at the proximal end of tube 1072. It is hypothesized that such proximal placement is particularly advantageous for system 1000, e.g., so as to reduce a likelihood of the flushing liquid escaping from the proximal end of tube 1072. For example, for applications in which system 1000 comprises membrane 1088, at certain points in the procedure aperture 1090 and/or aperture 1092 are open and unobstructed (e.g., see FIGS. 52A-D), and therefore, were flushing fluid to be introduced laterally at a point distal to proximal opening 1073, the flushing fluid may escape proximally rather than be forced distally through tube 1072.

The locking of flushing adapter 1100 to extracorporeal unit 1074 can be a snap fitting, e.g., facilitated by resilient wings 1110 that snap fit onto corresponding components of the extracorporeal unit, and which can be squeezed manually by the user in order to remove the flushing adapter from the extracorporeal unit.

Fluid fitting 1102 can be a Luer fitting, or any other suitable fitting to which a source of the flushing liquid can be connected.

In some applications, and as shown, the flushing position (i.e., the position in which flushing adapter 1100 is locked to extracorporeal unit 1074) is coincident with the deployment position (i.e., the position in which cartridge 1020 is disposed in order to hold anchor 120 opposite proximal opening 1073 of tube 1072). For example, the flushing adapter can be coupled to substantially the same region of the extracorporeal unit as cartridge 1020 in its deployment position.

As shown in FIG. 57B, even for applications in which (i) cartridge 1020 closes barrier 1030 upon arrival at the deployment position, and (ii) the flushing position is coincident with the deployment position, flushing adapter 1100 typically does not close the barrier upon placement at the flushing position. For example, and as shown, adapter 1100 can be shaped and sized such that channel 1106 extends distally past barrier 1030, e.g., without the adapter pushing the barrier closed. Thus, nozzle 1104 can become disposed distally beyond barrier 1030, such that it seals with port 1086.

In some applications, and as shown, nozzle 1104 seals with port 1086 proximally from membrane 1088. In some applications, and as shown, nozzle 1104 seals with the tapered inner wall of port 1086. Nozzle 1104 can comprise an O-ring 1108 or other seal that facilitates such sealing.

In some applications, if flushing is desired subsequently to anchoring of first anchor 120*f*, and therefore while tether 112 extends through port 1086, nozzle 1104 (e.g., O-ring 1108) can temporarily sandwich the tether against the tapered inner wall of the port, e.g., with the O-ring sealing against the tether.

Reference is additionally made to FIGS. 53A-E, 54, and 55A-C, which are schematic illustrations of apparatus and techniques for facilitating the use of a catheter having a lateral slit, in accordance with some applications. In some applications, when using a tube (e.g., a catheter) to implant an implant such as implant 110 in a curve, such as along/around the annulus of a heart valve, the rotational orientation of the distal end of the tube can remain constant with respect to the tissue as the tube is moved around the curve. Thus, the rotational orientation of the distal end of the tube can change relative to the part of the implant currently being secured to the tissue, e.g., relative to the tangent of the curve at that part of the implant. In some applications, this can be particularly material when the distal end of the tube has a lateral slit (e.g., lateral slit 156 or lateral slit 1056) and/or another feature that reduces rotational symmetry of the tube. For example, it is hypothesized that, when placing an anchor 120 other than the first anchor of the implant, it is advantageous to orient the lateral slit to face toward the preceding anchor such that tether 112 can extend cleanly through the lateral slit to the preceding anchor, e.g., rather than rubbing against the sides of the lateral slit, and/or curving around the outside of the tube. However, if the rotational orientation of the distal end of the tube were to remain constant with respect to the tissue as the implant is implanted around the curve, an orientation that is optimal for placing the second anchor can be suboptimal for placing a later anchor. This can be understood, for example, by comparing FIG. 53B to FIG. 53D. When placing the second anchor (FIG. 53B), lateral slit 1056 is facing substantially toward the first anchor, and tether 112 extends cleanly through the lateral slit, and in a generally straight line between the lateral slit and the first anchor. Were tube 1072 to remain in the same orientation for placement of the final anchor (FIG. 53D), lateral slit 1056 would be not face the preceding anchor (the penultimate anchor), but can face the anterior side of the valve.

FIGS. 53A-D show some steps in the implantation of implant 110 using catheter device 1070 of system 1000, in accordance with some applications. In some applications, and as shown, system 1000 (e.g., catheter device 1070 thereof) is configured to accommodate (e.g., to compensate for) the effect described in the preceding paragraph. For example, and as shown, extracorporeal unit 1074, which can be mounted on a platform 1002, can be mounted on the platform (e.g., via a bracket 1004) in a manner that facilitates rotation of the extracorporeal unit around a longitudinal axis ax15 defined by the proximal end of tube 1072. Extracorporeal unit 1074 can be rotationally fixed to tube 1072, and thus rotation of the extracorporeal unit around the longitudinal axis rotates the tube. It is hypothesized that such an arrangement facilitates rotation of the distal end of tube 1072 so as to optimally orient lateral slit 1056 according to the position of each anchor 120 with respect to the preceding anchor. For example, in each of FIGS. 53B, 53C, and 53D, extracorporeal unit 1074 is in a different rotational orientation and lateral slit 1056 is thus facing a different direction, each time substantially toward the preceding anchor.

In some applications, system 1000 defines an array of discrete rotational orientations around the longitudinal axis, with extracorporeal unit 1074 being mounted (or configured to be mounted) on platform 1002 in a manner that facilitates orienting the extracorporeal unit in each of the discrete rotational orientations. For example, and as shown, system 1000 (e.g., platform 1002, extracorporeal unit 1074, or bracket 1004) can comprise at least one detent 1006 (e.g., a spring-loaded detent), configured to secure the extracorporeal unit in each of the discrete rotational orientations, e.g., via a snap-fit. For example, system 1000 can also define an array of recesses 1008 corresponding to the array of discrete rotational orientations, such that in each of the discrete rotational orientations detent 1006 protrudes into a corresponding recess, thereby inhibiting rotation out of the discrete rotational orientation. In the example shown, recesses 1008 are defined by extracorporeal unit 1074 (e.g., by an exterior of casing of tensioner 1084), and detent 1006 is a component of, or is coupled to, bracket 1004.

As shown, bracket 1004 can be axially slidably coupled to platform 1002. Bracket 1004 can provide the rotational coupling of extracorporeal unit 1074 to platform 1002 by being rotatably coupled to the extracorporeal portion. This rotatable coupling can be facilitated by rotatable coupling between bracket 1004 and a proximal portion of tube 1072. For example, and as shown, bracket 1004 can define one or more channels 1005 through which the proximal portion of tube 1072 passes, e.g., defining a barrel hinge in which the proximal portion of tube 1072 serves as the "pin" of the hinge, and the part(s) of bracket 1004 that define channels 1005 serving as "knuckles" of the hinge.

Figure 53A:
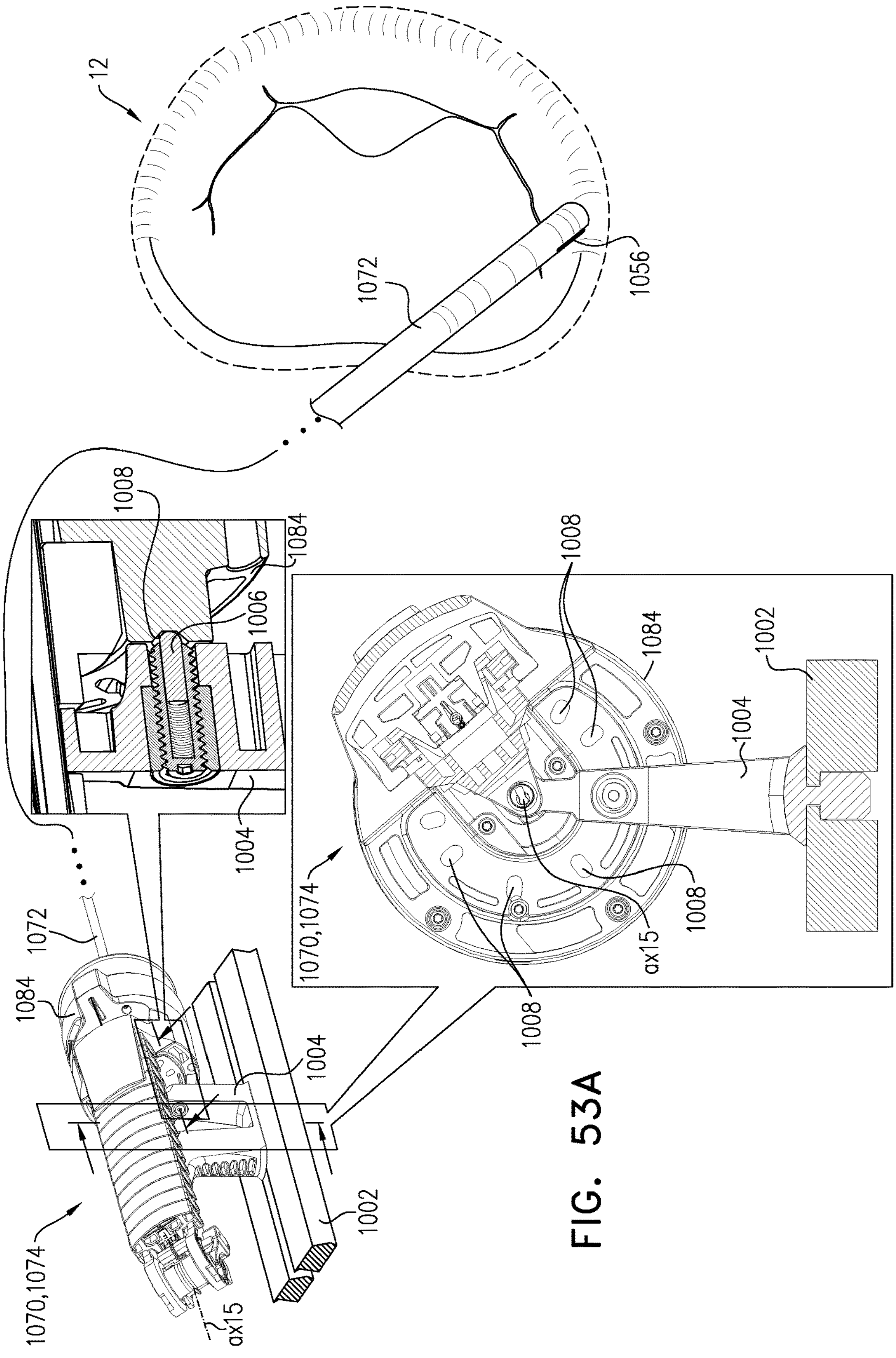
Figure 53B:
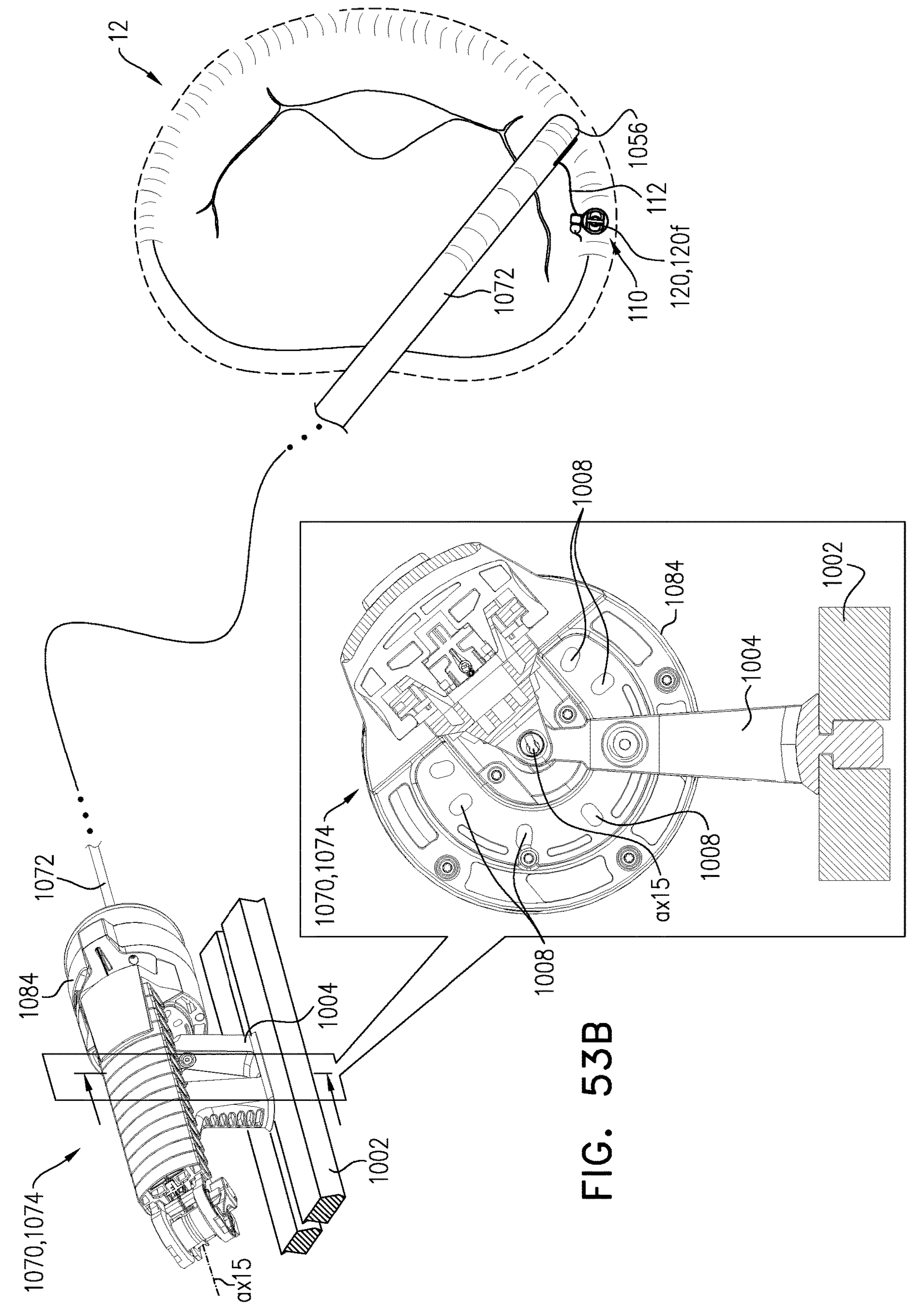
Figure 53C:
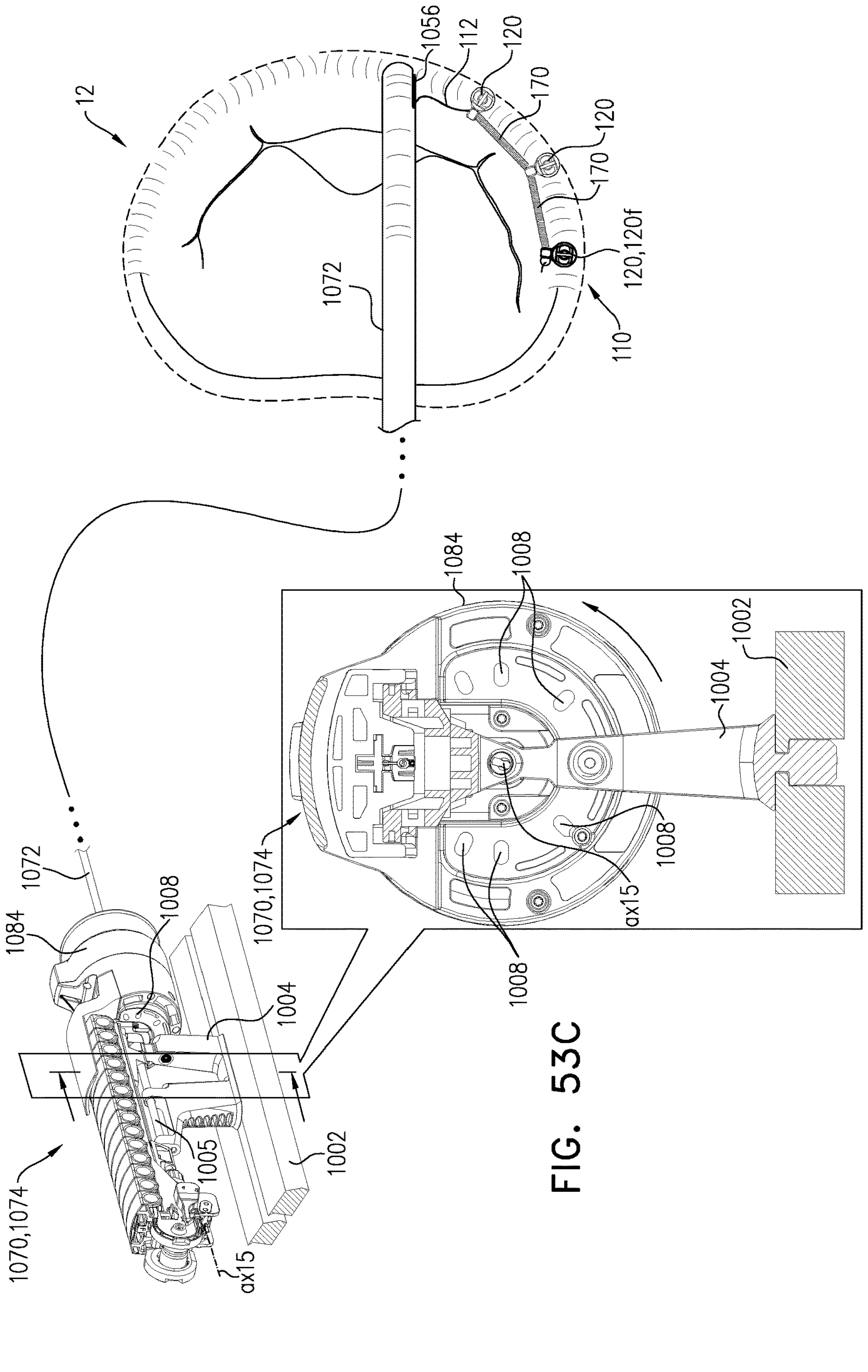
Figure 53D:
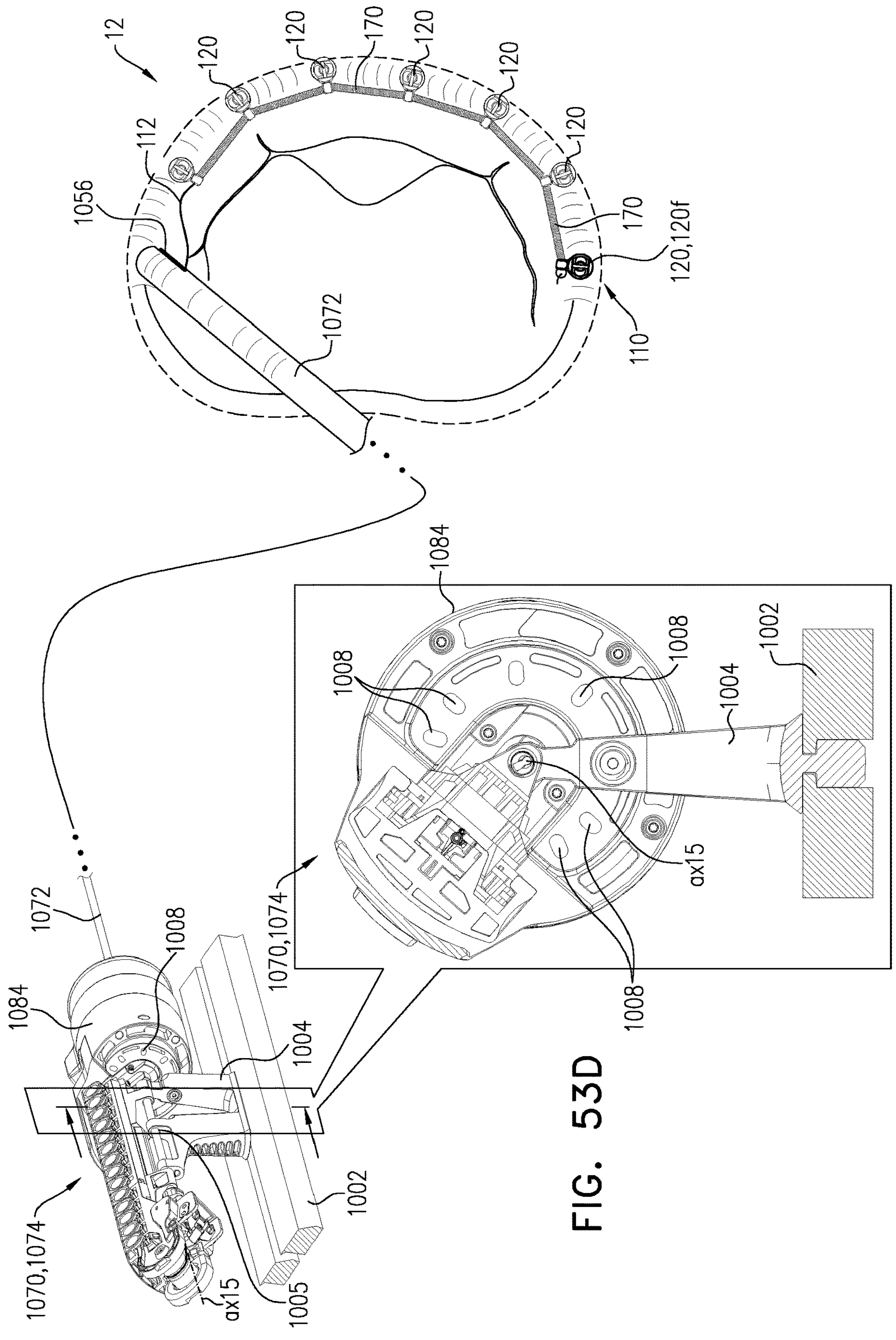

FIG. 53A shows the distal end of tube 1072 being positioned for placement of first anchor 120*f* of implant 110. FIG. 53B shows first anchor 120*f* having been anchored, and the distal end of tube 1072 being positioned for placement of the second anchor. In both FIGS. 53A and 53B extracorporeal unit 1074 is disposed in the same discrete rotational orientation, with detent 1006 protruding into the same recess 1008. FIG. 53C shows three anchors 120 having been anchored, with spacers or dividers 170 disposed therebetween, and the distal end of tube 1072 being positioned for placement of the fourth anchor. Extracorporeal unit 1074 has been rotated into another of its discrete rotational orientations (with detent 1006 protruding into another of recesses 1008) in order to orient the distal end of tube 1072 such that lateral slit 1056 faces substantially toward the fourth anchor. FIG. 53D shows seven anchors 120 having been anchored, with spacers or dividers 170 disposed therebetween, and the distal end of tube 1072 being positioned for placement of the eighth anchor. Extracorporeal unit 1074 has been rotated into yet another of its discrete rotational orientations (with detent 1006 protruding into yet another of recesses 1008) in order to orient the distal end of tube 1072 such that lateral slit 1056 faces substantially toward the eighth anchor. In the example shown, in which implant 110 is implanted along the posterior annulus of mitral valve 12 with first anchor 120*f* in the vicinity of the anterolateral commissure (e.g., in an anticlockwise curve), as the implant is progressively implanted, extracorporeal unit 1074 is rotated anticlockwise.

Figure 53E:
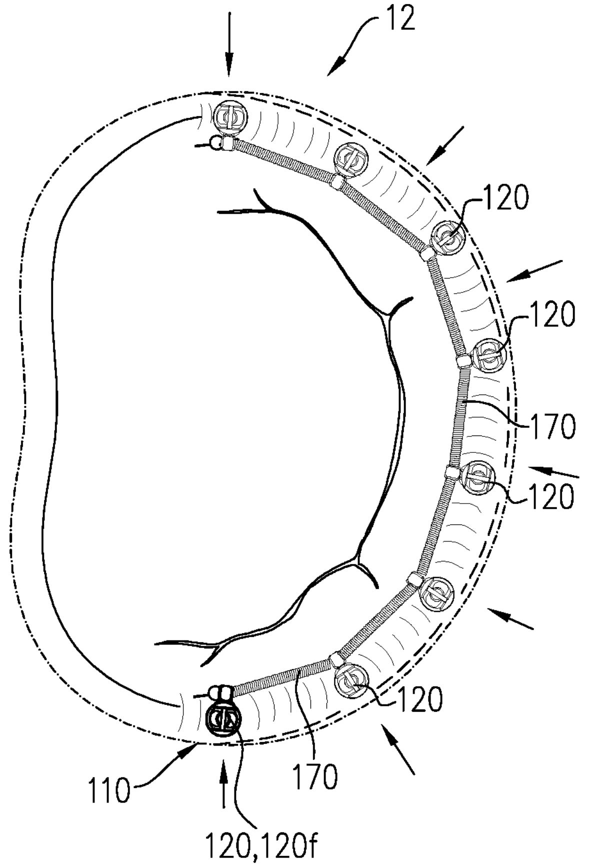
Figure 54:
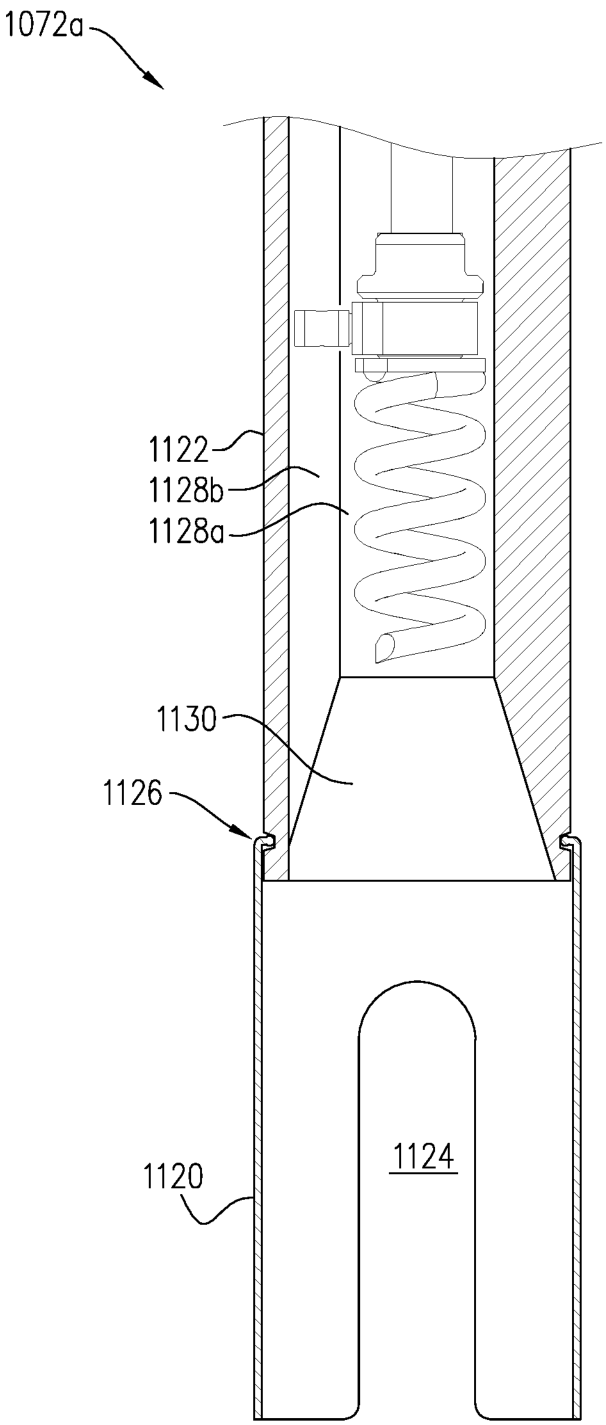
FIGS. 54 and 55A-C are schematic illustrations of a flexible tube having a rotatable distal portion, in accordance with some applications.

FIG. 53E shows implantation of implant 110 having been completed, and tether 112 having been tensioned in order to contract the annulus of valve 12 and reduce regurgitation through the valve.

It is to be noted that the features described with reference to FIGS. 53A-E can be applicable to other catheter devices, including, but not limited to, catheter devices that are not used to implant an implant such as implant 110, catheter devices that do not include and/or not used with cartridges such as cartridges 1020, and catheter devices that do not have a barrier such as barrier 1030. There is provided, in accordance with some applications, a system comprising a catheter device and a platform. The catheter device can comprise (1) a tube that has (a) a distal opening that is configured to be transluminally advanced to a tissue of the subject, and (b) a proximal portion that defines a longitudinal tube-axis, and (2) an extracorporeal unit that is coupled to the proximal portion of the tube. The system can define an array of discrete rotational orientations of the extracorporeal unit around the longitudinal tube-axis, the extracorporeal unit being configured to be mounted on the platform in a manner that facilitates rotation of the extracorporeal unit around the longitudinal tube-axis so as to become oriented in any of the discrete rotational orientations. For such applications, the extracorporeal unit can be rotationally fixed to the tube, such that rotation of the extracorporeal unit around the longitudinal tube-axis rotates the tube.

For some such applications, the system further comprises a series of anchors threaded on a tether by the tether being threaded through an eyelet of a head of each of the anchors. For some such applications, the system further comprises an anchor driver that, for each of the anchors, is configured to engage the head of the anchor, advance the anchor distally through the tube toward the distal opening, and anchor the anchor to the tissue.

FIGS. 54 and 55A-C show another approach in which, in accordance with some applications, the distal portion of the tube that defines the lateral slit is rotatable, e.g., with respect to more proximal portions of the tube. A typically flexible tube (e.g., catheter) 1072*a* is provided. Tube 1072*a* can be considered to be a variant of tube 1072 of system 1000, and/or of tube 152 of system 100, described hereinabove. Thus, in some applications, tube 1072 and/or tube 152 can be replaced with tube 1072*a*, mutatis mutandis. Tube 1072*a* has a proximal portion that includes a proximal end (not shown), a distal portion 1120, and an intermediate portion 1122 extending between the proximal portion and the distal portion. The proximal portion and/or intermediate portion 1122 can be as described for tube 1072 and/or tube 152, mutatis mutandis. Furthermore, distal portion 1120 defines a lateral slit 1124, e.g., as described for slit 156 and/or slit 1056, mutatis mutandis.

Like tubes 1072 and 152, tube 1072*a* defines a lumen therethrough, via which anchors (e.g., anchors 120) are advanceable. Distal portion 1120 is rotatably coupled to intermediate portion 1122 such that lateral slit 1124 is revolvable about the lumen. For example, tube 1072*a* can define a rotary bearing 1126 via which distal portion 1120 is coupled to intermediate portion 1122. Although rotary bearing 1126 is shown as distal portion 1120 being snap-fitted to a circumferential track defined by intermediate portion 1122, the scope of the disclosure includes alternatively or additionally using other bearing types including, but not limited to, a rolling element bearing (e.g., comprising ball bearings or roller bearings).

In some applications, and as shown, the lumen of tube 1072*a* defines a major channel region 1128*a* and a smaller minor channel region 1128*b*, e.g., such that an anchor comprising a tissue-engaging element and a lateral eyelet (e.g., anchor 120) is slidable through the tube with its tissue-engaging element through the major channel region, and its eyelet sliding through the minor channel region, e.g., as described hereinabove, mutatis mutandis. However, for some such applications, the distinction between the major and minor channel regions does not continue into distal portion 1120. For example, and as shown, a substantially conical region 1130 of the lumen of tube 1072*a* (e.g., at a distal part of intermediate portion 1122) can widen and/or circularize toward distal portion 1120.

Figure 55A:
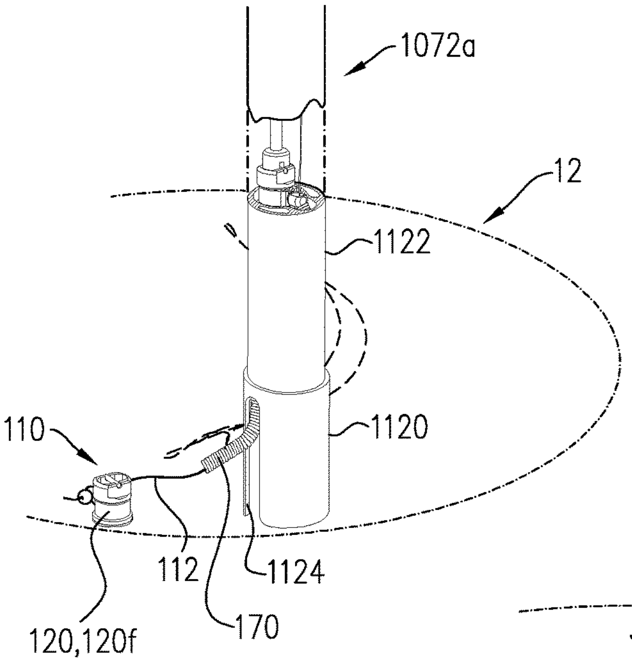
Figure 55B:
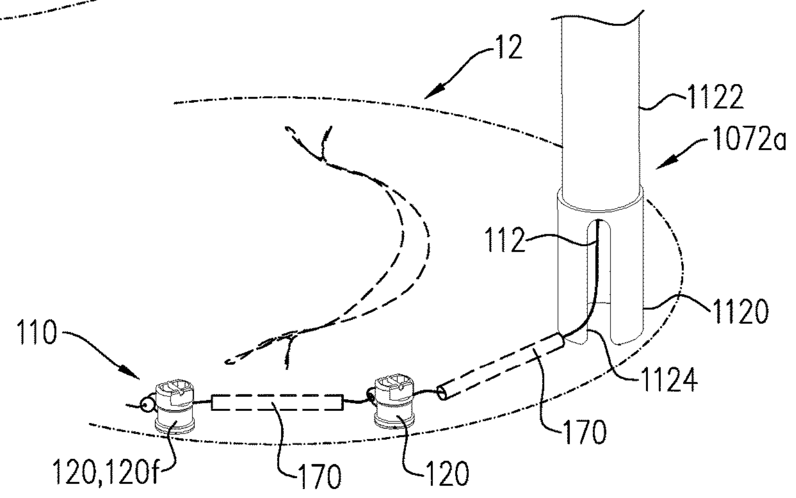
Figure 55C:
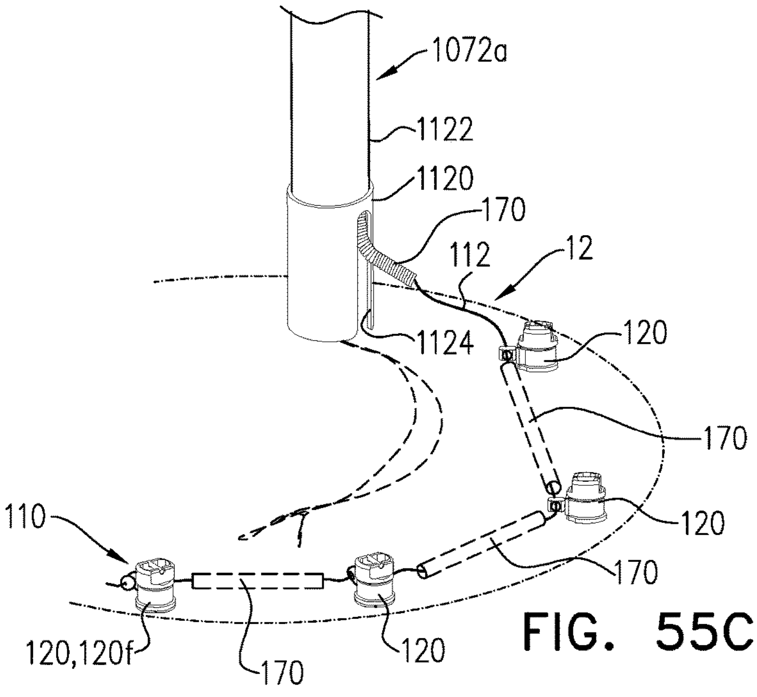

FIGS. 55A-C show steps in the implantation of implant 110 using a catheter tool that comprises tube 1072*a*. Similarly to as described with respect to FIGS. 53A-D, as the distal end of the tube is moved in a curve (e.g., in order to implant 110 around an annulus of valve 12), the lateral slit is maintained pointing generally toward the previously-anchored anchor via revolution of the lateral slit about the lumen of the tube. However, for tube 1072*a*, this revolution is achieved by rotation of distal portion 1120 with respect to intermediate portion 1122, e.g., in the absence of rotation of the intermediate portion. In some applications, this rotation is passive, e.g., lateral slit 1124 is moved into/retained in alignment by the tether 112, e.g., by the orientation/vector of the portion of the tether that is currently disposed between the previously-anchored anchor and the lateral slit.

Figure 58B:
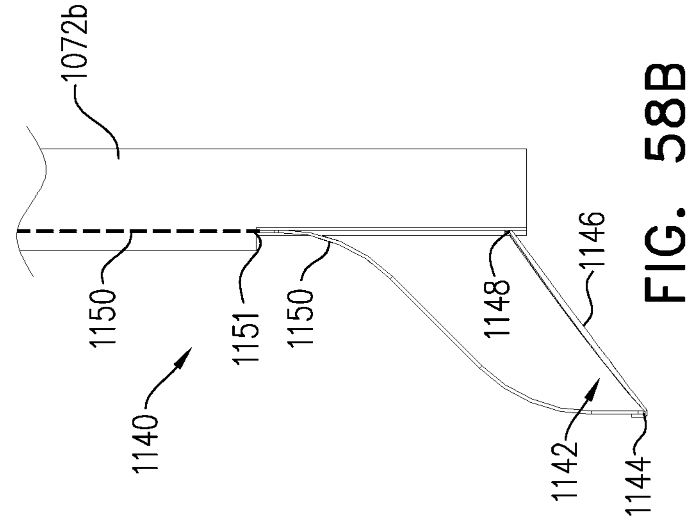
FIGS. 58A-C are schematic illustrations of a fluoroscopic guide, in accordance with some applications.
Figure 58A:
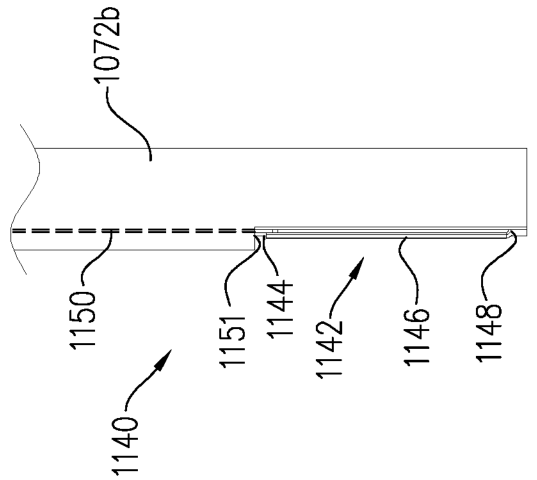
Figure 58C:
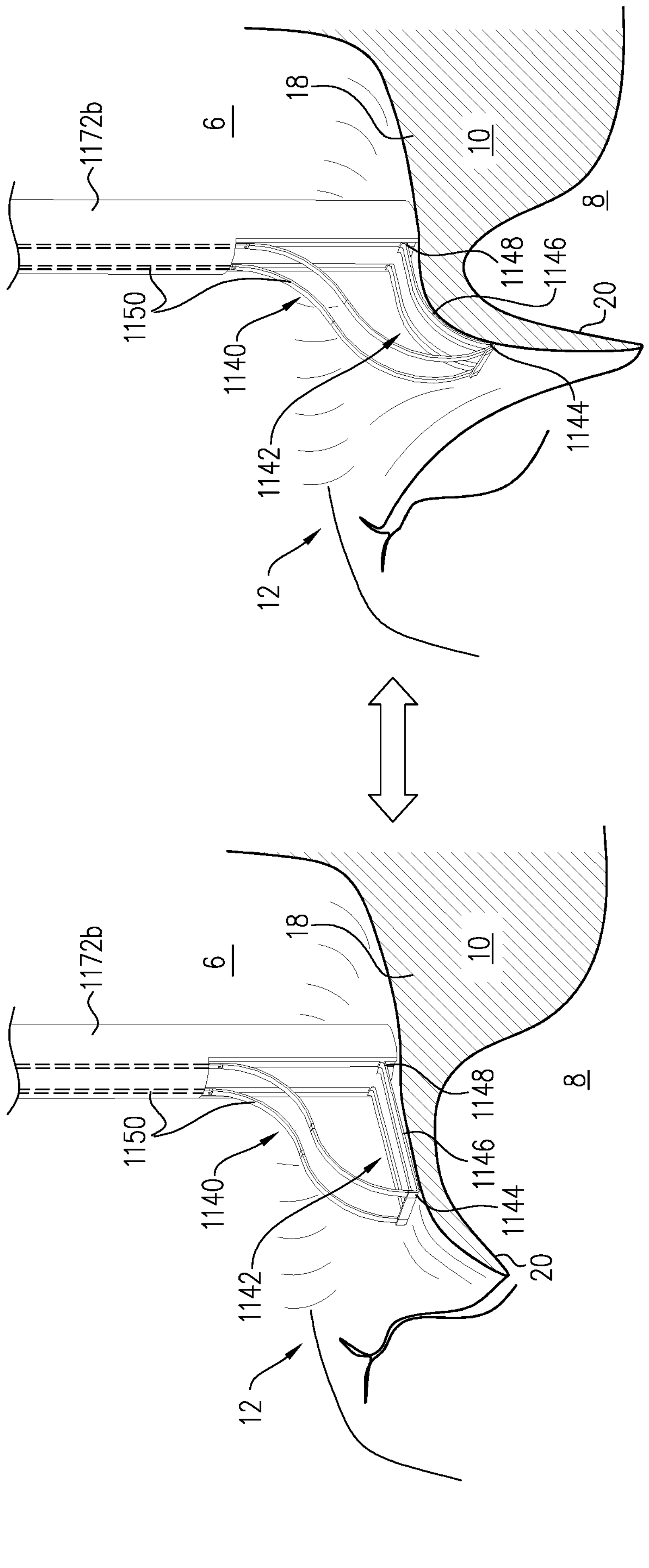

Reference is now made to FIGS. 58A-C, which are schematic illustrations of a fluoroscopic guide 1140, in accordance with some applications. Guide 1140 is configured to facilitate percutaneous (e.g., transluminal) positioning of the distal end of a tube (e.g., a catheter) against the annulus of a valve of a heart, e.g., in order to anchor an anchor into the annulus. In the example shown, guide 1140 is used with a tube 1072*b*, which can be considered to be a variant of tube 1072 or tube 152, with the addition of guide 1140. However, guide 1140 can be used with other tubes, mutatis mutandis. Similarly, although in the example shown guide is used to position the distal end of tube 1072*b* against annulus 18 of mitral valve 12, it can be used with other heart valves.

Valve 12 is disposed between an atrium (e.g., left atrium) 6 and a ventricle (e.g., left ventricle) 8 of the heart, and includes leaflets 20, the root of each leaflet being attached to annulus 18 of the valve. It is hypothesized that, for some procedures, such as annuloplasty and/or implantation of an implant at valve 12, it is advantageous to drive one or more anchors into tissue of the annulus, e.g., rather than into leaflet 20 or into a wall of atrium 6. Implantation of implant 110 is such a procedure. Thus, for such applications, it may be advantageous to position the end of the tube (via which the anchor will be anchored) close to the root of the leaflet but not on the leaflet. Guide 1140 is configured to facilitate such positioning.

Guide 1140 comprises a flap 1142, and at least one control rod (e.g., exactly one, exactly two, or more than two control rods) 1150. Flap 1142 has a tip 1144, a root 1148, and an intermediate portion 1146 extending between the tip and the root. At root 1148, flap 1142 is pivotably coupled to the distal portion of tube 1072*b* (e.g., to the distal end of the tube) in a manner in which the flap is deflectable with respect to the tube between (i) a retracted state in which the flap is substantially parallel with the tube (FIG. 58A), and (ii) an extended state in which the flap extends laterally from the tube (FIG. 58B). Intermediate portion 1146 is radiopaque, and is flexible, e.g., such that pressing on the intermediate portion changes its curvature. In some applications, flap 1142 (e.g., intermediate portion 1146 thereof) comprises a fabric with a radiopaque coating. In some applications, flap 1142 (e.g., intermediate portion 1146 thereof) comprises a thin strip of flexible metal.

Control rod 1150 extends from the distal portion of the tube to tip 1144 of flap 1142 such that (i) advancement of the control rod deflects the flap toward the extended state by pushing tip 1144 (e.g., distally), and (ii) retraction of the control rod deflects the flap toward the retracted state by pulling tip 1144 (e.g., proximally). In some applications, and as shown, control rod 1150 extends (e.g., from extracorporeal unit 1074; not shown) along tube 1072*b* to an exit point 1151 at which the control rod extends from the tube to tip 1144 of the flap. As shown, control rod 1150 can be sufficiently flexible that the advancement of the control rod that deflects the flap toward the extended state causes the control rod to flex laterally away from the distal portion of the tube (FIG. 58B).

In some applications, and as shown in FIG. 58A, in the retracted state tip 1144 is disposed proximally from root 1148 and/or is disposed against the distal portion of tube 1072*b*.

In some applications, and as shown in FIG. 58B, in the extended state flap 1142 extends distolaterally from tube 1072*b*—at least in the absence of other forces on the flap.

In some applications, in the extended state flap 1142 is disposed at 80-160 degrees (e.g., at 90-140 degrees, such as at 100-130 degrees) with respect to the tube.

In some applications, the pivotable coupling of flap 1142 to tube 1072*b* is such that an angular range of the flap (i.e., the angle through which the flap passes) between the retracted state and the extended state is 80-160 degrees (e.g., 90-40 degrees, such as 100-130 degrees)—at least in the absence of other forces on the flap.

FIG. 58C is a schematic illustration showing the distal end (i.e., the distal opening) of tube 1072*b* having been placed optimally on annulus 18 of valve 12, facilitated by guide 1140, in accordance with some applications. In this position, the region of intermediate portion 1146 of flap 1142 that is closest to root 1148 may become pushed proximally (relative to tube 1072*b*) by annulus 18, e.g., by the annulus resisting pushing of that region of the flap against the annulus. During ventricular systole (left frame of FIG. 58C), regions of intermediate portion 1146 that are closer to tip 1144 may also become pushed proximally/upstream, although by leaflet 20, responsively to ventricular pressure. However, during ventricular diastole (right frame of FIG. 58C), as leaflet 20 moves downstream the regions of intermediate portion 1146 that are closer to tip 1144 may move distally/downstream, e.g., due to control rod 1150 continuing to exert force on the tip. The curvature of flap 1142, which is radiopaque, provides a fluoroscopic indication regarding the optimality of the position of the distal end/opening of tube 1072*b*. For example, in some applications, optimal positioning can be fluoroscopically identified by (i) the region of intermediate portion 1146 of flap 1142 that is closest to root 1148 being pushed proximally (e.g., and remaining in a stable position), (ii) tip 1144 oscillating upstream and downstream with the cardiac cycle, and/or (iii) oscillating changes in the curvature of intermediate portion 1146.

There is provided, in accordance with some applications, a method, comprising transluminally advancing, to a heart of a subject, a distal portion of a tube of a catheter device, the catheter device including a fluoroscopic guide. In some applications, the fluoroscopic guide includes a flap having: (i) a tip, (ii) a root at which the flap is pivotably coupled to the distal portion of the tube, and (iii) a flexible intermediate portion extending between the tip and the root. In some applications, the fluoroscopic guide includes a control rod, extending from the distal portion of the tube to the tip of the flap.

In some applications, the method includes placing a distal end of the tube against a tissue site of the heart proximate to a valve of the heart.

In some applications, the method includes, within the heart, deflecting the flap toward an extended state thereof by advancing the control rod such that the control rod pushes the tip of the flap away from the tube.

In some applications, the method includes, while the distal end of the tube remains against the tissue site and the flap remains in its extended state, fluoroscopically observing a curvature of the intermediate portion. In some applications, the method includes, (i) responsively to the observing, determining whether to drive an anchor into the tissue site; and (ii) responsively to the determining, driving the anchor into the tissue site.

Figure 59A:
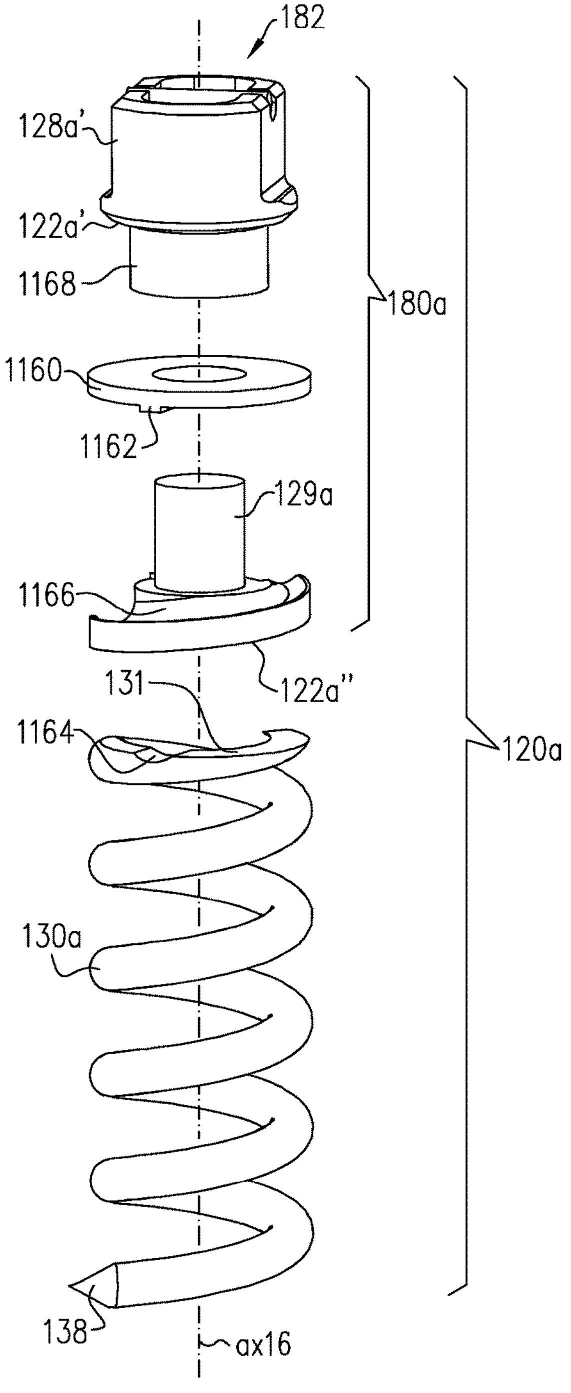
FIGS. 59A-B are schematic illustrations of an anchor, in accordance with some applications.
Figure 59B:
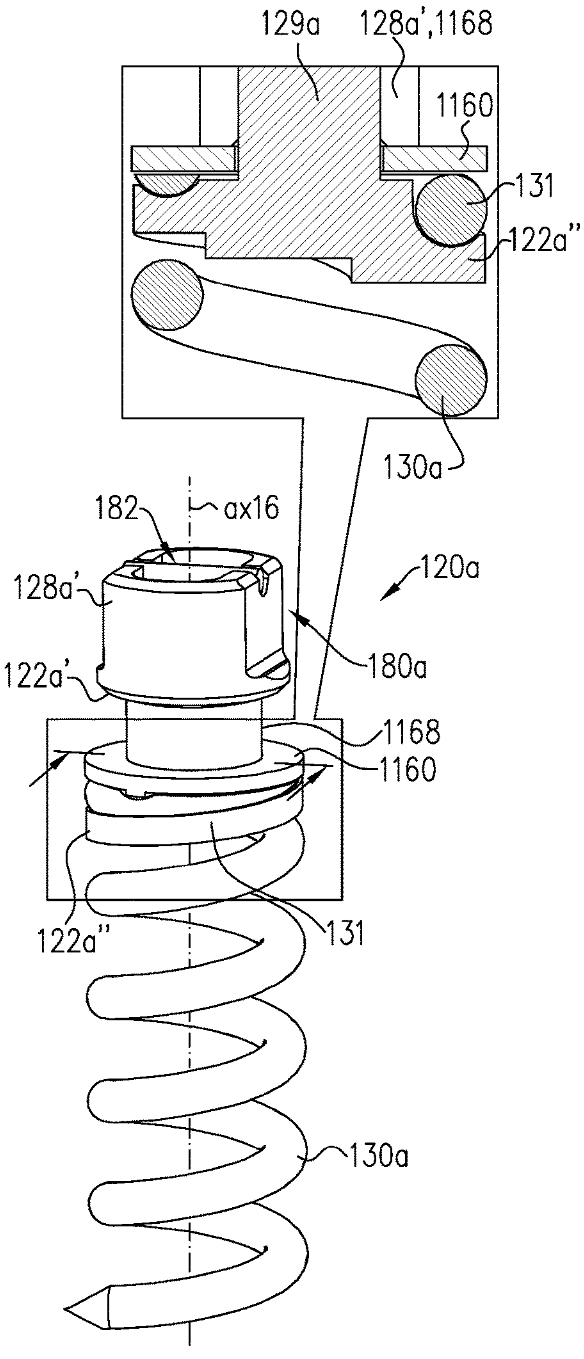

Reference is now made to FIGS. 59A-B, which are schematic illustrations of an anchor 120*a*, in accordance with some applications. Anchor 120*a* is a variant of anchor 120 and can be used as described hereinabove for anchor 120. Anchor 120*a* differs from anchor 120 primarily in its method of manufacture. Tissue-engaging element 130 of anchor 120 (e.g., a proximal turn of the tissue-engaging element) can be welded or brazed to head 180 (e.g., to a distal-facing surface of flange 122" thereof), e.g., in a manner that fixedly couples the tissue-engaging element to interface 182. Anchor 120*a* has reduced dependence on welding and may in fact not utilize welding at all.

Anchor 120*a* comprises a tissue-engaging element 130*a*, which is similar to tissue-engaging element 130 except that, in some applications, a proximal turn 131 of tissue-engaging element 130*a* can have a notch 1164 in it. Similarly to anchor 120, anchor 120*a* comprises a head 180*a* that comprises a core 129*a*, a flange 122*a*" fixed to the core, and a cap 128*a*' that defines interface 182. However, tissue-engaging element 130*a* is secured to head 180*a* primarily by (i) proximal turn 131 lying on a proximal-facing surface 1166 of flange 122*a*", and (ii) cap 128*a*' being fixed to core 129*a* in a manner that sandwiches the proximal turn against the proximal surface of the flange. Flange 122*a*" can be disposed between proximal turn 131 and a second turn of tissue-engaging element 130*a* that is immediately distal from the proximal turn.

Flange 122*a*" typically protrudes laterally (e.g., radially) beyond core 129*a*.

Flange 122*a*" can be shaped to receive proximal turn 131, e.g., by proximal surface 1166 being inclined with respect to axis ax16 and/or defining a groove shaped complementarily to the proximal turn. For example, and as shown, flange 122*a*" can be shaped such that proximal surface 1166 and/or the groove therein defines a partial helix.

In some applications, and as shown, anchor 120*a* (e.g., head 180*a* thereof) further comprises a washer 1160, and the sandwiching of proximal turn 131 is between the proximal surface of flange 122*a*" and the washer. For some such applications, washer 1160 is shaped to define a spur 1162 that further secures proximal turn 131 in place by being disposed in notch 1164. Alternatively or additionally, another flange, (e.g., defined by cap 128*a*') can serve a similar function to washer 1160.

In some applications, and as shown, core 129*a* is shaped as a post. In some applications, and as shown, cap 128*a*' is shaped to define a cavity in which the post is disposed. For example, cap 128*a*' can define a tubular wall 1168 that defines the cavity by circumscribing the cavity. In some applications, the fixing of cap 128*a*' to core 129*a* is at least in part provided by this positioning of the post within the cavity. For some such applications, the post of core 129*a* defines an external thread, and the cap (e.g., tubular wall 1168 thereof) defines an internal thread.

In some applications in which anchor 120*a* comprises washer 1160 and cap 128*a*' defines tubular wall 1168, the sandwiching of proximal turn 131 between washer 1160 and flange 122*a*" can be facilitated by the tubular wall being sufficiently long to extend distally over core 129*a* and push against the washer, i.e., a distal end of the tubular wall pushes against the washer.

In some applications, anchor 120*a* comprises a collar and an eyelet, e.g., as described for other anchors hereinabove. For such applications, the collar can circumscribe tubular wall 1168, such that the tubular wall is disposed coaxially between the collar and core 129*a* (e.g., the post thereof). The collar can be freely-rotatable, but can be axially restrained by a proximal flange 122*a*' defined by cap 128*a*'.

It is hypothesized that anchor 120*a* and the reduced-welding manufacturing technique therefor may advantageously facilitate more efficient manufacturing, and/or may confer the anchor with greater strength and/or post-implantation longevity. There is provided, in accordance with some applications, a method for manufacturing a tissue anchor that includes a head and helical tissue-engaging element, the method comprising (i) placing a proximal turn of the helical tissue-engaging element on a proximal surface of a flange of the head, the head including a core disposed on a central anchor-axis of the tissue anchor, and the tissue-engaging element extending helically around the central anchor-axis and having a distal turn that defines a sharpened distal tip, and (ii) sandwiching the proximal turn against the proximal surface of the flange by fixing a cap to the core.

Reference is again made to FIGS. 1A-59B. Each of the tissue anchors disclosed herein is described as comprising a tissue-engaging element and a head. Although each of the tissue anchors is shown and/or described as having a particular tissue-engaging element combined with a particular head, each of the heads described herein can optionally be combined with (i.e., coupled to) any of the tissue-engaging elements described herein or in any of the references incorporated herein by reference hereinabove. Similarly, each of the tissue-engaging elements described herein can optionally be combined with (i.e., coupled to) any of the heads described herein or in any of the references incorporated herein by reference hereinabove. Moreover, advantageous features described herein for a particular head or for a particular tissue-engaging element can be utilized by including that feature on another head or tissue-engaging element, including those described herein and those described in any of the references incorporated herein by reference hereinabove.

Reference is again made to FIGS. 1A-59B. The tools disclosed herein are typically described with (or in the context of) a particular implant, a particular tissue anchor, and/or a particular anchor head. It is to be noted that each such tool can be used, mutatis mutandis, with (or in the context of) other implants, other tissue anchors, and/or other anchor heads, including those described herein, and those described in any of the references incorporated herein by reference hereinabove. Moreover, advantageous features described herein for a particular tool can be utilized by including that feature on another tool, including those described herein and those described in any of the references incorporated herein by reference hereinabove.

The present invention is not limited to the examples that have been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Further, the treatment techniques, methods, steps, etc. described or suggested herein or references incorporated herein can be performed on a living animal or on a non-living simulation, such as on a cadaver, cadaver heart, simulator (e.g., with the body parts, tissue, etc. being simulated), etc.

Example Applications (some non-limiting examples of the concepts herein are recited below):

Example 1. A system for use with a subject, comprising: (A) a catheter device, comprising: (i) a tube that has a distal opening that is configured to be transluminally advanced into the subject and a proximal end that defines a proximal opening, and (ii) an extracorporeal unit that is coupled to the proximal end of the tube, defines a deployment position, and comprises: a track that leads to the deployment position; (B) a series of anchors; (C) a series of cartridges, each of the cartridges: (i) holding a respective anchor of the series of anchors, (ii) being coupled to the extracorporeal unit at a respective initial position of a series of initial positions, (iii) while remaining coupled to the extracorporeal unit, being moveable along the track from the respective initial position to the deployment position such that, in the deployment position, the cartridge holds the respective anchor opposite the proximal opening; and (D) an anchor driver that, for each of the anchors, is configured to: (i) while the anchor is held opposite the proximal opening by the respective cartridge in the deployment position, engage the anchor, and (ii) advance the anchor distally out of the respective cartridge, through the proximal opening, and through the tube toward the distal opening.

Example 2. The system according to example 1, wherein the extracorporeal unit includes a barrier movable between a closed state in which the barrier obstructs the proximal opening and an open state, and wherein the anchor driver, for each of the anchors, is configured to: (A) while the anchor is held opposite the proximal opening by the respective cartridge in the deployment position: (i) engage the anchor, and (ii) while engaged with the anchor, apply a force to the anchor that transitions the barrier into the open state, and (ii) while the barrier remains in the open state, advance the anchor distally out of the respective cartridge, through the proximal opening, and through the tube toward the distal opening.

Example 3. The system according to example 2, wherein the force is an engagement-verification force that challenges the engagement of the anchor by the anchor driver.

Example 4. The system according to any one of examples 2-3, wherein the force is a proximal pulling force, and wherein the anchor driver, for each of the anchors, is configured to, while engaged with the anchor, apply the proximal pulling force to the anchor.

Example 5. The system according to any one of examples 2-4, wherein the system is configured to define a threshold magnitude of the force, the barrier transitioning into the open state responsively to the force only upon the force exceeding the threshold magnitude.

Example 6. The system according to any one of examples 2-5, wherein, for each of the cartridges the cartridge is configured to undergo conformational change in response to the force, and the anchor driver is configured to transition the barrier into the open state by inducing the conformational change by applying the force to the respective anchor.

Example 7. The system according to any one of examples 2-6, wherein the barrier is biased toward being in the open state.

Example 8. The system according to any one of examples 2-7, wherein the extracorporeal unit comprises a spring-loaded displacement mechanism configured to transition the barrier into the open state responsively to the force applied to the anchor by the anchor driver.

Example 9. The system according to any one of examples 1-8, wherein each of the cartridges is configured to lock to the extracorporeal unit upon arriving at the deployment position.

Example 10. The system according to any one of examples 1-9, wherein each of the cartridges is shaped to be grasped by hand by a human operator and is configured to be moved along the track by hand by the operator.

Example 11. The system according to any one of examples 1-10, wherein the catheter device further comprises a port at the proximal opening of the tube, and the system further comprises a flushing adapter: (i) comprising a fluid fitting, a nozzle, and a channel therebetween, and (ii) reversibly lockable to the extracorporeal unit in a flushing position in which the fluid fitting is accessible from outside of the catheter device and the nozzle in fluid communication with the port such that fluid driven into the flushing adapter via the fluid fitting is directed distally through the tube.

Example 12. The system according to example 11, wherein, in the flushing position, a barrier of the extracorporeal unit is in the open state, and the channel extends distally past the barrier.

Example 13. The system according to example 11, wherein the flushing position is substantially coincident with the deployment position.

Example 14. The system according to example 11, wherein the fluid fitting is a Luer fitting.

Example 15. The system according to example 11, wherein the port comprises a sealing membrane, the anchor driver configured, for each of the anchors, to advance the anchor distally through the membrane and into the tube.

Example 16. The system according to example 15, wherein, in the flushing position, the nozzle seals with the port proximally from the membrane.

Example 17. The system according to example 16, wherein, the port has a tapered inner wall that defines a lumen proximal from the membrane, the lumen of the port tapering distally toward the membrane.

Example 18. The system according to example 17, wherein the nozzle is dimensioned such that, when the flushing adapter is locked to the extracorporeal unit in the flushing position, the nozzle seals against the tapered inner wall proximally from the membrane.

Example 19. The system according to example 15, wherein the membrane is shaped to define a first aperture through the membrane, a second aperture through the membrane, and a closed slit connecting the first aperture with the second aperture.

Example 20. The system according to example 19, wherein the first aperture is wider in diameter than the second aperture.

Example 21. The system according to example 20, wherein the first aperture is 3-10 times larger than the second aperture.

Example 22. The system according to example 20, wherein (A) each of the anchors comprises a tissue-engaging element, and a head that comprises an eyelet, and (B) the port is arranged such that, for each of the cartridges, while the cartridge is in the deployment position and holds the respective anchor opposite the proximal opening: (i) the tissue-engaging element of the respective tissue anchor is aligned with the first aperture, thereby defining an anchor-advancement axis from the respective tissue anchor, through the first aperture, and through the tube, and (ii) the eyelet of the respective tissue anchor is aligned with the second aperture.

Example 23. The system according to any one of examples 1-22, wherein (i) the system further comprises a platform, (ii) the proximal end of the tube defines a longitudinal axis, (iii) the extracorporeal unit is configured to be mounted on the platform in a manner that facilitates rotation of the extracorporeal unit around the longitudinal axis, and (iv) the extracorporeal unit is rotationally fixed to the tube, such that rotation of the extracorporeal unit around the longitudinal axis rotates the tube.

Example 24. The system according to example 23, wherein the system defines an array of discrete rotational orientations of the extracorporeal unit around the longitudinal axis, and the extracorporeal unit is configured to be mounted on the platform in a manner that facilitates orienting the extracorporeal unit in each of the discrete rotational orientations.

Example 25. The system according to example 24, further comprising at least one detent, configured to secure the extracorporeal unit in each of the discrete rotational orientations.

Example 26. The system according to example 25, wherein the at least one detent is configured to secure the extracorporeal unit in each of the discrete rotational orientations by providing a snap-fit of the extracorporeal unit in each of the discrete rotational orientations.

Example 27. The system according to example 25, wherein the extracorporeal unit defines an array of recesses corresponding to the array of discrete rotational orientations, and the at least one detent is configured to secure the extracorporeal unit in each of the discrete rotational orientations by, for each of the discrete rotational orientations, protruding into the corresponding recess.

Example 28. The system according to example 25, wherein (i) the system further comprises a bracket, the extracorporeal unit being configured to be mounted on the platform via coupling between the bracket and the platform, (ii) the extracorporeal unit is rotatably coupled to the bracket in a manner that facilitates rotation of the extracorporeal unit around the longitudinal axis, and (iii) the at least one detent is configured to secure the extracorporeal unit in each of the discrete rotational orientations by, while the extracorporeal unit is disposed in any of the discrete rotational orientations, inhibiting rotation of the extracorporeal unit with respect to the bracket.

Example 29. The system according to example 25, wherein the at least one detent is spring-loaded.

Example 30. The system according to any one of examples 1-29, wherein, for each of the cartridges, a barrier of the extracorporeal unit is configured to transition into a closed state responsively to movement of the cartridge toward the deployment position.

Example 31. The system according to example 30, wherein, for each of the cartridges, the barrier is configured to transition into the closed state responsively to arrival of the cartridge at the deployment position.

Example 32. The system according to example 31, wherein, for each of the cartridges, the cartridge is configured to push the barrier toward the closed state upon arrival of the cartridge at the deployment position.

Example 33. The system according to example 32, wherein, for each of the cartridges, the cartridge (i) comprises a first piece and a second piece that holds the respective anchor, (ii) defines a face that, upon arrival of the cartridge at the deployment position, pushes the barrier toward the closed state, and (iii) is configured such that, while the cartridge remains in the deployment position with the barrier in the closed state, application of a force to the respective anchor displaces the face such that the barrier responsively transitions into an open state.

Example 34. The system according to example 33, wherein the cartridge is configured such that, while the cartridge remains in the deployment position with the barrier in the closed state, application of the force to the respective anchor moves the face proximally, and the barrier is configured to transition into the open state responsively to the movement of the face proximally.

Example 35. The system according to example 33, wherein the face is defined by the second piece, and the cartridge is configured such that, while the cartridge remains in the deployment position with the barrier in the closed state, application of the force to the respective anchor displaces the face by sliding the second piece with respect to the first piece.

Example 36. The system according to example 33, wherein, for each of the cartridges, the cartridge is coupled to the extracorporeal unit via coupling between the first piece and the extracorporeal unit.

Example 37. The system according to example 33, wherein the second piece is mounted inside the first piece.

Example 38. The system according to example 37, wherein the first piece is shaped to be grasped by hand by a human operator.

Example 39. The system according to example 1, wherein, from the deployment position, each of the cartridges is removable such that the deployment position becomes vacant for a successive cartridge of the series.

Example 40. The system according to example 39, wherein, from the deployment position, each of the cartridges is removable by being removed from the extracorporeal unit.

Example 41. The system according to any one of examples 1-40, wherein the anchor driver is configured to, for each of the anchors, advance the anchor distally out of the respective cartridge, through the proximal opening, and through the tube toward the distal opening while the respective cartridge remains in the deployment position.

Example 42. The system according to example 41, wherein, for each of the cartridges, the cartridge is configured such that, while (i) the cartridge remains at the deployment position, and (ii) the anchor driver is extended distally beyond the cartridge and through the tube toward the distal opening, the anchor driver inhibits its removal of the cartridge from the deployment position.

Example 43. The system according to any one of examples 1-42, wherein each of the anchors comprises a tissue-engaging element and comprises a head that comprises an eyelet, and the system further comprises a tether: (i) threaded through the eyelet of each of the anchors, (ii) having a proximal portion that includes a proximal end of the tether, and (iii) having a distal portion that includes a distal end of the tether, the distal end of the tether being advanceable distally through the tube into the subject while the proximal end of the tether remains outside of the subject.

Example 44. The system according to example 43, wherein the tube defines a lateral slit extending proximally from the distal end of the tube, and the lateral slit is dimensioned to allow the tether, but not the anchors, to exit the tube laterally, proximally from the distal end of the tube.

Example 45. The system according to example 44, wherein the tube is shaped to define a narrowed inlet into the lateral slit, configured to inhibit but not preclude the tether from distally exiting the lateral slit via the narrowed inlet.

Example 46. The system according to example 45, wherein the tube comprises a tip frame that maintain the lateral slit and the narrowed inlet.

Example 47. The system according to example 46, wherein the tip frame is resilient.

Example 48. The system according to example 43, wherein, for each of the anchors: (i) the tissue-engaging element defines a central longitudinal axis of the anchor, has a sharpened distal tip, and is configured to be driven into tissue of the subject, (ii) the head is coupled to a proximal end of the tissue-engaging element, and further comprises an interface, configured to be reversibly engaged by the anchor driver, and (iii) the eyelet is mounted so as to be revolvable about the central longitudinal axis of the anchor.

Example 49. The system according to example 48, wherein, for each of the anchors, the eyelet: (i) defines an aperture and a slide axis through the aperture, (ii) is disposed laterally from the central longitudinal axis of the anchor thereby defining an eyelet axis that is orthogonal to the central longitudinal axis, and (iii) is mounted so as to be rotatable about the eyelet axis in a manner that constrains the slide axis to be orthogonal to the eyelet axis.

Example 50. The system according to example 48, wherein, for each of the anchors, the eyelet: (i) defines an aperture and a slide axis through the aperture, (ii) is disposed laterally from the central longitudinal axis of the anchor thereby defining an eyelet axis that is orthogonal to the central longitudinal axis, and (iii) is mounted so as to be revolvable about the central longitudinal axis while the slide axis remains constrained to be orthogonal to the eyelet axis.

Example 51. The system according to example 48, wherein the interface is disposed on the central longitudinal axis of the anchor.

Example 52. The system according to example 48, wherein the tissue-engaging element is helical, defines the central longitudinal axis by extending in a helix around and along the central longitudinal axis, and is configured to be screwed into the tissue of the subject.

Example 53. The system according to example 48, wherein the head comprises a collar that circumscribes the central longitudinal axis and is rotatably coupled to the tissue-engaging element, and wherein the eyelet is mounted on the collar, and is revolvable around the central longitudinal axis by rotation of the collar about the central longitudinal axis.

Example 54. The system according to example 43, further comprising a series of tubular spacers, threaded on the tether alternatingly with the anchors.

Example 55. The system according to example 54, wherein each of the spacers is elastically flexible in deflection.

Example 56. The system according to example 55, wherein each of the spacers comprises, at each end of the tubular spacer, a rigid ring.

Example 57. The system according to example 54, wherein each of the spacers resists axial compression.

Example 58. The system according to example 54, wherein each of the spacers is defined by a helical wire shaped as a coil.

Example 59. The system according to example 43, wherein the anchor driver, for each of the anchors, is configured to advance the anchor distally out of the respective cartridge, through the proximal opening, and through the tube toward the distal opening, while the eyelet of the anchor remains threaded on the tether.

Example 60. The system according to example 59, wherein: (i) the catheter device further comprises a port at the proximal opening of the tube, the port comprising a membrane, (ii) the membrane is shaped to define a first aperture through the membrane, a second aperture through the membrane, and a closed slit connecting the first aperture with the second aperture, and (iii) the port is arranged such that, for each of the anchors, the anchor driver is configured to advance the anchor distally out of the respective cartridge and through the membrane with the tissue-engaging element passing through the first aperture and the tether extending through the second aperture.

Example 61. The system according to example 43, wherein the catheter device further comprises a tensioner that comprises a spring-loaded winch, coupled to the proximal portion of the tether, and configured to maintain tension on the tether.

Example 62. A method for use with a catheter device, the method comprising: (i) transluminally advancing a distal portion of a tube of the catheter device to a heart of a subject, the catheter device including an extracorporeal unit coupled to a proximal end of the tube, a cartridge coupled to the extracorporeal unit at an initial position and holding an anchor; (ii) sliding the cartridge, from the initial position, along a track to a deployment position in which the cartridge holds the anchor opposite a proximal opening of the tube, the extracorporeal unit including a barrier that obstructs the proximal opening; (iii) subsequently, using an anchor driver engaged with the anchor, opening the barrier by applying a force to the anchor; and (iv) subsequently, using the anchor driver, advancing the anchor distally out of the cartridge, through the proximal opening, and through the tube toward the distal portion of the tube.

Example 63. A system for use with a subject, comprising: (A) a catheter device, comprising: (i) a tube that has a proximal opening, and a distal opening that is configured to be transluminally advanced into the subject, and (ii) an extracorporeal unit that comprises a track that leads to a deployment position; (B) a first cartridge holding a first anchor and being coupled to the extracorporeal unit and, while remaining coupled to the extracorporeal unit, being moveable along the track from a first initial position to the deployment position such that the first cartridge holds the first anchor opposite the proximal opening; (C) a second cartridge holding a second anchor and being coupled to the extracorporeal unit and, while remaining coupled to the extracorporeal unit, being moveable along the track from a second initial position to the deployment position such that the second cartridge holds the second anchor opposite the proximal opening; and (D) an anchor driver that is: (i) couplable to the first anchor while the first anchor is held by the first cartridge opposite the proximal opening, (ii) configured to advance the first anchor distally out of the first cartridge through the proximal opening and through the tube, (iii) subsequently couplable to the second anchor while the second anchor is held by the second cartridge opposite the proximal opening, and (iv) configured to advance the second anchor distally out of the second cartridge through the proximal opening and through the tube toward the first anchor.

Example 64. The system according to example 63, wherein the extracorporeal unit comprises a barrier movable between a closed state in which the barrier obstructs the proximal opening and an open state, and wherein the anchor driver is: (i) configured to, while coupled to the first anchor and while the barrier is in the open state, advance the first anchor distally out of the first cartridge through the proximal opening and through the tube, (ii) subsequently, configured to, while coupled to the second anchor and while the barrier is in the open state, advance the second anchor distally out of the second cartridge through the proximal opening and through the tube toward the first anchor.

Example 65. The system according to example 64, wherein the driver is configured to advance the first anchor distally out of the first cartridge through the proximal opening and through the tube while: (i) the first cartridge is in the deployment position, (ii) the barrier is in the open state, and (iii) the second cartridge remains in the second initial position.

Example 66. The system according to any one of examples 63-65, wherein each of the first cartridge and the second cartridge is configured to lock to the extracorporeal unit upon arriving at the deployment position.

Example 67. The system according to any one of examples 63-66, wherein each of the first cartridge and the second cartridge is shaped to be grasped by hand by a human operator and is configured to be moved along the track by hand by the human operator, and/or wherein each of the first cartridge and the second cartridge is removable from the deployment position by being removed from the extracorporeal unit.

Example 68. The system according to any one of examples 63-67, further comprising a third cartridge holding a third anchor and being coupled to the extracorporeal unit and, while remaining coupled to the extracorporeal unit, being moveable along the track from a third initial position to the deployment position such that the third cartridge holds the third anchor opposite the proximal opening.

Example 69. The system according to any one of examples 63-68, wherein the first anchor comprises a first tissue-engaging element and a first head comprising a first eyelet, and the second anchor comprises a second tissue-engaging element and a second head comprising a second eyelet.

Example 70. The system according to example 69, further comprising a tether threaded through the first eyelet and the second eyelet, the tether having a proximal portion that includes a proximal end of the tether and having a distal portion that includes a distal end of the tether, the distal end of the tether being advanceable distally through the tube into the subject while the proximal end of the tether remains outside of the subject.

Example 71. The system according to example 70, wherein the anchor driver is configured to advance the first anchor distally out of the first cartridge, through the proximal opening, and through the tube, while the first eyelet of the first anchor remains threaded on the tether, and wherein the anchor driver is configured to advance the second anchor distally out of the second cartridge, through the proximal opening, and through the tube, while the second eyelet of the second anchor remains threaded on the tether.

Example 72. The system according to example 71, wherein the catheter device further comprises a tensioning device configured to maintain tension on the tether during advancement of the first anchor and advancement of the second anchor.

Example 73. The system according to example 72, wherein the tensioning device comprises a spring and a spool, the spool coupled to the spring such that rotation of the spool in a first direction applies stress to the spring, and wherein the proximal portion of the tether is wound around the spool such that advancing of the distal portion of the tether distally through the tube rotates the spool in the first direction.

Example 74. A system, for use with a subject, the system comprising: (A) a catheter device, comprising: (i) a tube that has a distal opening that is configured to be transluminally advanced to a tissue of the subject and a proximal portion, and (ii) an extracorporeal unit that is coupled to the proximal portion of the tube; (B) a series of anchors, each of the anchors comprising: (i) a tissue-engaging element, and (ii) a head, coupled to a proximal end of the tissue-engaging element, and comprising an interface and an eyelet; (C) a tether, threaded through the eyelet of each of the anchors; and (D) an anchor driver that, for each of the anchors, is configured to: (i) engage the interface of the anchor, and (ii) while engaged with the anchor, advance the anchor distally through the tube toward the distal opening, and drive the tissue-engaging element into the tissue.

Example 75. The system according to example 74, wherein: (i) the system defines an array of discrete rotational orientations of the extracorporeal unit around a longitudinal tube-axis of the proximal portion of the tube, (ii) the extracorporeal unit is configured to be mounted on a platform in a manner that facilitates rotation of the extracorporeal unit around the longitudinal tube-axis so as to become oriented in any of the discrete rotational orientations, and (iii) the extracorporeal unit is rotationally fixed to the tube, such that rotation of the extracorporeal unit around the longitudinal tube-axis rotates the tube.

Example 76. The system according to any one of examples 74-75, wherein the tube defines a lateral slit extending proximally from the distal opening of the tube, and the lateral slit is dimensioned to allow the tether, but not the anchors, to exit the tube laterally, proximally from the distal opening of the tube.

Example 77. The system according to example 76, wherein the tube is shaped to define a narrowed inlet into the lateral slit, configured to inhibit but not preclude the tether from distally exiting the lateral slit via the narrowed inlet.

Example 78. The system according to example 77, wherein the tube comprises a tip frame that maintain the lateral slit and the narrowed inlet.

Example 79. The system according to example 78, wherein the tip frame is resilient.

Example 80. The system according to any one of examples 74-79, further comprising at least one detent, configured to secure the extracorporeal unit in each of the discrete rotational orientations.

Example 81. The system according to example 80, wherein the at least one detent is spring-loaded.

Example 82. The system according to example 80, wherein the at least one detent is configured to secure the extracorporeal unit in each of the discrete rotational orientations by providing a snap-fit of the extracorporeal unit in each of the discrete rotational orientations.

Example 83. The system according to example 80, wherein: (i) the extracorporeal unit defines an array of recesses corresponding to the array of discrete rotational orientations, and (ii) the at least one detent is configured to secure the extracorporeal unit in each of the discrete rotational orientations by, for each of the discrete rotational orientations, protruding into the corresponding recess.

Example 84. The system according to example 80, wherein: (i) the system further comprises a bracket, the extracorporeal unit being configured to be mounted on a platform via coupling between the bracket and the platform, (ii) the extracorporeal unit is rotatably coupled to the bracket in a manner that facilitates rotation of the extracorporeal unit around a longitudinal tube-axis of the proximal portion of the tube, and (iii) the at least one detent is configured to secure the extracorporeal unit in each of the discrete rotational orientations by, while the extracorporeal unit is disposed in any of the discrete rotational orientations, inhibiting rotation of the extracorporeal unit with respect to the bracket.

Example 85. The system according to any one of examples 74-84, further comprising a series of tubular spacers, threaded on the tether alternately with the anchors.

Example 86. The system according to example 85, wherein each of the spacers is elastically flexible in deflection.

Example 87. The system according to any one of examples 85-86, wherein each of the spacers comprises, at each end of the tubular spacer, a rigid ring.

Example 88. The system according to any one of examples 85-87, wherein each of the spacers resists axial compression.

Example 89. The system according any one of examples 85-88, wherein each of the spacers is defined by a helical wire shaped as a coil.

Example 90. The system according to any one of examples 74-89, wherein, for each of the anchors: (i) the tissue-engaging element defines a central longitudinal anchor-axis of the anchor, and (ii) the eyelet is mounted so as to be revolvable about the central longitudinal anchor axis.

Example 91. The system according to example 90, wherein, for each of the anchors, the eyelet: (i) defines an aperture and a slide axis through the aperture, (ii) is disposed laterally from the central longitudinal anchor-axis thereby defining an eyelet axis that is orthogonal to the central longitudinal anchor-axis, and (ii) is mounted so as to be rotatable about the eyelet axis in a manner that constrains the slide axis to be orthogonal to the eyelet axis.

Example 92. The system according to example 90, wherein, for each of the anchors, the eyelet: (i) defines an aperture and a slide axis through the aperture, (ii) is disposed laterally from the central longitudinal anchor-axis thereby defining an eyelet axis that is orthogonal to the central longitudinal axis, and (ii) is mounted so as to be revolvable about the central longitudinal anchor-axis while the slide axis remains constrained to be orthogonal to the eyelet axis.

Example 93. The system according to example 90, wherein the interface is disposed on the central longitudinal axis of the anchor.

Example 94. The system according to example 90, wherein the tissue-engaging element is helical, defines the central longitudinal anchor-axis by extending in a helix around and along the central longitudinal anchor-axis, and is configured to be screwed into the tissue of the subject.

Example 95. A system, for use with a subject, the system comprising: (A) a catheter device, comprising: (i) a tube that has a distal opening that is configured to be transluminally advanced to a tissue of the subject, and a proximal portion that defines a longitudinal tube-axis, and (ii) an extracorporeal unit that is coupled to the proximal portion of the tube; and (B) a platform; and wherein: (1) the system defines an array of discrete rotational orientations of the extracorporeal unit around the longitudinal tube-axis, (2) the extracorporeal unit is configured to be mounted on the platform in a manner that facilitates rotation of the extracorporeal unit around the longitudinal tube-axis so as to become oriented in any of the discrete rotational orientations, and (3) the extracorporeal unit is rotationally fixed to the tube, such that rotation of the extracorporeal unit around the longitudinal tube-axis rotates the tube.

Example 96. The system according to example 95, further comprising a series of anchors, each of the anchors being advanceable through the tube, and comprising: (i) a tissue-engaging element, and (ii) a head, coupled to a proximal end of the tissue-engaging element.

Example 97. The system according to example 96, wherein the head of each of the anchors and comprises an interface and an eyelet, and wherein the system further comprises a tether, threaded through the eyelet of each of the anchors.

Example 98. The system according to example 97, further comprising an anchor driver that, for each of the anchors, is configured to engage the interface of the anchor, and while engaged with the anchor, advance the anchor distally through the tube toward the distal opening, and drive the tissue-engaging element into the tissue.

Example 99. A method for use with a heart of a subject, the method comprising: (A) transluminally advancing, to the heart, a distal portion of a tube of a catheter device of a system, the catheter device further including an extracorporeal unit that is coupled to a proximal portion of the tube, the proximal portion of the tube defining a longitudinal tube-axis, and the system further including: (i) a series of anchors, (ii) a tether, threaded through an eyelet of each of the anchors, (iii) an anchor driver, and (iv) a platform, the extracorporeal unit mounted on the platform in a manner that defines an array of discrete rotational orientations of the extracorporeal unit around the longitudinal tube-axis; (B) while the extracorporeal unit is in a first of the discrete rotational orientations, and using an anchor driver, advancing a first anchor of the series distally through the tube toward a distal opening of the tube, and anchoring the first anchor to a first site of tissue of the heart; (C) subsequently, rotating the tube by a predetermined angle of rotation by rotating the extracorporeal unit into a second of the discrete rotational orientations; and (D) subsequently, while the extracorporeal unit remains in the second of the discrete rotational orientations, and using the anchor driver, advancing a second anchor of the series distally through the tube and over and along the tether toward the distal opening, and anchoring the second anchor to a second site of tissue of the heart.

Example 100. The method according to example 99, further comprising, subsequently drawing the first anchor and the second anchor toward each other by applying tension to the tether.

Example 101. A system, for use with a subject, the system comprising: (A) a catheter device, comprising: (i) a tube that has a proximal portion including a proximal end, a distal portion that is configured to be transluminally advanced to a tissue of the subject, and an intermediate portion extending between the proximal portion and the distal portion, and (ii) an extracorporeal unit that is coupled to the proximal portion of the tube; (B) a series of anchors, each of the anchors comprising: (i) a tissue-engaging element, and (ii) a head, coupled to a proximal end of the tissue-engaging element, and comprising an interface and an eyelet; (C) a tether, threaded through the eyelet of each of the anchors; (D) an anchor driver that, for each of the anchors, is configured to: (i) engage the interface of the anchor, and (ii) while engaged with the anchor, advance the anchor distally through the tube toward the distal portion, and drive the tissue-engaging element into the tissue; and wherein: (1) the distal portion defines a lumen, a distal opening, and a lateral slit extending proximally from the distal opening, (2) each of the anchors is dimensioned to be advanced by the anchor driver distally out of the lumen via the distal opening, (3) the lateral slit is dimensioned to allow the tether, but not the anchor, to exit the lumen laterally through the lateral slit, and (4) the distal portion is rotatably coupled to the intermediate portion such that the lateral slit is revolvable about the lumen.

Example 102. The system according to example 101, wherein the distal portion is shaped to define a narrowed inlet into the lateral slit, configured to inhibit but not preclude the tether from distally exiting the lateral slit via the narrowed inlet.

Example 103. The system according to any one of examples 101-102, wherein the tether has a proximal end, and a distal end that is advanceable distally through the tube into the subject while the proximal end of the tether remains outside of the subject.

Example 104. The system according to any one of examples 101-103, further comprising a series of tubular spacers, threaded on the tether alternately with the anchors.

Example 105. The system according to example 104, wherein each of the spacers is elastically flexible in deflection.

Example 106. The system according to example 105, wherein each of the spacers comprises, at each end of the tubular spacer, a rigid ring.

Example 107. The system according to example 104, wherein each of the spacers resists axial compression.

Example 108. The system according to example 104, wherein each of the spacers is defined by a helical wire shaped as a coil.

Example 109. The system according to any one of examples 101-108, wherein, for each of the anchors: (i) the tissue-engaging element defines a central longitudinal anchor-axis of the anchor, and (ii) the eyelet is mounted so as to be revolvable about the central longitudinal anchor axis.

Example 110. The system according to example 109, wherein, for each of the anchors, the eyelet: (i) defines an aperture and a slide axis through the aperture, (ii) is disposed laterally from the central longitudinal anchor-axis thereby defining an eyelet axis that is orthogonal to the central longitudinal anchor-axis, and (iii) is mounted so as to be rotatable about the eyelet axis in a manner that constrains the slide axis to be orthogonal to the eyelet axis.

Example 111. The system according to example 109, wherein, for each of the anchors, the eyelet: (i) defines an aperture and a slide axis through the aperture, (ii) is disposed laterally from the central longitudinal anchor-axis thereby defining an eyelet axis that is orthogonal to the central longitudinal axis, and (iii) is mounted so as to be revolvable about the central longitudinal anchor-axis while the slide axis remains constrained to be orthogonal to the eyelet axis.

Example 112. The system according to example 109, wherein the interface is disposed on the central longitudinal axis of the anchor.

Example 113. The system according to example 109, wherein the tissue-engaging element is helical, defines the central longitudinal anchor-axis by extending in a helix around and along the central longitudinal anchor-axis, and is configured to be screwed into the tissue of the subject.

Example 114. A tissue anchor comprising: (A) a helical tissue-engaging element: (i) having a proximal turn, and a distal turn that defines a sharpened distal tip, and (ii) extending helically around a central anchor-axis of the tissue anchor; and (B) a head, comprising: (i) a core, disposed on the central longitudinal axis, and (ii) a flange, fixed to the core, and having a proximal-facing surface, the proximal turn lying on the proximal-facing surface; and (iii) a cap, fixed to the core in a manner that secures the tissue-engaging element to the head by sandwiching the proximal turn against the proximal-facing surface of the flange.

Example 115. The tissue anchor according to example 114, wherein the cap is fixed to the core via complimentary screw threads defined by the cap and the core.

Example 116. The tissue anchor according to any one of examples 114-115, wherein the flange is a first flange, the cap is shaped to define a second flange, and the cap is fixed to the core in a manner that secures the tissue-engaging element to the head by sandwiching the proximal turn between the second flange and the proximal-facing surface of the first flange.

Example 117. The tissue anchor according to any one of examples 114-116, wherein the flange is shaped such that the proximal-facing surface is inclined with respect to the central anchor-axis.

Example 118. The tissue anchor according to any one of examples 114-117, wherein the flange is shaped such that the proximal-facing surface defines a partial helix.

Example 119. The tissue anchor according to any one of examples 114-118, wherein the tissue-engaging element has a second turn immediately distally from the proximal turn, and wherein the flange is disposed between the proximal turn and the second turn.

Example 120. The tissue anchor according to example any one of examples 114-119, wherein the flange protrudes laterally beyond the core.

Example 121. The tissue anchor according to any one of examples 114-120, wherein the flange protrudes radially beyond the core.

Example 122. The tissue anchor according to any one of examples 114-121, further comprising a washer, and wherein the cap is fixed to the core in a manner that secures the tissue-engaging element to the head by sandwiching the proximal turn between the washer and the proximal-facing surface of the flange.

Example 123. The tissue anchor according to example 122, wherein the proximal turn has a notch therein, the washer is shaped to define a spur, and the cap is fixed to the core in a manner that secures the tissue-engaging element to the head by sandwiching the proximal turn between the washer and the proximal-facing surface of the flange, with the spur disposed in the notch.

Example 124. The tissue anchor according to any one of examples 114-123, wherein the core is shaped as a post, and the cap is shaped to define a cavity in which the post is disposed.

Example 125. The tissue anchor according to example 124, wherein the head further comprises: (i) a collar, disposed axially between the flange and the cap, circumscribing the post and rotatable about the post, and (ii) an eyelet, mounted on the collar, and revolvable around the central anchor-axis by rotation of the collar about the post.

Example 126. The tissue anchor according to example 125, wherein the cap defines a tubular wall that defines the cavity and that is disposed coaxially between the post and the collar.

Example 127. The tissue anchor according to example 126, wherein the cap is fixed to the core in a manner that secures the tissue-engaging element to the head by sandwiching the proximal turn between a distal end of the tubular wall and the proximal-facing surface of the flange.

Example 128. A method for manufacturing a tissue anchor, the anchor including a head and helical tissue-engaging element, the method comprising: (i) placing a proximal turn of the helical tissue-engaging element on a proximal-facing surface of a flange of the head, the head including a core disposed on a central anchor-axis of the tissue anchor, and the tissue-engaging element extending helically around the central anchor-axis and having a distal turn that defines a sharpened distal tip, and (ii) sandwiching the proximal turn against the proximal-facing surface of the flange by fixing a cap to the core.

Example 129. The method according to example 128, wherein fixing the cap to the core comprises screwing the cap onto the core.

Example 130. The method according to any one of examples 128-129, wherein the flange is a first flange, the cap is shaped to define a second flange, and sandwiching the proximal turn against the proximal-facing surface of the flange comprises sandwiching the proximal turn between the second flange and the proximal-facing surface of the first flange.

Example 131. The method according to any one of examples 128-130, wherein sandwiching the proximal turn against the proximal-facing surface of the flange comprises sandwiching the proximal turn between a washer and the proximal-facing surface of the flange by fixing the cap to the core.

Example 132. The method according to example 131, wherein the proximal turn has a notch therein, the washer is shaped to define a spur, and sandwiching the proximal turn between the washer and the proximal-facing surface of the flange comprises sandwiching the proximal turn between the washer and the proximal-facing surface of the flange by fixing the cap to the core such that the spur is disposed in the notch.

Example 133. The method according to any one of examples 128-132, wherein the core is shaped as a post, the cap is shaped to define a cavity, and fixing the cap to the core comprises positioning the post in the cavity.

Example 134. The method according to example 133, further comprising placing a collar axially between the flange and the cap such that the collar circumscribes the post and is rotatable about the post, the collar having an eyelet mounted thereon such that the eyelet is revolvable around the central anchor-axis by rotation of the collar about the post.

Example 135. The method according to example 134, wherein the cap defines a tubular wall that defines the cavity, and wherein fixing the cap to the core comprises positioning the tubular wall coaxially between the post and the collar.

Example 136. The method according to example 135, wherein sandwiching the proximal turn against the proximal-facing surface of the flange by fixing the cap to the core comprises sandwiching the proximal turn between a distal end of the tubular wall and the proximal-facing surface of the flange by fixing the cap to the core.

Example 137. A system, for use with a subject, the system comprising a catheter device that comprises: (A) a tube that has: (i) a proximal portion including a proximal end, and (ii) a distal portion that is configured to be transluminally advanced to a tissue of the subject; (B) an extracorporeal unit that is coupled to the proximal portion of the tube; and (C) a fluoroscopic guide, comprising: (i) a flap, having (a) a tip, (b) a root at which the flap is pivotably coupled to the distal portion of the tube in a manner in which the flap is deflectable with respect to the tube between: a retracted state in which the flap is substantially parallel with the tube and an extended state in which the flap extends laterally from the tube, and (c) an intermediate portion extending between the tip and the root, the intermediate portion being: radiopaque and flexible such that pressing on the intermediate portion changes a curvature of the intermediate portion, and (ii) a control rod, extending from the distal portion of the tube to the tip of the flap such that: (a) advancement of the control rod deflects the flap toward the extended state by pushing the tip of flap, and (b) retraction of the control rod deflects the flap toward the retracted state by pulling the tip of the flap.

Example 138. The system according to example 137, wherein the fluoroscopic guide is configured such that advancement of the control rod deflects the flap toward the extended state by pushing the tip of flap distally.

Example 139. The system according to any one of examples 137-138, wherein the fluoroscopic guide is configured such that retraction of the control rod deflects the flap toward the extended state by pulling the tip of flap proximally.

Example 140. The system according to any one of examples 137-139, further comprising an anchor, and an anchor driver configured to advance the anchor distally through the tube toward the distal portion, and drive the anchor into the tissue.

Example 141. The system according to any one of examples 137-140, wherein the control rod extends from the extracorporeal unit, along the tube, to an exit point at which the control rod extends from the tube to the tip of the flap.

Example 142. The system according to any one of examples 137-141, wherein, in the retracted state, the tip of the flap is disposed against the distal portion of the tube.

Example 143. The system according to any one of examples 137-142, wherein, in the retracted state, the tip of the flap is disposed proximally from the root of the flap.

Example 144. The system according to any one of examples 137-143, wherein, in the extended state, the flap extends distolaterally from the tube.

Example 145. The system according to any one of examples 137-144, wherein the distal portion of the tube includes a distal end of the tube, and wherein the root of the flap is pivotably coupled to the distal portion of the tube at the distal end of the tube.

Example 146. The system according to any one of examples 137-145, wherein the control rod is flexible such that the advancement of the control rod that deflects the flap toward the extended state causes the control rod to flex laterally away from the distal portion of the tube.

Example 147. The system according to any one of examples 137-146, wherein the flap is pivotably coupled to the distal portion of the tube such that an angular range of the flap between the retracted state and the extended state is 80-160 degrees.

Example 148. The system according to example 147, wherein the flap is pivotably coupled to the distal portion of the tube such that the angular range of the flap between the retracted state and the extended state is 90-140 degrees.

Example 149. The system according to example 148, wherein the flap is pivotably coupled to the distal portion of the tube such that the angular range of the flap between the retracted state and the extended state is 100-130 degrees.

Example 150. The system according to any one of examples 137-149, wherein, in the extended state, the flap is disposed at 80-160 degrees with respect to the tube.

Example 151. The system according to example 150, wherein, in the extended state, the flap is disposed at 90-140 degrees with respect to the tube.

Example 152. The system according to example 151, wherein, in the extended state, the flap is disposed at 100-130 degrees with respect to the tube.

Example 153. A method, comprising: (A) transluminally advancing, to a heart of a subject, a distal portion of a tube of a catheter device, the catheter device including a fluoroscopic guide that includes: (i) a flap, having: (a) a tip, (b) a root at which the flap is pivotably coupled to the distal portion of the tube, and (c) a flexible intermediate portion extending between the tip and the root, and (ii) a control rod, extending from the distal portion of the tube to the tip of the flap; (B) placing a distal end of the tube against a tissue site of the heart proximate to a valve of the heart; (C) within the heart, deflecting the flap toward an extended state thereof by advancing the control rod such that the control rod pushes the tip of the flap away from the tube; (D) while the distal end of the tube remains against the tissue site and the flap remains in the extended state, fluoroscopically observing a curvature of the intermediate portion; (E) responsively to the observing, determining whether to drive an anchor into the tissue site; and (F) responsively to the determining, driving the anchor into the tissue site.

Example 154. The method according to example 153, wherein deflecting the flap toward the extended state comprises deflecting the flap toward the extended state by advancing the control rod such that the control rod pushes the tip of the flap distally.

Example 155. The method according to any one of examples 153-154, wherein fluoroscopically observing the curvature comprises fluoroscopically observing oscillation of the curvature.

Example 156. The method according to any one of examples 153-155, wherein: (i) the catheter device includes an extracorporeal unit that is coupled to a proximal portion of the tube, (ii) the control rod extends from the extracorporeal unit, along the tube, to an exit point at which the control rod extends from the tube to the tip of the flap, and (iii) deflecting the flap toward the extended state by advancing the control rod comprises deflecting the flap toward the extended state thereof by pushing the control rod from the extracorporeal unit.

Example 157. The method according to any one of examples 153-156, wherein transluminally advancing the distal portion of the tube comprises transluminally advancing the distal portion of the tube while the flap is in a retracted state in which the tip of the flap is disposed against the distal portion of the tube.

Example 158. The method according to any one of examples 153-157, wherein transluminally advancing the distal portion of the tube comprises transluminally advancing the distal portion of the tube while the flap is in a retracted state in which the tip of the flap is disposed proximally from the root of the flap.

Example 159. The method according to any one of examples 153-158, wherein, in the extended state, the flap extends distolaterally from the tube, and wherein deflecting the flap toward the extended state comprises deflecting the flap toward the extended state in which the flap extends distolaterally from the tube.

Example 160. The method according to any one of examples 153-159, wherein the root of the flap is pivotably coupled to the distal portion of the tube at a pivot point that is at the distal end of the tube, and deflecting the flap toward the extended state comprises deflecting the flap about the pivot point that is at the distal portion of the tube.

Example 161. The method according to any one of examples 153-160, wherein the control rod is flexible, and wherein advancing the control rod comprises advancing the control rod such that the control rod flexes laterally away from the distal portion of the tube and pushes the tip of the flap away from the distal portion of the tube.

Example 162. The method according to any one of examples 153-161, further comprising, subsequently to the observing, deflecting the flap toward a retracted state thereof by retracting the control rod such that the control rod pulls the tip of the flap toward the tube.

Example 163. The method according to example 162, wherein deflecting the flap toward the retracted state comprises deflecting the flap toward the retracted state by retracting the control rod such that the control rod pulls the tip of the flap proximally.

Example 164. The method according to any one of examples 153-163, wherein the tissue site is a site on an annulus of the valve, and wherein placing the distal end of the tube against the tissue site comprises placing the distal end of the tube against the site on the annulus of the valve.

Example 165. The method according to example 164, wherein deflecting the flap toward the extended state comprises deflecting the flap toward the extended state such that the intermediate portion of the flap becomes pressed against a hinge of the valve at which a leaflet of the valve connects to the annulus.

Example 166. The method according to example 164, further comprising pressing the intermediate portion of the flap against a hinge of the valve at which a leaflet of the valve connects to the annulus.

Example 167. The method according to any one of examples 153-166, wherein deflecting the flap toward the extended state comprises deflecting the flap by 80-160 degrees.

Example 168. The method according to example 167, wherein deflecting the flap toward the extended state comprises deflecting the flap by 90-140 degrees.

Example 169. The method according to example 168, wherein deflecting the flap toward the extended state comprises deflecting the flap by 100-130 degrees.

Example 170. The method according to any one of examples 153-169, wherein, in the extended state, the flap is disposed at 80-160 degrees with respect to the tube, and wherein deflecting the flap toward the extended state comprises deflecting the flap such that the flap becomes disposed at 80-160 degrees with respect to the tube.

Example 171. The method according to example 170, wherein, in the extended state, the flap is disposed at 90-140 degrees with respect to the tube, and wherein deflecting the flap toward the extended state comprises deflecting the flap such that the flap becomes disposed at degrees with respect to the tube.

Example 172. The method according to example 171, wherein, in the extended state, the flap is disposed at 100-130 degrees with respect to the tube, and wherein deflecting the flap toward the extended state comprises deflecting the flap such that the flap becomes disposed at 100-130 degrees with respect to the tube.

Example 173. An system, comprising an anchor for use with tissue of a subject, the anchor comprising: (A) a case, having a tissue-facing side that defines a tissue-facing opening from inside the case to outside the case; and (B) a tissue-engaging element: (i) shaped to define a helix that has multiple turns around an axis, (ii) axially compressed within the case, and positioned such that rotation of the tissue-engaging element about the axis feeds the helix distally out of the tissue-facing opening; and (iii) configured to be screwed into the tissue, and to anchor the case to the tissue, the tissue-facing side serving as an anchor head of the anchor.

Example 174. The system according to example 173, wherein a distal tip of the tissue-engaging element is sharpened.

Example 175. The system according to any one of examples 173-174, wherein the anchor is configured such that screwing of the tissue-engaging element into the tissue presses the tissue-facing side against the tissue.

Example 176. The system according to example 175, wherein the case side defines grips on the tissue-facing side, such that the screwing of the tissue-engaging element into the tissue presses the grips against the tissue.

Example 177. The system according to any one of examples 173-176, wherein the anchor is configured such that screwing of the tissue-engaging element into the tissue moves a proximal part of the tissue-engaging element toward the tissue-facing side.

Example 178. The system according to example 177, wherein: (i) the case further has a driver side opposite the tissue-facing side, and that defines a driver opening that provides access to the interface from outside the case, and (ii) the anchor is configured such that screwing of the tissue-engaging element into the tissue moves the proximal part of the tissue-engaging element away from the driver side.

Example 179. The system according to example 177, wherein: (i) the case further has a driver side opposite the tissue-facing side, and that defines a driver opening that provides access to the interface from outside the case, and (ii) the case is configured to automatically contract as the helix is fed distally out of the tissue-facing opening, such that the driver side follows the proximal part of the tissue-engaging element toward the tissue-facing side.

Example 180. The system according to example 177, wherein the anchor is configured such that screwing of the tissue-engaging element into the tissue sandwiches the tissue-facing side between the tissue and the proximal part of the tissue-engaging element.

Example 181. The system according to any one of examples 173-180, wherein the tissue-engaging element is configured such that, as the helix is fed out of the tissue-facing opening, progressively proximal portions of the helix axially expand as they become disposed outside of the case.

Example 182. The system according to example 181, wherein, while the helix is entirely disposed within the case, the helix has a compressed pitch, and portions of the helix disposed outside of the case have an expanded pitch that is at least twice as great as the compressed pitch.

Example 183. The system according to any one of examples 173-182, wherein: (i) the anchor comprises an interface at a proximal part of the tissue-engaging element, and (ii) the case further has a driver side that defines a driver opening from inside the case to outside the case, the driver opening providing access to the interface.

Example 184. The system according to any one of examples 173-183, wherein the anchor is configured such that screwing of the tissue-engaging element into the tissue moves the interface away from the driver side and toward the tissue-facing side.

Example 185. The system according to example 184, wherein the anchor is configured such that screwing of the tissue-engaging element into the tissue sandwiches the tissue-facing side between the tissue and the interface.

Example 186. The system according to example 183, wherein the interface is rotationally locked with the helix of the tissue-engaging element.

Example 187. The system according to example 183, wherein the driver opening is disposed in front of the interface.

Example 188. The system according to example 183, wherein the interface is visible via the driver opening.

Example 189. The system according to example 183, wherein the interface comprises a bar that is transverse to the axis and parallel to the driver opening.

Example 190. The system according to example 183, wherein the driver side is opposite the tissue-facing side.

Example 191. The system according to example 183, wherein the system further comprises a driver having a driver head at a distal portion of the driver, the driver head being: (i) dimensioned to access the interface from outside the case via the driver opening, and (ii) configured to engage the interface, and to rotate the tissue-engaging element by applying torque to the interface.

Example 192. The system according to example 191, wherein: (i) the driver head has an introduction state and a locking state; (ii) the anchor head is shaped to define a proximal opening via which the interface is accessible by the driver head while the driver head is in the introduction state, and (iii) the anchor driver is configured to lock the driver head to the interface by transitioning the driver head into the locking state by moving a part of the driver head laterally.

Example 193. The system according to example 192, wherein: (i) the anchor driver comprises a flexible shaft, and a rod extending through the shaft, (ii) the anchor head is disposed at a distal end of the shaft, and (iii) the rod is configured to transition the driver head into the locking state by applying a force to the driver head.

Example 194. The system according to example 193, wherein the driver head comprises fins, and the rod is configured to transition the driver head into the locking state by being advanced distally between the fins such that the rod pushes the fins radially outward such that the fins lock to the interface.

Example 195. The system according to example 194, wherein the fins are configured to, when pushed radially outward by the rod, lock to the interface via a friction fit.

Example 196. The system according to example 193, wherein the driver head comprises a cam, the rod being coupled to the cam, and configured to transition the driver head into the locking state by rotating the cam such that at least part of the cam protrudes laterally.

Example 197. The system according to example 196, wherein the rod is eccentric with respect to the shaft.

Example 198. The system according to example 196, wherein the rod is eccentric with respect to the cam.

Example 199. The system according to example 196, wherein in the introduction state the cam is flush with the shaft.

Example 200. The system according to example 196, wherein the anchor driver has a longitudinal axis defined by the shaft, and wherein the shaft and the cam are circular in transverse cross-section.

Example 201. The system according to example 196, wherein the interface is shaped to define multiple recesses, each dimensioned to receive the cam as it protrudes laterally.

Example 202. An apparatus comprising a tissue anchor for use with an anchor driver, the anchor comprising: (A) a tissue-engaging element defining a central longitudinal axis of the anchor, having a sharpened distal tip, and configured to be driven into tissue of a subject; and (B) an anchor head, coupled to a proximal end of the tissue-engaging element, the anchor head comprising: (i) an interface, configured to be reversibly engaged by the anchor driver, and (ii) an eyelet defining an aperture and a slide axis through the aperture, the eyelet disposed laterally from the central longitudinal axis thereby defining an eyelet axis that is orthogonal to the central longitudinal axis, and the eyelet mounted such that the eyelet is rotatable about the eyelet axis in a manner that constrains the slide axis to be orthogonal to the eyelet axis.

Example 203. The apparatus according to example 202, wherein the interface is disposed on the central longitudinal axis of the anchor.

Example 204. The apparatus according to example 202, wherein the tissue-engaging element is helical, defines the central longitudinal axis by extending in a helix around and along the central longitudinal axis, and is configured to be screwed into the tissue of the subject.

Example 205. The apparatus according to any one of examples 202-204, wherein the eyelet is mounted such that the eyelet is revolvable around the central longitudinal axis while the slide axis remains constrained to be orthogonal to the eyelet axis.

Example 206. The apparatus according to example 205, wherein the anchor head comprises a collar that circumscribes the central longitudinal axis and is rotatably coupled to the tissue-engaging element, and wherein the eyelet is mounted on the collar, and is revolvable around the central longitudinal axis by rotation of the collar about the central longitudinal axis.

Example 207. The apparatus according to example 206, wherein the eyelet defines:

a flange disposed medially to the collar, and a stem that extends laterally past the collar, and couples the flange to the aperture.

Example 208. The apparatus according to example 207, wherein the collar is a closed collar that defines a recess that supports the stem.

Example 209. The apparatus according to example 207, wherein the collar is an open collar that has free ends that together support the stem.

Example 210. The apparatus according to any one of examples 202-209, wherein the eyelet is shaped to define a first flat face and a second flat face, the aperture extending through the eyelet from the first flat face to the second flat face, and the second flat face being opposite the first flat face.

Example 211. The apparatus according to example 210, wherein the apparatus comprises an implant that comprises the anchor, and a tether threaded through the aperture.

Example 212. The apparatus according to example 210, wherein the first flat face is parallel with the eyelet axis.

Example 213. The apparatus according to example 210, wherein the first flat face is orthogonal to the slide axis.

Example 214. The apparatus according to example 210, wherein the first flat face is parallel with the second flat face.

Example 215. The apparatus according to example 210, wherein the eyelet has an inner surface that defines the aperture between the first flat face and the second flat face, such that a narrowest part of the aperture is midway between the first flat face and the second flat face.

Example 216. The apparatus according to example 215, wherein the eyelet defines the inner surface of the eyelet as a hyperboloid.

Example 217. The apparatus according to example 215, wherein the eyelet defines the inner surface of the eyelet as a catenoid.

Example 218. The apparatus according to any one of examples 202-217, wherein the apparatus comprises an implant that comprises the anchor, and a tether threaded through the aperture.

Example 219. The apparatus according to example 218, wherein the anchor is a first anchor of the implant, and the implant further comprises: (i) a second anchor, and (ii) a spacer that is tubular, having two spacer-ends and a spacer-lumen therebetween, wherein the spacer is threaded on the tether between the first anchor and the second anchor, with the tether passing through the spacer-lumen.

Example 220. The apparatus according to example 219, wherein the spacer is elastically flexible in deflection.

Example 221. The apparatus according to example 219, wherein the spacer resists axial compression.

Example 222. The apparatus according to example 219, wherein the spacer is defined by a helical wire shaped as a coil that defines the spacer-lumen.

Example 223. The apparatus according to example 219, wherein the spacer is configured to limit a proximity between the first anchor and the second anchor.

Example 224. The apparatus according to example 219, wherein: (i) for each of the anchors, the eyelet is shaped to define two flat faces, the aperture extending through the eyelet between the flat faces, (ii) the spacer is threaded on the tether between the first anchor and the second anchor such that one of the spacer-ends faces one of the flat faces of the eyelet of the first anchor, and the other of the spacer-ends faces one of the flat faces of the eyelet of the second anchor, and (iii) each of the spacer-ends is dimensioned to abut, flush against, the flat face that it faces.

Example 225. The apparatus according to any one of examples 202-224, further comprising the anchor driver.

Example 226. The apparatus according to example 225, wherein: (i) the anchor driver has a driver head that has an introduction state and a locking state, (ii) the anchor head is shaped to define a proximal opening via which the interface is accessible by the driver head while the driver head is in the introduction state, and (iii) the anchor driver is configured to lock the driver head to the interface by transitioning the driver head into the locking state by moving a part of the driver head laterally.

Example 227. The apparatus according to example 226, wherein: (i) the anchor driver comprises a flexible shaft, and a rod extending through the shaft, (ii) the anchor head is disposed at a distal end of the shaft, and (iii) the rod is configured to transition the driver head into the locking state by applying a force to the driver head.

Example 228. The apparatus according to example 227, wherein the driver head comprises fins, and the rod is configured to transition the driver head into the locking state by being advanced distally between the fins such that the rod pushes the fins radially outward such that the fins lock to the interface.

Example 229. The apparatus according to example 228, wherein the fins are configured to, when pushed radially outward by the rod, lock to the interface via a friction fit.

Example 230. The apparatus according to example 227, wherein the driver head comprises a cam, the rod being coupled to the cam, and configured to transition the driver head into the locking state by rotating the cam such that at least part of the cam protrudes laterally.

Example 231. The apparatus according to example 230, wherein the rod is eccentric with respect to the shaft.

Example 232. The apparatus according to example 230, wherein the rod is eccentric with respect to the cam.

Example 233. The apparatus according to example 230, wherein in the introduction state the cam is flush with the shaft.

Example 234. The apparatus according to example 230, wherein the anchor driver has a longitudinal axis defined by the shaft, and wherein the shaft and the cam are circular in transverse cross-section.

Example 235. The apparatus according to example 230, wherein the interface is shaped to define multiple recesses, each dimensioned to receive the cam as it protrudes laterally.

Example 236. The apparatus according to any one of examples 226-235, wherein: (i) the apparatus comprises a delivery tool that comprises the anchor driver and a percutaneously-advanceable tube, and (ii) while the anchor driver is engaged with the anchor, the anchor driver and the anchor are slidable through the tube.

Example 237. The apparatus according to example 236, wherein: (i) the tube defines an internal channel that has a keyhole-shaped orthogonal cross-section that defines a major channel region and a minor channel region, (ii) the major channel-region has a larger cross-sectional area than does the minor channel region, and (iii) the anchor is slidable through the channel with the tissue-engaging element sliding snugly through the major channel region, and the eyelet sliding snugly through the minor channel region.

Example 238. The apparatus according to example 237, wherein: (A) the apparatus comprises an implant that comprises a tether and the tissue anchor, and (B) the eyelet is shaped to facilitate smooth sliding of the eyelet simultaneously (i) snugly though the minor channel region, and (ii) over the tether, while the tether is disposed within the minor channel region and is parallel with the central longitudinal axis.

Example 239. The apparatus according to example 238, wherein: (i) the anchor is advanceable out of a distal end of the tube, (ii) the tube defines a lateral slit extending proximally from the distal end of the tube, (iii) the lateral slit is adjacent to the minor channel region, and (iv) the lateral slit allows the tether, but not the anchor, to exit the tube laterally, proximally from the distal end of the tube.

Example 240. The apparatus according to example 239, wherein the tube is shaped to define a narrowed inlet into the lateral slit, configured to inhibit but not preclude the tether from distally exiting the lateral slit via the narrowed inlet.

Example 241. The apparatus according to example 240, wherein the tube comprises a tip frame that maintain the narrowed slit and the narrowed inlet.

Example 242. The apparatus according to example 241, wherein the tip frame is resilient.

Example 243. The apparatus according to any one of examples 202-239, wherein: (A) the apparatus comprises an implant comprising a tether and the tissue anchor, and (B) the eyelet is shaped to facilitate smooth sliding of the tether through the aperture both (i) while the tether is parallel with the central longitudinal axis, and (ii) while the tether is oriented orthogonal to the central longitudinal axis.

Example 244. The apparatus according to example 243, wherein the tether has a thickness, and a narrowest part of the aperture is no more than twice as wide as the thickness of the tether.

Example 245. The apparatus according to example 244, wherein the narrowest part of the aperture is no more than 50 percent wider than the thickness of the tether.

Example 246. The apparatus according to example 245, wherein the narrowest part of the aperture is no more than 20 percent wider than the thickness of the tether.

Example 247. A system comprising an implant for use in a heart of a subject, the implant comprising: (A) a first anchor; (B) a second anchor; (C) at least one tether coupling the first anchor to the second anchor; and (D) a tensioner, coupled to the at least one tether between the first anchor and the second anchor, and comprising: (i) a spring; and (ii) a restraint, restraining the spring in an elastically-deformed shape of the spring; and wherein: (1) the restraint is bioresorbable, such that after implantation of the implant within the heart, disintegration of the restraint releases the spring from the restraint, (2) the spring is configured to, upon release from the restraint, automatically move away from the elastically-deformed state toward a second shape, and (3) the coupling of the spring to the at least one tether is such that the movement of the spring away from the elastically-deformed state toward the second shape pulls, via the at least one tether, the first anchor and the second anchor toward each other.

Example 248. The system according to example 247, wherein the restraint comprises a suture.

Example 249. The system according to example 247, wherein the restraint comprises a band.

Example 250. The system according to example 247, wherein the restraint comprises a spacer.

Example 251. The system according to example 247, wherein the restraint restrains the spring by holding portions of the spring together.

Example 252. The system according to example 247, wherein the restraint restrains the spring by holding portions of the spring apart from each other.

Example 253. The system according to example 247, wherein the first anchor is a tissue-piercing anchor.

Example 254. The system according to example 247, wherein the first anchor is a clip.

Example 255. The system according to example 247, wherein the spring is a tension spring.

Example 256. The system according to example 247, wherein the spring has a coiled structure.

Example 257. The system according to any one of examples 247-256, wherein the spring defines a cell, and the movement of the spring away from the elastically-deformed state toward the second shape includes the cell becoming smaller in a first dimension and larger in a second direction.

Example 258. The system according to any one of examples 247-256, wherein the spring is a foreshortening spring, and the movement of the spring away from the elastically-deformed state toward the second shape includes foreshortening of the spring.

Example 259. The system according to any one of examples 247-258, wherein: (i) the at least one tether defines a path from the first anchor via the spring to the second anchor, and (ii) the coupling of the spring to the at least one tether is such that the movement of the spring away from the elastically-deformed state toward the second shape pulls the first anchor and the second anchor toward each other by introducing tortuosity to the path of the at least one tether.

Example 260. The system according to any one of examples 247-259, wherein: (i) the restraint is a first restraint, (ii) the tensioner further comprises a second restraint, (iii) the second restraint is configured to limit the movement of the spring away from the elastically-deformed state upon release of the spring from the first restraint, thereby applying a limit to the pulling of the first anchor and the second anchor toward each other, (iv) the second restraint is bioresorbable, such that disintegration of the second restraint releases the spring from the second restraint, thereby allowing the spring to further pull, beyond the limit, the first anchor and the second anchor toward each other, (v) the first restraint is bioresorbable at a first rate, such that release of the spring from the first restraint occurs after a first duration after implantation of the implant within the heart, and (vi) the second restraint is bioresorbable at a second rate, such that release of the spring from the second restraint occurs after a second duration after implantation of the implant within the heart, the second duration being longer than the first duration.

Example 261. The system according to example 260, wherein the first rate is such that the first duration is between 1 and 3 months.

Example 262. The system according to example 260, wherein the second rate is such that the second duration is between 3 months and 1 year.

Example 263. The system according to any one of examples 247-262, wherein the implant is an annuloplasty structure, the first anchor and the second anchor are configured to be driven into tissue of an annulus of a valve of the heart, and the implant is configured to reshape the annulus by the pulling of the first anchor and the second anchor toward each other.

Example 264. The system according to example 263, wherein: (i) the at least one tether is a first at least one tether, (ii) the tensioner is a first tensioner, and (iii) the implant further comprises: a third anchor, a second at least one tether coupled to the third anchor, and a second tensioner coupled to the second at least one tether.

Example 265. The system according to example 264, wherein the second at least one tether couples the third anchor to the second anchor, and the second tensioner is coupled to the second at least one tether between the third anchor and the second anchor.

Example 266. The system according to any one of examples 247-265, wherein the at least one tether includes: (i) a first tether that tethers the first anchor to a first part of the spring; and (ii) a second tether that is distinct from the first tether, and that tethers the second anchor to a second part of the spring, the first and second tethers thereby coupling the first anchor to the second anchor via the spring.

Example 267. The system according to example 266, wherein an inter-part distance between the first part and the second part is smaller in the second state than in the elastically-deformed state.

Example 268. An apparatus, comprising an anchor for use with tissue of a subject, the anchor comprising: (A) a sharpened distal tip; (B) a hollow body proximal from the distal tip, and shaped to define: (i) a chamber, (ii) a lateral wall around the chamber, an anchor axis of the anchor passing through the chamber and the tip, and (iii) two ports in the lateral wall; and (C) a spring, comprising an elongate element having two ends and defining a loop therebetween, at least the loop being disposed within the chamber; and wherein the anchor: (1) has a first state in which the spring is constrained by the lateral wall, and (2) is transitionable from the first state into a second state in which, relative to the first state, the elongate element is under less strain, and the ends are disposed further apart from each other, each of the ends protruding laterally from the hollow body via a respective one of the ports.

Example 269. The apparatus according to example 268, wherein the ends are sharpened.

Example 270. The apparatus according to example 268, wherein in the first state, the ends do not protrude laterally from the hollow body.

Example 271. The apparatus according to any one of examples 268-270, wherein the anchor is configured such that, when the anchor transitions from the first state to the second state, the loop becomes smaller.

Example 272. The apparatus according to any one of examples 268-270, wherein the anchor is configured such that, when the anchor transitions from the first state to the second state, the loop moves axially within the chamber.

Example 273. The apparatus according to any one of examples 268-272, wherein the anchor further comprises a head that defines an interface, configured to be reversibly engaged by an anchor driver.

Example 274. The apparatus according to example 273, further comprising a tether, wherein the head defines an eyelet that is threaded onto the tether.

Example 275. The apparatus according to any one of examples 268-274, wherein, in the first state, the ends are disposed distally from the loop.

Example 276. The apparatus according to example 275, wherein, in the second state, the ends are disposed distally from the loop.

Example 277. The apparatus according to example 275, wherein, in the second state, the ends are disposed proximally from the loop.

Example 278. The apparatus according to any one of examples 268-277, further comprising a retainer, wherein: (i) the hollow body is shaped to define at least one window in the lateral wall, and (ii) the retainer is configured to retain the anchor in the first state by extending through the window and into the loop.

Example 279. The apparatus according to example 278, wherein: (i) in the first state, each of the ends is disposed at the respective port, (ii) the anchor is configured such that, when the anchor transitions from the first state to the second state, the loop moves axially within the chamber, and (iii) the retainer is configured to retain the anchor in the first state by inhibiting the loop from moving axially within the chamber.

Example 280. The apparatus according to example 278, wherein the hollow body is shaped to define two windows in the lateral wall, the two windows being opposite each other and rotationally offset from the two ports.

Example 281. The apparatus according to example 280, wherein the retainer extends through one of the windows, through the loop, and out of the other of the windows.

Example 282. The apparatus according to example 280, wherein: (i) a port axis passes through the two ports and the anchor axis, and (ii) a window axis passes through the two windows and the anchor axis and is orthogonal to the port axis.

Example 283. The apparatus according to example 280, wherein the windows are axially offset from the ports.

Example 284. An apparatus for use with tissue of a heart of a subject, the apparatus comprising: (A) a tool, transluminally advanceable to the heart and comprising a tube having a distal end that defines an opening; and (B) an anchor, disposed at least partly within the tube, and comprising a tissue-engaging element, the anchor being configured to be anchored to the tissue by the tissue-engaging element being driven into the tissue; and (C) a driver, extending through at least part of the tube, a distal end of the driver being reversibly engaged with the anchor within the tube, the driver being configured to drive the tissue-engaging element out of the opening and into the tissue, while the opening is disposed within the tissue; and wherein: the tool is configured to, while the anchor remains disposed at least partly within the tube, penetrate the distal end of the tube into the tissue such that the opening becomes submerged within the tissue.

Example 285. The apparatus according to example 284, wherein the distal end is tapered.

Example 286. The apparatus according to example 284, wherein the distal end is sharpened.

Example 287. The apparatus according to example 284, wherein the anchor is disposed entirely within the tube.

Example 288. The apparatus according to example 284, wherein the anchor further comprises a head, the driver being reversibly engaged with the anchor by being reversibly engaged with the head.

Example 289. The apparatus according to any one of examples 284-288, further comprising a tether, wherein the anchor further comprises a head that defines an eyelet through which the tether is threaded.

Example 290. The apparatus according to any one of examples 284-289, wherein at least a part of the tissue-engaging element is constrained by the tube and is configured to automatically change shape within the tissue upon exiting the opening.

Example 291. The apparatus according to example 290, wherein the part of the tissue-engaging element is a tine.

Example 292. The apparatus according to example 290, wherein the part of the tissue-engaging element is a flange.

Example 293. The apparatus according to example 292, wherein the flange comprises a polymer.

Example 294. The apparatus according to example 292, wherein the flange comprises a sheet and a self-expanding frame supporting the sheet.

Example 295. The apparatus according to any one of examples 284-294, wherein a distal tip of the tissue-engaging element is disposed outside of the opening, and the tool is configured to, while the distal tip is disposed outside of the opening, penetrate the distal end of the tube into the tissue such that the opening becomes submerged within the tissue.

Example 296. The apparatus according to example 295, wherein the tissue-engaging element is shaped to fit snugly within the opening such that, while the tool penetrates the distal end of the tube into the tissue, the tissue-engaging element blocks the opening.

Example 297. The apparatus according to example 295, wherein the distal tip is sharpened, and wherein the distal tip of the tissue-engaging element and the distal end of the tube together define a tapered point, the distal tip being a distal portion of the tapered point and the distal end of the tube being a proximal portion of the tapered point.

Example 298. The apparatus according to any one of examples 284-297, wherein: (i) the tube defines a channel that has a central channel region and lateral channel regions; and (ii) the anchor comprises a head and tines, the head disposed in the central channel region and each of the tines disposed in a respective lateral channel region, such that, within the channel, the anchor is slidable axially but is inhibited from rotating.

Example 299. The apparatus according to example 298, wherein the channel is wider at the central channel region than at the lateral channel region.

Example 300. The apparatus according to example 298, wherein the opening is defined by the channel reaching the distal end of the tube, and wherein the shape of the opening shapes the distal end of the tube to resemble a beak.

Example 301. A system for use with tissue of a heart of a subject, the system comprising a tissue anchor that comprises: (A) a head: (i) having a tissue-facing side, shaped to define a plurality of grips, and (ii) an opposing side that defines an eyelet; and (B) multiple tissue-engaging elements, disposed laterally from the grips: (i) each having a sharpened tip, (ii) each having: a delivery state in which the tissue-engaging element is configured to be driven linearly into the tissue until the grips contact the tissue and a gripping state, and (iii) collectively configured such that, while the multiple tissue-engaging elements are disposed within the tissue with the grips contacting the tissue, transitioning of the tissue-engaging elements toward the gripping state brings the tips toward each other and presses the grips against the tissue.

Example 302. The system according to example 301, wherein the multiple tissue-engaging elements are collectively configured such that, while the multiple tissue-engaging elements are disposed within the tissue with the grips contacting the tissue, transitioning of the tissue-engaging elements toward the gripping state squeezes the tissue between the multiple tissue-engaging elements.

Example 303. The system according to any one of examples 301-302, wherein each of the tissue-engaging elements has a deflecting portion, and a static portion that connects the deflecting portion to the head, both the deflecting portion and the static portion being configured to be driven linearly into the tissue while the tissue-engaging element is in the delivery state, and the tissue-engaging element is configured such that, when the tissue-engaging element transitions toward the gripping state: (i) the static portion remains static with respect to the head, and (ii) the deflecting portion deflects with respect to the static portion and with respect to the head.

Example 304. The system according to any one of examples 301-303, wherein the system comprises an implant that comprises: (i) the tissue anchor, and (ii) a tether threaded through the eyelet.

Example 305. The system according to any one of examples 301-304, wherein: (i) in the delivery state, each of the tissue-engaging elements has a medial side and a lateral side, the medial side being closer than the lateral side to the other tissue-engaging elements; and (ii) each of the tissue-engaging elements is shaped to define a barb on the lateral side.

Example 306. The system according to example 305, wherein each of the tissue-engaging elements is configured such that, in the delivery state the barb is obscured, and in the gripping state the barb is exposed.

Example 307. The system according to example 305, wherein each of the tissue-engaging elements has a deflecting portion, and a static portion that connects the deflecting portion to the head, both the deflecting portion and the static portion being configured to be driven linearly into the tissue while the tissue-engaging element is in the delivery state, and the tissue-engaging element is configured such that, when the tissue-engaging element transitions toward the gripping state: (i) the static portion remains static with respect to the head, and (ii) the deflecting portion deflects with respect to the static portion and with respect to the head.

Example 308. The system according to example 307, wherein, for each of the tissue-engaging elements, the barb is defined by the static portion.

Example 309. The system according to example 307, wherein, for each of the tissue-engaging elements, the barb is defined by the deflecting portion.

Example 310. A system for use with tissue of a heart of a subject, the system comprising: (A) an anchor; (B) a tether, coupled to the anchor, the anchor being configured to be anchored to the tissue such that the tether extends proximally from the anchor; (C) a tether-handling device, comprising: (i) a housing, shaped to define a passage therethrough, the tether extending through the passage in a manner that facilitates transluminal sliding of the housing distally over and along the tether to the anchor; (ii) a clamp, coupled to the housing, and biased to clamp onto the tether within the passage in a manner that inhibits sliding of the housing with respect to the tether; and (iii) an arm, extending proximally from the housing, and comprising: a conduit, shaped to receive a portion of the tether proximally from the housing, and a lever, coupling the conduit to the housing, and biased to place the conduit in an offset position with respect to the passage; and (D) a tool, comprising a tube; and wherein the system has a delivery state in which (1) the tool is coupled to the tether-handling device, with the tube disposed: (a) within the passage in a manner that inhibits the clamp from clamping, and (b) within the conduit in a manner that constrains the conduit in an in-line position with respect to the passage, and (2) is configured to transluminally advance the tether-handling device distally over and along the tether toward the anchor.

Example 311. The system according to example 310, wherein the conduit has an open lateral side.

Example 312. The system according to example 310, wherein the tether extends out of a proximal side of the housing, and wherein the lever is biased to place the conduit against the proximal side of the housing.

Example 313. The system according to any one of examples 310-312, wherein the bias of the clamp is such that, absent the tube being disposed in the passage, the clamp automatically clamps onto the tether within the passage in the manner that inhibits sliding of the housing with respect to the tether.

Example 314. The system according to example 313, wherein, in the delivery state, the tube is disposed within the passage and within the conduit by extending distally through the conduit and into the passage.

Example 315. The system according to example 313, wherein the system is transitionable from the delivery state into an intermediate state by proximally retracting the tube out of the passage but not out of the conduit.

Example 316. The system according to example 313, wherein in the intermediate state a distal part of the tube remains disposed in the housing.

Example 317. The system according to any one of examples 313-316, wherein the tether has sufficient tensile strength relative to the bias of the lever that, absent the tube being disposed in the conduit, the lever is inhibitable from moving the conduit into the offset position by tensioning the tether proximally from the clamp.

Example 318. The system according to example 317, further comprising a cutter, advanceable over and along the tether, axially moveable with respect to the tube, and configured to cut the tether proximally from the conduit.

Example 319. The system according to example 318, wherein, while the tether is tensioned proximally from the clamp, cutting of the tether proximally from the conduit triggers the lever to move the conduit into the offset position.

Example 320. The system according to example 319, wherein: (i) the cutter is configured to cut the tether proximally from the conduit in a manner that leaves a vestigial piece of the tether protruding proximally from the conduit, and (ii) the arm is configured such that the lever moving the conduit into the offset position draws the vestigial piece of the tether into the conduit.

Example 321. The system according to example 318, wherein the tube is slidable within the cutter.

Example 322. An apparatus for use with a tether, the apparatus comprising a clamp, comprising: (A) a chuck, having a longitudinal axis, and comprising: (i) a sleeve, circumscribing the longitudinal axis, and having a tapered inner surface, and (ii) a collet, disposed within the sleeve, and dimensioned to receive the tether therethrough; and (B) a spring, axially pushing the collet against the tapered inner surface such that the collet is squeezed medially by the sleeve.

Example 323. The apparatus according to example 322, wherein the sleeve and the collet are concentric with the longitudinal axis.

Example 324. The apparatus according to example 323, wherein the spring is concentric with the longitudinal axis.

Example 325. The apparatus according to any one of examples 322-324, wherein the spring is a compression spring.

Example 326. The apparatus according to example 325, wherein the spring is helical.

Example 327. The apparatus according to example 325, wherein the spring circumscribes the longitudinal axis, the clamp configured to be threaded onto the tether such that the sleeve, the collet, and the spring circumscribe the tether.

Example 328. The apparatus according to example 325, wherein the sleeve has an opposing surface, and the spring is maintained under compression between the opposing surface and the collet.

Example 329. The apparatus according to any one of examples 322-328, further comprising the tether, wherein: (i) the clamp is configured to receive the tether through the collet and the sleeve, and (ii) the spring axially pushes the collet against the tapered inner surface by pushing the collet in a first axial direction with respect to the sleeve, such that the collet clamps the tether thereby inhibiting sliding of the tether through the collet in at least the first axial direction.

Example 330. The apparatus according to example 329, wherein the clamp is configured to facilitate sliding of the tether through the collet in a second axial direction that is opposite to the first axial direction, by movement of the tether through the sleeve in the second axial direction axially pushing the collet away from the tapered inner surface, thereby reducing clamping of the tether by the collet.

Example 331. The apparatus according to any one of examples 322-330, wherein the sleeve has an opposing surface against which the spring applies an opposing force while axially pushing the collet.

Example 332. The apparatus according to example 331, further comprising the tether, wherein: (i) the clamp has a proximal end and a distal end, the tapered inner surface tapering toward the distal end, (ii) the chuck facilitates sliding of the clamp along the tether in a distal direction in which the distal end leads the proximal end, and (iii) the chuck inhibits sliding of the clamp along the tether in a proximal direction in which the proximal end leads the distal end.

Example 333. The apparatus according to example 332, further comprising a sheath that extends proximally from the sleeve, and that is elastically coupled to the sleeve in a manner in which: (i) the sheath is retractable distally over the sleeve by application of a distally-directed force to the sheath, and (ii) in response to removal of the distally-directed force, the sheath automatically re-extends proximally.

Example 334. The apparatus according to example 333, wherein the sheath is rigid.

Example 335. The apparatus according to example 333, further comprising a tool that comprises a cutter, the tool being configured to: (i) retract the sheath distally over the sleeve by applying the distally-directed force to the sheath; (ii) while maintaining the distally-directed force on the sheath: (a) tension the tether by applying a proximally-directed force to the tether, such that the tether slides proximally through the collet, and (b) subsequently, cut the tether proximally from the sleeve in a manner that leaves a vestigial piece of the tether protruding proximally from the sleeve, and (iii) remove the distally-directed force such that the sheath automatically re-extends proximally and ensheathes the vestigial piece of the tether.

Example 336. The apparatus according to example 335, wherein the tool is configured to cut the tether proximally from the sleeve in a manner that leaves a vestigial piece of the tether protruding proximally from the chuck.

Example 337. The apparatus according to example 333, wherein the spring is a first spring, and wherein the clamp further comprises a second spring, disposed laterally from the sleeve, and providing the elastic coupling of the sheath to the sleeve.

Example 338. The apparatus according to example 337, wherein: (i) the sleeve defines a flange extending laterally from the sleeve, and (ii) the second spring is a compression spring, disposed laterally from the sleeve such that application of the distally-directed force to the sheath compresses the spring against the flange.

Example 339. The apparatus according to example 337, wherein the second spring is a helical spring.

Example 340. The apparatus according to example 337, wherein the second spring circumscribes the sleeve.

Example 341. A system comprising an implant configured to be implanted in a heart of a subject, the implant comprising: (A) a tether; (B) anchors slidably coupled to the tether, and configured to anchor the tether to tissue of the heart; (C) a spring, having a resting state, and coupled to the tether in a manner in which movement of the spring toward the resting state applies tension to the tether; and (D) a restraint: (i) coupled to the spring in a manner that inhibits the spring from moving toward the resting state, (ii) comprising a material that is configured to disintegrate within the heart, and (iii) configured such that disintegration of the material reduces the inhibition of the spring by the restraint.

Example 342. The system according to example 341, wherein the spring is a helical coil spring.

Example 343. The system according to any one of examples 341-342, wherein: (i) the restraint is configured such that, after a threshold amount of disintegration of the restraint, the restraint no longer inhibits the spring, and (ii) the material is configured such that the threshold amount of disintegration is reached between 1 day and 2 years after implantation of the implant in the heart.

Example 344. The system according to example 343, wherein the material is configured such that the threshold amount of disintegration is reached between 15 days and 2 years after implantation of the implant in the heart.

Example 345. The system according to example 344, wherein the material is configured such that the threshold amount of disintegration is reached between 15 days and 1 year after implantation of the implant in the heart.

Example 346. The system according to example 345, wherein the material is configured such that the threshold amount of disintegration is reached between 15 days and 6 s after implantation of the implant in the heart.

Example 347. The system according to example 346, wherein the material is configured such that the threshold amount of disintegration is reached between 1 and 3 months after implantation of the implant in the heart.

Example 348. The system according to example 347, wherein the material is configured such that the threshold amount of disintegration is reached between 1 and 2 months after implantation of the implant in the heart.

Example 349. The system according to any one of examples 341-348, wherein: (i) the restraint is a first restraint and is configured to have a first lifespan after implantation of the implant such that, upon expiry of the first lifespan, the first restraint no longer inhibits the spring; and (ii) the implant further comprises a second restraint, configured to have a second lifespan after implantation of the implant, the second lifespan being greater than the first lifespan.

Example 350. The system according to example 349, wherein the second restraint is coupled to the spring in a manner that inhibits the spring from moving toward the resting state, thereby configuring the system such that, after implantation of the implant: (i) upon expiry of the first lifespan, the spring moves partway toward the resting state but remains inhibited by the second restraint; and (ii) upon expiry of the second lifespan, the second restraint no longer inhibits the spring, and the spring moves further toward the resting state.

Example 351. The system according to example 349, wherein: (i) the spring is a first spring, (ii) the implant further comprises a second spring, having a resting state, and coupled to the tether in a manner in which movement of the second spring toward the resting state applies tension to the tether, and (iii) the second restraint is coupled to the second spring in a manner that inhibits the second spring from moving toward the resting state of the second spring, and is configured such that upon expiry of the second lifespan, the second restraint no longer inhibits the second spring.

Example 352. The system according to example 349, wherein the first restraint and the second restraint are configured such that second lifespan is at least twice as great as the first lifespan.

Example 353. The system according to example 349, wherein the first restraint and the second restraint are configured such that second lifespan is at least three times as great as the first lifespan.

Example 354. The system according to example 349, wherein the first restraint and the second restraint are configured such that the first lifespan is between 1 and 3 months, and the second lifespan is between 3 months and 1 year.

Example 355. The system according to example 354, wherein the first restraint and the second restraint are configured such that the first lifespan is between 1 and 3 months, and the second lifespan is between 3 and 6 months.

Example 356. The system according to example 354, wherein the first restraint and the second restraint are configured such that the first lifespan is between 1 and 2 months, and the second lifespan is between 3 months and 1 year.

Example 357. The system according to example 356, wherein the first restraint and the second restraint are configured such that the first lifespan is between 1 and 2 months, and the second lifespan is between 3 and 6 months.

Example 358. The system according to any one of examples 341-357, wherein the restraint is extension-resistant, and is coupled to the spring in a manner that inhibits the spring from moving toward the resting state by the restraint resisting extension.

Example 359. The system according to example 358, wherein the restraint is a tether that tethers one part of the spring to another part of the spring, thereby inhibiting the one part of the spring from moving away from the other part of the spring.

Example 360. The system according to example 358, wherein the restraint is a tube in which the spring is disposed.

Example 361. The system according to any one of examples 341-360, wherein the restraint is compression-resistant, and is coupled to the spring in a manner that inhibits the spring from moving toward the resting state by the restraint resisting compression.

Example 362. The system according to example 361, wherein the restraint is an obstruction disposed between one part of the spring and another part of the spring, thereby inhibiting the one part of the spring from moving toward from the other part of the spring.

Example 363. The system according to any one of examples 341-362, wherein the spring: (i) is shaped to define a cell that has a first dimension and a second dimension, and (i) is configured to move toward the resting state by contracting in the first dimension and expanding in the second dimension.

Example 364. The system according to example 363, wherein, while inhibited by the restraint, the spring is longer in the first dimension than in the second dimension.

Example 365. The system according to example 363, wherein the cell is a first cell, and the spring is shaped to further define a second cell.

Example 366. A system, for use with tissue of a heart of a subject, the system comprising: (A) an anchor, comprising: (i) a tissue-engaging element having a sharpened distal tip, and configured to anchor the anchor to the tissue by being driven into the tissue; and (ii) an anchor head, coupled to a proximal end of the tissue-engaging element, and comprising an interface; and (B) an anchor-handling assembly, comprising: (i) a sleeve having a distal portion that includes a distal end of the sleeve, the distal portion being transluminally advanceable to the anchor anchored to the tissue, and the distal end being dimensioned to snugly fit over the anchor head; and (ii) a tool, comprising: (1) a flexible shaft, and (2) a tool head coupled to a distal end of the flexible shaft, comprising jaws that are biased to assume an open state, and that are reversibly squeezable into a closed state, and dimensioned, relative to an inner dimension of the distal portion of the sleeve, such that disposition of the tool head in the distal portion of the sleeve squeezes the jaws into the closed state; and wherein the tool is configured to: (a) advance the tool head distally through the sleeve to the distal portion, (b) while the jaws remain in the closed state, lock the jaws to the interface, and (c) while the jaws remain locked to the interface, apply a de-anchoring force to the anchor head.

Example 367. The system according to example 366, wherein, while the tool head is locked to the interface and the distal end of the sleeve is disposed snugly over the anchor head, the jaws are unlockable from the interface by retracting the sleeve proximally with respect to the anchor head and the tool head, such that the distal portion of the sleeve ceases to squeeze the jaws into the closed state, and the jaws automatically move apart.

Example 368. The system according to example 366, wherein the tool is configured to lock the jaws to the interface while the jaws remain in the closed state by pushing the driver head against the anchor head.

Example 369. The system according to any one of examples 366-368, wherein: (i) in the closed state, the jaws define a gap therebetween; and (ii) while remaining in the closed state, the jaws are configured: (a) to become locked to the interface by receiving the interface into the gap in response to the jaws being pushed onto the interface with a distally-directed force having a magnitude, by the interface deflecting the jaws apart; and (b) to resist becoming unlocked from the interface by the interface leaving the gap, wherein pulling of the jaws with a proximally-directed force having the magnitude is insufficient to pull the jaws off of the interface.

Example 370. The system according to any one of examples 366-369, wherein the sleeve has an intermediate portion that is proximal from the distal portion, and that is internally dimensioned such that disposition of the tool head in the intermediate portion of the sleeve does not squeeze the jaws into the closed state.

Example 371. The system according to any one of examples 366-370, wherein the jaws and the interface are configured to define a snap-fitting, and the tool is configured to lock the jaws to the interface while the jaws remain in the closed state by snap-fitting the jaws to the interface.

Example 372. The system according to any one of examples 366-371, wherein the de-anchoring force is a de-anchoring torque, and wherein the tool is configured to apply the de-anchoring torque to the anchor head while the jaws remain locked to the interface.

Example 373. A system for use with a tether secured along tissue of a heart of a subject, the system comprising: (A) an anchor comprising: (i) a tissue-engaging element having a sharpened distal tip; and (ii) a head, coupled to a proximal part of the tissue-engaging element, and comprising a shackle having a reversibly openable opening; and (B) an anchor-handling assembly, transluminally advanceable to the heart, and comprising: (i) a driver, configured to drive the tissue-engaging element into the tissue; and (ii) a link tool, configured to, within the heart, temporarily open the opening and pass the tether laterally through the opening.

Example 374. The system according to example 373, wherein the link tool is configured to, within the heart, slidably couple the anchor to the tether by temporarily opening the opening and passing the tether laterally through the opening and into the shackle.

Example 375. The system according to example 373, wherein the driver is configured to drive the tissue-engaging element into the tissue by screwing the tissue-engaging element into the tissue.

Example 376. The system according to any one of examples 373-375, wherein, at the opening, the shackle comprises a spring-loaded gate.

Example 377. The system according to example 376, wherein the spring-loaded gate is a single gate.

Example 378. The system according to example 376, wherein the spring-loaded gate is a double gate.

Example 379. The system according to example 376, wherein the spring-loaded gate is configured to open inwardly but not outwardly.

Example 380. The system according to any one of examples 373-379, wherein the link tool is configured to, within the heart, decouple the anchor from the tether by temporarily opening the opening and passing the tether laterally through the opening and out of the shackle.

Example 381. The system according to example 380, wherein the head further comprises a magnet, and wherein the tool is configured to be magnetically-attracted to the magnet.

Example 382. A method for use with tissue of a heart of a subject, the method comprising: (i) transluminally securing a tether along the tissue by anchoring a plurality of anchors to respective sites of the tissue such that the tether extends between the anchors of the plurality and along the tissue, each anchor of the plurality having a respective eyelet through which the tether passes; and (ii) while the plurality of anchors remains anchored to the tissue, transluminally: (a) slidably coupling an additional anchor to the tether between two of the anchors of the plurality; and (b) anchoring the additional anchor to the tissue.

Example 383. The method according to example 382, wherein anchoring the additional anchor to the tissue comprises anchoring the additional anchor to the tissue subsequently to slidably coupling the additional anchor to the tether.

Example 384. The method according to example 382, wherein anchoring the additional anchor to the tissue comprises anchoring the additional anchor to the tissue prior to slidably coupling the additional anchor to the tether.

Example 385. The method according to any one of examples 382-384, wherein, for each anchor of the plurality, anchoring the anchor to the respective site of the tissue comprises driving a tissue-engaging element of the anchor into the respective site of the tissue.

Example 386. The method according to example 385, wherein, for each anchor of the plurality, driving the tissue-engaging element of the anchor into the respective site of the tissue comprises screwing the tissue-engaging element of the anchor into the respective site of the tissue.

Example 387. The method according to any one of examples 382-386, further comprising contracting the tissue by tensioning the tether.

Example 388. The method according to example 387, wherein tensioning the tether comprises tensioning the tether subsequently to anchoring the additional anchor to the tissue.

Example 389. The method according to example 387, wherein tensioning the tether comprises tensioning the tether prior to slidably coupling the additional anchor to the tether.

Example 390. The method according to example 389, further comprising relaxing the tether subsequently to tensioning the tether and prior to slidably coupling the additional anchor to the tether.

Example 391. The method according to example 390, further comprising re-tensioning the tether subsequently to anchoring the additional anchor to the tissue.

Example 392. The method according to any one of examples 382-391, wherein slidably coupling the additional anchor to the tether comprises clipping the additional anchor to the tether.

Example 393. The method according to example 392, wherein the additional anchor includes a head that includes a shackle, and wherein clipping the additional anchor to the tether comprises, subsequently to anchoring the additional anchor to the tissue, transluminally grasping the tether and pressing the tether laterally into the shackle such that the shackle becomes slidably coupled to the tether.

Example 394. The method according to example 393, wherein the shackle is a snap shackle, and wherein pressing the tether laterally into the shackle comprises pressing the tether laterally into the snap shackle such that the tether snaps into the snap shackle.

Example 395. A method for use with tissue of a heart of a subject, the method comprising: (i) transluminally securing a tether along the tissue by anchoring a plurality of anchors to respective sites of the tissue such that the tether extends between the anchors of the plurality and along the tissue, each anchor of the plurality having a respective eyelet through which the tether passes; and (ii) transluminally decoupling from the tether one anchor of the plurality from between two other anchors of the plurality.

Example 396. The method according to example 395, wherein: (i) the one anchor includes a tissue-engaging element having a sharpened distal tip, and a head coupled to a proximal part of the tissue-engaging element, the head including a magnetic element, and (ii) the method further comprises transluminally advancing a tool to the one anchor, facilitated by magnetic attraction between the tool and the magnetic element, wherein decoupling the one anchor from the tether comprises decoupling the one anchor from the tether using the tool.

Example 397. The method according to any one of examples 395-396, further comprising, while the two other anchors of the plurality remain anchored to the tissue, de-anchoring the one anchor from the tissue.

Example 398. The method according to example 397, wherein de-anchoring the one anchor from the tissue comprises de-anchoring the one anchor from the tissue prior to decoupling the one anchor from the tether.

Example 399. The method according to example 397, wherein de-anchoring the one anchor from the tissue comprises de-anchoring the one anchor from the tissue subsequently to decoupling the one anchor from the tether.

Example 400. The method according to any one of examples 395-399, wherein, for each anchor of the plurality, anchoring the anchor to the respective site of the tissue comprises driving a tissue-engaging element of the anchor into the respective site of the tissue.

Example 401. The method according to example 400, wherein, for each anchor of the plurality, driving the tissue-engaging element of the anchor into the respective site of the tissue comprises screwing the tissue-engaging element of the anchor into the respective site of the tissue.

Example 402. The method according to any one of examples 395-401, further comprising contracting the tissue by tensioning the tether.

Example 403. The method according to example 402, wherein tensioning the tether comprises tensioning the tether subsequently to decoupling the one anchor from the tether.

Example 404. The method according to example 402, wherein tensioning the tether comprises tensioning the tether prior to decoupling the one anchor from the tether.

Example 405. The method according to example 404, further comprising relaxing the tether subsequently to tensioning the tether and prior to decoupling the one anchor from the tether.

Example 406. The method according to example 405, further comprising re-tensioning the tether subsequently to decoupling the one anchor from the tether.

Example 407. The method according to example 395, wherein decoupling the one anchor from the tether comprises unclipping the additional anchor from the tether.

Example 408. The method according to example 407, wherein the one anchor includes a head that includes a shackle, and wherein unclipping the one anchor from the tether comprises transluminally opening the shackle.

Example 409. An apparatus comprising a tissue anchor, the anchor comprising: (A) a tissue-engaging element defining a central longitudinal axis of the anchor, having a sharpened distal tip, and configured to be driven into tissue of a subject; and (B) an anchor head, coupled to a proximal end of the tissue-engaging element, the anchor head comprising: (i) a stock, (ii) a ball joint, and (iii) an eyelet, coupled to the stock via the ball joint.

Example 410. The apparatus according to example 409, wherein the ball joint is disposed on the central longitudinal axis.

Example 411. The apparatus according to any one of examples 409-410, wherein the anchor head defines an eyelet axis through the ball joint and the eyelet, and the ball joint allows the eyelet to be moved into a position in which the eyelet axis is orthogonal to the central longitudinal axis.

Example 412. The apparatus according to any one of examples 409-411, wherein the stock is fixedly coupled to the tissue-engaging element.

Example 413. The apparatus according to any one of examples 409-412, wherein the tissue-engaging element is helical, defines the central longitudinal axis by extending in a helix around and along the central longitudinal axis, and is configured to be screwed into the tissue of the subject.

Example 414. The apparatus according to any one of examples 409-413, wherein the eyelet is disposed laterally from the central longitudinal axis.

Example 415. The apparatus according to example 414, wherein the ball joint is disposed laterally from the central longitudinal axis.

Example 416. The apparatus according to example 415, wherein the anchor head comprises a collar that circumscribes and is rotatably coupled to the stock, and wherein the ball joint is mounted on the collar such that the ball joint is revolvable around the central longitudinal axis by rotation of the collar about the stock.

Example 417. The apparatus according to example 415, wherein the stock is disposed on the central longitudinal axis.

Example 418. The apparatus according to any one of examples 409-417, wherein: (i) the ball joint comprises a socket, and a bearing stud, (ii) the bearing stud defines a ball at a first end of the stud, the ball disposed within the socket, (iii) a second end of the stud defines the eyelet, and (iv) the ball joint defines: (a) a spherical-sector of deflection within which the ball joint allows deflection of the bearing stud into any angular disposition with respect to the socket, and (b) a deflection plane on which the ball joint allows deflection of the bearing stud beyond the spherical-sector of deflection, outside of the deflection plane the ball joint inhibiting deflection of the bearing stud beyond spherical-sector of deflection.

Example 419. The apparatus according to example 418, wherein the spherical-sector of deflection has a midpoint, and the ball joint is positioned such that the midpoint lies on the central longitudinal axis.

Example 420. The apparatus according to example 418, wherein the ball joint is disposed on the central longitudinal axis.

Example 421. The apparatus according to example 418, wherein the ball joint defines the spherical-sector of deflection to have a solid angle of at least one steradian.

Example 422. The apparatus according to example 421, wherein the ball joint defines the solid angle to be least two steradians.

Example 423. The apparatus according to example 422, wherein the ball joint defines the solid angle to be 2-5 steradians.

Example 424. The apparatus according to example 423, wherein the ball joint defines the solid angle to be 3-5 steradians.

Example 425. The apparatus according to example 418, wherein: (i) the ball joint defines, on the deflection plane, a planar angular arc of deflection of at least 110 degrees, and (ii) on the deflection plane, the ball joint allows deflection of the bearing stud beyond the boundary only within the planar angular arc of deflection.

Example 426. The apparatus according to example 425, wherein the ball joint defines the planar angular arc of deflection to be at least 120 degrees.

Example 427. The apparatus according to example 426, wherein the ball joint defines the planar angular arc of deflection to be at least 140 degrees.

Example 428. The apparatus according to example 427, wherein the ball joint defines the planar angular arc of deflection to be at least 160 degrees.

Example 429. The apparatus according to example 428, wherein the ball joint defines the planar angular arc of deflection to be at least 180 degrees.

Example 430. The apparatus according to example 429, wherein the ball joint defines the planar angular arc of deflection to be at least 200 degrees.

Example 431. The apparatus according to example 425, wherein the ball joint defines the planar angular arc of deflection to be no greater than 180 degrees.

Example 432. The apparatus according to example 431, wherein the ball joint defines the planar angular arc of deflection to be no greater than 160 degrees.

Example 433. The apparatus according to example 432, wherein the ball joint defines the planar angular arc of deflection to be no greater than 140 degrees.

Example 434. The apparatus according to any one of examples 409-433, wherein: (i) the eyelet is shaped to define a first face, and a second face opposite the first face, and (ii) the eyelet has an aperture defined by an inner surface of the eyelet, the aperture extending between the first face and the second face, and a narrowest part of the aperture being midway between the first face and the second face.

Example 435. The apparatus according to example 434, wherein the inner surface of the eyelet is a hyperboloid.

Example 436. The apparatus according to example 434, wherein the inner surface of the eyelet is a catenoid.

Example 437. The apparatus according to any one of examples 409-436, wherein the apparatus comprises an implant that comprises a tether and the anchor, the eyelet being threaded onto the tether.

Example 438. The apparatus according to example 437, wherein: (i) the anchor is a first anchor of the implant, and (ii) the implant further comprises a second anchor, an eyelet of the second anchor being threaded onto the tether.

Example 439. The apparatus according to example 438, wherein: (i) the implant further comprises a spacer that is tubular, having two spacer-ends and a lumen therebetween, and (ii) the spacer is threaded on the tether between the first anchor and the second anchor, with the tether passing through the spacer-lumen.

Example 440. The apparatus according to example 439, wherein the spacer is elastically flexible in deflection.

Example 441. The apparatus according to example 439, wherein the spacer resists axial compression.

Example 442. The apparatus according to example 439, wherein the spacer is defined by a helical wire shaped as a coil that defines the spacer-lumen.

Example 443. The apparatus according to example 437, wherein the eyelet defines an aperture therethrough, the eyelet being threaded onto the tether by the tether being threaded through the aperture, and the anchor head being configured to facilitate smooth sliding of the tether through the aperture both (i) while the tether is parallel with the central longitudinal axis, and (ii) while the tether is oriented orthogonal to the central longitudinal axis.

Example 444. The apparatus according to example 443, wherein the tether has a thickness, and a narrowest part of the aperture is no more than twice as wide as the thickness of the tether.

Example 445. The apparatus according to example 444, wherein the narrowest part of the aperture is no more than 50 percent wider than the thickness of the tether.

Example 446. The apparatus according to example 445, wherein the narrowest part of the aperture is no more than 20 percent wider than the thickness of the tether.

Example 447. The apparatus according to any one of examples 409-446, wherein the anchor head further comprises a driver interface, and wherein the apparatus further comprises an anchor driver, configured to reversibly engage the driver interface, and configured to, while engaged with the driver interface, (i) transluminally advance the anchor to the tissue, and (ii) drive the tissue-engaging element into the tissue.

Example 448. The apparatus according to example 447, wherein the interface is disposed on the central longitudinal axis of the anchor.

Example 449. The apparatus according to example 447, wherein: (i) the apparatus comprises a delivery tool that comprises a percutaneously-advanceable tube and the anchor driver, and (ii) the anchor driver is, while engaged with the driver interface, configured to transluminally advance the anchor to the tissue by sliding the anchor through the tube.

Example 450. The apparatus according to example 449, wherein: (i) the tube defines an internal channel that has a cross-section that defines a major channel region and a minor channel region, (ii) the major channel-region has a larger cross-sectional area than does the minor channel region, and (iii) the anchor is slidable through the channel with the tissue-engaging element sliding through the major channel region, and the eyelet sliding through the minor channel region.

Example 451. An apparatus comprising a tissue anchor, the anchor comprising: (A) a tissue-engaging element defining a central longitudinal axis of the anchor, having a sharpened distal tip, and configured to be driven into tissue of a subject; and (B) an anchor head, comprising: (i) a stock, coupled to a proximal end of the tissue-engaging element, (ii) a driver interface coupled to the stock, and (iii) an eyelet, hingedly coupled to the stock such that the eyelet is pivotable over the driver interface.

Example 452. The apparatus according to example 451, wherein the stock is fixedly coupled to the proximal end of the tissue-engaging element.

Example 453. The apparatus according to any one of examples 451-452, wherein the driver interface is fixedly coupled to the stock.

Example 454. The apparatus according to any one of examples 451-453, wherein the stock is coupled to the proximal end of the tissue-engaging element and to the driver interface in a manner that transfers torque from the driver interface to the tissue-engaging element.

Example 455. The apparatus according to any one of examples 451-454, wherein the eyelet is positionable on the central longitudinal axis.

Example 456. The apparatus according to any one of examples 451-455, wherein the hinged coupling of the eyelet to the stock is such that the eyelet is positionable on a first side of the driver interface, and is pivotable over the driver interface to a second side of the driver interface, the second side being opposite the first side.

Example 457. The apparatus according to any one of examples 451-456, wherein the hinged coupling of the eyelet to the stock is such that the eyelet is pivotable over the driver interface in an arc that is greater than 180 degrees.

Example 458. The apparatus according to any one of examples 451-457, wherein the tissue-engaging element is helical, defines the central longitudinal axis by extending in a helix around and along the central longitudinal axis, and is configured to be screwed into the tissue of the subject.

Example 459. The apparatus according to any one of examples 451-456, wherein the anchor head comprises an arch that defines at least part of the eyelet, the arch having two base termini, each of the base termini being hingedly coupled to the stock at respective hinge points opposite each other.

Example 460. The apparatus according to example 459, wherein: (i) the anchor head comprises a collar that circumscribes and is rotatably coupled to the stock, and (ii) the eyelet is hingedly coupled to the stock by each of the base termini being hingedly coupled to the collar at a respective one of the hinge points.

Example 461. The apparatus according to example 460, wherein, at each of the hinge points, the collar defines a respective recess, and the respective base terminus is hingedly coupled to the collar by protruding into the recess.

Example 462. The apparatus according to example 459, wherein the eyelet is disposed centrally on the arch.

Example 463. The apparatus according to example 459, wherein the eyelet is disposed eccentrically on the arch.

Example 464. The apparatus according to any one of examples 451-463, wherein the apparatus comprises an implant that comprises a tether and the anchor, the eyelet being threaded onto the tether.

Example 465. The apparatus according to example 464, wherein: (i) the anchor is a first anchor of the implant, and (ii) the implant further comprises a second anchor, an eyelet of the second anchor being threaded onto the tether.

Example 466. The apparatus according to example 465, wherein: (i) the implant further comprises a spacer that is tubular, having two spacer-ends and a lumen therebetween, and (ii) the spacer is threaded on the tether between the first anchor and the second anchor, with the tether passing through the spacer-lumen.

Example 467. The apparatus according to example 466, wherein the spacer is elastically flexible in deflection.

Example 468. The apparatus according to example 466, wherein the spacer resists axial compression.

Example 469. The apparatus according to example 466, wherein the spacer is defined by a helical wire shaped as a coil that defines the spacer-lumen.

Example 470. The apparatus according to example 464, wherein the eyelet defines an aperture therethrough, the eyelet being threaded onto the tether by the tether being threaded through the aperture, and the anchor head being configured to facilitate smooth sliding of the tether through the aperture both (i) while the tether is parallel with the central longitudinal axis, and (ii) while the tether is oriented orthogonal to the central longitudinal axis.

Example 471. The apparatus according to any one of examples 451-470, wherein the apparatus further comprises an anchor driver, configured to reversibly engage the driver interface, and configured to, while engaged with the driver interface, (i) transluminally advance the anchor to the tissue, and (ii) drive the tissue-engaging element into the tissue.

Example 472. The apparatus according to example 471, wherein the interface is disposed on the central longitudinal axis of the anchor.

Example 473. The apparatus according to example 471, wherein: (i) the apparatus comprises a delivery tool that comprises a percutaneously-advanceable tube and the anchor driver, and (ii) the anchor driver is, while engaged with the driver interface, configured to transluminally advance the anchor to the tissue by sliding the anchor through the tube.

Example 474. A method, comprising: (A) to an implant that is coupled to a heart of a subject, transluminally advancing an elongate tool that includes a holder and a cutter, the implant including: (i) a tether under tension, and (ii) a stopper locking the tension in the tether by being locked to a first portion of the tether; (B) securing the stopper to the holder; and (C) while the stopper remains secured to the holder and locked to the first portion of the tether: (i) relieving the tension on the tether by cutting the tether with the cutter; and (ii) withdrawing the tool, the stopper, and the first portion of the tether from the subject while leaving a second portion of the tether coupled to the heart.

Example 475. The method according to example 474, wherein the implant includes an anchor coupled to the tether and anchored to the heart, and wherein withdrawing the tool, the stopper, and the first portion of the tether comprises withdrawing the tool, the stopper, and the first portion of the tether from the subject while leaving the anchor anchored to the heart.

Example 476. The method according to any one of examples 474-475, wherein the holder includes a chamber and an opening into the chamber, the cutter is disposed at the opening, and securing the stopper comprises advancing the stopper past the cutter and the opening and into the chamber.

Example 477. The method according to example 476, wherein securing the stopper comprises using the cutter to inhibit the stopper from exiting the chamber via the opening.

Example 478. The method according to example 477, wherein using the cutter to inhibit the stopper from exiting the chamber via the opening comprises actuating the cutter to obstruct the opening.

Example 479. The method according to example 478, wherein actuating the cutter to obstruct the opening comprises moving a blade of the cutter to obstruct the opening, and wherein cutting the tether comprises cutting the tether with the blade by moving further the blade of the cutter.

Example 480. The method according to any one of examples 474-479, wherein the implant is disposed inside the heart, and transluminally advancing the elongate tool to the implant comprises transluminally advancing the elongate tool to the implant that is disposed inside the heart.

Example 481. The method according to example 480, wherein the implant is an annuloplasty implant, coupled to an annulus of a valve of the heart, and transluminally advancing the elongate tool to the implant comprises transluminally advancing the elongate tool to the annuloplasty implant that is coupled to the annulus.

Example 482. The method according to example 481, further comprising, subsequently to relieving the tension on the tether, deploying a prosthetic valve within the annulus of the valve of the heart.

Example 483. The method according to example 481, wherein the annuloplasty implant extends in a path at least partway around the annulus and is coupled to the annulus at multiple sites along the path, and transluminally advancing the elongate tool to the implant comprises transluminally advancing the elongate tool to the annuloplasty implant that extends in the path at least partway around the annulus and is coupled to the annulus at the multiple sites along the path.

Example 484. The method according to any one of examples 474-483, wherein the implant includes an anchor slidably coupled to the tether and anchored to the heart, the stopper locking the tension in the tether by inhibiting the first portion of the tether from sliding with respect to the anchor, and transluminally advancing the elongate tool to the implant comprises transluminally advancing the elongate tool to the implant that includes the anchor slidably coupled to the tether and anchored to the heart, the stopper locking the tension in the tether by inhibiting the first portion of the tether from sliding with respect to the anchor.

Example 485. The method according to example 484, wherein the stopper inhibits the first portion of the tether from sliding with respect to the anchor by the stopper abutting the anchor, and transluminally advancing the elongate tool to the implant comprises transluminally advancing the elongate tool to the implant in which the stopper inhibits the first portion of the tether from sliding with respect to the anchor by the stopper abutting the anchor.

Example 486. The method according to example 484, wherein cutting the tether comprises cutting the tether between the stopper and the anchor.

Example 487. The method according to example 486, wherein: (i) relieving the tension on the tether by cutting the tether comprises cutting the tether such that the cutting forms first and second cut ends of the tether, and the second portion of the tether pulls the second cut end away from the cutter and past the anchor, (ii) withdrawing the first portion of the tether comprises withdrawing the first portion of the tether along with the first cut end, and (iii) leaving the second portion of the tether comprises leaving the second portion of the tether along with the second cut end.

Example 488. The method according to example 487, wherein: (i) the anchor is a first anchor, (ii) the implant includes a second anchor, slidably coupled to the tether and anchored to the heart, and (iii) cutting the tether comprises cutting the tether such that the second portion of the tether pulls the second cut end away from the cutter, past the first anchor, but not past the second anchor.

Example 489. The method according to example 487, wherein cutting the tether such that the second portion of the tether pulls the second cut end away from the cutter and past the anchor, comprises cutting the tether such that the second portion of the tether decouples the anchor from the tether by pulling the second cut end away from the cutter and past the anchor.

Example 490. The method according to example 489, wherein: (i) the anchor is slidably coupled to the tether by an eyelet of the anchor being threaded onto the tether, and (ii) cutting the tether such that the second portion of the tether decouples the anchor from the tether comprises cutting the tether such that the second portion of the tether unthreads the anchor from the tether by pulling the second cut end away from the cutter and through the eyelet.

Example 491. A method, comprising: (A) transluminally advancing an elongate tool to a tether that is under tension and disposed within a heart of a subject, the elongate tool including a holder and a cutter; (B) securing a first portion of the tether to the holder; and (C) while the first portion of the tether remains secured to the holder: (i) relieving the tension on the tether by cutting the tether with the cutter, thereby separating the first portion of the tether from a second portion of the tether; and (ii) withdrawing the tool and the first portion of the tether from the subject while leaving the second portion of the tether coupled to the heart.

Example 492. The method according to example 491, wherein the first portion of the tether includes a knot that locks the tension in the tether, and wherein withdrawing the first portion of the tether comprises withdrawing the knot from the subject.

Example 493. The method according to example 491, wherein the first portion of the tether has a stopper locked thereto, the stopper locking the tension in the tether, and wherein withdrawing the first portion of the tether comprises withdrawing the stopper from the subject.

Example 494. The method according to any one of examples 491-493, wherein the tether is coupled to an anchor that is anchored to the heart, and wherein withdrawing the tool and the first portion of the tether comprises withdrawing the tool and the first portion of the tether from the subject while leaving the anchor anchored to the heart.

Example 495. An apparatus, comprising a tissue anchor, the anchor comprising: (A) a revolute joint defining a hinge axis; (B) a first arm, defining: (i) a first coupling, and (ii) a first hook that curves about and away from the hinge axis, terminating in a first tip, the curving of the first hook being in a first direction about the hinge axis; and (C) a second arm, hingedly coupled to the first arm via the revolute joint, and defining: (i) a second coupling, and (ii) a second hook that curves about and away from the hinge axis, terminating in a second tip, the curving of the second hook being in a second direction about the hinge axis, the second direction being opposite to the first direction; and wherein the hinged coupling of the second arm to the first arm is such that the anchor is transitionable between: (1) an open state in which: (a) the first arm is in a first rotational position about the hinge axis; (b) the first hook and the second hook define a space therebetween, (c) the first tip and the second tip define therebetween a gap into the space, and (d) the first coupling and the second coupling are disengaged from each other, and (2) a closed state in which: (a) the first arm is in a second rotational position about the hinge axis; (b) the gap is smaller than in the open state; and (c) the first coupling and the second coupling are engaged with each other, the engagement between the first coupling and the second coupling inhibiting the anchor from transitioning out of the closed state.

Example 496. The apparatus according to example 495, wherein, for each of the first hook and the second hook, a radius of curvature of the hook increases with distance from the revolute joint.

Example 497. The apparatus according to any one of examples 495-496, wherein, in the closed state, the first tip and the second tip face away from each other.

Example 498. The apparatus according to any one of examples 495-496, wherein the anchor further comprises a spring, configured to bias the first arm toward a given rotational position about the hinge axis.

Example 499. The apparatus according to example 498, wherein the spring is configured to bias the lock toward the closed state.

Example 500. The apparatus according to example 498, wherein the spring is a torsion spring.

Example 501. The apparatus according to example 500, wherein the revolute joint comprises a pin that extends through the first arm and the second arm, and wherein the torsion spring is mounted on the pin.

Example 502. The apparatus according to any one of examples 495-501, wherein: (i) the first arm defines a first beam, (ii) the second arm defines a second beam, and (iii) the revolute joint is disposed between the first beam and the first hook, and between the second beam and the second hook, such that the first arm is a class I lever whose fulcrum is the revolute joint.

Example 503. The apparatus according to example 502, wherein the anchor is a class I double-lever whose fulcrum is the revolute joint.

Example 504. The apparatus according to example 502, wherein the anchor is transitionable from the open state toward the closed state by driving the first beam about the hinge axis.

Example 505. The apparatus according to example 504, wherein the anchor is transitionable from the open state toward the closed state by increasing an alignment between the first beam and the second beam.

Example 506. The apparatus according to example 505, wherein: (i) the first coupling is disposed on the first beam, (ii) the second coupling is disposed on the second beam, and (iii) the hinged coupling of the second arm to the first arm is such that the anchor is transitionable into the closed state by bringing the first beam into alignment with the second beam such that the first coupling and the second coupling responsively engage each other.

Example 507. The apparatus according to example 506, wherein the first coupling comprises a protrusion and the second coupling comprises a recess.

Example 508. An apparatus for use with tissue of a heart, the apparatus comprising: (A) a tether; and (B) a tissue anchor comprising: (i) a stem, (ii) an arm, (iii) a hinge, the arm being coupled to a distal end of the stem via the hinge, and (iv) a head coupled to a proximal part of the stem, the tether being slidably coupled to the head, and the stem having an intermediate part between the distal end and the proximal part; and wherein: (1) the anchor is anchorable into the tissue by advancing into the tissue, in succession, a first side of the arm, the hinge, and the intermediate part of the stem, such that stem extends, from the distal end and the hinge within the tissue, to the proximal part above the tissue, (2) the arm is pivotable about the hinge within the tissue such that the anchor is transitionable, within the tissue, toward a restraining state in which the arm extends transversally across the distal end of the stem, and (3) the head is configured to sandwich the tissue between the arm and the head by being moved distally along the stem toward the hinge.

Example 509. The apparatus according to example 508, further comprising a hollow needle, wherein: (i) the needle has a sharpened tip, configured to be penetrated into the tissue, (ii) the arm is configured to be delivered, within the needle, into the tissue, (iii) the stem is biased to automatically curve, upon deployment from the needle within the tissue, and (iv) the needle is configured to inhibit the curving of the stem while the stem is disposed within the needle.

Example 510. The apparatus according to any one of examples 508-509, wherein the arm has a second side, the hinge coupled to the arm between the first side and the second side, such that transitioning of the anchor toward the restraining state pivots, within the tissue, the arm with respect to the stem such that the first side of the arm moves proximally with respect to the stem, and the second side of the arm moves distally with respect to the stem.

Example 511. The apparatus according to example 510, wherein the anchor is configured to, while the arm is disposed within the tissue, automatically transition toward the restraining state upon application of a proximal pulling force to the stem.

Example 512. The apparatus according to example 511, wherein the second side, measured between a tip of the second side and the hinge, is longer than the first side, measured between a tip of the first side and the hinge.

Example 513. The apparatus according to example 511, wherein the second side has an eccentric tip.

Example 514. The apparatus according to example 513, wherein the eccentric tip is sharpened.

Example 515. The apparatus according to example 513, wherein the first side has a centralized tip.

Example 516. The apparatus according to example 515, wherein the centralized tip is sharpened.

Example 517. The apparatus according to example 510, further comprising a retrieval line, coupled to the second side in a manner in which proximal pulling of the retrieval line transitions the anchor away from the restraining state by pivoting, within the tissue, the arm with respect to the stem such that the first side of the arm moves distally with respect to the stem, and the second side of the arm moves proximally with respect to the stem.

Example 518. The apparatus according to example 517, further comprising a tube, advanceable distally over and along the retrieval line and the stem, and wherein the anchor is configured to be de-anchored from the tissue by pulling of the retrieval line, the stem, and the second side of the arm, into the tube.

Example 519. The apparatus according to example 517, wherein the retrieval line is intracorporeally decouplable from the anchor.

Example 520. A method for implanting an implant into tissue of a heart of a subject, the method comprising: (A) into the subject, introducing a tissue anchor including a stem, a head coupled to a proximal part of the stem, an arm, and a hinge via which the arm is coupled to the stem, the stem having an intermediate part between the distal end and the proximal part, (B) toward the heart, transluminally advancing the anchor along a tether with the head sliding over the tether; (C) advancing into the tissue, in succession, a first side of the arm, the hinge, and the intermediate part of the stem, such that a proximal part of the stem extends above the tissue; (D) within the tissue, transitioning the anchor toward a restraining state thereof by pivoting the arm about the hinge such that the arm extends transversally across the distal end of the stem; and (E) subsequently, sandwiching the tissue between the arm and the head by moving the head distally along the stem toward the hinge.

Example 521. The method according to example 520, further comprising advancing into the tissue a needle that has a sharpened tip, wherein advancing into the tissue the first end of the arm, the hinge, and the intermediate part of the stem comprises advancing out of the needle and into the tissue, in succession, the first end of the arm, the hinge, and the intermediate part of the stem.

Example 522. The method according to any one of examples 520-521, wherein advancing the first side of the arm into the tissue comprises advancing the first side of the arm into an annulus of an atrioventricular valve of the heart while the arm is generally orthogonal to a coronary artery disposed alongside the annulus.

Example 523. The method according to example 522, wherein pivoting the arm about the hinge comprises pivoting the arm about the hinge such that the arm becomes generally parallel with the coronary artery.

Example 524. The method according to any one of examples 520-523, wherein the arm has a second side, the hinge coupled to the arm between the first side and the second side, and wherein transitioning the anchor toward the retaining state comprises, within the tissue, pivoting the arm with respect to the stem such that the first side of the arm moves proximally with respect to the stem, and the second side of the arm moves distally with respect to the stem.

Example 525. The method according to example 524, wherein pivoting the arm about the hinge comprises pivoting the arm about the hinge while a retrieval line is coupled to the second side, and wherein the method further comprises subsequently intracorporeally decoupling the retrieval line from the anchor.

Example 526. The method according to example 524, wherein pivoting the arm with respect to the stem comprises applying a proximal pulling force to the stem such that the anchor automatically transitions toward the restraining state.

Example 527. The method according to example 526, wherein the second side, measured between a tip of the second side and the hinge, is longer than the first side, measured between a tip of the first side and the hinge, and wherein pivoting the arm with respect to the stem comprises applying a proximal pulling force to the stem such that interaction between the tissue and the longer second side pivots the arm with respect to the stem.

Example 528. The method according to example 526, wherein the second side has an eccentric tip, and wherein pivoting the arm with respect to the stem comprises applying a proximal pulling force to the stem such that interaction between the tissue and the eccentric tip side pivots the arm with respect to the stem.

Example 529. The method according to example 528, wherein the first side of the arm has a centralized tip, and wherein advancing the first side of the arm into the tissue comprises penetrating the tissue with the centralized tip.

Example 530. The method according to example 524, further comprising de-anchoring the anchor from the tissue by: (i) pivoting the arm with respect to the stem by proximally pulling on a retrieval line that is coupled to the second side such that, within the tissue, the first side of the arm moves distally with respect to the stem and the second side of the arm moves proximally with respect to the stem; and (ii) subsequently, pulling the arm, second-side first, out of the tissue.

Example 531. The method according to example 530, further comprising advancing a tube over and along the retrieval line and the stem, wherein pulling the arm out of the tissue comprises pulling the arm, second-side first, into the tube and out of the tissue.

Example 532. An implant comprising: (A) a tether; (B) a first anchor and a second anchor, each of the first and second anchors comprising: (i) a head, slidably coupled to the tether, and (ii) a tissue-engaging element, configured to anchor the anchor and the tether to the tissue; and (C) a tubular spacer defining a lumen along a spacer-axis, and having: (i) a primary region that is flexible in deflection; and (ii) at each end of the primary region, a secondary region that is less flexible in deflection than the primary region, the lumen extending through the primary region and both secondary regions; and wherein the tubular spacer is threaded onto the tether between the first anchor and the second anchor, by the tether passing through the lumen.

Example 533. The implant according to example 532, wherein the primary region is elastically flexible in deflection.

Example 534. The implant according to any one of examples 532-533, wherein the primary region resists axial compression.

Example 535. The implant according to example 534, wherein each of the secondary regions are more resistant than the primary region to axial compression.

Example 536. The implant according to any one of examples 532-535, wherein each of the secondary regions is shorter than the primary region.

Example 537. The implant according to example 536, wherein a combined length of both of the secondary regions is shorter than the primary region.

Example 538. The implant according to example 536, wherein each of the secondary regions is less than 30 percent as long as the primary region.

Example 539. The implant according to example 538, wherein each of the secondary regions is less than 20 percent as long as the primary region.

Example 540. The implant according to example 539, wherein each of the secondary regions is less than 10 percent as long as the primary region.

Example 541. The implant according to example 540, wherein each of the secondary regions is at least 2 percent as long as the primary region.

Example 542. The implant according to example 540, wherein each of the secondary regions is at least 5 percent as long as the primary region.

Example 543. The implant according to any one of examples 532-542, wherein the spacer comprises a helical coil that extends along the primary region.

Example 544. The implant according to example 543, wherein the helical coil comprises a wire that is coiled to form the helical coil, and wherein the wire has a core that comprises a radiopaque material.

Example 545. The implant according to example 544, wherein the wire comprises cobalt chrome, and wherein the core comprises platinum.

Example 546. The implant according to example 543, wherein the coil extends into the secondary regions.

Example 547. The implant according to example 543, wherein the helical coil comprises a wire that is coiled to form the helical coil, the wire having a wire thickness, and wherein, in a resting state of the helical coil, the helical coil has a pitch that is 1.4-2 times the wire thickness.

Example 548. The implant according to example 547, wherein, in the resting state, the pitch of the helical coil is 1.6-1.8 times the wire thickness.

Example 549. The implant according to example 543, wherein the spacer comprises, at each of the secondary regions, a rigid ring coupled to the end of the helical coil.

Example 550. The implant according to example 549, wherein the helical coil comprises a wire that is coiled to form the helical coil, the wire having a wire thickness, and wherein each of the rings has a length, along the spacer-axis, that is at least twice as great as the wire thickness.

Example 551. The implant according to example 549, wherein each of the rings is disposed at least partly inside of the helical coil.

Example 552. The implant according to example 549, wherein each of the rings has a flange disposed outside of the helical coil, the flange providing a bearing surface configured to facilitate sliding of the tether thereagainst.

Example 553. A system, for use with a subject, the system comprising: (A) a delivery tool, percutaneously advanceable into the subject, and having a cavity; and (B) a stopper comprising: (i) a first element comprising a first plate that defines a first passageway therethrough; (ii) a second element comprising a second plate that defines a second passageway therethrough; and (iii) a torsion bar, connecting the first plate to the second plate in a manner in which: (a) the torsion bar biases the stopper toward a grip state in which the first passageway and the second passageway are offset with respect to each other, and (b) the stopper is dimensioned such that, while the stopper is disposed in the cavity, the delivery tool retains the stopper in an open state, the stopper being transitionable into the open state by increasing stress on the torsion bar and alignment between the first passageway and the second passageway.

Example 554. The system according to example 553, wherein, in both the grip state and the open state, both the first passageway and the second passageway are parallel with the torsion bar.

Example 555. The system according to any one of examples 553-554, wherein: (i) the cavity is defined by an inner surface of the delivery tool, and (ii) the stopper is dimensioned to be disposed within the cavity in a manner in which the first plate and the second plate are disposed within the cavity, with the inner surface retaining the stopper in the open state by pressing against the first plate and the second plate.

Example 556. The system according to example 555, wherein: (i) while the stopper is disposed within the cavity, the inner surface pressing against the first plate and the second state inhibits torsional de-stressing of the torsion bar, and (ii) the stopper is configured to, in response to being ejected from the cavity, transition toward the grip state by torsional de-stressing of the torsion bar moving the first plate with respect to the second plate.

Example 557. The system according to example 555, wherein: (i) in the open state of the stopper, the stopper defines a central longitudinal axis that passes through a center of the first plate and a center of the second plate, and (ii) transitioning of the stopper toward the grip state offsets the center of at least one of the first plate and the second plate with respect to the central longitudinal axis.

Example 558. The system according to example 557, wherein, in both the open state and the grip state, both the first passageway and the second passageway are parallel with the longitudinal axis.

Example 559. The system according to example 557, wherein, in the grip state, the first plate is nonaxial with the second plate.

Example 560. The system according to example 557, wherein the delivery tool is a catheter.

Example 561. The system according to any one of examples 553-560, further comprising a tether, and wherein: (i) while the stopper is in the open state, the alignment between the first passageway and the second passageway is sufficient for the tether to be slidable through the stopper, and (ii) while the tether is disposed through the stopper, transitioning of the stopper into the grip state grips the tether within the stopper, thereby inhibiting sliding of the tether through the stopper.

Example 562. The system according to example 561, wherein the system comprises an implant that comprises the tether, implant being contractable by applying tension to the tether, and wherein, in the grip state of the stopper, the stopper is configured to lock the tension in the tether by gripping the tether.

Example 563. The system according to any one of examples 553-562, wherein, in the open state of the stopper, the first element and the second element are aligned with respect to each other such that the stopper is cylindrical.

Example 564. The system according to example 563, wherein in the grip state, the first element is offset with respect to the second element such that the stopper is non-cylindrical.

Example 565. A system for use with a subject, comprising: (A) a catheter device, comprising: (i) a tube that has a proximal opening, and a distal opening that is configured to be transluminally advanced into the subject, and (ii) an extracorporeal unit that comprises: a track that leads to a deployment position, and a barrier, movable between a closed state in which the barrier obstructs the proximal opening and an open state; (B) a first cartridge holding a first anchor and being coupled to the extracorporeal unit and, while remaining coupled to the extracorporeal unit, being moveable along the track from a first initial position to the deployment position such that: (i) the first cartridge holds the first anchor opposite the proximal opening, and (ii) the barrier is in the closed state; (C) a second cartridge holding a second anchor and being coupled to the extracorporeal unit and, while remaining coupled to the extracorporeal unit, being moveable along the track from a second initial position to the deployment position such that: (i) the second cartridge holds the second anchor opposite the proximal opening, and (ii) the barrier is in the closed state; and (D) an anchor driver that is: (i) couplable to the first anchor while the first anchor is held by the first cartridge opposite the proximal opening, (ii) configured to, while the barrier is in the open state, advance the first anchor distally out of the first cartridge through the proximal opening and through the tube, (iii) subsequently couplable to the second anchor while the second anchor is held by the second cartridge opposite the proximal opening, and (iv) configured to, while the barrier is in the open state, advance the second anchor distally out of the second cartridge through the proximal opening and through the tube toward the first anchor.

Example 566. The system according to example 565, wherein the driver is configured to advance the first anchor distally out of the first cartridge through the proximal opening and through the tube while: (i) the first cartridge is in the deployment position, (ii) the barrier is in the open state, and (iii) the second cartridge remains in the second initial position.

Example 567. The system according to any one of examples 565-566, wherein each of the first cartridge and the second cartridge is configured to lock to the extracorporeal unit upon arriving at the deployment position.

Example 568. The system according to any one of examples 565-567, wherein each of the first cartridge and the second cartridge is shaped to be grasped by hand by a human operator and is configured to be moved along the track by hand by the human operator, and/or wherein each of the first cartridge and the second cartridge is removable from the deployment position by being removed from the extracorporeal unit.

Example 569. The system according to any one of examples 565-568, further comprising a third cartridge holding a third anchor and being coupled to the extracorporeal unit and, while remaining coupled to the extracorporeal unit, being moveable along the track from a third initial position to the deployment position such that the third cartridge holds the third anchor opposite the proximal opening.

Example 570. The system according to any one of examples 565-569, wherein the first anchor comprises a first tissue-engaging element and a first head comprising a first eyelet, and the second anchor comprises a second tissue-engaging element and a second head comprising a second eyelet.

Example 571. The system according to example 570, further comprising a tether threaded through the first eyelet and the second eyelet, the tether having a proximal portion that includes a proximal end of the tether and having a distal portion that includes a distal end of the tether, the distal end of the tether being advanceable distally through the tube into the subject while the proximal end of the tether remains outside of the subject.

Example 572. The system according to example 571, wherein the anchor driver is configured to advance the first anchor distally out of the first cartridge, through the proximal opening, and through the tube, while the first eyelet of the first anchor remains threaded on the tether, and wherein the anchor driver is configured to advance the second anchor distally out of the second cartridge, through the proximal opening, and through the tube, while the second eyelet of the second anchor remains threaded on the tether.

Example 573. The system according to example 572, wherein the catheter device further comprises a tensioning device configured to maintain tension on the tether during advancement of the first anchor and advancement of the second anchor.

Example 574. The system according to example 573, wherein the tensioning device comprises a spring and a spool, the spool coupled to the spring such that rotation of the spool in a first direction applies stress to the spring, and wherein the proximal portion of the tether is wound around the spool such that advancing of the distal portion of the tether distally through the tube rotates the spool in the first direction.

The invention claimed is:

1. A system for use with a subject, comprising:
- a catheter device, comprising:
  - a tube that has:
    - a distal opening that is configured to be transluminally advanced into the subject, and
    - a proximal end that defines a proximal opening and defines a tube axis, and
  - an extracorporeal unit that is coupled to the proximal end of the tube; and
- a series of anchors;
- a series of cartridges arranged in a row along the extracorporeal unit that defines a cartridge axis, the cartridge axis being parallel with the tube axis, each of the cartridges:
  - having an initial position in which the cartridge holds a respective anchor of the series of anchors,
  - while remaining coupled to the extracorporeal unit, being moveable from the initial position to a deployment position; and
- an anchor driver that is configured to, for each of the anchors, sequentially:
  - engage the anchor, and
  - while the respective cartridge is in the deployment position, move the anchor out of the respective cartridge, through the proximal opening, and through the tube toward the distal opening.

2. The system according to claim 1, wherein, for each of the anchors:
- the respective cartridge is configured to restrain the anchor therein,
- the anchor driver is configured to, while engaged with the anchor, apply a proximal pulling force to the anchor, and
- the respective cartridge is configured to, upon the proximal pulling force exceeding a threshold magnitude, responsively undergo a conformational change that allows the anchor driver to move the anchor out of the respective cartridge.

3. The system according to claim 1, wherein, for each of the anchors:
- the respective cartridge comprises a first piece and a second piece,
- the anchor driver is configured to, while engaged with the anchor, apply a proximal pulling force to the anchor, and
- the respective cartridge is configured such that, upon the proximal pulling force exceeding a threshold magnitude, the second piece responsively slides with respect to the first piece in a manner that allows the anchor driver to move the anchor out of the respective cartridge.

4. The system according to claim 1, wherein:
- the catheter device further comprises a port at the proximal opening of the tube, and
- the system further comprises a flushing adapter:
  - comprising a fluid fitting, a nozzle, and a channel therebetween, and
  - reversibly lockable to the extracorporeal unit in a flushing position in which:
    - the fluid fitting is accessible from outside of the catheter device, and
    - the nozzle in fluid communication with the port such that fluid driven into the flushing adapter via the fluid fitting is directed distally through the tube.

5. The system according to claim 4, wherein the port comprises a sealing membrane, the anchor driver configured, for each of the anchors, to advance the anchor distally through the membrane and into the tube.

6. The system according to claim 5, wherein, in the flushing position, the nozzle seals with the port proximally from the membrane.

7. The system according to claim 1, wherein each of the cartridges is removable from the extracorporeal unit.

8. The system according to claim 1, wherein the anchor driver is configured to, for each of the anchors, move the anchor out of the respective cartridge, through the proximal opening, and through the tube toward the distal opening while the respective cartridge remains in the deployment position.

9. The system according to claim 1, wherein:

each of the anchors comprises a tissue-engaging element, and a head that comprises an eyelet, and the system further comprises a tether:

threaded through the eyelet of each of the anchors, having a proximal portion that includes a proximal end of the tether, and having a distal portion that includes a distal end of the tether, the distal end of the tether being advanceable distally through the tube into the subject while the proximal end of the tether remains outside of the subject.

10. The system according to claim 9, wherein, for each of the anchors:

the tissue-engaging element defines a central longitudinal axis of the anchor, has a sharpened distal tip, and is configured to be driven into tissue of the subject, the head is coupled to a proximal end of the tissue-engaging element, and further comprises an interface, configured to be reversibly engaged by the anchor driver, and the eyelet is mounted so as to be revolvable, with respect to the interface, about the central longitudinal axis of the anchor.

11. The system according to claim 10, wherein the eyelet is mounted so as to be pivotable with respect to the longitudinal axis of the anchor.

12. The system according to claim 10, wherein the tissue-engaging element defines the central longitudinal axis by extending in a helix around and along the central longitudinal axis, and is configured to be screwed into the tissue of the subject.

13. The system according to claim 12, wherein the tissue-engaging element is configured to be screwed into the tissue such that a distal portion of the helix enters the tissue prior to a proximal portion of the helix, the distal portion having a greater pitch than the proximal portion.

14. The system according to claim 10, wherein:

the head comprises a collar that circumscribes the central longitudinal axis, and is rotatably coupled to the interface, and the eyelet is mounted on the collar and is revolvable around the central longitudinal axis by rotation of the collar about the central longitudinal axis.

15. The system according to claim 9, further comprising a series of tubular spacers, threaded on the tether alternatingly with the anchors.

16. The system according to claim 15, wherein each of the spacers is elastically flexible in deflection.

17. The system according to claim 15, wherein each of the spacers resists axial compression.

18. The system according to claim 15, wherein each of the spacers is defined by a helical wire shaped as a coil.

19. The system according to claim 9, wherein the anchor driver, for each of the anchors, is configured to move the anchor out of the respective cartridge, through the proximal opening, and through the tube toward the distal opening, while the eyelet of the anchor remains threaded on the tether.

20. The system according to claim 9, wherein the catheter device further comprises a tensioner that comprises a spring-loaded winch, coupled to the proximal portion of the tether, and configured to maintain tension on the tether.

* * * * *